United States Patent
Flynn et al.

(10) Patent No.: US 9,187,474 B2
(45) Date of Patent: Nov. 17, 2015

(54) RAF INHIBITOR COMPOUNDS

(71) Applicants: Deciphera Pharmaceuticals, LLC, Lawrence, KS (US); Eli Lilly and Company, Windlesham, Surrey (GB)

(72) Inventors: Daniel L. Flynn, Lawrence, KS (US); Michael D. Kaufman, Lawrence, KS (US); Lakshminarayana Vogeti, Lawrence, KS (US); Scott Wise, Lawrence, KS (US); Wei-Ping Lu, Lawrence, KS (US); Bryan Smith, Lawrence, KS (US); Timothy Malcolm Caldwell, Fishers, IN (US); William C. Patt, Lawrence, KS (US); James R. Henry, Indianapolis, IN (US); Philip A. Hipskind, Indianapolis, IN (US); Sheng-Bin Peng, Indianapolis, IN (US)

(73) Assignees: Deciphera Pharmaceuticals, LLC KS (US); Eli Lilly and Company IN (US)

( * ) Notice: Subject to any disclaimer, the term of this patent is extended or adjusted under 35 U.S.C. 154(b) by 0 days.

(21) Appl. No.: 14/383,803

(22) PCT Filed: Mar. 5, 2013

(86) PCT No.: PCT/US2013/029176
§ 371 (c)(1),
(2) Date: Sep. 8, 2014

(87) PCT Pub. No.: WO2013/134298
PCT Pub. Date: Sep. 12, 2013

(65) Prior Publication Data
US 2015/0105367 A1    Apr. 16, 2015

Related U.S. Application Data

(60) Provisional application No. 61/607,807, filed on Mar. 7, 2012.

(51) Int. Cl.
*C07D 471/04* (2006.01)

(52) U.S. Cl.
CPC .................. *C07D 471/04* (2013.01)

(58) Field of Classification Search
None
See application file for complete search history.

(56) References Cited

U.S. PATENT DOCUMENTS 8,188,113 B2 * 5/2012 Flynn et al. ............ 514/300
2007/0054916 A1 3/2007 Patel et al.
2008/0114006 A1 5/2008 Flynn et al.

OTHER PUBLICATIONS

Advanced Organic Chemistry: Reactions, Mechanisms and Structures, 4th Ed., John Wiley & Sons, pp. 69-74 (1992).

Berge, et al., "Pharmaceutical Salts" Journal of 'Pharmaceutical Sciences, vol. 66, No. 1, Jan. 1977.
Davies et al, "Mutations of the BRAF Gene in Human Cancer" Nature, 2002, 417: 949-954.
Hatzivassiliou G, et al. "RAF Inhibitors Prime Wild-Type RAF to Activate the MAPK Pathway and Enhance Growth" Nature, 2010, 464: 431-435.
Heidorn, et al, "Kinase-Dead Braf and Oncogenic RAS Cooperative to Drive Tumor Progression Through CRAF" Cell, 2010, 140: 209-221.
Johannessen et al, "COT/MAP3K8 Drives Resistance to RAF Inhibition Through MAP Kinase Pathway Reactivation" Nature. 2010, 468: 968-72.
Lennartsson et al, "The Stem Cell Factor Receptor/C-Kit As a Drug Target in Cancer" Current Cancer Drug Targets, 2006, 6: 65.
Montagut et al, "Elevated CRAF as a Potential Mechanism of Acquired Resistance to BRAF Inhibition in Melanoma" Cancer Res. 2008, 68: 4853-61.
Moss, G.P. "Basic Terminology of Stereochemistry" Pure Appl. Chem. 1996, 68, pp. 2193-2222.
Muller, P. "Glossary of Terms Used in Physical Organic Chemistry" Pure Appl. Chem. 1994, 66, pp. 1077-1184.
Nazarian et al, "Melanomas Acquire Resistance to B-RAF (V600e) Inhibition by RTK or N-RAS Upregulation" Nature. 2010, 468: 973-7.
Poulikakos et al, "RAF Inhibitors Transactivate RAF Dimers and ERK Signalling in Cells With Wild-Type BRAF" Nature, 2010, 464: 427-430.
Poulikakos et al, RAF Inhibitor Resistance Is Mediated by Dimerization of Aberrantly Spliced BRAF (V600E) Nature. 2011, 480: 387-390.
Pylayeva-Gupta et al, "RAS Oncogenes: Waving a Tumorigenic Web" Nature Reviews Cancer, 2011, 11: 761.
Remington: The Science and Practice of Pharmacy (A. Gennaro, et al, eds., 19th ed., Mack Publishing Co., 1995).
Rominger, et al, "An Intrinsic ATPASE Activity of Phospho-Mek-1 Uncoupled From Downstream ERK Phosphorylation" Arch. Biochem. Biophys. 2007, 464: 130-137.

(Continued)

*Primary Examiner* — Timothy R Rozof
(74) *Attorney, Agent, or Firm* — Cooley LLP

(57) ABSTRACT

This invention provides compounds of Formula (I) or a pharmaceutically acceptable salt thereof; pharmaceutical compositions comprising a compound of Formula (I); and use of a compound of Formula (I) for treating specified cancers.

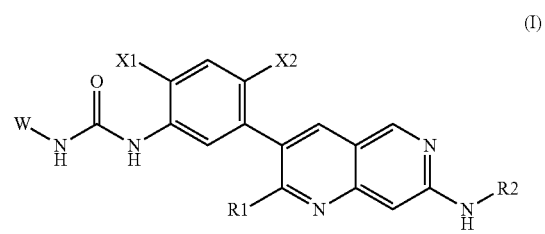

(I)

19 Claims, No Drawings

(56) References Cited

OTHER PUBLICATIONS

Roskoski, Jr., "RAF Protein-Serine/Threonine Kinases: Structure and Regulation", Biochemical and Biophysical Research Communications 399 (2010) 313-317.
Schindler et al, "Structural Mechanism for STI-571 Inhibition of Abelson Tyrosine Kinase" Science, 2000, 289: 1938-1942.
Schubbert et al, "Hyperactive RAS in Developmental Disorders and Cancer" Nature Reviews Cancer, 2007, 7: 295;.
Sebolt-Leopold et al, "Targeting the Mitogen Activated Protein Kinase Casecade to Treat Cancer" Nat Rev Cancer, 2004, 4: 937-947;.
Shi et al, "Combinatorial Treatments That Overcome PDGFRβ-Driven Resistance of Melanoma Cells to $^{V600E}$ B-RAF Inhibition" Cancer Res. 2011, 71: 5067-74.
Stahl, P.H., Wermuth, C.G., Eds. Handbook of Pharmaceutical Salts: Properties, Selection and Use; Verlag Helvetica Chimica Acta/Wiley-VCH: Zurich, 2002.
Su et al, "RAS Mutations in Cutaneous Squamous-Cell Carcinomas in Patients Treated With BRAF Inhibitors" New England Journal of Medicine. 2012 366:207-215.
Villanueva et al, "Acquired Resistance to BRAF Inhibitors Mediated by a RAF Kinase Switch in Melanoma Can Be Overcome by Cotargeting MEDK and IGF-1R/P13K" Cancer Cell. 2010, 18: 683-95.
Wagle et al, "Dissecting Therapeutic Resistance to RAF Inhibition in Melanoma by Tumor Genomic Profiling" Journal of Clinical Oncology, 2011, 29: 3085-96.
Wan et al, "Mechanism of Activation of the RAF-ERK Signaling Pathway by Onvogenic Mutations of B-RAF"Cell, 2004, 116: 855-867.
Wellbrock et al, "The RAF Proteins Take Centre Stage" Nat Rev Mol Cell Biol, 2004, 5: 875-885.
Whittaker et al, "Gatekeeper Mutations Mediate Resistance to Braftargeted Therapies" Sci Transl Med. 2010, 2: 35-41.

* cited by examiner

SEQUENCE LISTING

```
<160> NUMBER OF SEQ ID NOS: 8

<210> SEQ ID NO 1
<211> LENGTH: 307
<212> TYPE: PRT
<213> ORGANISM: Artificial Sequence
<220> FEATURE:
<223> OTHER INFORMATION: B-Raf-V600E

<400> SEQUENCE: 1

Met Asp Arg Gly Ser His His His His His His Gly Ser Glu Asp Arg
1               5                   10                  15

Asn Arg Met Lys Thr Leu Gly Arg Arg Asp Ser Ser Asp Asp Trp Glu
            20                  25                  30

Ile Pro Asp Gly Gln Ile Thr Val Gly Gln Arg Ile Gly Ser Gly Ser
        35                  40                  45

Phe Gly Thr Val Tyr Lys Gly Lys Trp His Gly Asp Val Ala Val Lys
    50                  55                  60

Met Leu Asn Val Thr Ala Pro Thr Pro Gln Gln Leu Gln Ala Phe Lys
65                  70                  75                  80

Asn Glu Val Gly Val Leu Arg Lys Thr Arg His Val Asn Ile Leu Leu
                85                  90                  95

Phe Met Gly Tyr Ser Thr Lys Pro Gln Leu Ala Ile Val Thr Gln Trp
            100                 105                 110

Cys Glu Gly Ser Ser Leu Tyr His His Leu His Ile Ile Glu Thr Lys
        115                 120                 125

Phe Glu Met Ile Lys Leu Ile Asp Ile Ala Arg Gln Thr Ala Gln Gly
    130                 135                 140

Met Asp Tyr Leu His Ala Lys Ser Ile Ile His Arg Asp Leu Lys Ser
145                 150                 155                 160

Asn Asn Ile Phe Leu His Glu Asp Leu Thr Val Lys Ile Gly Asp Phe
                165                 170                 175

Gly Leu Ala Thr Glu Lys Ser Arg Trp Ser Gly Ser His Gln Phe Glu
            180                 185                 190

Gln Leu Ser Gly Ser Ile Leu Trp Met Ala Pro Glu Val Ile Arg Met
        195                 200                 205

Gln Asp Lys Asn Pro Tyr Ser Phe Gln Ser Asp Val Tyr Ala Phe Gly
    210                 215                 220

Ile Val Leu Tyr Glu Leu Met Thr Gly Gln Leu Pro Tyr Ser Asn Ile
225                 230                 235                 240

Asn Asn Arg Asp Gln Ile Ile Phe Met Val Gly Arg Gly Tyr Leu Ser
                245                 250                 255

Pro Asp Leu Ser Lys Val Arg Ser Asn Cys Pro Lys Ala Met Lys Arg
            260                 265                 270

Leu Met Ala Glu Cys Leu Lys Lys Lys Arg Asp Glu Arg Pro Leu Phe
```

```
            275                 280                 285
Pro Gln Ile Leu Ala Ser Ile Glu Leu Leu Ala Arg Ser Leu Pro Lys
        290                 295                 300

Ile His Arg
305

<210> SEQ ID NO 2
<211> LENGTH: 307
<212> TYPE: PRT
<213> ORGANISM: Artificial Sequence
<220> FEATURE:
<223> OTHER INFORMATION: B-Raf-V600E+T529I

<400> SEQUENCE: 2

Met Asp Arg Gly Ser His His His His His Gly Ser Glu Asp Arg
1               5                   10                  15

Asn Arg Met Lys Thr Leu Gly Arg Arg Asp Ser Ser Asp Asp Trp Glu
                20                  25                  30

Ile Pro Asp Gly Gln Ile Thr Val Gly Gln Arg Ile Gly Ser Gly Ser
            35                  40                  45

Phe Gly Thr Val Tyr Lys Gly Lys Trp His Gly Asp Val Ala Val Lys
    50                  55                  60

Met Leu Asn Val Thr Ala Pro Thr Pro Gln Gln Leu Gln Ala Phe Lys
65                  70                  75                  80

Asn Glu Val Gly Val Leu Arg Lys Thr Arg His Val Asn Ile Leu Leu
                85                  90                  95

Phe Met Gly Tyr Ser Thr Lys Pro Gln Leu Ala Ile Val Ile Gln Trp
            100                 105                 110

Cys Glu Gly Ser Ser Leu Tyr His His Leu His Ile Ile Glu Thr Lys
        115                 120                 125

Phe Glu Met Ile Lys Leu Ile Asp Ile Ala Arg Gln Thr Ala Gln Gly
130                 135                 140

Met Asp Tyr Leu His Ala Lys Ser Ile Ile His Arg Asp Leu Lys Ser
145                 150                 155                 160

Asn Asn Ile Phe Leu His Glu Asp Leu Thr Val Lys Ile Gly Asp Phe
                165                 170                 175

Gly Leu Ala Thr Glu Lys Ser Arg Trp Ser Gly Ser His Gln Phe Glu
            180                 185                 190

Gln Leu Ser Gly Ser Ile Leu Trp Met Ala Pro Glu Val Ile Arg Met
        195                 200                 205

Gln Asp Lys Asn Pro Tyr Ser Phe Gln Ser Asp Val Tyr Ala Phe Gly
    210                 215                 220

Ile Val Leu Tyr Glu Leu Met Thr Gly Gln Leu Pro Tyr Ser Asn Ile
225                 230                 235                 240

Asn Asn Arg Asp Gln Ile Ile Phe Met Val Gly Arg Gly Tyr Leu Ser
                245                 250                 255

Pro Asp Leu Ser Lys Val Arg Ser Asn Cys Pro Lys Ala Met Lys Arg
            260                 265                 270

Leu Met Ala Glu Cys Leu Lys Lys Lys Arg Asp Glu Arg Pro Leu Phe
        275                 280                 285

Pro Gln Ile Leu Ala Ser Ile Glu Leu Leu Ala Arg Ser Leu Pro Lys
    290                 295                 300

Ile His Arg
305
```

```
<210> SEQ ID NO 3
<211> LENGTH: 307
<212> TYPE: PRT
<213> ORGANISM: Artificial Sequence
<220> FEATURE:
<223> OTHER INFORMATION: B-Raf-V600E+G468A

<400> SEQUENCE: 3

Met Asp Arg Gly Ser His His His His His His Gly Ser Glu Asp Arg
1               5                   10                  15

Asn Arg Met Lys Thr Leu Gly Arg Arg Asp Ser Ser Asp Asp Trp Glu
            20                  25                  30

Ile Pro Asp Gly Gln Ile Thr Val Gly Gln Arg Ile Gly Ser Gly Ser
        35                  40                  45

Phe Ala Thr Val Tyr Lys Gly Lys Trp His Gly Asp Val Ala Val Lys
    50                  55                  60

Met Leu Asn Val Thr Ala Pro Thr Pro Gln Gln Leu Gln Ala Phe Lys
65                  70                  75                  80

Asn Glu Val Gly Val Leu Arg Lys Thr Arg His Val Asn Ile Leu Leu
                85                  90                  95

Phe Met Gly Tyr Ser Thr Lys Pro Gln Leu Ala Ile Val Thr Gln Trp
            100                 105                 110

Cys Glu Gly Ser Ser Leu Tyr His His Leu His Ile Ile Glu Thr Lys
        115                 120                 125

Phe Glu Met Ile Lys Leu Ile Asp Ile Ala Arg Gln Thr Ala Gln Gly
    130                 135                 140

Met Asp Tyr Leu His Ala Lys Ser Ile Ile His Arg Asp Leu Lys Ser
145                 150                 155                 160

Asn Asn Ile Phe Leu His Glu Asp Leu Thr Val Lys Ile Gly Asp Phe
                165                 170                 175

Gly Leu Ala Thr Glu Lys Ser Arg Trp Ser Gly Ser His Gln Phe Glu
            180                 185                 190

Gln Leu Ser Gly Ser Ile Leu Trp Met Ala Pro Glu Val Ile Arg Met
        195                 200                 205

Gln Asp Lys Asn Pro Tyr Ser Phe Gln Ser Asp Val Tyr Ala Phe Gly
    210                 215                 220

Ile Val Leu Tyr Glu Leu Met Thr Gly Gln Leu Pro Tyr Ser Asn Ile
225                 230                 235                 240

Asn Asn Arg Asp Gln Ile Ile Phe Met Val Gly Arg Gly Tyr Leu Ser
                245                 250                 255

Pro Asp Leu Ser Lys Val Arg Ser Asn Cys Pro Lys Ala Met Lys Arg
            260                 265                 270

Leu Met Ala Glu Cys Leu Lys Lys Lys Arg Asp Glu Arg Pro Leu Phe
        275                 280                 285

Pro Gln Ile Leu Ala Ser Ile Glu Leu Leu Ala Arg Ser Leu Pro Lys
    290                 295                 300

Ile His Arg
305

<210> SEQ ID NO 4
<211> LENGTH: 1008
<212> TYPE: PRT
<213> ORGANISM: Unknown
<220> FEATURE:
<223> OTHER INFORMATION: B-Raf-wild type

<400> SEQUENCE: 4
```

-continued

```
Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
210                 215                 220

His Asn Gln Thr Ser Leu Tyr Lys Lys Ala Gly Ser Ala Ala Ala Val
225                 230                 235                 240

Val Glu Glu Asn Leu Tyr Phe Gln Gly Ser Phe Thr Met Ala Ala Leu
                245                 250                 255

Ser Gly Gly Gly Gly Gly Ala Glu Pro Gly Gln Ala Leu Phe Asn
        260                 265                 270

Gly Asp Met Glu Pro Glu Ala Gly Ala Gly Ala Ala Ala Ser
    275                 280                 285

Ser Ala Asn Ile Lys Gln Met Ile Lys Leu Thr Gln Glu His Ile Glu
    290                 295                 300

Ala Leu Leu Asp Lys Phe Gly Gly Glu His Asn Pro Pro Ser Ile Tyr
305                 310                 315                 320

Leu Glu Ala Tyr Glu Glu Tyr Thr Ser Lys Leu Asp Ala Leu Gln Gln
                325                 330                 335

Arg Glu Gln Gln Leu Leu Glu Ser Leu Gly Asn Gly Thr Asp Phe Ser
            340                 345                 350

Val Ser Ser Ser Ala Ser Met Asp Thr Val Thr Ser Ser Ser Ser Ser
        355                 360                 365

Ser Leu Ser Val Leu Pro Ser Ser Leu Ser Val Phe Gln Asn Pro Thr
    370                 375                 380

Asp Val Ala Arg Ser Asn Pro Lys Ser Pro Gln Lys Pro Ile Val Arg
385                 390                 395                 400

Val Phe Leu Pro Asn Lys Gln Arg Thr Val Val Pro Ala Arg Cys Gly
                405                 410                 415

Val Thr Val Arg Asp Ser Leu Lys Lys Ala Leu Met Met Arg Gly Leu
```

```
            420              425              430
Ile Pro Glu Cys Cys Ala Val Tyr Arg Ile Gln Asp Gly Glu Lys Lys
            435              440              445
Pro Ile Gly Trp Asp Thr Asp Ile Ser Trp Leu Thr Gly Glu Glu Leu
450              455              460
His Val Glu Val Leu Glu Asn Val Pro Leu Thr Thr His Asn Phe Val
465              470              475              480
Arg Lys Thr Phe Phe Thr Leu Ala Phe Cys Asp Phe Cys Arg Lys Leu
            485              490              495
Leu Phe Gln Gly Phe Arg Cys Gln Thr Cys Gly Tyr Lys Phe His Gln
            500              505              510
Arg Cys Ser Thr Glu Val Pro Leu Met Cys Val Asn Tyr Asp Gln Leu
            515              520              525
Asp Leu Leu Phe Val Ser Lys Phe Phe Glu His His Pro Ile Pro Gln
            530              535              540
Glu Glu Ala Ser Leu Ala Glu Thr Ala Leu Thr Ser Gly Ser Ser Pro
545              550              555              560
Ser Ala Pro Ala Ser Asp Ser Ile Gly Pro Gln Ile Leu Thr Ser Pro
            565              570              575
Ser Pro Ser Lys Ser Ile Pro Ile Pro Gln Pro Phe Arg Pro Ala Asp
            580              585              590
Glu Asp His Arg Asn Gln Phe Gly Gln Arg Asp Arg Ser Ser Ser Ala
            595              600              605
Pro Asn Val His Ile Asn Thr Ile Glu Pro Val Asn Ile Asp Asp Leu
610              615              620
Ile Arg Asp Gln Gly Phe Arg Gly Asp Gly Gly Ser Thr Thr Gly Leu
625              630              635              640
Ser Ala Thr Pro Pro Ala Ser Leu Pro Gly Ser Leu Thr Asn Val Lys
            645              650              655
Ala Leu Gln Lys Ser Pro Gly Pro Gln Arg Glu Arg Lys Ser Ser Ser
            660              665              670
Ser Ser Glu Asp Arg Asn Arg Met Lys Thr Leu Gly Arg Arg Asp Ser
            675              680              685
Ser Asp Asp Trp Glu Ile Pro Asp Gly Gln Ile Thr Val Gly Gln Arg
690              695              700
Ile Gly Ser Gly Ser Phe Gly Thr Val Tyr Lys Gly Lys Trp His Gly
705              710              715              720
Asp Val Ala Val Lys Met Leu Asn Val Thr Ala Pro Thr Pro Gln Gln
            725              730              735
Leu Gln Ala Phe Lys Asn Glu Val Gly Val Leu Arg Lys Thr Arg His
            740              745              750
Val Asn Ile Leu Leu Phe Met Gly Tyr Ser Thr Lys Pro Gln Leu Ala
            755              760              765
Ile Val Thr Gln Trp Cys Glu Gly Ser Ser Leu Tyr His His Leu His
            770              775              780
Ile Ile Glu Thr Lys Phe Glu Met Ile Lys Leu Ile Asp Ile Ala Arg
785              790              795              800
Gln Thr Ala Gln Gly Met Asp Tyr Leu His Ala Lys Ser Ile Ile His
            805              810              815
Arg Asp Leu Lys Ser Asn Asn Ile Phe Leu His Glu Asp Leu Thr Val
            820              825              830
Lys Ile Gly Asp Phe Gly Leu Ala Thr Val Lys Ser Arg Trp Ser Gly
            835              840              845
```

-continued

```
Ser His Gln Phe Glu Gln Leu Ser Gly Ser Ile Leu Trp Met Ala Pro
    850                 855                 860

Glu Val Ile Arg Met Gln Asp Lys Asn Pro Tyr Ser Phe Gln Ser Asp
865                 870                 875                 880

Val Tyr Ala Phe Gly Ile Val Leu Tyr Glu Leu Met Thr Gly Gln Leu
                885                 890                 895

Pro Tyr Ser Asn Ile Asn Asn Arg Asp Gln Ile Ile Phe Met Val Gly
            900                 905                 910

Arg Gly Tyr Leu Ser Pro Asp Leu Ser Lys Val Arg Ser Asn Cys Pro
        915                 920                 925

Lys Ala Met Lys Arg Leu Met Ala Glu Cys Leu Lys Lys Lys Arg Asp
    930                 935                 940

Glu Arg Pro Leu Phe Pro Gln Ile Leu Ala Ser Ile Glu Leu Leu Ala
945                 950                 955                 960

Arg Ser Leu Pro Lys Ile His Arg Ser Ala Ser Glu Pro Ser Leu Asn
                965                 970                 975

Arg Ala Gly Phe Gln Thr Glu Asp Phe Ser Leu Tyr Ala Cys Ala Ser
            980                 985                 990

Pro Lys Thr Pro Ile Gln Ala Gly Gly Tyr Gly Ala Phe Pro Val His
        995                 1000                1005
```

<210> SEQ ID NO 5
<211> LENGTH: 568
<212> TYPE: PRT
<213> ORGANISM: Unknown
<220> FEATURE:
<223> OTHER INFORMATION: C-Raf

<400> SEQUENCE: 5

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Lys Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Leu Val Pro Arg
        210                 215                 220

Gly Ser Gln Pro Lys Thr Pro Val Pro Ala Gln Arg Glu Arg Ala Pro
225                 230                 235                 240

Val Ser Gly Thr Gln Glu Lys Asn Lys Ile Arg Pro Arg Gly Gln Arg
                245                 250                 255

Asp Ser Ser Asp Asp Trp Glu Ile Glu Ala Ser Glu Val Met Leu Ser
                260                 265                 270

Thr Arg Ile Gly Ser Gly Ser Phe Gly Thr Val Tyr Lys Gly Lys Trp
            275                 280                 285

His Gly Asp Val Ala Val Lys Ile Leu Lys Val Val Asp Pro Thr Pro
        290                 295                 300

Glu Gln Phe Gln Ala Phe Arg Asn Glu Val Ala Val Leu Arg Lys Thr
305                 310                 315                 320

Arg His Val Asn Ile Leu Leu Phe Met Gly Tyr Met Thr Lys Asp Asn
                325                 330                 335

Leu Ala Ile Val Thr Gln Trp Cys Glu Gly Ser Ser Leu Tyr Lys His
                340                 345                 350

Leu His Val Gln Glu Thr Lys Phe Gln Met Phe Gln Leu Ile Asp Ile
            355                 360                 365

Ala Arg Gln Thr Ala Gln Gly Met Asp Tyr Leu His Ala Lys Asn Ile
        370                 375                 380

Ile His Arg Asp Met Lys Ser Asn Asn Ile Phe Leu His Glu Gly Leu
385                 390                 395                 400

Thr Val Lys Ile Gly Asp Phe Gly Leu Ala Thr Val Lys Ser Arg Trp
                405                 410                 415

Ser Gly Ser Gln Gln Val Glu Gln Pro Thr Gly Ser Val Leu Trp Met
                420                 425                 430

Ala Pro Glu Val Ile Arg Met Gln Asp Asn Asn Pro Phe Ser Phe Gln
            435                 440                 445

Ser Asp Val Tyr Ser Tyr Gly Ile Val Leu Tyr Glu Leu Met Thr Gly
        450                 455                 460

Glu Leu Pro Tyr Ser His Ile Asn Asn Arg Asp Gln Ile Ile Phe Met
465                 470                 475                 480

Val Gly Arg Gly Tyr Ala Ser Pro Asp Leu Ser Lys Leu Tyr Lys Asn
                485                 490                 495

Cys Pro Lys Ala Met Lys Arg Leu Val Ala Asp Cys Val Lys Lys Val
                500                 505                 510

Lys Glu Glu Arg Pro Leu Phe Pro Gln Ile Leu Ser Ser Ile Glu Leu
            515                 520                 525

Leu Gln His Ser Leu Pro Lys Ile Asn Arg Ser Ala Ser Glu Pro Ser
530                 535                 540

Leu His Arg Ala Ala His Thr Glu Asp Ile Asn Ala Cys Thr Leu Thr
545                 550                 555                 560

Thr Ser Pro Arg Leu Pro Val Phe
                565

<210> SEQ ID NO 6
<211> LENGTH: 333
<212> TYPE: PRT
<213> ORGANISM: Unknown
<220> FEATURE:
<223> OTHER INFORMATION: MEK1 protein sequence used for screening

<400> SEQUENCE: 6
```

```
Met Glu Leu Lys Asp Asp Phe Glu Lys Ile Ser Glu Leu Gly Ala
1               5                   10                  15

Gly Asn Gly Gly Val Val Phe Lys Val Ser His Lys Pro Ser Gly Leu
                20                  25                  30

Val Met Ala Arg Lys Leu Ile His Leu Glu Ile Lys Pro Ala Ile Arg
            35                  40                  45

Asn Gln Ile Ile Arg Glu Leu Gln Val Leu His Glu Cys Asn Ser Pro
        50                  55                  60

Tyr Ile Val Gly Phe Tyr Gly Ala Phe Tyr Ser Asp Gly Glu Ile Ser
65                  70                  75                  80

Ile Cys Met Glu His Met Asp Gly Gly Ser Leu Asp Gln Val Leu Lys
                85                  90                  95

Lys Ala Gly Arg Ile Pro Glu Gln Ile Leu Gly Lys Val Ser Ile Ala
                100                 105                 110

Val Ile Lys Gly Leu Thr Tyr Leu Arg Glu Lys His Lys Ile Met His
            115                 120                 125

Arg Asp Val Lys Pro Ser Asn Ile Leu Val Asn Ser Arg Gly Glu Ile
        130                 135                 140

Lys Leu Cys Asp Phe Gly Val Ser Gly Gln Leu Ile Asp Ser Met Ala
145                 150                 155                 160

Asn Ser Phe Val Gly Thr Arg Ser Tyr Met Ser Pro Glu Arg Leu Gln
                165                 170                 175

Gly Thr His Tyr Ser Val Gln Ser Asp Ile Trp Ser Met Gly Leu Ser
            180                 185                 190

Leu Val Glu Met Ala Val Gly Arg Tyr Pro Ile Pro Pro Pro Asp Ala
        195                 200                 205

Lys Glu Leu Glu Leu Met Phe Gly Cys Gln Val Glu Gly Asp Ala Ala
210                 215                 220

Glu Thr Pro Pro Arg Pro Arg Thr Pro Gly Arg Pro Leu Ser Ser Tyr
225                 230                 235                 240

Gly Met Asp Ser Arg Pro Pro Met Ala Ile Phe Glu Leu Leu Asp Tyr
                245                 250                 255

Ile Val Asn Glu Pro Pro Pro Lys Leu Pro Ser Gly Val Phe Ser Leu
            260                 265                 270

Glu Phe Gln Asp Phe Val Asn Lys Cys Leu Ile Lys Asn Pro Ala Glu
        275                 280                 285

Arg Ala Asp Leu Lys Gln Leu Met Val His Ala Phe Ile Lys Arg Ser
        290                 295                 300

Asp Ala Glu Glu Val Asp Phe Ala Gly Trp Leu Cys Ser Thr Ile Gly
305                 310                 315                 320

Leu Asn Gln Pro Ser Thr Pro Thr His Ala Ala Gly Val
                325                 330

<210> SEQ ID NO 7
<211> LENGTH: 676
<212> TYPE: PRT
<213> ORGANISM: Unknown
<220> FEATURE:
<223> OTHER INFORMATION: c-KIT with N-terminal GST fusion

<400> SEQUENCE: 7

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
                20                  25                  30
```

-continued

Glu Gly Asp Lys Trp Arg Asn Lys Lys Phe Glu Leu Gly Leu Glu Phe
        35                  40                  45

Pro Asn Leu Pro Tyr Tyr Ile Asp Gly Asp Val Lys Leu Thr Gln Ser
    50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
                100                 105                 110

Leu Lys Val Asp Phe Leu Ser Lys Leu Pro Glu Met Leu Lys Met Phe
            115                 120                 125

Glu Asp Arg Leu Cys His Lys Thr Tyr Leu Asn Gly Asp His Val Thr
130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
                180                 185                 190

Tyr Ile Trp Pro Leu Gln Gly Trp Gln Ala Thr Phe Gly Gly Gly Asp
    195                 200                 205

His Pro Pro Lys Ser Asp Leu Val Pro Arg His Asn Gln Thr Ser Leu
    210                 215                 220

Tyr Lys Lys Ala Gly Ser Ala Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
                260                 265                 270

Pro Thr Gln Leu Pro Tyr Asp His Lys Trp Glu Phe Pro Arg Asn Arg
    275                 280                 285

Leu Ser Phe Gly Lys Thr Leu Gly Ala Gly Ala Phe Gly Lys Val Val
    290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
                325                 330                 335

Leu Met Ser Glu Leu Lys Val Leu Ser Tyr Leu Gly Asn His Met Asn
                340                 345                 350

Ile Val Asn Leu Leu Gly Ala Cys Thr Ile Gly Gly Pro Thr Leu Val
    355                 360                 365

Ile Thr Glu Tyr Cys Cys Tyr Gly Asp Leu Leu Asn Phe Leu Arg Arg
    370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
                420                 425                 430

Pro Thr Lys Ala Asp Lys Arg Arg Ser Val Arg Ile Gly Ser Tyr Ile
            435                 440                 445

```
Glu Arg Asp Val Thr Pro Ala Ile Met Glu Asp Glu Leu Ala Leu
    450             455             460

Asp Leu Glu Asp Leu Leu Ser Phe Ser Tyr Gln Val Ala Lys Gly Met
465             470             475             480

Ala Phe Leu Ala Ser Lys Asn Cys Ile His Arg Asp Leu Ala Ala Arg
                485             490             495

Asn Ile Leu Leu Thr His Gly Arg Ile Thr Lys Ile Cys Asp Phe Gly
            500             505             510

Leu Ala Arg Asp Ile Lys Asn Asp Ser Asn Tyr Val Val Lys Gly Asn
        515             520             525

Ala Arg Leu Pro Val Lys Trp Met Ala Pro Glu Ser Ile Phe Asn Cys
    530             535             540

Val Tyr Thr Phe Glu Ser Asp Val Trp Ser Tyr Gly Ile Phe Leu Trp
545             550             555             560

Glu Leu Phe Ser Leu Gly Ser Ser Pro Tyr Pro Gly Met Pro Val Asp
                565             570             575

Ser Lys Phe Tyr Lys Met Ile Lys Glu Gly Phe Arg Met Leu Ser Pro
                580             585             590

Glu His Ala Pro Ala Glu Met Tyr Asp Ile Met Lys Thr Cys Trp Asp
            595             600             605

Ala Asp Pro Leu Lys Arg Pro Thr Phe Lys Gln Ile Val Gln Leu Ile
        610             615             620

Glu Lys Gln Ile Ser Glu Ser Thr Asn His Ile Tyr Ser Asn Leu Ala
625             630             635             640

Asn Cys Ser Pro Asn Arg Gln Lys Pro Val Val Asp His Ser Val Arg
                645             650             655

Ile Asn Ser Val Gly Ser Thr Ala Ser Ser Ser Gln Pro Leu Leu Val
                660             665             670

His Asp Asp Val
            675

<210> SEQ ID NO 8
<211> LENGTH: 13
<212> TYPE: PRT
<213> ORGANISM: Artificial Sequence
<220> FEATURE:
<223> OTHER INFORMATION: N-terminal purification tag

<400> SEQUENCE: 8

Met Asp Arg Gly Ser His His His His His His Gly Ser
1               5                   10
```

RAF INHIBITOR COMPOUNDS

This application claims priority to U.S. Patent Application Ser. No. 61/607,807, filed Mar. 7, 2012, entitled "(1,6-NAPH-THYRIDIN-3-YL) PHENYL UREAS EXHIBITING ANTI-CANCER AND ANTI-PROLIFERATIVE ACTIVITIES," the contents of which are incorporated herein in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_058_01US_SeqList_ST25.txt, date recorded: Jul. 7, 2015, file size 31 kilobytes).

The Ras/Raf/mitogen-activated protein kinase kinase (also known as MAP2K; MAPK kinase; and MAPK/ERK kinase or MEK)/extracellular signal-regulated kinase (ERK) signaling cascade (referred to herein as "Ras/Raf/MEK/ERK" or "Ras/Raf/MEK/MAPK") is an evolutionary conserved pathway that plays an integral role in development and tissue homeostasis in mammals. This signaling pathway consists of a kinase cascade that relays extracellular signals to the nucleus for gene expression and key cellular functions. Gene expression controlled by the Ras/Raf/MEK/ERK signaling pathway regulates fundamental cellular processes including proliferation, differentiation, apoptosis, and angiogenesis. These diverse roles of Ras/Raf/MEK/ERK signaling are aberrantly activated in various types of cancer. Mutations in genes within this pathway may lead to constitutively active proteins resulting in increased cell proliferation, and resistance to apoptosis.

Raf (a serine/threonine-protein kinase) is encoded by a gene family consisting of three genes affording three Raf isoform members (B-Raf, C-Raf (Raf-1) and A-Raf). Each of these proteins share highly conserved amino-terminal regulatory regions and catalytic domains at the carboxy terminus. Unless otherwise indicated, Raf refers to all three members. Although each isoform plays a role in the Ras/Raf/MEK/ERK pathway, B-Raf is the main activator of the kinase MEK. B-Raf is recruited by Ras:GTP to the intracellular cell membrane where B-Raf becomes activated. In turn, B-Raf is responsible for activation of MEK1/2 and MEK1/2 for activation of the kinases ERK1/ERK2. Mutations in the B-Raf gene allow for B-Raf to signal independently of upstream signals. As a result, mutated B-Raf protein (such as V600E) causes excessive downstream signaling of MEK and ERK. This leads to excessive cell proliferation and survival and oncogenesis. Overactivation of the signaling cascade by mutated B-Raf has been implicated in multiple malignancies.

The receptor tyrosine kinase (RTK) c-KIT (also called CD117), is expressed on a wide variety of cell types. The ligand for c-KIT is stem cell factor (SCF). The binding of SCF to the extracellular domain of c-KIT induces receptor dimerization and activation of downstream signaling pathways, including the RAS/RAF/MEK/ERK pathway. Mutant c-KIT has been implicated in the pathogenesis of several cancers.

Despite B-Raf specific inhibitors (such as vemurafenib), and compounds such as those disclosed in WO 2006/039718 and WO 2008/034008, there is a need for a Raf inhibitor active in inhibiting all isoforms of Raf proteins including A-Raf, B-Raf, C-Raf, and B-Raf V600E mutation. There is a further need for a Raf inhibitor that is active against tumor cells with upstream pathway activation by N-Ras mutations, K-Ras mutations, or cKIT mutations. Furthermore, there remains a need to provide alternative B-Raf inhibitors for treatment of cancer. Accordingly, the present invention provides Raf inhibitors which may be active in inhibiting all isoforms of Raf proteins. Also, the present invention provides Raf inhibitors which may be active against tumor cells with upstream pathway activation by N-Ras mutations, K-Ras mutations, or cKIT mutations. Additionally, the present invention provides alternative inhibitors of B-Raf. Furthermore, the present invention provides alternative inhibitors of B-Raf which may be useful for treating cancer.

One aspect of the present invention provides a compound of Formula I:

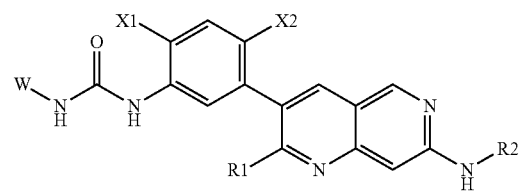

wherein

W is C1-C6 alkyl, optionally substituted with one or more of Z1A, Z1B, Z1C, Z1D, or Z1E; C4-C8 cycloalkyl optionally substituted with one or two Z2A or Z2B substituents; or C4-C8 heterocyclyl optionally substituted with one or two Z2A or Z2B substituents;

Each Z1A, Z1B, Z1C, Z1D, Z1E is individually and independently C1-C6 alkyl, halogen, fluoro-C1-C6 alkyl wherein the alkyl chain is partially or completely fluorinated, C1-C4alkoxy, hydroxyl, fluoroC1-C4alkoxy wherein the alkyl chain is partially or completely fluorinated, cyano, C3-C8 cycloalkyl optionally substituted with one or two Z2A or Z2B substituents, phenyl optionally substituted with one to three Z2A or Z2B, or R5;

each Z2A and Z2B is individually and independently hydrogen, C1-C6 alkyl, halogen, fluoro-C1-C6 alkyl wherein the alkyl chain is partially or completely fluorinated, hydrogen, C1-C4alkoxy, hydroxyl, or cyano;

X1 is fluoro or H;

X2 is methyl, halogen, or hydrogen;

R1 is selected from C1-C4alkyl, or hydrogen;

R2 is C1-C6 alkyl, hydrogen, —(CH$_2$)$_n$—OR3, —(CH$_2$)$_n$—NR3(R4), —(CH$_2$)$_q$—R5, —C(O)—R7, or R6-substituted C5-C6heteroaryl;

each R3 and R4 is individually and independently H, C1-C6 alkyl;

each R5 is independently and individually selected from the group consisting of

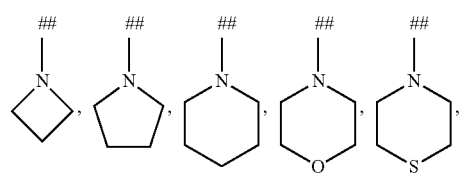

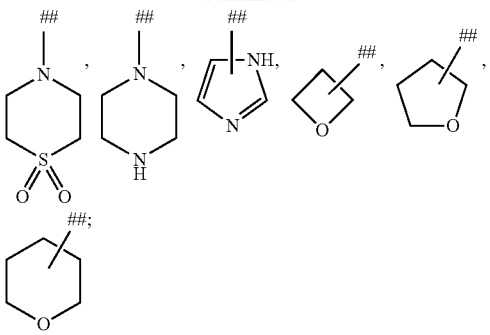

and wherein the symbol (##) is the point of attachment to —(CH₂)q— or Z1A-E;

each R5 is optionally substituted with —(R6)p;

each R6 is individually and independently C1-C6 alkyl, —(CH₂)m—CN, —(CH₂)m—OR3, —(CH₂)m—NR3(R4), —(CH₂)m—C(O)NR3(R4), or —(CH₂)m—C(O)—R3, wherein each alkyl or alkylene is optionally substituted with one or two C1-C6 alkyl;

R7 is C1-C6alkyl, C3-C8 cycloalkyl, hydrogen, —(CH₂)m—NR3(R4), —(CH₂)m—R5, or —(CH₂)m—OR3;

each m is individually and independently 0, 1, 2, or 3;

n is 2, 3, or 4;

p is 0, 1, 2, 3, or 4;

q is 0, 1, or 2;

or a pharmaceutically acceptable salt thereof.

A second aspect of the present invention provides a pharmaceutical composition comprising a compound of Formula I, or a pharmaceutically acceptable salt thereof, in association with a pharmaceutically acceptable carrier.

A third aspect of the present invention provides a method of inhibiting Raf in a cancer patient in need thereof, comprising administering a therapeutically effective amount of a compound of Formula I, or a pharmaceutically acceptable salt thereof, to said patient.

A fourth aspect of the present invention provides a method of treating a cancer which is acute myelogenous leukemia (AML), chronic myelogenous leukemia (CML), chronic lymphoblastic leukemia (CLL), myelodysplastic syndrome, ovarian cancer, melanoma, small-cell lung cancer, non-small-cell lung cancer, colorectal cancer, pancreatic cancer, prostate cancer, liver cancer or thyroid cancer in a patient comprising administering to a patient in need thereof a therapeutically effective amount of a compound of Formula I, or a pharmaceutically acceptable salt thereof.

A fifth aspect of the present invention provides a method of treating a cancer which is thyroid cancer, ovarian cancer, melanoma, AML or colorectal cancer in a patient comprising administering to a patient in need thereof a therapeutically effective amount of a compound of Formula I, or a pharmaceutically acceptable salt thereof.

A sixth aspect of the present invention provides a compound of Formula I, or a pharmaceutically acceptable salt thereof, for use in therapy.

A seventh aspect of the present invention provides a compound of Formula I, or a pharmaceutically acceptable salt thereof, for use in the treatment of a cancer which is acute myelogenous leukemia (AML), chronic myelogenous leukemia (CML), chronic lymphoblastic leukemia (CLL), myelodysplastic syndrome, ovarian cancer, melanoma, small-cell lung cancer, non-small-cell lung cancer, colorectal cancer, pancreatic cancer, prostate cancer, liver cancer or thyroid cancer.

An eighth aspect of the present invention provides a compound of Formula I, or a pharmaceutically acceptable salt thereof, for use in the treatment of a cancer which is thyroid cancer, ovarian cancer, melanoma, AML or colorectal cancer.

A ninth aspect of the present invention provides use of a compound of Formula I or a pharmaceutically acceptable salt thereof, for the manufacture of a medicament for the treatment of a cancer which is acute myelogenous leukemia (AML), chronic myelogenous leukemia (CML), chronic lymphoblastic leukemia (CLL), myelodysplastic syndrome, ovarian cancer, melanoma, small-cell lung cancer, non-small-cell lung cancer, colorectal cancer, pancreatic cancer, prostate cancer, liver cancer or thyroid cancer.

A tenth aspect of the present invention provides use of a compound of Formula I, or a pharmaceutically acceptable salt thereof, for the manufacture of a medicament for the treatment of a cancer which is thyroid cancer, ovarian cancer, melanoma, AML or colorectal cancer.

In one embodiment, the compound of Formula I is a compound wherein: W is C1-C6 alkyl, optionally substituted with one or more of Z1A, Z1B, Z1C, Z1D, or Z1E; or a pharmaceutically acceptable salt thereof.

In one embodiment, the compound of Formula I is a compound wherein: W is C4-C8 cycloalkyl optionally substituted with one or two Z2A or Z2B substituents; or a pharmaceutically acceptable salt thereof.

In one embodiment, the compound of Formula I is a compound wherein: W is C4-C8 heterocyclyl optionally substituted with one or two Z2A or Z2B substituents; or a pharmaceutically acceptable salt thereof.

In one embodiment, the compound of Formula I is a compound wherein: Each Z1A, Z1B, Z1C, Z1D, Z1E is individually and independently C1-C6 alkyl, halogen, fluoro-C1-C6 alkyl wherein the alkyl chain is partially or completely fluorinated, C1-C4alkoxy, hydroxyl, fluoroC1-C4alkoxy wherein the alkyl chain is partially or completely fluorinated, cyano, C3-C8 cycloalkyl optionally substituted with one or two Z2A or Z2B substituents, phenyl optionally substituted with one to three Z2A or Z2B, or R5; or a pharmaceutically acceptable salt thereof.

In one embodiment, the compound of Formula I is a compound wherein: each Z2A and Z2B is individually and independently C1-C6 alkyl, halogen, fluoro-C1-C6 alkyl wherein the alkyl chain is partially or completely fluorinated, hydrogen, C1-C4alkoxy, hydroxyl, or cyano; or a pharmaceutically acceptable salt thereof.

In one embodiment, the compound of Formula I is a compound wherein: X1 is fluoro or H; or a pharmaceutically acceptable salt thereof.

In one embodiment, the compound of Formula I is a compound wherein: X1 is fluoro; or a pharmaceutically acceptable salt thereof.

In one embodiment, the compound of Formula I is a compound wherein: X2 is methyl, halogen, or hydrogen; or a pharmaceutically acceptable salt thereof.

In one embodiment, the compound of Formula I is a compound wherein: X2 is methyl; or a pharmaceutically acceptable salt thereof.

In one embodiment, the compound of Formula I is a compound wherein: X2 is fluoro; or a pharmaceutically acceptable salt thereof.

In one embodiment, the compound of Formula I is a compound wherein: X2 is hydrogen; or a pharmaceutically acceptable salt thereof.

In one embodiment, the compound of Formula I is a compound wherein: R1 is C1-C4alkyl, or H; or a pharmaceutically acceptable salt thereof.

In one embodiment, the compound of Formula I is a compound wherein: R1 is methyl; or a pharmaceutically acceptable salt thereof.

In one embodiment, the compound of Formula I is a compound wherein: R1 is hydrogen; or a pharmaceutically acceptable salt thereof.

In one embodiment, the compound of Formula I is a compound wherein: R2 is C1-C6 alkyl, hydrogen, —(CH$_2$)$_n$—OR3, —(CH$_2$)$_n$—NR3(R4), —(CH$_2$)$_q$—R5, —C(O)—R7, or R6-substituted C5-C6heteroaryl; or a pharmaceutically acceptable salt thereof.

In one embodiment, the compound of Formula I is a compound wherein: R2 is C1-C6 alkyl; or a pharmaceutically acceptable salt thereof.

In one embodiment, the compound of Formula I is a compound wherein: R2 is hydrogen; or a pharmaceutically acceptable salt thereof.

In one embodiment, the compound of Formula I is a compound wherein: R2 is —(CH$_2$)$_n$—OR3 and n is 2-4; or a pharmaceutically acceptable salt thereof.

In one embodiment, the compound of Formula I is a compound wherein: R2 is —C(O)—R7 and R7 is C1-C6alkyl, C3-C8 cycloalkyl, hydrogen, —(CH$_2$)$_m$—NR3(R4), —(CH$_2$)$_m$—R5, or —(CH$_2$)$_m$—OR3; or a pharmaceutically acceptable salt thereof.

In one embodiment, the compound of Formula I is a compound wherein: R2 is —C(O)—R7 and R7 is C1-C6alkyl, hydrogen or C3-C8 cycloalkyl; or a pharmaceutically acceptable salt thereof.

In one embodiment, the compound of Formula I is a compound wherein: R2 is —C(O)—R7 and R7 is —(CH$_2$)$_m$—NR3(R4), or —(CH$_2$)$_m$—R5 and m is 0-3; or a pharmaceutically acceptable salt thereof.

In one embodiment, the compound of Formula I is a compound wherein: R2 is —C(O)—R7 and R7 is —(CH$_2$)$_m$—NR3(R4), or —(CH$_2$)$_m$—R5 and m is 0; or a pharmaceutically acceptable salt thereof.

In one embodiment, the compound of Formula I is a compound of Formula Ia

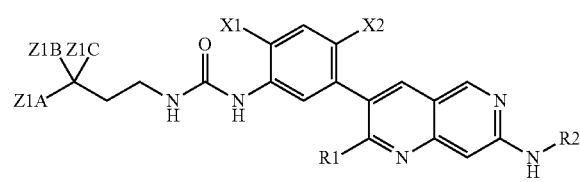

Ia wherein: each Z1A, Z1B, Z1C is individually and independently C1-C2 alkyl, fluorine, trifluoromethyl, C1-C2alkoxy, hydroxyl, or cyano and X1, X2, R1 and R2 are as defined above for formula I; or a pharmaceutically acceptable salt thereof.

In one embodiment, the compound of Formula Ia is a compound wherein: Z1A, Z1B, Z1C are methyl and X1, X2, R1 and R2 are as defined above for formula I.

In one embodiment, the compound of Formula Ia is a compound wherein: Z1A and Z1B are methyl and Z1C is fluorine, trifluoromethyl, C1-C2alkoxy, hydroxyl, or cyano and X1, X2, R1 and R2 are as defined above for formula I.

In one embodiment, the compound of Formula Ia is a compound wherein: X1 is fluoro, X2 is methyl, fluoro, or hydrogen, and Z1A, Z1B, Z1C, R1 and R2 are as defined above for formula I; or a pharmaceutically acceptable salt thereof.

In one embodiment, the compound of Formula Ia is a compound wherein: R1 is methyl or hydrogen and Z1A, Z1B, Z1C, X1, X2, and R2 are as defined above for formula I; or a pharmaceutically acceptable salt thereof.

In one embodiment, the compound of Formula Ia is a compound wherein: R2 is C1-C6alkyl or hydrogen; or a pharmaceutically acceptable salt thereof.

In one embodiment, the compound of Formula Ia is a compound wherein: R2 is —(CH$_2$)$_n$—OR3, —(CH$_2$)$_n$—NR3(R4), —(CH$_2$)$_q$—R5, and R3, R4, R5, n, and q are as defined above for formula I; or a pharmaceutically acceptable salt thereof.

In one embodiment, the compound of Formula Ia is a compound wherein: R2 is —C(O)—R7, and R7 is as defined above for formula I; or a pharmaceutically acceptable salt thereof.

In one embodiment, the compound of Formula Ia is a compound wherein: R2 is R6-substituted C5-C6heteroaryl and R6 is as defined above for formula I; or a pharmaceutically acceptable salt thereof.

In one embodiment, the compound of Formula I is a compound of Formula Ib

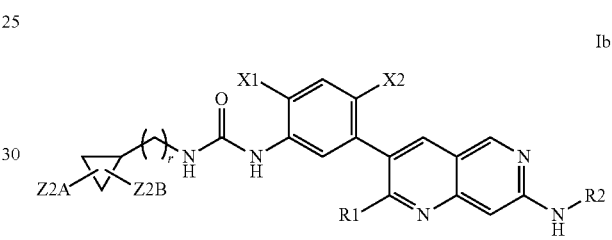

Ib wherein:
Z2A and Z2B are individually and independently hydrogen, C1-C2 alkyl, trifluoromethyl, or C1-C2 alkoxy; and wherein r is 1 or 2, and X1, X2, R1 and R2 are as defined above for formula I; or a pharmaceutically acceptable salt thereof.

In one embodiment, the compound of Formula Ib is a compound wherein: X1 is fluoro, X2 is methyl, fluoro, or hydrogen, and Z2A, Z2B, R1 and R2 are as defined above for formula I; or a pharmaceutically acceptable salt thereof.

In one embodiment, the compound of Formula Ib is a compound wherein: R1 is methyl or hydrogen and Z2A, Z2B, X1, X2, and R2 are as defined above for formula I; or a pharmaceutically acceptable salt thereof.

In one embodiment, the compound of Formula Ib is a compound wherein: R2 is C1-C6alkyl or hydrogen; or a pharmaceutically acceptable salt thereof.

In one embodiment, the compound of Formula Ib is a compound wherein: R2 is —(CH$_2$)$_n$—OR3, —(CH$_2$)$_n$—NR3(R4), —(CH$_2$)$_q$—R5, and R3, R4, R5, n, and q are as defined above for formula I; or a pharmaceutically acceptable salt thereof.

In one embodiment, the compound of Formula Ib is a compound wherein: R2 is —C(O)—R7, and R7 is as defined above for formula I; or a pharmaceutically acceptable salt thereof.

In one embodiment, the compound of Formula Ib is a compound wherein: R2 is R6-substituted C5-C6heteroaryl and R6 is as defined above for formula I; or a pharmaceutically acceptable salt thereof.

In one embodiment, the compounds of Formula I is a compound of Formula Ic

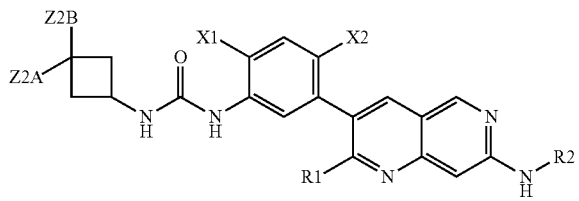

Ic wherein:
Z2A and Z2B are individually and independently C1-C2 alkyl, hydrogen, trifluoromethyl, or C1-C2 alkoxy, and X1, X2, R1 and R2 are as defined above for formula I; or a pharmaceutically acceptable salt thereof.

In one embodiment, the compound of Formula Ic is a compound wherein: X1 is fluoro, X2 is methyl, fluoro, or hydrogen, and Z2A, Z2B, R1 and R2 are as defined above for formula I; or a pharmaceutically acceptable salt thereof.

In one embodiment, the compound of Formula Ic is a compound wherein: R1 is methyl or hydrogen and Z2A, Z2B, X1, X2, and R2 are as defined above for formula I; or a pharmaceutically acceptable salt thereof.

In one embodiment, the compound of Formula Ic is a compound wherein: R2 is C1-C6alkyl or hydrogen; or a pharmaceutically acceptable salt thereof.

In one embodiment, the compound of Formula Ic is a compound wherein: R2 is —(CH$_2$)$_n$—OR3, —(CH$_2$)$_n$—NR3(R4), —(CH$_2$)$_q$—R5, and R3, R4, R5, n, and q are as defined above for formula I; or a pharmaceutically acceptable salt thereof.

In one embodiment, the compound of Formula Ic is a compound wherein: R2 is —C(O)—R7, and R7 is as defined above for formula I; or a pharmaceutically acceptable salt thereof.

In one embodiment, the compound of Formula Ic is a compound wherein: R2 is R6-substituted C5-C6heteroaryl and R6 is as defined above for formula I; or a pharmaceutically acceptable salt thereof.

In one embodiment, the compound of Formula Ib is a compound of Formula Id

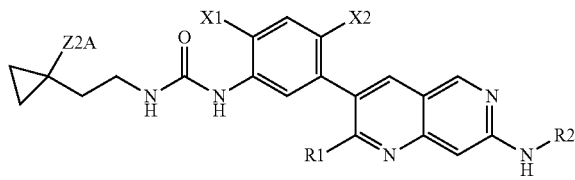

Id wherein:
Z2A is C1-C2 alkyl, trifluoromethyl, C1-C2 alkoxy, or hydrogen; and wherein X1, X2, R1 and R2 are as defined above for formula I; or a pharmaceutically acceptable salt thereof.

In one embodiment, the compound of Formula Id is a compound wherein: X1 is fluoro, X2 is methyl, fluoro, or hydrogen, and Z2A, Z2B, R1 and R2 are as defined above for formula I; or a pharmaceutically acceptable salt thereof.

In one embodiment, the compound of Formula Id is a compound wherein: R1 is methyl or hydrogen and Z2A, Z2B, X1, X2, and R2 are as defined above for formula I; or a pharmaceutically acceptable salt thereof.

In one embodiment, the compound of Formula Id is a compound wherein: R2 is C1-C6alkyl or hydrogen; or a pharmaceutically acceptable salt thereof.

In one embodiment, the compound of Formula Id is a compound wherein: R2 is —(CH$_2$)$_n$—OR3, —(CH$_2$)$_n$—NR3(R4), —(CH$_2$)$_q$—R5, and R3, R4, R5, n, and q are as defined above for formula I; or a pharmaceutically acceptable salt thereof.

In one embodiment, the compound of Formula Id is a compound wherein: R2 is —C(O)—R7, and R7 is as defined above for formula I; or a pharmaceutically acceptable salt thereof.

In one embodiment, the compound of Formula Id is a compound wherein: R2 is R6-substituted C5-C6heteroaryl and R6 is as defined above for formula I; or a pharmaceutically acceptable salt thereof.

In one embodiment, the compound of Formula I is a compound of Formula Ie

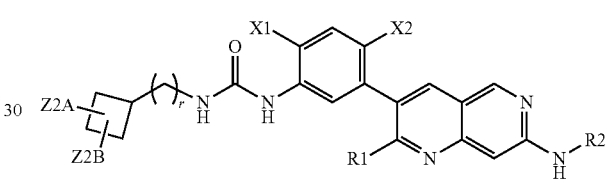

Ie wherein:
Z2A and Z2B are individually and independently hydrogen, C1-C2 alkyl, trifluoromethyl, or C1-C2 alkoxy; and wherein r is 1 or 2, and X1, X2, R1 and R2 are as defined above for formula I; or a pharmaceutically acceptable salt thereof.

In one embodiment, the compound of Formula Ie is a compound wherein: X1 is fluoro, X2 is methyl, fluoro, or hydrogen, and Z2A, Z2B, R1 and R2 are as defined above for formula I; or a pharmaceutically acceptable salt thereof.

In one embodiment, the compound of Formula Ie is a compound wherein: R1 is methyl or hydrogen and Z2A, Z2B, X1, X2, and R2 are as defined above for formula I; or a pharmaceutically acceptable salt thereof.

In one embodiment, the compound of Formula Ie is a compound wherein: R2 is C1-C6alkyl or hydrogen; or a pharmaceutically acceptable salt thereof.

In one embodiment, the compound of Formula Ie is a compound wherein: R2 is —(CH$_2$)$_n$—OR3, —(CH$_2$)$_n$—NR3(R4), —(CH$_2$)$_q$—R5, and R3, R4, R5, n, and q are as defined above for formula I; or a pharmaceutically acceptable salt thereof.

In one embodiment, the compound of Formula Ie is a compound wherein: R2 is —C(O)—R7, and R7 is as defined above for formula I; or a pharmaceutically acceptable salt thereof.

In one embodiment, the compound of Formula Ie is a compound wherein: R2 is R6-substituted C5-C6heteroaryl and R6 is as defined above for formula I; or a pharmaceutically acceptable salt thereof.

In one embodiment, the compound of Formula I is a compound of Formula If

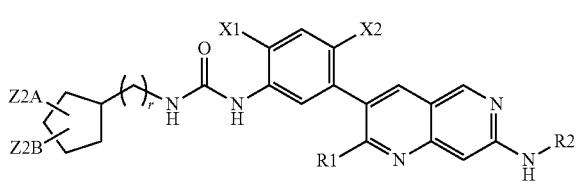

wherein:
Z2A and Z2B are individually and independently hydrogen, C1-C2 alkyl, trifluoromethyl, or C1-C2 alkoxy; and wherein r is 1 or 2, and X1, X2, R1 and R2 are as defined above for formula I; or a pharmaceutically acceptable salt thereof.

In one embodiment, the compound of Formula If is a compound wherein: X1 is fluoro, X2 is methyl, fluoro, or hydrogen, and Z2A, Z2B, R1 and R2 are as defined above for formula I; or a pharmaceutically acceptable salt thereof.

In one embodiment, the compound of Formula If is a compound wherein: R1 is methyl or hydrogen and Z2A, Z2B, X1, X2, and R2 are as defined above for formula I; or a pharmaceutically acceptable salt thereof.

In one embodiment, the compound of Formula If is a compound wherein: R2 is C1-C6alkyl or hydrogen; or a pharmaceutically acceptable salt thereof.

In one embodiment, the compound of Formula If is a compound wherein: R2 is —(CH$_2$)$_n$—OR3, —(CH$_2$)$_n$—NR3 (R4), —(CH$_2$)$_q$—R5, and R3, R4, R5, n, and q are as defined above for formula I; or a pharmaceutically acceptable salt thereof.

In one embodiment, the compound of Formula If is a compound wherein: R2 is —C(O)—R7, and R7 is as defined above for formula I; or a pharmaceutically acceptable salt thereof.

In one embodiment, the compound of Formula If is a compound wherein: R2 is R6-substituted C5-C6heteroaryl and R6 is as defined above for formula I; or a pharmaceutically acceptable salt thereof.

In one embodiment, the compound of Formula I is a compound of Formula Ig

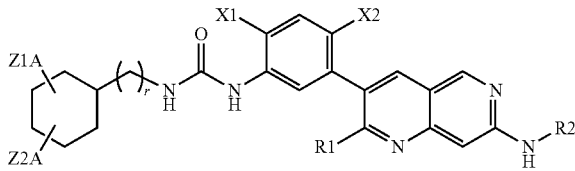

wherein:
Z2A and Z2B are individually and independently hydrogen, C1-C2 alkyl, trifluoromethyl, or C1-C2 alkoxy; and wherein r is 1 or 2, and X1, X2, R1 and R2 are as defined above for formula I; or a pharmaceutically acceptable salt thereof.

In one embodiment, the compound of Formula Ig is a compound wherein: X1 is fluoro, X2 is methyl, fluoro, or hydrogen, and Z2A, Z2B, R1 and R2 are as defined above for formula I; or a pharmaceutically acceptable salt thereof.

In one embodiment, the compound of Formula Ig is a compound wherein: R1 is methyl or hydrogen and Z2A, Z2B, X1, X2, and R2 are as defined above for formula I; or a pharmaceutically acceptable salt thereof.

In one embodiment, the compound of Formula Ig is a compound wherein: R2 is C1-C6alkyl or hydrogen; or a pharmaceutically acceptable salt thereof.

In one embodiment, the compound of Formula Ig is a compound wherein: R2 is —(CH$_2$)$_n$—OR3, —(CH$_2$)$_n$—NR3 (R4), —(CH$_2$)$_q$—R5, and R3, R4, R5, n, and q are as defined above for formula I; or a pharmaceutically acceptable salt thereof.

In one embodiment, the compound of Formula Ig is a compound wherein: R2 is —C(O)—R7, and R7 is as defined above for formula I; or a pharmaceutically acceptable salt thereof.

In one embodiment, the compound of Formula Ig is a compound wherein: R2 is R6-substituted C5-C6heteroaryl and R6 is as defined above for formula I; or a pharmaceutically acceptable salt thereof.

In some embodiments, any one or more hydrogens of the alkyl substituents of W, X2, R1, and R2 may be substituted with deuterium.

In some embodiments, the invention comprises a compound selected from the group consisting of a compound selected from 1-(3,3-dimethylbutyl)-3-(2-fluoro-5-(2-methyl-7-(methylamino)-1,6-naphthyridin-3-yl)phenyl)urea, 1-(3-cyano-3-methylbutyl)-3-(2,4-difluoro-5-(2-methyl-7-(methylamino)-1,6-naphthyridin-3-yl)phenyl)urea, 1-(3,3-dimethylbutyl)-3-(5-(2-ethyl-7-(methylamino)-1,6-naphthyridin-3-yl)-2,4-difluorophenyl)urea, 1-(3,3-dimethylbutyl)-3-(5-(2-ethyl-7-(methylamino)-1,6-naphthyridin-3-yl)-2-fluoro-4-methylphenyl)urea, 1-cycloheptyl-3-(2-fluoro-4-methyl-5-(2-methyl-7-(methylamino)-1,6-naphthyridin-3-yl)phenyl)urea,
1-(3,3-dimethylbutyl)-3-(4-methyl-3-(2-methyl-7-(methylamino)-1,6-naphthyridin-3-yl)phenyl)urea, 1-(3,3-dimethylbutyl)-3-(5-(2-ethyl-7-(methylamino)-1,6-naphthyridin-3-yl)-2-fluorophenyl)urea, 1-cycloheptyl-3-(2,4-difluoro-5-(2-methyl-7-(methylamino)-1,6-naphthyridin-3-yl)phenyl)urea, 1-(3-cyano-3-methylbutyl)-3-(2-fluoro-4-methyl-5-(2-methyl-7-(methylamino)-1,6-naphthyridin-3-yl)phenyl)urea, 1-(3-cyano-3-methylbutyl)-3-(2-fluoro-5-(2-methyl-7-(methylamino)-1,6-naphthyridin-3-yl)phenyl) urea, 1-(2-fluoro-4-methyl-5-(2-methyl-7-(methylamino)-1,6-naphthyridin-3-yl)phenyl)-3-(2-(trifluoromethoxy)ethyl) urea, 1-(4,4-difluorocyclohexyl)-3-(2-fluoro-4-methyl-5-(2-methyl-7-(methylamino)-1,6-naphthyridin-3-yl)phenyl) urea, 1-(2,4-difluoro-5-(2-methyl-7-(methylamino)-1,6-naphthyridin-3-yl)phenyl)-3-(3,3-dimethylcyclobutyl) methyl)urea, 1-(3,3-dimethylcyclobutyl)-3-(2-fluoro-4-methyl-5-(2-methyl-7-(methylamino)-1,6-naphthyridin-3-yl)phenyl)urea, 1-(3,3-dimethylcyclobutyl)-3-(2-fluoro-5-(2-methyl-7-(methylamino)-1,6-naphthyridin-3-yl)phenyl) urea, 1-(2,4-difluoro-5-(2-methyl-7-(methylamino)-1,6-naphthyridin-3-yl)phenyl)-3-(3-methyl-trans(3-fluorocyclobutyl))urea, 1-(3,3-dimethylbutyl)-3-(2-fluoro-4-methyl-5-(2-methyl-7-(methylamino)-1,6-naphthyridin-3-yl)phenyl)urea, 1-(2,4-difluoro-5-(2-methyl-7-(methylamino)-1,6-naphthyridin-3-yl)phenyl)-3-(3,3-dimethylbutyl)urea, 1-(3,3-dimethylbutyl)-3-(4-fluoro-3-(2-methyl-7-(methylamino)-1,6-naphthyridin-3-yl)phenyl) urea, 1-(2,2-dimethyltetrahydro-2H-pyran-4-yl)-3-(2-fluoro-4-methyl-5-(2-methyl-7-(methylamino)-1,6-naphthyridin-3-yl)phenyl)urea, 1-((3,3-dimethylcyclobutyl) methyl)-3-(2-fluoro-4-methyl-5-(2-methyl-7-(methylamino)-1,6-naphthyridin-3-yl)phenyl)urea, 1-(4,4-difluorocyclohexyl)-3-(2-fluoro-4-methyl-5-(7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-(1-(trifluoromethyl)

cyclopropyl)ethyl)urea, 1-(2,4-difluoro-5-(2-methyl-7-(methylamino)-1,6-naphthyridin-3-yl)phenyl)-3-(3-methoxy-3-methylbutyl)urea, 1-(trans-4-cyano-4-methylcyclohexyl)-3-(2-fluoro-4-methyl-5-(2-methyl-7-(methylamino)-1,6-naphthyridin-3-yl)phenyl)urea, 1-(cis-4-cyano-4-methylcyclohexyl)-3-(2-fluoro-4-methyl-5-(2-methyl-7-(methylamino)-1,6-naphthyridin-3-yl)phenyl) urea, 1-(2-fluoro-4-methyl-5-(2-methyl-7-(methylamino)-1,6-naphthyridin-3-yl)phenyl)-3-(2-(1-methylcyclopropyl)ethyl)urea, 1-(2,4-difluoro-5-(2-methyl-7-(methylamino)-1,6-naphthyridin-3-yl)phenyl)-3-(2-(1-methoxycyclopropyl)ethyl)urea, 1-(cyclohexylmethyl)-3-(2-fluoro-4-methyl-5-(2-methyl-7-(methylamino)-1,6-naphthyridin-3-yl)phenyl)urea, 1-(3-ethoxy-3-methylbutyl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-(1-methoxycyclopropyl)ethyl)urea, 1-(2-fluoro-4-methyl-5-(7-(methylamino)-1,6-naphthyridin-3-yl)phenyl)-3-(3-methoxy-3-methylbutyl)urea, 1-(2-fluoro-4-methyl-5-(2-methyl-7-(methylamino)-1,6-naphthyridin-3-yl)phenyl)-3-(4-methoxy-4-methylpentyl)urea, 1-(2,4-difluoro-5-(2-methyl-7-((6-methylpyridin-3-yl)amino)-1,6-naphthyridin-3-yl)phenyl)-3-(3,3-dimethylbutyl)urea, N-(3-(5-(3-(3,3-dimethylbutyl)ureido)-2-fluorophenyl)-2-methyl-1,6-naphthyridin-7-yl)acetamide, N-(3-(3-(3-(3,3-dimethylbutyl)ureido)-4-fluorophenyl)-2-ethyl-1,6-naphthyridin-7-yl)acetamide, N-(3-(5-(3-(3,3-dimethylbutyl)ureido)-2-fluorophenyl)-2-ethyl-1,6-naphthyridin-7-yl)acetamide, N-(3-(4-fluoro-3-(3-(3-fluoro-3-methylbutyl)ureido)phenyl)-2-methyl-1,6-naphthyridin-7-yl)isobutyramide, N-(3-(5-(3-(4,4-difluorocyclohexyl)ureido)-4-fluoro-2-methylphenyl)-2-methyl-1,6-naphthyridin-7-yl)cyclopropanecarboxamide, N-(3-(5-(3-(2-cyclopropylethyl)ureido)-4-fluoro-2-methylphenyl)-2-methyl-1,6-naphthyridin-7-yl)cyclopropanecarboxamide, N-(3-(3-(3-(4,4-difluorocyclohexyl)ureido)-4-fluorophenyl)-2-methyl-1,6-naphthyridin-7-yl)cyclopropanecarboxamide, N-(3-(4-fluoro-2-methyl-5-(3-(2-(trifluoromethoxy)ethyl)ureido)phenyl)-2-methyl-1,6-naphthyridin-7-yl)cyclopropanecarboxamide, N-(3-(5-(3-(3-cyano-3-methylbutyl)ureido)-2,4-difluorophenyl)-2-methyl-1,6-naphthyridin-7-yl)acetamide, 1-(5-(7-amino-2-methyl-1,6-naphthyridin-3-yl)-2-fluoro-4-methylphenyl)-3-(3-cyano-3-methylbutyl)urea, 1-(3-fluoro-3-methylbutyl)-3-(2-fluoro-4-methyl-5-(2-methyl-7-(methylamino)-1,6-naphthyridin-3-yl)phenyl)urea, 1-fluoro-cis(3-methylcyclobutyl))-3-(2-fluoro-4-methyl-5-(2-methyl-7-(methylamino)-1,6-naphthyridin-3-yl)phenyl)urea, 1-(2,4-difluoro-5-(2-methyl-7-(methylamino)-1,6-naphthyridin-3-yl)phenyl)-3-(3,3-dimethylcyclobutyl)urea, 1-(5-(7-amino-2-methyl-1,6-naphthyridin-3-yl)-2-fluoro-4-methylphenyl)-3-(3-fluoro-3-methylbutyl)urea, 1-(5-(7-amino-2-methyl-1,6-naphthyridin-3-yl)-2-fluoro-4-methylphenyl)-3-(3-methoxy-3-methylbutyl)urea, 1-(5-(7-amino-1,6-naphthyridin-3-yl)-2-fluoro-4-methylphenyl)-3-(3-fluoro-3-methylbutyl)urea, 1-(5-(7-amino-2-methyl-1,6-naphthyridin-3-yl)-2-fluoro-4-methylphenyl)-3-cycloheptylurea, 1-(5-(7-amino-2-methyl-1,6-naphthyridin-3-yl)-2-fluoro-4-methylphenyl)-3-(2-(1-(trifluoromethyl)cyclopropyl)ethyl)urea, 1-(2-cyclopropylethyl)-3-(2-fluoro-4-methyl-5-(2-methyl-7-(methylamino)-1,6-naphthyridin-3-yl)phenyl)urea, 1-cycloheptyl-3-(2-fluoro-5-(2-methyl-7-(methylamino)-1,6-naphthyridin-3-yl)phenyl)urea, 1-(3-fluoro-3-methylbutyl)-3-(2-fluoro-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(3,3,3-trifluoropropyl)urea, 1-(2,4-difluoro-5-(2-methyl-7-(methylamino)-1,6-naphthyridin-3-yl)phenyl)-3-(4,4-difluorocyclohexyl)urea, 1-(2-fluoro-4-methyl-5-(2-methyl-7-(methylamino)-1,6-naphthyridin-3-yl)phenyl)-3-(4,4,4-trifluoro-3,3-dimethylbutyl)urea, 1-(2,4-difluoro-5-(2-methyl-7-(methylamino)-1,6-naphthyridin-3-yl)phenyl)-3-(4,4,4-trifluorobutyl)urea, 1-(2-fluoro-4-methyl-5-(2-methyl-7-(methylamino)-1,6-naphthyridin-3-yl)phenyl)-3-(3,3,3-trifluoropropyl)urea, 1-(2-fluoro-4-methyl-5-(2-methyl-7-(methylamino)-1,6-naphthyridin-3-yl)phenyl)-3-(3-methoxy-3-methylbutyl)urea, 1-(3-fluoro-3-methylbutyl)-3-(2-fluoro-4-methyl-5-(7-(methylamino)-1,6-naphthyridin-3-yl)phenyl)urea, 1-(2,4-difluoro-5-(2-methyl-7-(methylamino)-1,6-naphthyridin-3-yl)phenyl)-3-(2-(1-methylcyclopropyl)ethyl)urea, 1-(5-(7-(ethylamino)-2-methyl-1,6-naphthyridin-3-yl)-2-fluoro-4-methylphenyl)-3-(3-fluoro-3-methylbutyl)urea, 1-(3-fluoro-3-methylbutyl)-3-(2-fluoro-5-(7-(isopropylamino)-2-methyl-1,6-naphthyridin-3-yl)-4-methylphenyl)urea, 1-(2-cyclobutylethyl)-3-(2-fluoro-4-methyl-5-(2-methyl-7-(methylamino)-1,6-naphthyridin-3-yl)phenyl)urea, 1-(2-cyclobutylethyl)-3-(2-fluoro-5-(2-methyl-7-(methylamino)-1,6-naphthyridin-3-yl)phenyl)urea, 1-(4,4-difluoropentyl)-3-(2-fluoro-4-methyl-5-(2-methyl-7-(methylamino)-1,6-naphthyridin-3-yl)phenyl)urea, 1-(3-fluoro-trans(3-methylcyclobutyl))-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(4-fluoro-4-methylpentyl)urea, 1-(2,4-difluoro-5-(2-methyl-7-(methylamino)-1,6-naphthyridin-3-yl)phenyl)-3-(4,4,4-trifluoro-3,3-dimethylbutyl)urea, N-(3-(3-(3-(3,3-dimethylbutyl)ureido)-4-fluorophenyl)-2-methyl-1,6-naphthyridin-7-yl)acetamide, N-(3-(5-(3-(3,3-dimethylbutyl)ureido)-4-fluoro-2-methylphenyl)-2-methyl-1,6-naphthyridin-7-yl)acetamide, N-(3-(5-(3-(3,3-dimethylbutyl)ureido)-2,4-difluorophenyl)-2-methyl-1,6-naphthyridin-7-yl)acetamide, N-(3-(5-(3-(3,3-dimethylbutyl)ureido)-2-methylphenyl)-2-methyl-1,6-naphthyridin-7-yl)acetamide, N-(3-(3-(3-cycloheptylureido)-4-fluorophenyl)-2-methyl-1,6-naphthyridin-7-yl)acetamide, N-(3-(3-(3-cyclohexylureido)-4-fluorophenyl)-2-methyl-1,6-naphthyridin-7-yl)acetamide, N-(3-(3-(3-cyclopentylureido)-4-fluorophenyl)-2-methyl-1,6-naphthyridin-7-yl)acetamide, N-(3-(3-(3-(2-cyclopentylethyl)ureido)-4-fluorophenyl)-2-methyl-1,6-naphthyridin-7-yl)acetamide, N-(3-(3-(3-(2-cyclopropylethyl)ureido)-4-fluorophenyl)-2-methyl-1,6-naphthyridin-7-yl)acetamide, N-(3-(3-(3-(3,3-dimethylcyclobutyl)ureido)-4-fluorophenyl)-2-methyl-1,6-naphthyridin-7-yl)acetamide, N-(3-(4-fluoro-5-(3-(3-fluoro-3-methylbutyl)ureido)-2-methylphenyl)-2-methyl-1,6-naphthyridin-7-yl)propionamide, N-(3-(2,4-difluoro-5-(3-(3-fluoro-3-methylbutyl)ureido)phenyl)-2-methyl-1,6-naphthyridin-7-yl)acetamide, N-(3-(2,4-difluoro-5-(3-(3-hydroxy-3-methylbutyl)ureido)phenyl)-2-methyl-1,6-naphthyridin-7-yl)acetamide, N-(3-(4-fluoro-2-methyl-5-(3-(3,3,3-trifluoropropyl)ureido)phenyl)-2-methyl-1,6-naphthyridin-7-yl)cyclopropanecarboxamide, N-(3-(4-fluoro-5-(3-(3-fluoro-3-methylbutyl)ureido)-2-methylphenyl)-2-methyl-1,6-naphthyridin-7-yl)acetamide, N-(3-(4-fluoro-5-(3-(3-fluoro-3-methylbutyl)ureido)-2-methylphenyl)-2-methyl-1,6-naphthyridin-7-yl)cyclopropanecarboxamide, N-(3-(4-fluoro-5-(3-(3-fluoro-3-methylbutyl)ureido)-2-methylphenyl)-2-methyl-1,6-naphthyridin-7-yl)isobutyramide, N-(3-(4-fluoro-3-(3-(3,3,3-trifluoropropyl)ureido)phenyl)-2-methyl-1,6-naphthyridin-7-yl)cyclopropanecarboxamide, N-(3-(2,4-difluoro-5-(3-(3-fluoro-3-methylbutyl)ureido)phenyl)-2-methyl-1,6-naphthyridin-7-yl)cyclopropanecarboxamide, N-(3-(2,4-difluoro-5-(3-(4,4,4-trifluorobutyl)ureido)phenyl)-2-methyl-1,6-naphthyridin-7-yl)cyclopropanecarboxamide, N-(3-(5-(3-(2-cyclopropylethyl)ureido)-2,4-difluorophenyl)-2-methyl-1,6-naphthyridin-7-yl)cyclopropanecarboxamide, N-(3-(4-fluoro-5-(3-(3-fluoro-3-methylbutyl)ureido)-2-methylphenyl)-2-methyl-1,6-naphthyridin-7-yl)formamide, 1-(5-(7-amino-2-methyl-1,6-naphthyridin-3-yl)-2-fluorophenyl)-3-(3,3-dimethylbutyl)urea, 1-(5-(7-amino-2-methyl-1,6-naphthyridin-3-yl)-2-fluoro-4-methylphenyl)-3-(4,4,4-trifluoro-3,3-dimethylbutyl)urea, 1-(5-(7-amino-2-methyl-1,6-naphthyridin-3-yl)-2,4-difluorophenyl)-3-(3,3-dimethylbutyl)urea, 1-(5-(7-amino-2-methyl-1,6-naphthyridin-3-yl)-2-fluoro-4-methylphenyl)-3-(3,3-dimethylbutyl)urea, 1-(5-(7-amino-2-methyl-1,6-naphthyridin-3-yl)-2,4-difluorophenyl)-3-(3-fluoro-3-methylbutyl)urea, 1-(2-fluoro-4-methyl-5-(2-methyl-7-(methylamino)-1,6-naphthyridin-3-yl)phenyl)-3-phenethylurea, 3-(3-(3-(3-(3,3-dimethylbutyl)ureido)-4-fluorophenyl)-2-methyl-1,6-naphthyridin-7-yl)-1,1-dimethylurea, N-(3-(3-(3-(3,3-dimethylbutyl)ureido)-4-fluorophenyl)-2-methyl-1,6-naphthyridin-7-yl)azetidine-1-carboxamide, 3-(3-(4-fluoro-5-(3-(3-fluoro-3-methylbutyl)ureido)-2-methylphenyl)-2-methyl-1,6-naphthyridin-7-yl)-1,1-dimethylurea, 1-(3,3-dimethylbutyl)-3-(2-fluoro-5-(7-((2-hydroxyethyl)amino)-2-methyl-1,6-naphthyridin-3-yl)-4-methylphenyl)urea, 1-(2,4-difluoro-5-(7-(2-hydroxyethylamino)-2-methyl-1,6-naphthyridin-3-yl)phenyl)-3-(3,3-dimethylbutyl)urea, 1-(2-fluoro-4-methyl-5-(2-methyl-7-(methylamino)-1,6-naphthyridin-3-yl)phenyl)-3-(2-hydroxy-3,3-dimethylbutyl)urea, 1-(2-fluoro-4-methyl-5-(2-methyl-7-(methylamino)-1,6-naphthyridin-3-yl)phenyl)-3-isopentylurea, 1-(2-fluoro-4-methyl-5-(2-methyl-7-(methylamino)-1,6-naphthyridin-3-yl)phenyl)-3-(2,4,4-trimethylpentan-2-yl)urea, 1-(2,4-difluoro-5-(2-methyl-7-(methylamino)-1,6-naphthyridin-3-yl)phenyl)-3-isopentylurea, 1-(3-fluoro-3-methylbutyl)-3-(2-fluoro-5-(7-((2-hydroxyethyl)amino)-2-methyl-1,6-naphthyridin-3-yl)-4-methylphenyl)urea, 1-((3,3-difluorocyclobutyl)methyl)-3-(2-fluoro-5-(7-((2-hydroxyethyl)amino)-2-methyl-1,6-naphthyridin-3-yl)-4-methylphenyl)urea, 1-(3-cyano-3-methylbutyl)-3-(2-fluoro-5-(7-((2-hydroxyethyl)amino)-2-methyl-1,6-naphthyridin-3-yl)-4-methylphenyl)urea, (S)-1-(2-fluoro-4-methyl-5-(2-methyl-7-(methylamino)-1,6-naphthyridin-3-yl)phenyl)-3-(2-hydroxy-3,3-dimethylbutyl)urea, (R)-1-(2-fluoro-4-methyl-5-(2-methyl-7-(methylamino)-1,6-naphthyridin-3-yl)phenyl)-3-(2-hydroxy-3,3-dimethylbutyl)urea, 1-(2-fluoro-4-methyl-5-(2-methyl-7-(methylamino)-1,6-naphthyridin-3-yl)phenyl)-3-(2-morpholinoethyl)urea, 1-(2-fluoro-4-methyl-5-(2-methyl-7-(methylamino)-1,6-naphthyridin-3-yl)phenyl)-3-(2-(1-hydroxycyclopropyl)ethyl)urea, 1-(4,4-dimethylpentan-2-yl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-hydroxy-3-methylbutyl)urea, 1-(2-fluoro-4-methyl-5-(2-methyl-7-(methylamino)-1,6-naphthyridin-3-yl)phenyl)-3-(3,3,3-trifluoro-2-hydroxypropyl)urea, (R)-1-(4,4-dimethylpentan-2-yl)-3-(2-fluoro-4-methyl-5-(2-methyl-7-(methylamino)-1,6-naphthyridin-3-yl)phenyl)urea, (S)-1-(4,4-dimethylpentan-2-yl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(tetrahydro-2H-pyran-4-yl)urea, 1-(3-cyano-3-methylbutyl)-3-(2,4-difluoro-5-(7-((2-hydroxyethyl)amino)-2-methyl-1,6-naphthyridin-3-yl)phenyl)urea, 1-(2,4-difluoro-5-(7-((2-hydroxyethyl)amino)-2-methyl-1,6-naphthyridin-3-yl)phenyl)-3-(3-fluoro-3-methylbutyl)urea, 1-(2,4-difluoro-5-(7-((2-hydroxyethyl)amino)-2-methyl-1,6-naphthyridin-3-yl)phenyl)-3-((3,3-difluorocyclobutyl)methyl)urea, (R)-1-(2-fluoro-4-methyl-5-(2-methyl-7-(methylamino)-1,6-naphthyridin-3-yl)phenyl)-3-(2-hydroxy-3-methylbutyl)urea, (S)-1-(2-fluoro-4-methyl-5-(2-methyl-7-(methylamino)-1,6-naphthyridin-3-yl)phenyl)-3-(2-hydroxy-3-methylbutyl)urea, (R)-1-(5-(7-amino-2-methyl-1,6-naphthyridin-3-yl)-2-fluoro-4-methylphenyl)-3-(2-hydroxy-3,3-dimethylbutyl)urea, (S)-1-(5-(7-amino-2-methyl-1,6-naphthyridin-3-yl)-2-fluoro-4-methylphenyl)-3-(2-hydroxy-3,3-dimethylbutyl)urea, 1-(5-(7-amino-2-methyl-1,6-naphthyridin-3-yl)-2-fluoro-4-methylphenyl)-3-(2-hydroxy-3,3-dimethylbutyl)urea, 1-(2-cyclopropyl-2-hydroxyethyl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(oxetan-2-ylmethyl)urea, 1-(2-fluoro-4-methyl-5-(2-methyl-7-(methylamino)-1,6-naphthyridin-3-yl)phenyl)-3-((tetrahydro-2H-pyran-2-yl)methyl)urea, or 1-(2-fluoro-4-methyl-5-(2-methyl-7-(methylamino)-1,6-naphthyridin-3-yl)phenyl)-3-(tetrahydrofuran-3-yl)urea.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, and pharmaceutically acceptable salts of the disclosed compounds. Thus, the terms "compound," "compounds", "test compound" or "test compounds" as used in this disclosure refer to the compounds of this disclosure and any and all possible isomers, stereoisomers, enantiomers, diastereomers, tautomers, and pharmaceutically acceptable salts.

DEFINITIONS

The term "alkyl" as used herein refers to both a straight chain alkyl, wherein alkyl chain length is indicated by a range of numbers, and a branched alkyl, wherein a branching point in the chain exists, and the total number of carbons in the chain is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, iso-propyl, butyl, iso-butyl, secondary-butyl, tertiary-butyl, pentyl, and hexyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —CH₂—, —CH₂CH₂—, and —CH₂CH₂CH₂—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or 10 ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" or "halo" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands. For example, in some embodiments, a ring N atom from the heterocyclyl is the bonding atom of the heterocylic moiety. In exemplary embodiments, "heterocyclyl" refers to a cyclic hydrocarbon as described above containing 4, 5, or 6 ring atoms (i.e., C4-C6 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the terms "patient" or "subject" include, without limitation, a human or an animal. Exemplary animals include, but are not limited to, mammals such as mouse, rat, guinea pig, dog, cat, horse, cow, pig, monkey, chimpanzee, baboon, or rhesus monkey.

"Therapeutically effective amount" or "effective amount" means the dosage of the compound, or pharmaceutically acceptable salt thereof, or pharmaceutical composition containing an exemplified compound of Formula I, or pharmaceutically acceptable salt thereof, necessary to inhibit B-Raf, C-Raf, A-Raf and B-Raf V600E signaling in a cancer patient, and either destroy the target cancer cells or slow or arrest the progression of the cancer in a patient. The exact dosage required to treat a patient and the length of treatment time will be determined by a physician in view of the stage and severity of the disease as well as the specific needs and response of the individual patient and the particular compound administered. Although expressed as dosage on a per day basis, the dosing regimen may be adjusted to provide a more optimal therapeutic benefit to a patient. In addition to daily dosing, twice-a-day (BID) or thrice-a-day (TID) dosing may be appropriate. BID dosing is currently preferred.

The terms "treatment," "treat," and "treating," are meant to include the full spectrum of intervention for the cancer from which the patient is suffering, such as administration of the active compound to alleviate, slow or reverse one or more of the symptoms and to delay progression of the cancer even if the cancer is not actually eliminated. Treating can be curing, improving, or at least partially ameliorating the disorder. The patient to be treated is a mammal, in particular a human being.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is H$^+$, is also known as "prototropy." Tautomers are defined as isomers that arise from tautomerism, independent of whether the isomers are isolable.

The exemplified compounds of the present invention are preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995).

The exemplified compounds of the present invention are capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

The compounds of Formula I, or a pharmaceutically acceptable salt thereof, may be prepared by a variety of procedures known in the art, as well as those described below. The specific synthetic steps may be combined in different ways to prepare the Formula I compounds, or a pharmaceutically acceptable salt thereof.

The compounds employed as initial starting materials in the synthesis of the compounds of Formula I are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

ChemDraw version 10 or 12 (CambridgeSoft Corporation, Cambridge, Mass.) was used to name the structures of intermediates and exemplified compounds.

The following abbreviations are used in this disclosure and have the following definitions: "ADP" is adenosine diphosphate, "ATP" is adenosine triphosphate, "BippyPhos" refers to (5-(di-tert-butylphosphino)-1',3',5'-triphenyl-1'H-[1,4]bipyrazole), "DCM" is dichloromethane, "DIEA" is N,N-diisopropylethylamine, "DMA" is N,N-dimethylacetamide, "DMF" is N,N-dimethylformamide, "DMSO" is dimethylsulfoxide, "DPPA" is diphenylphosphryl azide, "DTT" is dithiothreitol, "ESI" is electrospray ionization, "EtOAc" is ethyl acetate, "EtOH" is ethanol, "GST" is glutathione S-transferase, "h" is hour or hours, "IC$_{50}$" is half maximal inhibitory concentration, min is minutes, "Hex" refers to hexanes, "IPA" refers to isopropyl alcohol, "MeCN" is acetonitrile, "MeOH" is methanol, "MS" is mass spectrometry, "MTBE" is tert-butyl methyl ether, "NADH" is nicotinamide adenine dinucleotide, "NMR" is nuclear magnetic resonance, "PBS" is phosphate buffered saline, "Pd$_2$(dba)$_3$" refers to tris(dibenzylideneacetone)dipalladium(0), "Pd(PPh$_3$)$_4$" is tetrakis(triphenylphosphine)palladium, "Pet" is petroleum, "satd." refers to saturated, "RT" is room temperature which is also known as "ambient temp," which will be understood to consist of a range of normal laboratory temperatures ranging from 15-25° C., "TBTU" is O-(Benzotriazol-1-yl)-N,N,N',N'-tetramethyluronium tetrafluoroborate, "TEA" is triethylamine, "TFA" is trifluoroacetic acid, "THF" is tetrahydrofuran, "Tris" is tris(hydroxymethyl)aminomethane, and "XantPhos" is (4,5-bis(diphenylphosphino)-9,9-dimethylxanthene).

General Chemistry

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the ordinary skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties, as is well appreciated by the ordinary skilled chemist. All substituents, unless otherwise indicated, are as previously defined, and all reagents are well known and appreciated in the art.

Scheme 1

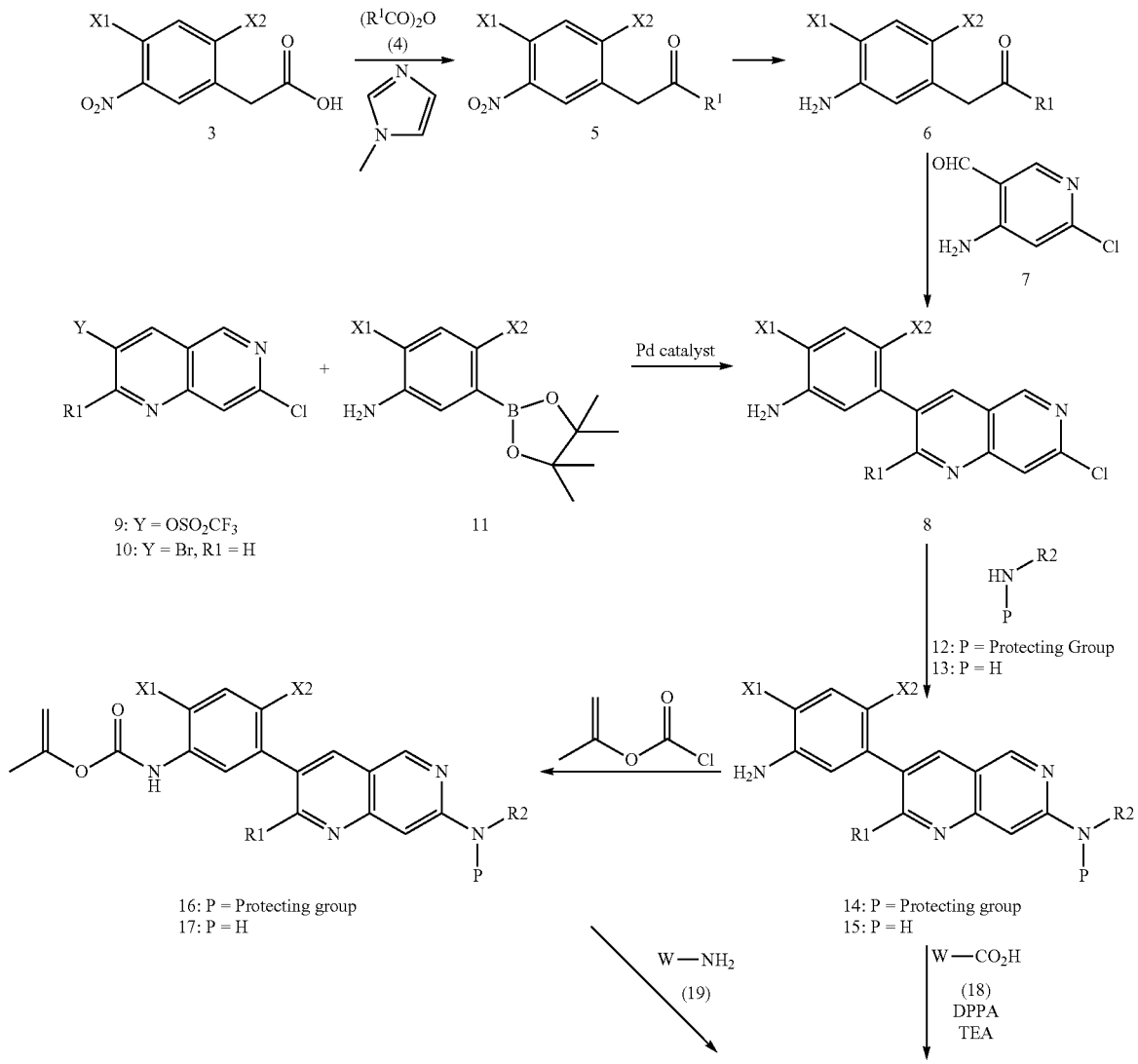

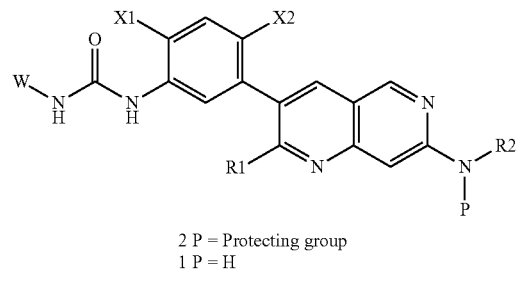

2 P = Protecting group
1 P = H

Compounds of Formula 1 can be prepared as illustrated in Scheme 1.

Compound 3 can react with a carboxylic acid anhydride 4 in the presence of 1-methylimidazole to provide 5. Nitro compound 5 in turn can be exposed to standard reducing conditions, for example hydrogenation in the presence of palladium on carbon, to provide amine 6. Treatment of 6 with aldehyde 7 in the presence of a base, for example potassium hydroxide or sodium hydroxide, provides compound 8. Compound 8 can also be synthesized by an alternative route. More specifically, triflate 9 or bromide 10 is reacted with boronate 11 in the presence of a palladium catalyst, such as tetrakis (triphenylphosphine)palladium (Pd(PPh$_3$)$_4$), in the presence of a base such as sodium bicarbonate or potassium carbonate, in a suitable solvent mixture such as dioxane and water at elevated temperature to provide compound 8.

Compound 8 can then react with compound 12 or 13 to provide 14 or 15 respectively. Those skilled in the art will appreciate that in some instances it will be preferable to mask hydrogen of the NHR2 moiety of compound 1 with a protecting group ("P") and the "P" moiety of compounds 12, 14, 16, and 2 represents a standard protecting group. Examples of protecting groups include 4-methoxybenzyl, tert-butoxycarbonyl and trifluoroacetyl. Those skilled in art will understand that the protecting groups of intermediates 14 and 16 can be removed immediately after synthesis to provide 15 or 17 respectively, or alternately may be carried forward in Scheme 1. In one embodiment, the reaction of 12 or 13 with 8 is accomplished by heating the two components in a suitable solvent such as N-methylpyrrolidinone (NMP) or ethanol, optionally with microwave irradiation and optionally on the presence of an added base, for example diisopropylethylamine. In another embodiment, the reaction of 12 or 13 with 8 is accomplished by heating the partners in the presence of a palladium catalyst, such as Pd$_2$(dba)$_3$ or palladium acetate, in the presence of a ligand such as XantPhos (4,5-bis(diphenylphosphino)-9,9-dimethylxanthene) or BippyPhos (5-(di-tert-butylphosphino)-1',3',5'-triphenyl-1'H-[1,4]bipyrazole), and a base, for example cesium carbonate, in a suitable solvent such as dioxane.

Compound 14 or 15 can be converted to compound 2 or 1 directly by reaction with a carboxylic acid of formula 18 under conditions of the Curtius rearrangement to provide urea 2 or 1. More specifically, compound 14 or 15 is reacted with 18 in the presence of a base, such as triethylamine, and diphenylphosphoryl azide (DPPA), in a suitable solvent such as dioxane with heating to provide 2 or 1 respectively. The protecting group of 2, in turn, is removed by standard conditions appropriate for said protecting group, for example by exposure to trifluoroacetic acid in the instance in which P is 4-methoxybenzyl or tert-butoxycarbonyl. In an alternate synthesis, compound 14 or 15 can react with isopropenyl chloroformate to provide 16 or 17 respectively. More specifically, treatment of 14 or 15 with ispropenyl chloroformate under Schotten-Baumann conditions, for example in a mixture of saturated aqueous sodium bicarbonate and ethyl acetate, or alternately in a mixture of pyridine and dichloromethane, provides 16 and 17 respectively. Further reaction of 16 or 17 with amine 19 in the presence of a base, for example N-methylpyrrolidine, in a suitable solvent, such as dioxane or tetrahydrofuran, at elevated temperature provides 2 or 1 respectively.

Scheme 2

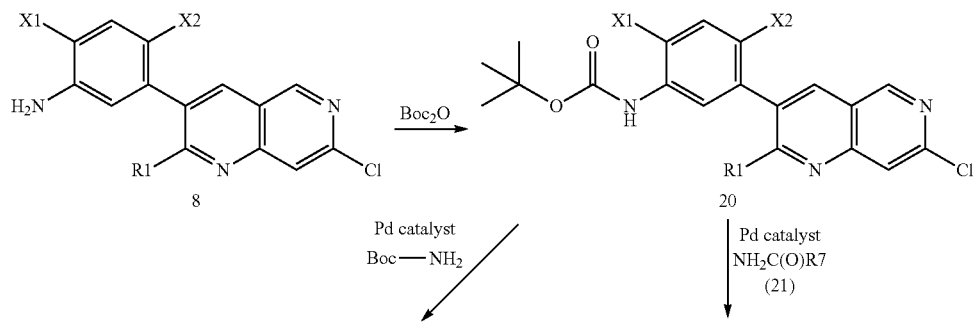

23

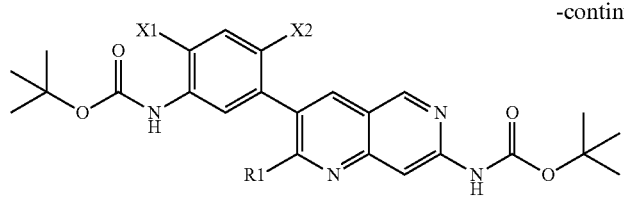

24

|TFA

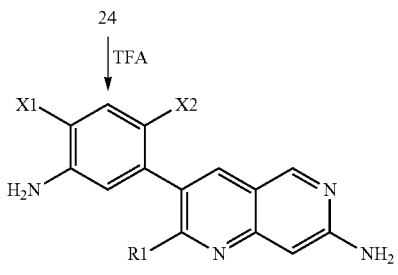

25

24

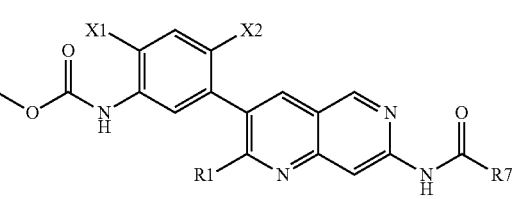

22

|TFA

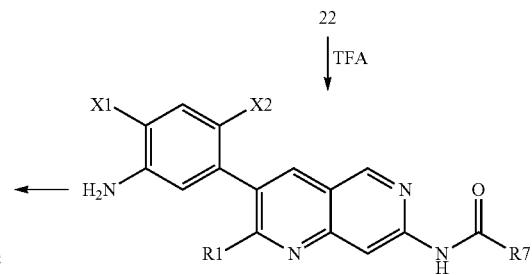

23

Compounds of Formula 15 wherein R2 is H (25) or —C(O)R7 (23) can also be synthesized as illustrated in Scheme 2.

Compound 8 can react with di-tert-butyl dicarbonate (Boc$_2$O) to provide Boc-protected 20. Compound 20 can react with compound 21 in the presence of a palladium catalyst, as described above, to provide 22. The Boc protecting group of 22 can be removed by treatment with acid to provide 23, an example of general intermediate 15 (Scheme 1) wherein R2 is C(O)R7. If desired, the C(O)R7 moiety can also be removed by appropriate conditions specific to the nature of R7 to provide 25. In an analogous manner, 20 can react with tert-butyl carbamate and a palladium catalyst to provide 24. Compound 24 can react with acid, for example trifluoroacetic acid, to effect removal of both Boc protecting groups to afford 25, an example of general intermediate 15 wherein R2 is H.

Scheme 3

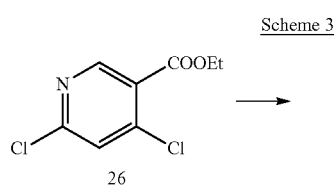
26

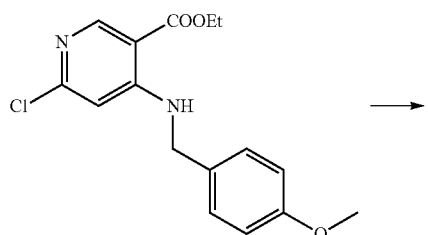
27

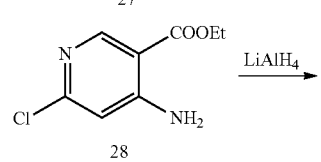
28

-continued

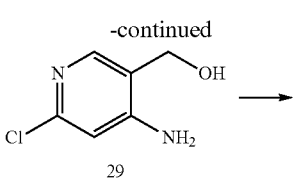
29

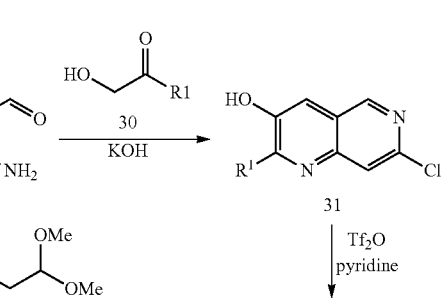

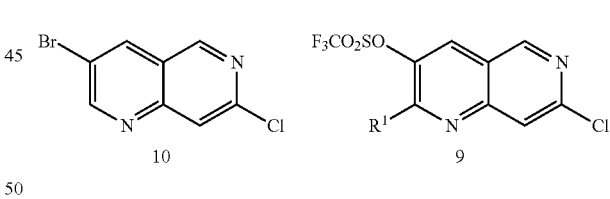
10        9

Compounds 7, 9 and 10 can be prepared as illustrated in Scheme 3.

Ethyl 4,6-dichloronicotinate (26) is reacted with (4-methoxybenzyl)amine to provide 27. Compound 27 is treated with acid to provide compound 28. Compound 28 is reacted with lithium aluminum hydride (LAH) to provide alcohol 29. Compound 29 is oxidized with manganese dioxide to provide aldehyde 7. Reaction of compound 7 with 2-bromo-1,1-dimethoxyethane and ytterbium(III) trifluoromethanesulfonate in acetontirile at elevated temperature provides compound 10. Reaction of compound 7 with compound 30 provides compound 31. Reaction of compound 31 with trifluoromethanesulfonyl chloride and pyridine provides compound 9.

Scheme 4

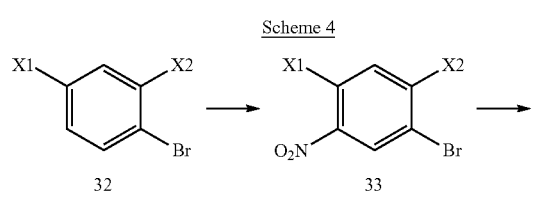

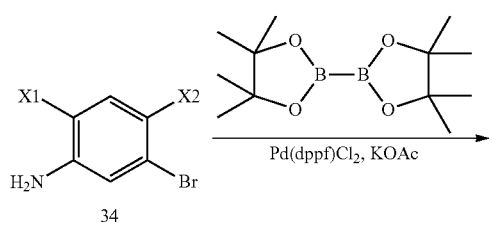

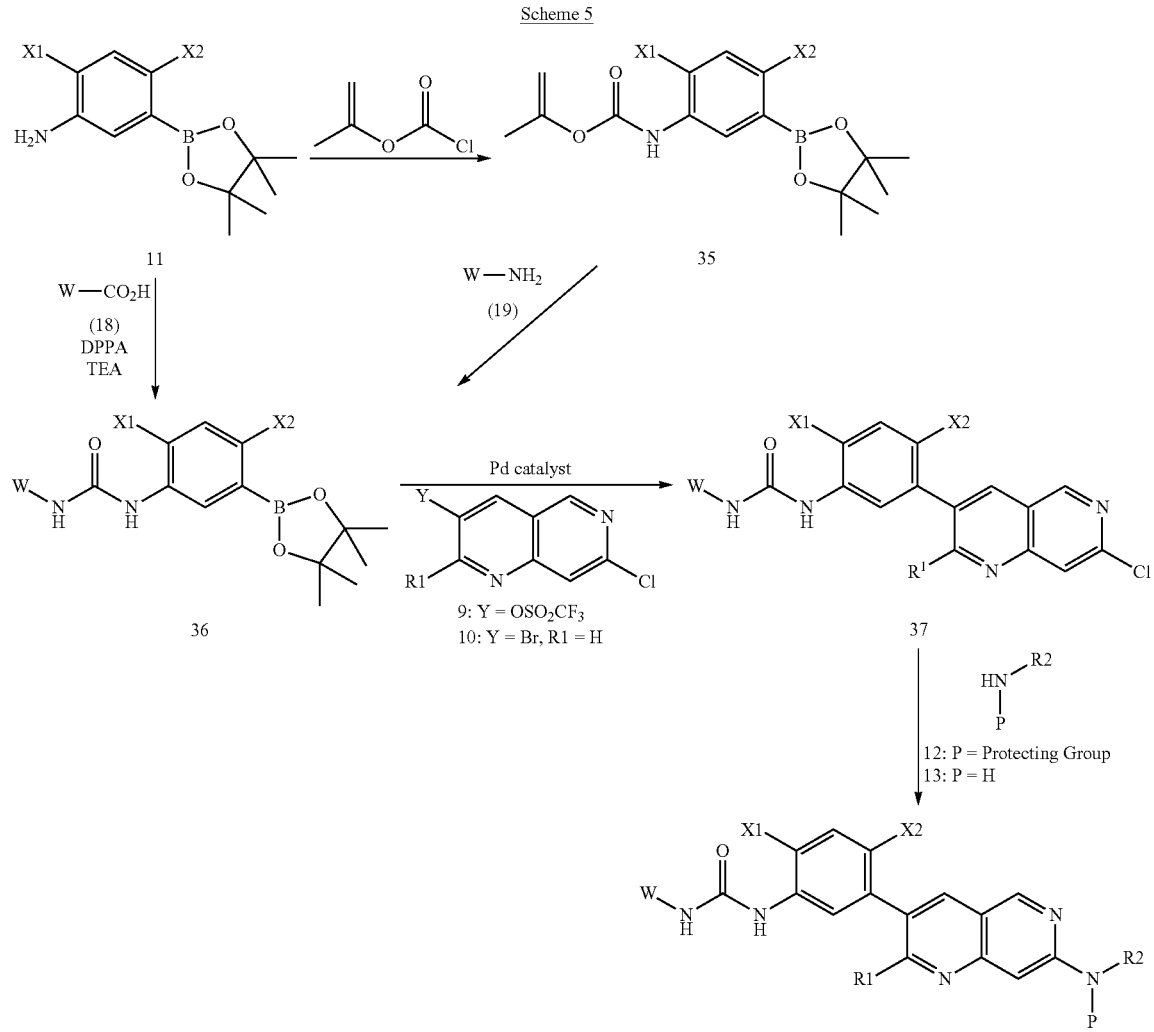

Compound 11 can be synthesized as illustrated in Scheme 4.

Compound 32 is nitrated by conditions familiar to the skilled artisan to provide 33. Compound 33 is subjected to reducing conditions, for example Raney Nickel in tetrandrofuarn, to provide 34. Compound 34 is reacted with bis(pinacolato)diboron, a suitable base such as potassium acetate, and a suitable catalyst such as [1,1'-bis(diphenylphosphino)ferrocene]-dichloropalladium(II)-dichloromethane complex in an appropriate solvent such as dioxane or DMF at elevated temperature to provide compound 11.

Compounds of Formula 1 can also be prepared as illustrated in Scheme 5.

Compound 11 is reacted with isopropenyl choroformate under conditions described above to provide compound 35, which is further reacted with amine 19 to provide compound 36. Alternately, compound 11 is directly converted to compound 36 by reaction with acid 18 under Curtius rearrangement conditions as described above. Compound 36 is reacted with 9 or 10 and a palladium catalyst as described above to provide 37. Further reaction of 37 with 12 or 13 is accomplished by heating the partners in the presence of a palladium catalyst, such as $Pd_2(dba)_3$ or palladium acetate, in the presence of a ligand such as XantPhos (4,5-bis(diphenylphosphino)-9,9-dimethylxanthene), tert-butyl XPhos (2-di-tert-butylphosphino-2',4',6'-triisopropylbiphenyl) or BippyPhos (5-(Di-tert-butylphosphino)-1',3',5'-triphenyl-1'H-[1,4]bipyrazole), a base, for example cesium carbonate, in a suitable solvent such as dioxane to provide compound 2 or 1 respectively.

an amine (42: R*s are alkyl or H) or heterocyclic amine (42: R*s joined to form a ring) provides a compound of formula 41.

Preparation 1

Synthesis of 1-(4-fluoro-3-nitrophenyl)propan-2-one

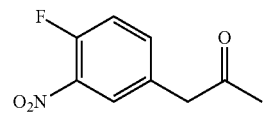

Treat a −35° C. solution of fuming nitric acid (32.3 mL, 723 mmol) with 4-fluorophenylacetone (1.756 ml, 13.14 mmol)

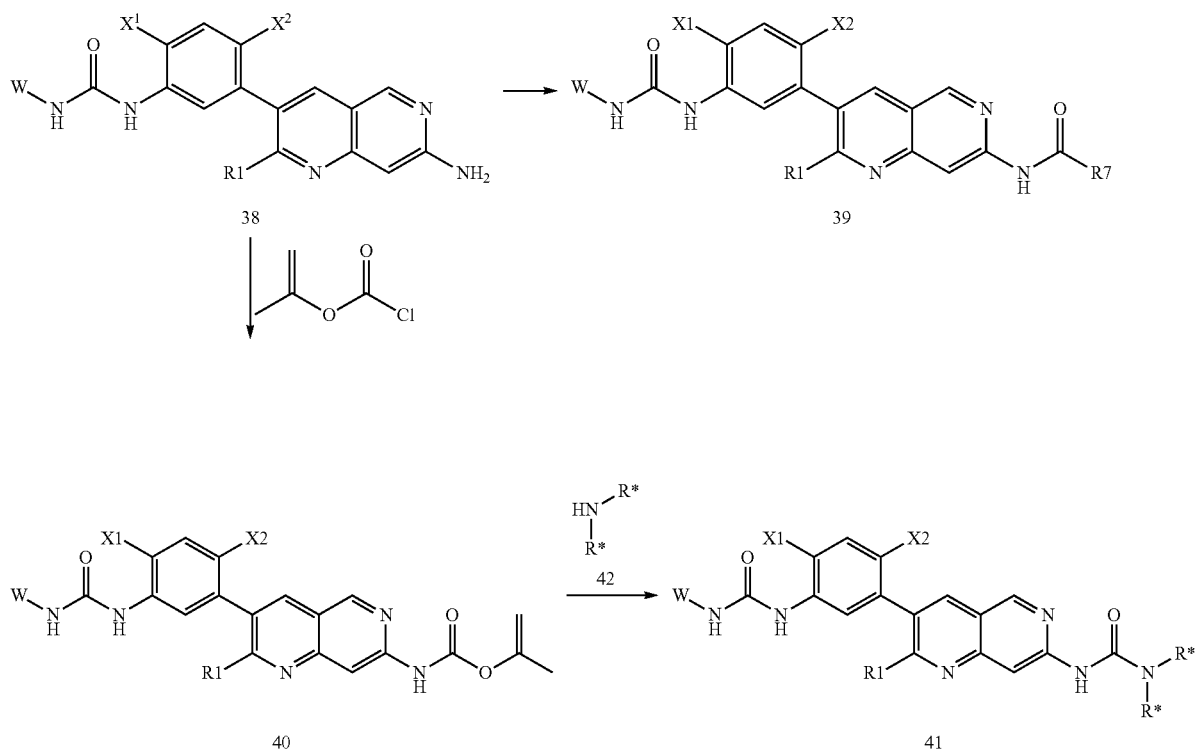

Scheme 6

Compounds of Formula 1 wherein R2 is C(O)R7 can also be prepared from compounds of formula 1 (R2=H, 38) as illustrated in Scheme 6. Thus, 38 is reacted with a suitable carbonylation reagent such as an acid halide or isocyanate to provide compound 39. As an alternative, compound 38 can be reacted with isopropenyl chloroformate as described above to provide carbamate 40. Further reaction of compound 40 with and stir at −35° C. for 1 h. Pour the mixture onto ice, extract with DCM (2×), dry the combined organics over $MgSO_4$, concentrate to dryness and purify via silica gel chromatography (EtOAc/Hex) to afford the title compound (1.07 g, 41%). $^1$H NMR (400 MHz, DMSO-$d_6$): δ 7.97 (dd, J=7.4, 2.2 Hz, 1H), 7.58 (ddd, J=8.6, 4.6, 2.2 Hz, 1H), 7.52 (dd, J=11.3, 8.6 Hz, 1H), 3.95 (s, 2H), 2.17 (s, 3H).

Preparation 2

Synthesis of 2-(4-fluoro-3-nitrophenyl)acetic acid

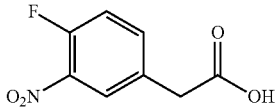 [SMILES: O=C(O)Cc1ccc(F)c([N+](=O)[O-])c1]

Treat a 0° C. solution of 4-fluorophenylacetic acid (3 g, 19.46 mmol) in $H_2SO_4$ (20 mL) drop wise with nitric acid (0.913 mL, 20.44 mmol) and stir for 1 h. Pour the mixture onto ice, extract with DCM (2×), wash the combined organics with brine, dry over $MgSO_4$ and concentrate to dryness to afford the title compound (3.48 g, 90%). MS (ESI) m/z: 198.1 (M−H$^+$).

The following compounds are prepared essentially by the method of Preparation 2.

| Prep No. | Chemical Name | Structure | Physical Data |
|---|---|---|---|
| 3 | 2-(2,4-difluoro-5-nitrophenyl)acetic acid | 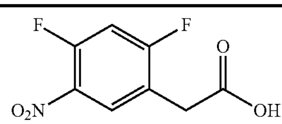 | MS (ESI) m/z: 218.0 (M + H$^+$) |
| 4 | 2-(4-fluoro-2-methyl-5-nitrophenyl)acetic acid | 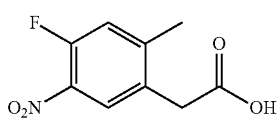 | MS (ESI) m/z: 214.1 (M + H$^+$) |
| 5 | 2-(2-fluoro-5-nitrophenyl)acetic acid | 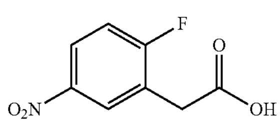 [SMILES: O=C(O)Cc1cc([N+](=O)[O-])ccc1F] | $^1$H NMR (400 MHz, CDCl$_3$): δ 8.16 (m, 2 H), 7.18 (m, 1 H), 3.76 (s, 2 H) |

Preparation 6

Synthesis of 1-(4-fluoro-3-nitrophenyl)butan-2-one

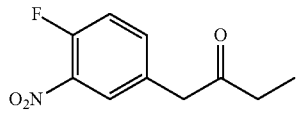

Treat a solution of 2-(4-fluoro-3-nitrophenyl)acetic acid (1.5 g, 7.53 mmol) in propionic anhydride (5.40 mL, 45.2 mmol) with 1-methylimidazole (0.600 mL, 7.53 mmol) and stir at RT overnight. Quench the mixture with $H_2O$, stir for 1 h, extract with EtOAc (2×), wash the combined organics with satd. $Na_2CO_3$, then brine, dry the organics over $MgSO_4$, concentrate to dryness and purify via silica gel chromatography (EtOAc/Hex) to afford the title compound (830 mg, 52%). $^1$H NMR (400 MHz, DMSO-d$_6$): δ 8.00 (dd, J=7.4, 2.2 Hz, 1H), 7.61 (ddd, J=8.6, 4.6, 2.2 Hz, 1H), 7.53 (dd, J=11.4, 8.6 Hz, 1H), 3.95 (s, 2H), 2.56 (q, J=7.3 Hz, 2H), 0.96 (t, J=7.3 Hz, 3H); MS (ESI) m/z: 212.1 (M+H$^+$).

The following compounds are prepared essentially by the method of Preparation 6.

| Prep No. | Chemical Name | Structure | Physical Data |
|---|---|---|---|
| 7 | 1-(2,4-difluoro-5-nitrophenyl)propan-2-one | 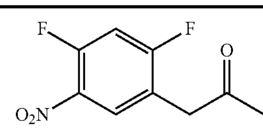 | MS (ESI) m/z: 216.1 (M + H$^+$) |
| 8 | 1-(2,4-difluoro-5-nitrophenyl)butan-2-one | 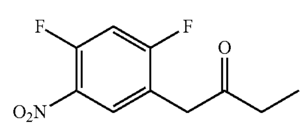 | MS (ESI) m/z: 230.1 (M + H$^+$) |
| 9 | 1-(4-fluoro-2-methyl-5-nitrophenyl)butan-2-one | 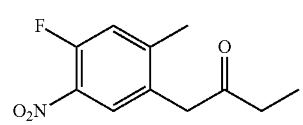 | $^1$H NMR (400 MHz, DMSO-d$_6$): δ 7.93 (d, J = 8.0 Hz, 1 H), 7.40 (d, J = 12.4 Hz, 1 H), 3.94 (s, 2 H), 2.54 (q, J = 7.2 Hz, 2 H), 2.18 (s, 3 H), 0.93 (t, J = 7.2 Hz, 3 H) |

| Prep No. | Chemical Name | Structure | Physical Data |
|---|---|---|---|
| 10 | 1-(2-fluoro-5-nitrophenyl)propan-2-one | 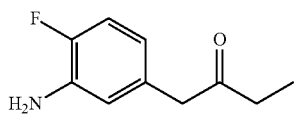 | $^1$H NMR (400 MHz, CDCl$_3$): δ 8.20 (m, 1 H), 8.17 (m, 1 H), 7.24 (s, 1 H), 3.84 (s, 2 H), 2.28 (s, 3 H) |

Preparation 11

Synthesis of 1-(3-amino-4-fluorophenyl)butan-2-one

Treat a solution of 1-(4-fluoro-3-nitrophenyl)butan-2-one (0.83 g, 3.93 mmol) in EtOAc (30 mL) with 10% Pd/C (0.209 g, 0.197 mmol) and hydrogenate at atmospheric pressure (balloon) overnight. Remove the solids via filtration through diatomaceous earth, rinse well with EtOAc, concentrate the filtrate to dryness and purify via silica gel chromatography (EtOAc/Hex) to afford the title compound (536 mg, 75%). $^1$H NMR (400 MHz, DMSO-d$_6$): δ 6.88 (dd, J=11.6, 8.2 Hz, 1H), 6.57 (dd, J=8.9, 2.1 Hz, 1H), 6.32 (m, 1H), 5.07 (s, 2H), 3.55 (s, 2H), 2.46 (q, J=7.3 Hz, 2H), 0.89 (t, J=7.3 Hz, 3H); MS (ESI) m/z: 182.1 (M+H$^+$).

The following compounds are prepared essentially by the method of Preparation 11.

Preparation 17

Synthesis of ethyl 6-chloro-4-(4-methoxybenzylamino)nicotinate

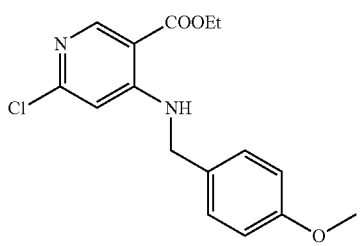

Stir a mixture of ethyl 4,6-dichloronicotinate (16 g, 73.1 mmol), (4-methoxybenzyl)amine (10 g, 73.1 mmol), and TEA (15.2 g, 146 mmol) in DMSO (150 mL) at RT overnight. Add EtOAc, wash with water (2×), then brine (1×), dry the organics over MgSO$_4$ and concentrate to afford the title compound (21 g, 90%). $^1$H NMR (300 MHz, CDCl$_3$): δ 8.62 (s,

| Prep No. | Chemical Name | Structure | Physical Data |
|---|---|---|---|
| 12 | 1-(3-amino-4-fluorophenyl)propan-2-one | 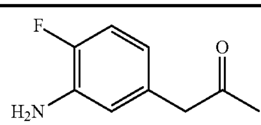 | MS (ESI) m/z: 168.1 (M + H$^+$) |
| 13 | 1-(5-amino-2,4-difluorophenyl)propan-2-one | 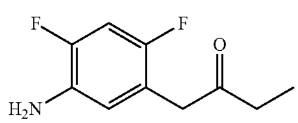 | MS (ESI) m/z: 186.1 (M + H$^+$) |
| 14 | 1-(5-amino-2,4-difluorophenyl)butan-2-one | 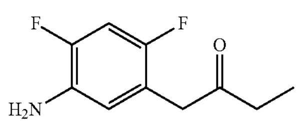 | MS (ESI) m/z: 200.1 (M + H$^+$) |
| 15 | 1-(5-amino-4-fluoro-2-methylphenyl)butan-2-one | 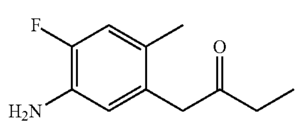 | $^1$H NMR (400 MHz, DMSO-d$_6$): δ 6.75 (d, J = 12.4 Hz, 1 H), 6.51 (d, J = 9.2 Hz, 1 H), 4.81 (s, 2 H), 3.55 (s, 2 H), 2.43 (q, J = 7.2 Hz, 2 H), 1.96 (s, 3 H), 0.89 (t, J = 7.2 Hz, 3 H). |
| 16 | 1-(5-amino-2-fluorophenyl)propan-2-one | 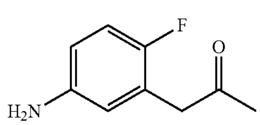 | $^1$H NMR (400 MHz, CDCl$_3$): δ 6.86 (t, 1 H), 6.53 (m, 1 H), 6.46 (m, 1 H), 3.36 (s, 2 H), 3.25 (s, 2 H), 2.13 (s, 3 H) |

1H), 8.39 (s, 1H), 7.16 (d, J=8.7 Hz, 2H), 6.85-6.80 (m, 2H), 6.49 (s, 1H), 4.33-4.25 (m, 4H), 3.77 (s, 3H), 1.31 (t, J=6.9 Hz, 3H).

Preparation 18

Synthesis of ethyl 4-amino-6-chloronicotinate

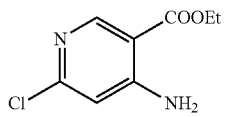

Heat a mixture of ethyl 6-chloro-4-(4-methoxybenzylamino)nicotinate (21 g, 65.6 mmol) and TFA (150 mL) at 50° C. overnight. Cool the mixture to RT, concentrate to dryness, dissolve the residue in EtOAc, wash with satd. NaHCO₃ (2×), then brine (1×), dry over MgSO₄, concentrate and purify via silica gel chromatography to give the title compound (10 g, 76%). ¹H NMR (400 MHz, DMSO-d₆): δ 8.49 (s, 1H), 7.47 (s, 2H), 6.76 (s, 1H), 4.29 (q, J=7.2 Hz, 2H), 1.31 (t, J=7.2 Hz, 3H).

Preparation 19

Synthesis of (4-amino-6-chloropyridin-3-yl)methanol

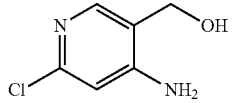

Treat a 0° C. suspension of lithium aluminum hydride (5.7 g, 150 mmol) in THF (150 mL), under N₂, drop-wise with a solution of ethyl 4-amino-6-chloronicotinate (15 g, 75 mmol) in THF (50 mL), allow to warm to RT and stir for 3 h. Quench the mixture with 10% NaOH (5.7 mL), then water (5.7 mL), filter to remove solids, add water to the filtrate and extract with EtOAc (3×). Wash the combined organics with brine, dry and concentrate to give the title compound (10 g, 84%). ¹H NMR (300 MHz, DMSO-d₆): δ 7.79 (s, 1H), 6.53 (s, 1H), 6.17 (s, 2H), 5.10 (t, J=5.4 Hz, 1H), 4.36 (d, J=5.4 Hz, 2H).

Preparation 20

Synthesis of 4-amino-6-chloronicotinaldehyde

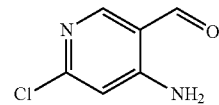

Treat a solution of (4-amino-6-chloropyridin-3-yl)methanol (10 g, 63.3 mmol) in DCM (150 mL) with activated manganese dioxide (38 g, 443 mmol) and stir at RT overnight. Remove solids via filtration, concentrate the filtrate and purify by silica gel chromatography to afford the title compound (7.2 g, 73%). ¹H NMR (400 MHz, DMSO-d₆): δ 9.88 (s, 1H), 8.44 (s, 1H), 7.84 (s, 2H), 6.73 (s, 1H); MS (ESI) m/z: 157.0 (M+H⁺).

Preparation 21

Synthesis of 5-(7-chloro-2-methyl-1,6-naphthyridin-3-yl)-2-fluoroaniline

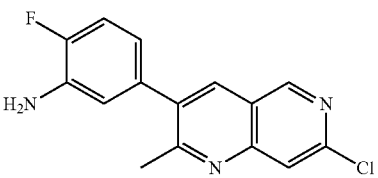 [SMILES: Cc1nc2cc(Cl)ncc2cc1-c1ccc(F)c(N)c1]

Heat a solution of 1-(3-amino-4-fluorophenyl)propan-2-one (0.34 g, 2.034 mmol), 4-amino-6-chloronicotinaldehyde (0.318 g, 2.034 mmol) and KOH (0.057 g, 1.017 mmol) in EtOH (12 mL) at 60° C. for 1 h. Cool the mixture to RT, add brine and extract with EtOAc (3×). Dry the combined organics over MgSO₄, concentrate to dryness and purify via silica gel chromatography (EtOAc/Hex) to afford the title compound (353 mg, 60%). MS (ESI) m/z: 288.1 (M+H⁺).

The following compounds are prepared essentially by the method of Preparation 21.

| Prep No. | Chemical Name | Structure | Physical Data |
|---|---|---|---|
| 22 | 5-(7-chloro-2-methyl-1,6-naphthyridin-3-yl)-2,4-difluoroaniline | 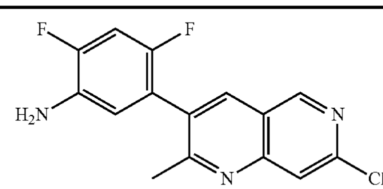 | MS (ESI) m/z: 305.8 (M + H⁺) |
| 23 | 5-(7-chloro-2-ethyl-1,6-naphthyridin-3-yl)-2,4-difluoroaniline | 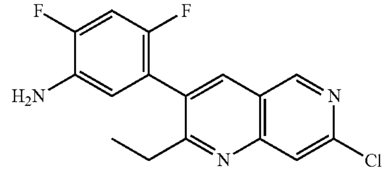 [SMILES: CCc1nc2cc(Cl)ncc2cc1-c1cc(N)c(F)cc1F] | MS (ESI) m/z: 320.1 (M + H⁺) |

| Prep No. | Chemical Name | Structure | Physical Data |
|---|---|---|---|
| 24 | 5-(7-chloro-2-ethyl-1,6-naphthyridin-3-yl)-2-fluoro-4-methylaniline | 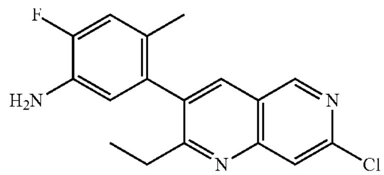 [SMILES: CCc1nc2cc(Cl)ncc2cc1-c1cc(N)c(F)cc1C] | MS (ESI) m/z: 316.1 (M + H+) |
| 25 | 5-(7-chloro-2-ethyl-1,6-naphthyridin-3-yl)-2-fluoroaniline | 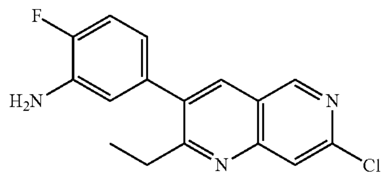 [SMILES: CCc1nc2cc(Cl)ncc2cc1-c1ccc(F)c(N)c1] | MS (ESI) m/z: 302.0 (M + H+) |
| 26 | 3-(7-chloro-2-methyl-1,6-naphthyridin-3-yl)-4-fluorobenzenamine | 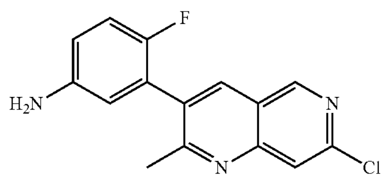 [SMILES: Cc1nc2cc(Cl)ncc2cc1-c1cc(N)ccc1F] | $^1$H NMR (400 MHz, CDCl$_3$): δ 8.96 (s, 1 H), 8.01 (s, 1 H), 7.89 (s, 1 H), 6.93 (dd, J = 8.8 Hz, 1 H), 6.72 (m, 1 H), 6.52 (m, 1 H), 2.59 (s, 3 H) |

Preparation 27

Synthesis of 5-bromo-2-fluoro-4-methylaniline

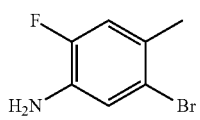

Combine 1-bromo-4-fluoro-2-methylbenzene (30.0 g, 159 mmol) in concentrated sulfuric acid (100 mL), cool to about −5° C., and treat drop wise with nitric acid (11.00 mL, 174 mmol) over 20 minutes. Allow reaction mixture to warm to RT and stir for 30 min. Pour onto crushed ice with stirring and partition with tert-butyl methyl ether (MTBE) (200 mL). Separate the aqueous layer and extract with MTBE (2×50 mL). Combine organic layers, dry and concentrate under reduced pressure to provide 1-bromo-4-fluoro-2-methyl-5-nitrobenzene as an orange-colored viscous oil (39.0 g).

Combine crude 1-bromo-4-fluoro-2-methyl-5-nitrobenzene (32.4 g, 138 mmol), ethanol (100 mL) and Raney Nickel (1.00 g, 17.04 mmol) in a shaker flask. Charge the flask with hydrogen (275 kPa) and agitate until the absorption of hydrogen ceases. De-pressurize the reaction vessel, remove the catalyst by filtration, and evaporate the filtrate to dryness. Add MTBE, then filter again and evaporate the filtrate. Stir residue in hexanes. Collect the solids by filtration, wash with cold hexanes and dry in vacuo to provide the title compound (17.8 g, 63%) as a dark solid. MS (m/z): 204.0 (M+H+)/206.0 (M+H+).

Preparation 28

Synthesis of 2-fluoro-4-methyl-5-(4,4,5,5-tetramethyl-1,3,2-dioxaborolan-2-yl)aniline Combine 5-bromo-2-fluoro-4-methylaniline (3.1 g, 15.2 mmol), bis(pinacolato)diboron (4.24 g, 16.7 mmol), and potassium acetate (4.47 g, 45.6 mmol) in dioxane (40 mL) and sparge with argon. Add [1,1'-bis(diphenylphosphino)ferrocene]-dichloropalladium(II)-dichloromethane complex (0.620 g, 0.760 mmol), sparge again with argon and heat at 100° C. overnight. Filter the reaction mixture and concentrate in vacuo. Purify by silica gel chromatography (EtOAc/hexanes) to give the title compound (3.24 g, 85%). MS (m/z): 252.1 (M+H+).

The following compounds are prepared essentially by the method of Preparation 28.

| Prep No. | Chemical Name | Structure | Physical data MS (m/z): |
|---|---|---|---|
| 29 | 2,4-difluoro-5-(4,4,5,5-tetramethyl-1,3,2-dioxaborolan-2-yl)aniline | 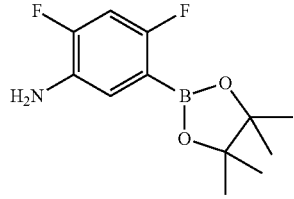 [SMILES: CC1(C)OB(c2cc(N)c(F)cc2F)OC1(C)C] | 256.2 (M + H$^+$) |
| 30 | 2-fluoro-5-(4,4,5,5-tetramethyl-1,3,2-dioxaborolan-2-yl)aniline | 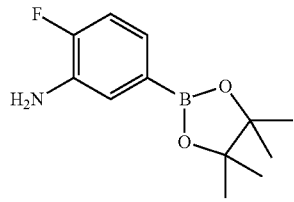 [SMILES: CC1(C)OB(c2ccc(F)c(N)c2)OC1(C)C] | 238.1 (M + H$^+$) |

Preparation 31

Synthesis of prop-1-en-2-yl 2-fluoro-4-methyl-5-(4,4,5,5-tetramethyl-1,3,2-dioxaborolan-2-yl)phenylcarbamate

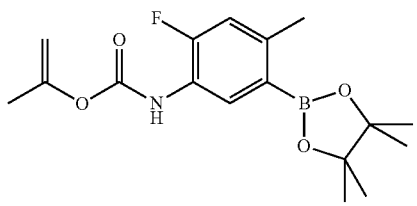 [SMILES: C=C(C)OC(=O)Nc1cc(B2OC(C)(C)C(C)(C)O2)c(C)cc1F]

Combine 2-fluoro-4-methyl-5-(4,4,5,5-tetramethyl-1,3,2-dioxaborolan-2-yl)aniline (5.0 g, 19.91 mmol) and isopropenyl chloroformate (2.40 mL, 21.90 mmol) in EtOAc (60 mL) and saturated NaHCO$_3$ (60 mL) and stir at RT for 6 h. Separate the layers, extract the aqueous layer with EtOAc (2×), wash the combined organics with brine, dry over Na$_2$SO$_4$ and concentrate to obtain the title compound. Use for the next reaction without further purification (assuming 100% yield). MS (m/z): 336.2 (M+H$^+$).

The following compounds are prepared essentially by the method of Preparation 31.

| Prep No. | Chemical Name | Structure | Physical data |
|---|---|---|---|
| 32 | Prop-1-en-2-yl (2,4-difluoro-5-(4,4,5,5-tetramethyl-1,3,2-dioxaborolan-2-yl)phenyl)carbamate | 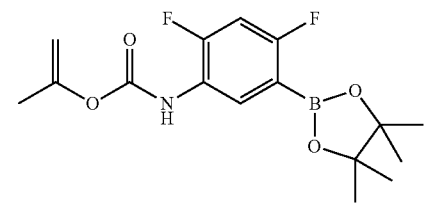 [SMILES: C=C(C)OC(=O)Nc1cc(B2OC(C)(C)C(C)(C)O2)c(F)cc1F] | MS (m/z): 340.1 (M + H$^+$) |
| 33 | Prop-1-en-2-yl (2-fluoro-5-(4,4,5,5-tetramethyl-1,3,2-dioxaborolan-2-yl)phenyl)carbamate | 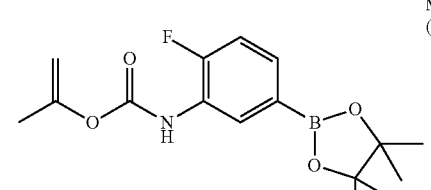 | MS (m/z): 322.1 (M + H$^+$) |

Preparation 34

Synthesis of 7-chloro-2-methyl-[1,6]naphthyridin-3-ol

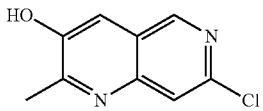

Treat a mixture of 4-amino-6-chloro-pyridine-3-carbaldehyde (39 g, 0.25 mol) and 2-hydroxy acetone (28 g, 0.375 mol) in THF (400 mL) with KOH (52.5 g, 0.75 mol), stir at RT for 1 h, add water and acidify with 1N HCl. Collect the resulting solids by filtration, wash with water (3×), then EtOAc (2×) and dry to afford the title compound (45 g, 93%) as a white solid. $^1$H NMR (400 MHz, DMSO-$d_6$): δ 9.00 (s, 1H), 7.77 (s, 1H), 7.53 (s, 1H), 2.54 (s, 3H).

The following compound is prepared essentially by the method of Preparation 34.

| Prep No. | Chemical Name | Structure | Physical Data |
|---|---|---|---|
| 35 | 7-chloro-2-ethyl-1,6-naphthyridin-3-ol | 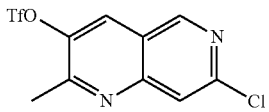 | MS (ESI) m/z: 209.1 (M + H$^+$) |

Preparation 36

Synthesis of 7-chloro-2-methyl-1,6-naphthyridin-3-yl trifluoromethanesulfonate Treat a 0° C. solution of 7-chloro-2-methyl-[1,6]naphthyridin-3-ol (30 g, 154.6 mmol) in DCM (300 mL), under Ar, with pyridine (24.4 g, 309.2 mmol) and trifluoromethanesulfonic anhydride [Tf$_2$O] (65.4 g, 232 mmol), stir for 2 h, then wash with water. Extract the aqueous layer with DCM (1×), wash the combined organics with brine, dry over Na$_2$SO$_4$, concentrate and purify by silica gel chromatography to give the title compound (40.2 g, 80%). $^1$H NMR (400 MHz, DMSO-$d_6$): δ 9.10 (d, J=0.8 Hz, 1H), 8.15 (s, 1H), 7.96 (t, J=0.8 Hz, 1H), 2.83 (s, 3H).

The following compound is prepared essentially by the method of Preparation 36.

| Prep No. | Chemical Name | Structure | Physical Data |
|---|---|---|---|
| 37 | 7-chloro-2-ethyl-1,6-naphthyridin-3-yl trifluoromethanesulfonate | 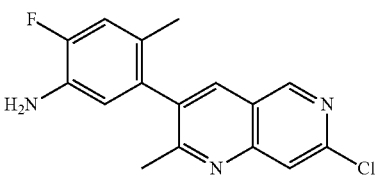 | MS (ESI) m/z: 341.0 (M + H$^+$) |

Preparation 38

Synthesis of 5-(7-chloro-2-methyl-1,6-naphthyridin-3-yl)-2-fluoro-4-methylaniline Sparge a mixture of 7-chloro-2-methyl-1,6-naphthyridin-3-yl trifluoromethanesulfonate (2.250 g, 6.89 mmol) and 2-fluoro-4-methyl-5-(4,4,5,5-tetramethyl-1,3,2-dioxaborolan-2-yl)aniline (1.729 g, 6.89 mmol) in dioxane (32 mL) with argon, add a solution of K$_2$CO$_3$ (2.86 g, 20.66 mmol) in H$_2$O (16 mL) followed by Pd(PPh$_3$)$_4$ (252 mg, 0.689 mmol) and heat at 60° C. for 1 h. Cool to RT, add EtOAc, wash successively with H$_2$O, satd. NaHCO$_3$, then brine, dry over Na$_2$SO$_4$, concentrate to dryness and purify via silica gel chromatography (EtOAc/Hex) to afford the title compound (1.277 g, 61%) as a solid. $^1$H NMR (400 MHz, DMSO-$d_6$): δ 9.21 (d, J=0.8 Hz, 1H), 8.28 (s, 1H), 8.00 (s, 1H), 7.00 (d, J=12.4 Hz, 1H), 6.59 (d, J=9.3 Hz, 1H), 5.08 (s, 2H), 2.42 (s, 3H), 1.85 (s, 3H); MS (ESI) m/z: 302.1 (M+H$^+$).

The following compounds are prepared essentially by the method of Preparation 38.

| Prep No. | Chemical Name | Structure | Physical Data |
|---|---|---|---|
| 39 | 3-(7-chloro-2-methyl-1,6-naphthyridin-3-yl)-4-methylaniline | 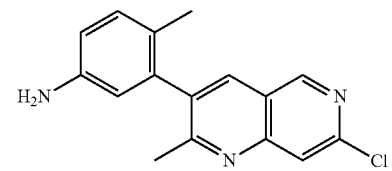 [SMILES: Cc1ccc(N)cc1-c1cc2cnc(Cl)cc2nc1C] | MS (ESI) m/z: 284.1 (M + H$^+$) |

| Prep No. | Chemical Name | Structure | Physical Data |
|---|---|---|---|
| 40 | 3-(7-chloro-2-ethyl-1,6-naphthyridin-3-yl)-4-fluoroaniline | 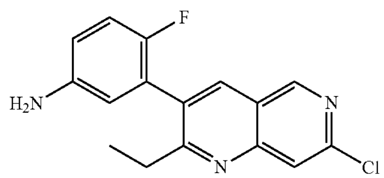 [SMILES: CCc1nc2cc(Cl)ncc2cc1-c1cc(N)ccc1F] | MS (ESI) m/z: 302.1 (M + H+) |

Preparation 41

Synthesis of 3-bromo-7-chloro-1,6-naphthyridine

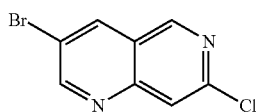

Heat a mixture of 4-amino-6-chloronicotinaldehyde (2.00 g, 12.77 mmol), 2-bromo-1,1-dimethoxyethane (6.48 g, 38.3 mmol) and ytterbium(III) trifluoromethanesulfonate (1.981 g, 3.19 mmol) in MeCN (25 mL) at 80° C. overnight. Cool to RT, dilute with EtOAc, collect the solids via filtration, rinse with EtOAc and dry. Wash the filtrate with H$_2$O, then brine, dry over Na$_2$SO$_4$, concentrate to dryness and purify via silica gel chromatography (EtOAc/Hex). Combine the two solids to afford the title compound (1.67 g, 53%) as an off-white solid. MS(ESI) m/z: 244.9 (M+H+).

Preparation 42

Synthesis of 5-(7-chloro-1,6-naphthyridin-3-yl)-2-fluoro-4-methylaniline

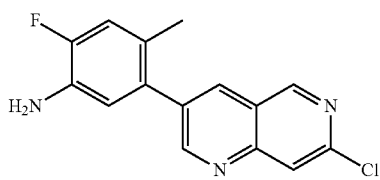 [SMILES: Cc1cc(F)c(N)cc1-c1cnc2cc(Cl)ncc2c1]

Sparge a solution of 3-bromo-7-chloro-1,6-naphthyridine (0.5 g, 2.053 mmol) and 2-fluoro-4-methyl-5-(4,4,5,5-tetramethyl-1,3,2-dioxaborolan-2-yl)aniline (0.516 g, 2.053 mmol) in dioxane (15 mL) with Ar, add a solution of K$_2$CO$_3$ (0.568 g, 4.11 mmol) in H$_2$O (3 mL), followed by Pd(PPh$_3$)$_4$ (0.237 g, 0.205 mmol), heat at 75° C. for 8 h, then cool to RT. Add H$_2$O, extract with EtOAc (2×), wash the combined organics with brine, dry over Na$_2$SO$_4$, concentrate to dryness and purify via silica gel chromatography (EtOAc/Hex) to afford the title compound (470 mg, 80%) as an off-white solid. MS(ESI) m/z: 288.1 (M+H+).

Preparation 43

Synthesis of 3-(3-amino-4-fluorophenyl)-N-(4-methoxybenzyl)-N,2-dimethyl-1,6-naphthyridin-7-amine

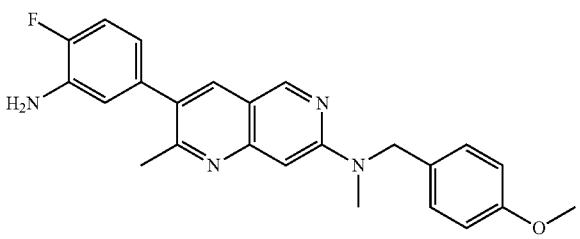

Treat a solution of 5-(7-chloro-2-methyl-1,6-naphthyridin-3-yl)-2-fluoroaniline (0.353 g, 1.227 mmol) and 4-methoxy-N-methylbenzylamine (0.371 g, 2.454 mmol) in NMP (6 mL) in a sealed tube with N,N-diisopropylethylamine (DIEA) (0.429 mL, 2.454 mmol), sparge with argon and heat at 170° C. overnight. Add additional 4-methoxy-N-methylbenzylamine (0.371 g, 2.454 mmol) and heat at 185° C. for 24 h. Add more 4-methoxy-N-methylbenzylamine (0.15 g, 1 mmol) and heat the mixture overnight at 185° C. Cool to RT, dilute with EtOAc and wash with satd. NaHCO$_3$, water, and then brine. Dry the organics over MgSO$_4$, concentrate to dryness and purify via silica gel chromatography (EtOAc/Hex) to afford the title compound (334 mg, 68%). $^1$H NMR (400 MHz, DMSO-d$_6$): δ 8.95 (s, 1H), 7.95 (s, 1H), 7.15 (d, J=8.4 Hz, 2H), 7.05 (dd, J=11.5, 8.2 Hz, 1H), 6.85 (m, 2H), 6.78 (dd, J=8.8, 2.3 Hz, 1H), 6.71 (s, 1H), 6.54 (ddd, J=8.2, 4.4, 2.2 Hz, 1H), 5.24 (s, 2H), 4.85 (s, 2H), 3.69 (s, 3H), 3.08 (s, 3H), 2.47 (s, 3H); MS (ESI) m/z: 403.2 (M+H+).

The following compounds are prepared essentially by the method of Preparation 43.

| Prep No. | Chemical Name | Structure | Physical Data |
|---|---|---|---|
| 44 | 3-(5-amino-2,4-difluorophenyl)-N-(4-methoxybenzyl)-N,2-dimethyl-1,6-naphthyridin-7-amine | 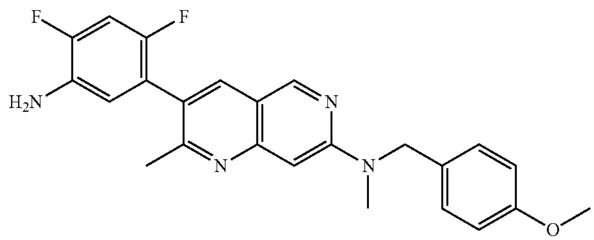 [SMILES: COc1ccc(CN(C)c2cc3nc(C)c(-c4cc(N)c(F)cc4F)cc3cn2)cc1] | MS (ESI) m/z: 421.2 (M + H$^+$) |
| 45 | 3-(5-amino-2,4-difluorophenyl)-2-ethyl-N-(4-methoxybenzyl)-N-methyl-1,6-naphthyridin-7-amine | 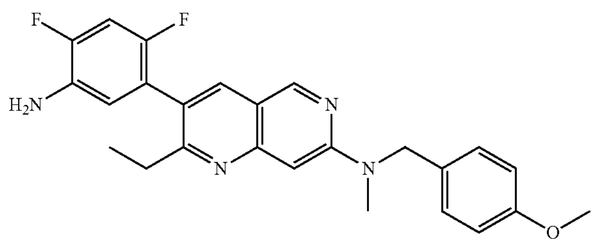 [SMILES: CCc1nc2cc(N(C)Cc3ccc(OC)cc3)ncc2cc1-c1cc(N)c(F)cc1F] | MS (ESI) m/z: 435.2 (M + H$^+$) |
| 46 | 3-(5-amino-4-fluoro-2-methylphenyl)-2-ethyl-N-(4-methoxybenzyl)-N-methyl-1,6-naphthyridin-7-amine | 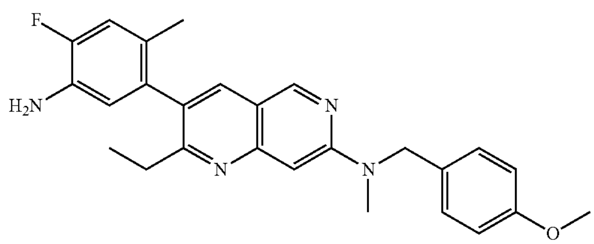 [SMILES: CCc1nc2cc(N(C)Cc3ccc(OC)cc3)ncc2cc1-c1cc(N)c(F)cc1C] | MS (ESI) m/z: 431.2 (M + H$^+$) |
| 47 | 3-(5-amino-4-fluoro-2-methylphenyl)-N-(4-methoxybenzyl)-N,2-dimethyl-1,6-naphthyridin-7-amine | 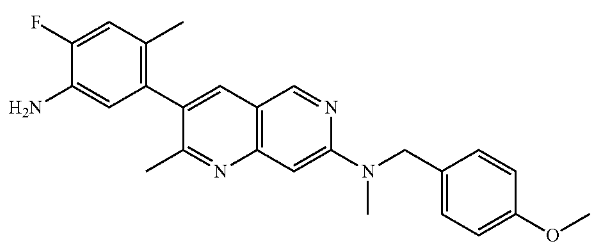 [SMILES: COc1ccc(CN(C)c2cc3nc(C)c(-c4cc(N)c(F)cc4C)cc3cn2)cc1] | MS (ESI) m/z: 417.2 (M + H$^+$) |
| 48 | 3-(5-amino-2-methylphenyl)-N-(4-methoxybenzyl)-N,2-dimethyl-1,6-naphthyridin-7-amine | 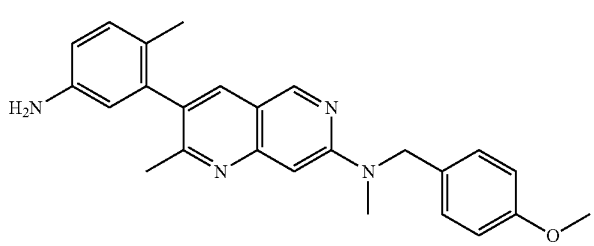 [SMILES: COc1ccc(CN(C)c2cc3nc(C)c(-c4cc(N)ccc4C)cc3cn2)cc1] | MS (ESI) m/z: 399.2 (M + H$^+$) |
| 49 | 3-(3-amino-4-fluorophenyl)-2-ethyl-N-(4-methoxybenzyl)-N-methyl-1,6-naphthyridin-7-amine | 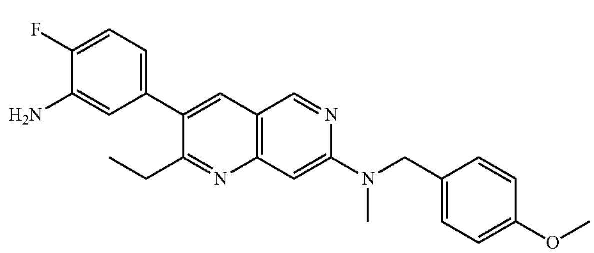 [SMILES: CCc1nc2cc(N(C)Cc3ccc(OC)cc3)ncc2cc1-c1ccc(F)c(N)c1] | MS (ESI) m/z: 417.2 (M + H$^+$) |

Preparation 50

Synthesis of 3-(5-amino-2,4-difluorophenyl)-N,2-dimethyl-1,6-naphthyridin-7-amine

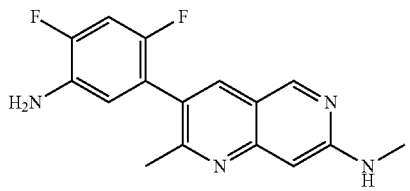 [SMILES: CNc1cc2nc(C)c(-c3cc(N)c(F)cc3F)cc2cn1]

Heat a solution of 5-(7-chloro-2-methyl-1,6-naphthyridin-3-yl)-2,4-difluorobenzenamine (0.55 g, 1.799 mmol) in methylamine (33% in EtOH, 10 mL, 1.799 mmol) at 120° C. with microwave irradiation for 12 h. Add additional methylamine (33% in EtOH, 2 mL), heat the mixture at 120° C. for 12 h, add more methylamine (33% in EtOH, 2 mL) and irradiate at 120° C. for 15 h. Dilute the mixture with EtOAc, wash with satd. NaHCO$_3$ (2×), dry and evaporated to yield the title compound (0.53 g, 98%). MS(ESI) m/z: 301.1 (M+H$^+$).

The following compounds are prepared essentially by the method of Preparation 50.

| Prep No. | Chemical Name | Structure | Physical Data |
|---|---|---|---|
| 51 | 3-(5-amino-2-fluorophenyl)-N,2-dimethyl-1,6-naphthyridin-7-amine | 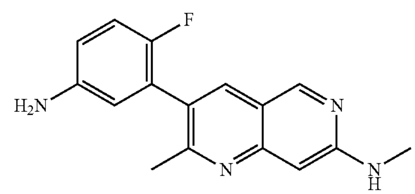 [SMILES: CNc1cc2nc(C)c(-c3cc(N)ccc3F)cc2cn1] | MS (ESI) m/z: 283.2 (M + H$^+$) |
| 52 | 3-(5-amino-4-fluoro-2-methylphenyl)-N,2-dimethyl-1,6-naphthyridin-7-amine | 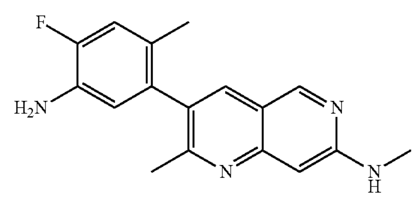 [SMILES: CNc1cc2nc(C)c(-c3cc(N)c(F)cc3C)cc2cn1] | MS (ESI) m/z: 297.0 (M + H$^+$) |
| 53 | 3-(5-amino-4-fluoro-2-methylphenyl)-N-methyl-1,6-naphthyridin-7-amine | 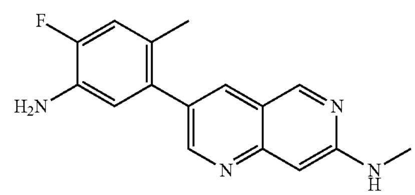 [SMILES: CNc1cc2ncc(-c3cc(N)c(F)cc3C)cc2cn1] | MS (ESI) m/z: 283.1 (M + H$^+$) |
| 54 | 2-((3-(5-amino-4-fluoro-2-methylphenyl)-2-methyl-1,6-naphthyridin-7-yl)amino)ethanol | 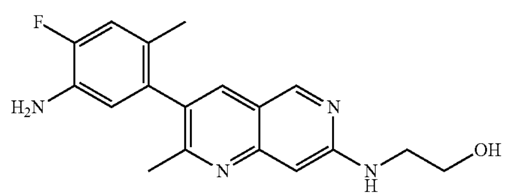 [SMILES: Cc1cc(F)c(N)cc1-c1cc2cnc(NCCO)cc2nc1C] | MS (ESI) m/z: 327.2 (M + H$^+$) |
| 55 | 2-((3-(5-amino-2,4-difluorophenyl)-2-methyl-1,6-naphthyridin-7-yl)amino)ethan-1-ol | 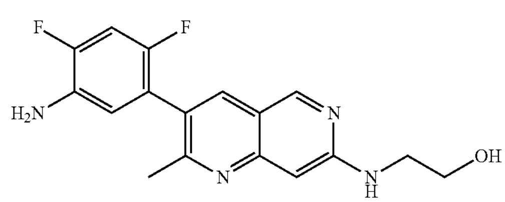 [SMILES: Cc1nc2cc(NCCO)ncc2cc1-c1cc(N)c(F)cc1F] | MS (ESI) m/z: 331.1 (M + H$^+$) |

Preparation 56

Synthesis of N-(3-(3-amino-4-fluorophenyl)-2-methyl-1,6-naphthyridin-7-yl)cyclopropanecarboxamide

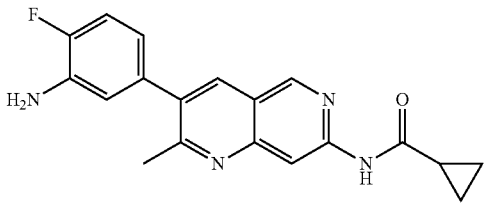 [SMILES: Cc1nc2cc(NC(=O)C3CC3)ncc2cc1-c1ccc(F)c(N)c1]

Sparge a solution of 5-(7-chloro-2-methyl-1,6-naphthyridin-3-yl)-2-fluoroaniline (0.5 g, 1.738 mmol) in dioxane (15 mL) with argon, add cyclopropanecarboxamide (0.739 g, 8.69 mmol), XantPhos (0.101 g, 0.174 mmol), $Cs_2CO_3$ (1.699 g, 5.21 mmol) and $Pd_2(dba)_3$ (0.080 g, 0.087 mmol) and heat at 80° C. overnight. Cool to RT, add EtOAc and MeOH, remove the solids via filtration through diatomaceous earth, rinse well with EtOAc and $H_2O$ and separate the layers of the filtrate. Wash the organic layer with brine, dry over $Na_2SO_4$, concentrate to dryness and purify via silica gel chromatography (EtOAc/Hex) to afford the title compound (200 mg, 34%) as a white amorphous solid. $^1$H NMR (400 MHz, DMSO-$d_6$): δ 11.01 (s, 1H), 9.13 (d, J=0.9 Hz, 1H), 8.44 (m, 1H), 8.17 (s, 1H), 7.08 (m, 1H), 6.82 (dd, J=8.7, 2.2 Hz, 1H), 6.59 (m, 1H), 5.28 (s, 2H), 2.56 (s, 3H), 2.02 (m, 1H), 0.88-0.81 (m, 4H); MS(ESI) m/z: 337.1 (M+H$^+$).

The following compounds are prepared essentially by the method of Preparation 56.

Preparation 60

Synthesis of N-(3-(3-amino-4-fluorophenyl)-2-ethyl-1,6-naphthyridin-7-yl)acetamide

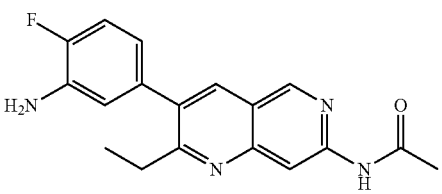

Sparge a solution of 5-(7-chloro-2-ethyl-1,6-naphthyridin-3-yl)-2-fluoroaniline (0.63 g, 2.088 mmol) in dioxane (20 mL) with argon, add acetamide (0.987 g, 16.70 mmol), $K_3PO_4$ (1.773 g, 8.35 mmol), $Pd_2(dba)_3$ (0.096 g, 0.104 mmol) and BippyPhos (0.106 g, 0.209 mmol) and heat at 80° C. for 16 h. Cool to RT, remove the solids via filtration through diatomaceous earth, rinse well with EtOAc and $H_2O$, and separate the layers of the filtrate. Extract the aqueous layer with EtOAc (1×), wash the combined organics with brine, dry over $Na_2SO_4$, concentrate to dryness and purify via silica gel chromatography (EtOAc/Hex) to afford the title compound (250 mg, 37%) as an off-white solid. MS(ESI) m/z: 325.1 (M+H$^+$).

| Prep No. | Chemical Name | Structure | Physical Data |
|---|---|---|---|
| 57 | N-(3-(5-amino-2-fluorophenyl)-2-methyl-1,6-naphthyridin-7-yl)acetamide | 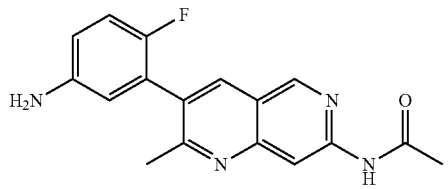 [SMILES: CC(=O)Nc1cc2nc(C)c(-c3cc(N)ccc3F)cc2cn1] | MS (ESI) m/z: 311.1 (M + H$^+$) |
| 58 | N-(3-(3-amino-4-fluorophenyl)-2-methyl-1,6-naphthyridin-7-yl)isobutyramide | 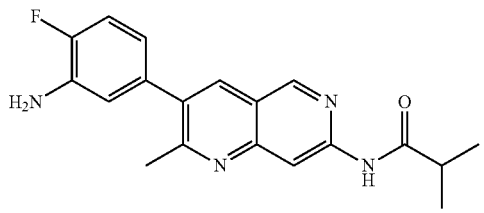 [SMILES: Cc1nc2cc(NC(=O)C(C)C)ncc2cc1-c1ccc(F)c(N)c1] | MS (ESI) m/z: 339.2 (M + H$^+$) |
| 59 | N-(3-(5-amino-4-fluoro-2-methylphenyl)-2-methyl-1,6-naphthyridin-7-yl)cyclopropanecarboxamide | 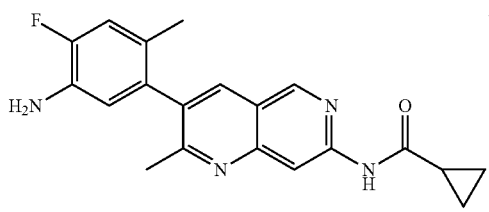 [SMILES: Cc1cc(F)c(N)cc1-c1cc2cnc(NC(=O)C3CC3)cc2nc1C] | MS (ESI) m/z: 351.2 (M + H$^+$) |

The following compounds are prepared essentially by the method of Preparation 60.

| Prep No. | Chemical Name | Structure | Physical Data |
|---|---|---|---|
| 61 | 3-(5-amino-2,4-difluorophenyl)-2-methyl-N-(6-methylpyridin-3-yl)-1,6-naphthyridin-7-amine | 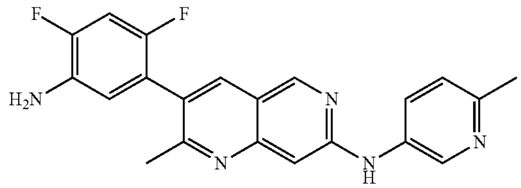 [SMILES: Cc1ccc(Nc2cc3nc(C)c(-c4cc(N)c(F)cc4F)cc3cn2)cn1] | MS (ESI) m/z: 378.1 (M + H⁺) |
| 62 | N-(3-(5-amino-2-fluorophenyl)-2-ethyl-1,6-naphthyridin-7-yl)acetamide | 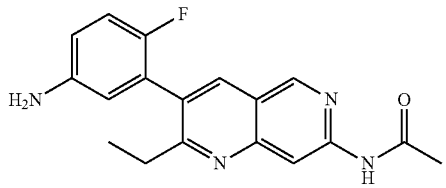 [SMILES: CCc1nc2cc(NC(C)=O)ncc2cc1-c1cc(N)ccc1F] | MS (ESI) m/z: 325.1 (M + H⁺) |

Preparation 63

Synthesis of tert-butyl (5-(7-chloro-2-methyl-1,6-naphthyridin-3-yl)-2,4-difluorophenyl)carbamate

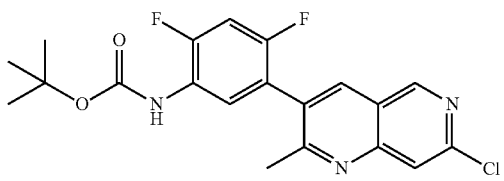 [SMILES: Cc1nc2cc(Cl)ncc2cc1-c1cc(NC(=O)OC(C)(C)C)c(F)cc1F]

Heat a solution of 5-(7-chloro-2-methyl-1,6-naphthyridin-3-yl)-2,4-difluoroaniline (0.5 g, 1.636 mmol) and di-tert-butyl dicarbonate [Boc$_2$O] (0.759 mL, 3.27 mmol) in toluene (10 mL) at 110° C. for 16 h, add additional Boc$_2$O (0.36 g, 1.65 mmol) and heat for an additional 40 h. Cool to RT, concentrate to dryness and purify via silica gel chromatography (EtOAc/Hex) to afford the title compound (750 mg, 113%) as a viscous oil. MS (ESI) m/z: 406.1 (M+H⁺).

The following compound is prepared essentially by the method of Preparation 63.

Preparation 65

Synthesis of tert-butyl (5-(7-acetamido-2-methyl-1,6-naphthyridin-3-yl)-2,4-difluorophenyl)carbamate

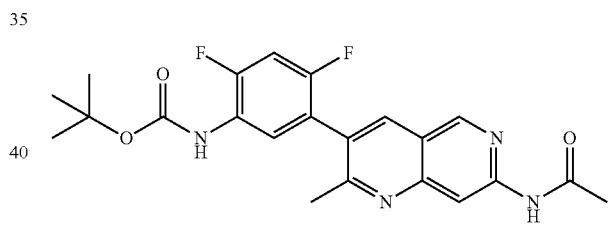

Sparge a mixture of tert-butyl (5-(7-chloro-2-methyl-1,6-naphthyridin-3-yl)-2,4-difluorophenyl)carbamate (0.664 g, 1.636 mmol), XantPhos (0.189 g, 0.327 mmol), Cs$_2$CO$_3$ (1.066 g, 3.27 mmol) and acetamide (0.483 g, 8.18 mmol) in dioxane (16 mL) with Ar, add Pd$_2$(dba)$_3$ (0.150 g, 0.164 mmol) and heat at 100° C. overnight. Cool to RT, remove the solids via filtration through diatomaceous earth, rinse well with THF, concentrate the filtrate to dryness and purify via

| Prep No. | Chemical Name | Structure | Physical Data |
|---|---|---|---|
| 64 | tert-butyl (5-(7-chloro-2-methyl-1,6-naphthyridin-3-yl)-2-fluoro-4-methylphenyl)carbamate | | MS (ESI) m/z: 402.1 (M + H⁺). | silica gel chromatography (EtOAc/Hex) to afford the title compound (630 mg, 90%) as a glass. MS (ESI) m/z: 429.2 (M+H+).

The following compound is prepared essentially by the method of Preparation 65.

| Prep No. | Chemical Name | Structure | Physical Data |
|---|---|---|---|
| 66 | tert-butyl (5-(7-(tert-butoxycarbonylamino)-2-methyl-1,6-naphthyridin-3-yl)-2-fluoro-4-methylphenyl)carbamate | 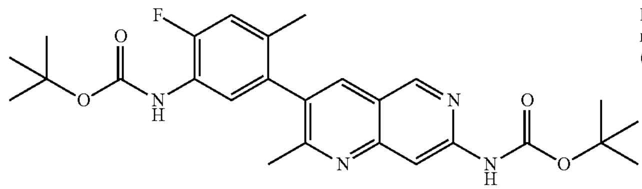 [SMILES: Cc1cc(F)c(NC(=O)OC(C)(C)C)cc1-c1cc2cnc(NC(=O)OC(C)(C)C)cc2nc1C] | MS (ESI) m/z: 483.2 (M + H+). |

Preparation 67

Synthesis of N-(3-(5-amino-2,4-difluorophenyl)-2-methyl-1,6-naphthyridin-7-yl)acetamide

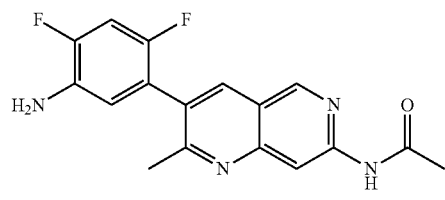 [SMILES: CC(=O)Nc1cc2nc(C)c(-c3cc(N)c(F)cc3F)cc2cn1]

Add TFA (5 mL, 64.9 mmol) to a solution of tert-butyl (5-(7-acetamido-2-methyl-1,6-naphthyridin-3-yl)-2,4-difluorophenyl)carbamate (0.63 g, 1.470 mmol) in DCM (5 mL), stir at RT for 16 h, then concentrate to dryness. Neutralize with satd. NaHCO₃, extract with EtOAc/THF (1×), wash the organic layer with brine, dry over MgSO₄ and concentrate to dryness. Triturate with THF/Hex, collect the solids via filtration and dry to afford the title compound (391 mg, 81%) as a tan solid. $^1$H NMR (400 MHz, DMSO-$d_6$): δ 10.76 (s, 1H), 9.13 (d, J=0.84 Hz, 1H), 8.49 (s, 1H), 8.25 (s, 1H), 7.21 (dd, J=11.28, 9.65 Hz, 1H), 6.76 (dd, J=9.87, 7.72 Hz, 1H), 5.18 (s, 2H), 2.49 (s, 3H), 2.15 (s, 3H); MS (ESI) m/z: 329.1 (M+H+).

The following compound is prepared essentially by the method of Preparation 67.

Preparation 69

Synthesis of prop-1-en-2-yl(2-fluoro-5-(7-((4-methoxybenzyl)(methyl)amino)-2-methyl-1,6-naphthyridin-3-yl)phenyl)carbamate Treat a solution of 3-(3-amino-4-fluorophenyl)-N-(4-methoxybenzyl)-N,2-dimethyl-1,6-naphthyridin-7-amine (0.334 g, 0.830 mmol) in EtOAc (10 mL) with satd. NaHCO₃ (10 mL), add isopropenyl chloroformate (0.100 mL, 0.913 mmol) and stir at RT for 2 h. Separate the layers, extract the aqueous layer with EtOAc (2×), dry the combined organics over MgSO₄ and concentrate to dryness to afford the title compound (398 mg, 99%). MS (ESI) m/z: 487.2 (M+H+).

| Prep No. | Chemical Name | Structure | Physical Data |
|---|---|---|---|
| 68 | 3-(5-amino-4-fluoro-2-methylphenyl)-2-methyl-1,6-naphthyridin-7-amine | 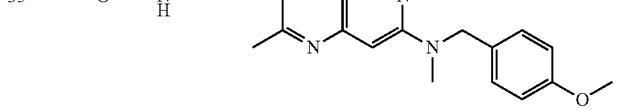 | MS (ESI) m/z: 283.1 (M + H+) |

The following compounds are prepared essentially by the method of Preparation 69.

| Prep No. | Chemical Name | Structure | Physical Data |
|---|---|---|---|
| 70 | prop-1-en-2-yl (2,4-difluoro-5-(7-((4-methoxybenzyl)(methyl)amino)-2-methyl-1,6-naphthyridin-3-yl)phenyl)carbamate | 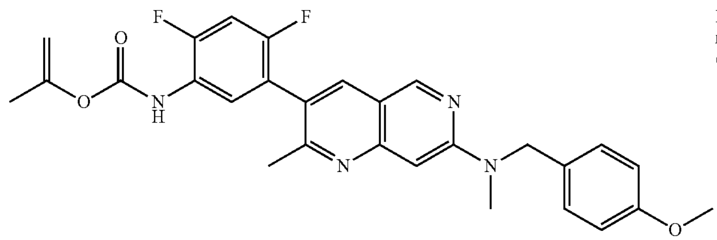 | MS (ESI) m/z: 505.2 (M + H$^+$) |
| 71 | prop-1-en-2-yl (5-(2-ethyl-7-((4-methoxybenzyl)(methyl)amino)-1,6-naphthyridin-3-yl)-2,4-difluorophenyl)carbamate | 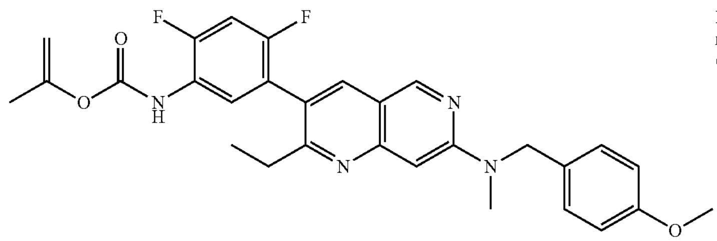 [SMILES: C=C(C)OC(=O)Nc1cc(-c2cc3cnc(N(C)Cc4ccc(OC)cc4)cc3nc2CC)c(F)cc1F] | MS (ESI) m/z: 519.2 (M + H$^+$) |
| 72 | prop-1-en-2-yl (5-(2-ethyl-7-((4-methoxybenzyl)(methyl)amino)-1,6-naphthyridin-3-yl)-2-fluoro-4-methylphenyl)carbamate | 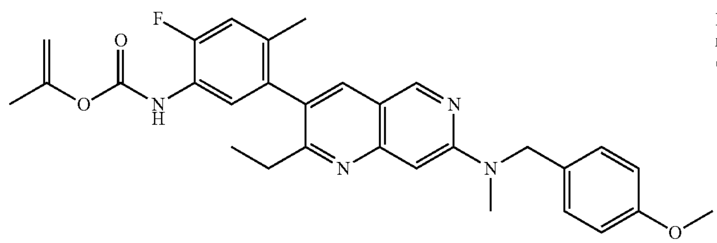 [SMILES: C=C(C)OC(=O)Nc1cc(-c2cc3cnc(N(C)Cc4ccc(OC)cc4)cc3nc2CC)c(C)cc1F] | MS (ESI) m/z: 515.3 (M + H$^+$) |
| 73 | prop-1-en-2-yl (2-fluoro-5-(7-((4-methoxybenzyl)(methyl)amino)-2-methyl-1,6-naphthyridin-3-yl)-4-methylphenyl)carbamate | 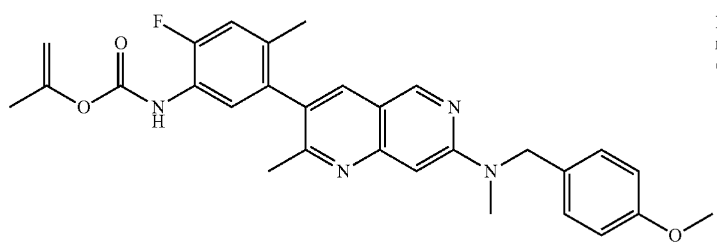 [SMILES: C=C(C)OC(=O)Nc1cc(-c2cc3cnc(N(C)Cc4ccc(OC)cc4)cc3nc2C)c(C)cc1F] | MS (ESI) m/z: 501.2 (M + H$^+$) |
| 74 | prop-1-en-2-yl (3-(7-((4-methoxybenzyl)(methyl)amino)-2-methyl-1,6-naphthyridin-3-yl)-4-methylphenyl)carbamate | 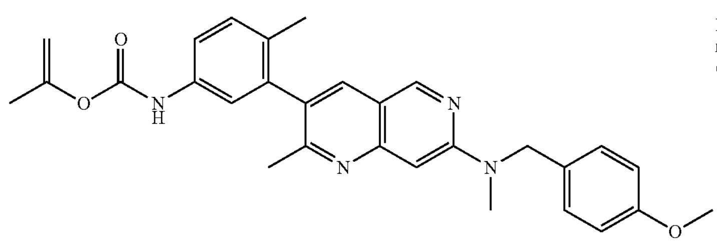 [SMILES: C=C(C)OC(=O)Nc1ccc(C)c(-c2cc3cnc(N(C)Cc4ccc(OC)cc4)cc3nc2C)c1] | MS (ESI) m/z: 483.3 (M + H$^+$) |
| 75 | prop-1-en-2-yl (5-(2-ethyl-7-((4-methoxybenzyl)(methyl)amino)-1,6-naphthyridin-3-yl)-2-fluorophenyl)carbamate | 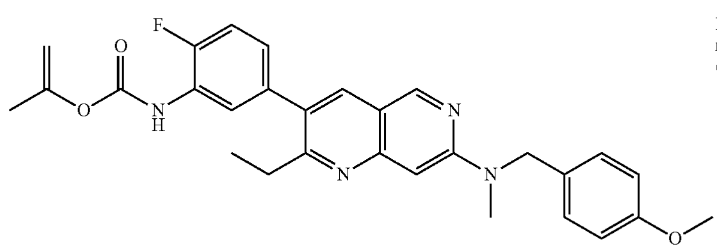 [SMILES: C=C(C)OC(=O)Nc1cc(-c2cc3cnc(N(C)Cc4ccc(OC)cc4)cc3nc2CC)ccc1F] | MS (ESI) m/z: 501.2 (M + H$^+$) |

-continued

| Prep No. | Chemical Name | Structure | Physical Data |
|---|---|---|---|
| 76 | prop-1-en-2-yl (4-fluoro-3-(2-methyl-7-(methylamino)-1,6-naphthyridin-3-yl)phenyl)carbamate | 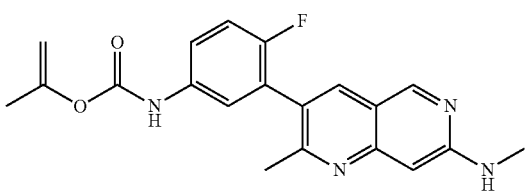 [SMILES: C=C(C)OC(=O)Nc1ccc(F)c(-c2cc3cnc(NC)cc3nc2C)c1] | MS (ESI) m/z: 367.2 (M + H⁺) |
| 77 | prop-1-en-2-yl (3-(7-acetamido-2-methyl-1,6-naphthyridin-3-yl)-4-fluorophenyl)carbamate | 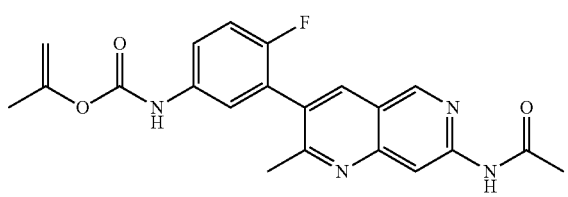 [SMILES: C=C(C)OC(=O)Nc1ccc(F)c(-c2cc3cnc(NC(C)=O)cc3nc2C)c1] | MS (ESI) m/z: 395.1 (M + H⁺) |
| 78 | prop-1-en-2-yl (5-(7-acetamido-2-ethyl-1,6-naphthyridin-3-yl)-2-fluorophenyl)carbamate | 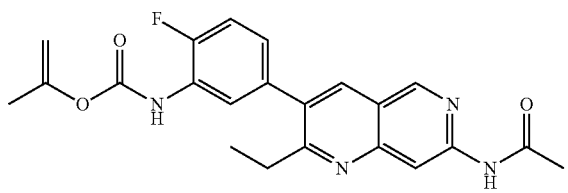 [SMILES: C=C(C)OC(=O)Nc1cc(-c2cc3cnc(NC(C)=O)cc3nc2CC)ccc1F] | MS (ESI) m/z: 409.2 (M + H⁺) |
| 79 | prop-1-en-2-yl (3-(7-acetamido-2-ethyl-1,6-naphthyridin-3-yl)-4-fluorophenyl)carbamate | 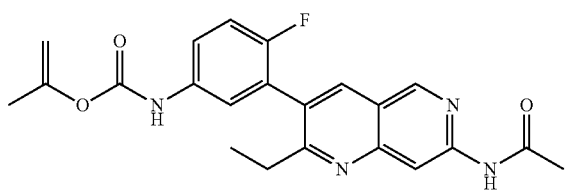 [SMILES: C=C(C)OC(=O)Nc1ccc(F)c(-c2cc3cnc(NC(C)=O)cc3nc2CC)c1] | MS (ESI) m/z: 409.2 (M + H⁺) |
| 80 | prop-1-en-2-yl (2-fluoro-5-(7-isobutyramido-2-methyl-1,6-naphthyridin-3-yl)phenyl)carbamate | 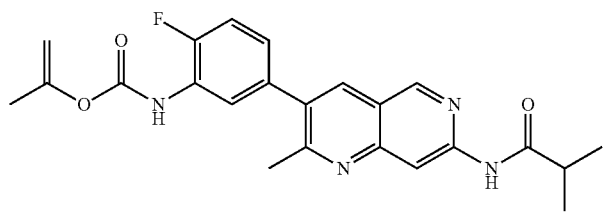 [SMILES: C=C(C)OC(=O)Nc1cc(-c2cc3cnc(NC(=O)C(C)C)cc3nc2C)ccc1F] | MS (ESI) m/z: 423.2 (M + H⁺) |
| 81 | prop-1-en-2-yl (5-(7-(cyclopropanecarboxamido)-2-methyl-1,6-naphthyridin-3-yl)-2-fluoro-4-methylphenyl)carbamate | 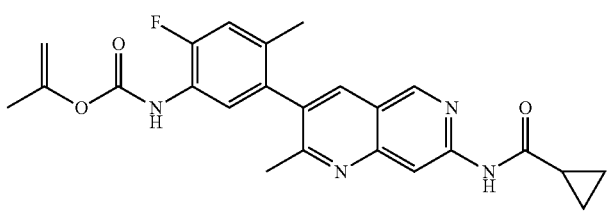 [SMILES: C=C(C)OC(=O)Nc1cc(-c2cc3cnc(NC(=O)C4CC4)cc3nc2C)c(C)cc1F] | MS (ESI) m/z: 435.2 (M + H⁺) |
| 82 | prop-1-en-2-yl (5-(7-(cyclopropanecarboxamido)-2-methyl-1,6-naphthyridin-3-yl)-2-fluorophenyl)carbamate | 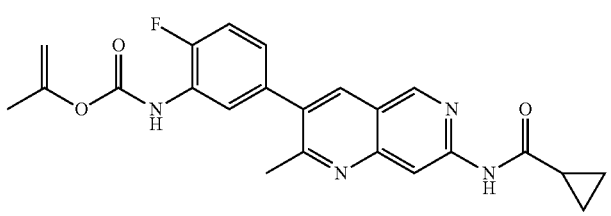 [SMILES: C=C(C)OC(=O)Nc1cc(-c2cc3cnc(NC(=O)C4CC4)cc3nc2C)ccc1F] | MS (ESI) m/z: 421.2 (M + H⁺) |

| Prep No. | Chemical Name | Structure | Physical Data |
|---|---|---|---|
| 83 | prop-1-en-2-yl (5-(7-acetamido-2-methyl-1,6-naphthyridin-3-yl)-2,4-difluorophenyl)carbamate | 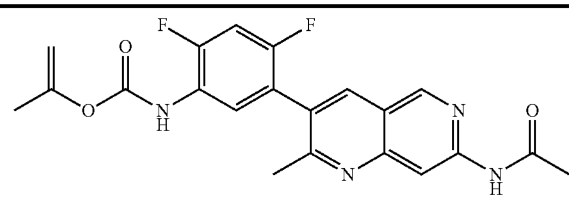 | MS (ESI) m/z: 413.2 (M + H⁺) |

Preparation 84

Synthesis of prop-1-en-2-yl 2,4-difluoro-5-(2-methyl-7-(methylamino)-1,6-naphthyridin-3-yl)phenylcarbamate

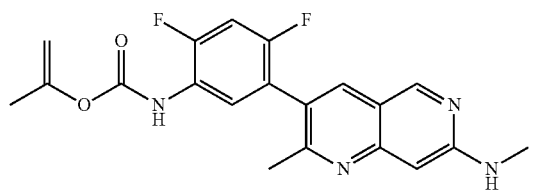

Treat a 0° C. solution of 3-(5-amino-2,4-difluorophenyl)-N,2-dimethyl-1,6-naphthyridin-7-amine (1.45 g, 4.83 mmol) in pyridine (30 mL) drop-wise with isopropenyl chloroformate (0.528 mL, 4.83 mmol), warm to RT and stir overnight. Add EtOAc, wash with satd. NaHCO₃ (2×), dry, concentrate and purify by silica gel chromatography (EtOAc/TEA pre-wash, EtOAc/Hex) to afford the title compound (1.449 g, 78%). $^1$H NMR (400 MHz, DMSO-$d_6$): δ 9.77 (s, 1H), 8.85 (s, 1H), 8.03 (s, 1H), 7.67-7.63 (m, 1H), 7.49 (t, 1H), 6.87-6.84 (m, 1H), 6.52 (s, 1H), 4.73 (s, 1H), 4.70 (s, 1H), 2.82 (d, 3H), 2.38 (s, 3H), 1.91 (s, 3H); MS (ESI) m/z: 385.2 (M+H⁺). The following compounds are prepared essentially by the method of Preparation 84.

| Prep No. | Chemical Name | Structure | Physical Data |
|---|---|---|---|
| 85 | prop-1-en-2-yl (2-fluoro-4-methyl-5-(2-methyl-7-(methylamino)-1,6-naphthyridin-3-yl)phenyl)carbamate | 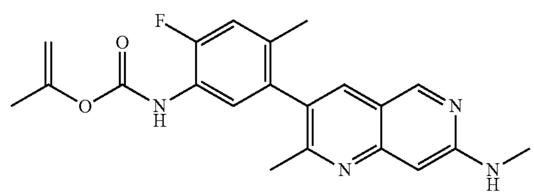 | MS (ESI) m/z: 381.1 (M + H⁺) |
| 86 | prop-1-en-2-yl (2-fluoro-4-methyl-5-(7-(methylamino)-1,6-naphthyridin-3-yl)phenyl)carbamate | 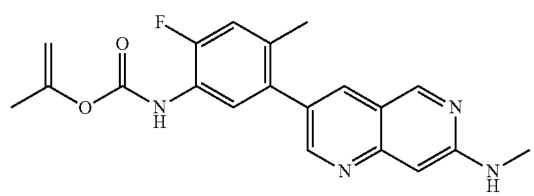 [SMILES: C=C(C)OC(=O)Nc1cc(-c2cnc3cc(NC)ncc3c2)c(C)cc1F] | MS (ESI) m/z: 367.1 (M + H⁺) |
| 87 | prop-1-en-2-yl (2,4-difluoro-5-(2-methyl-7-((6-methylpyridin-3-yl)amino)-1,6-naphthyridin-3-yl)phenyl)carbamate | 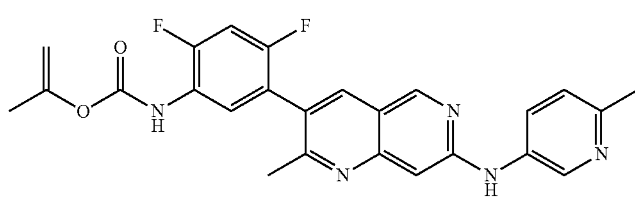 [SMILES: C=C(C)OC(=O)Nc1cc(-c2cc3cnc(Nc4ccc(C)nc4)cc3nc2C)c(F)cc1F] | MS (ESI) m/z: 462.2 (M + H⁺) |
| 88 | prop-1-en-2-yl (5-(7-amino-2-methyl-1,6-naphthyridin-3-yl)-2-fluoro-4-methylphenyl)carbamate | 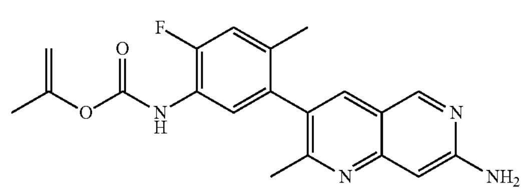 [SMILES: C=C(C)OC(=O)Nc1cc(-c2cc3cnc(N)cc3nc2C)c(C)cc1F] | MS (ESI) m/z: 367.1 (M + H⁺) |

| Prep No. | Chemical Name | Structure | Physical Data |
|---|---|---|---|
| 89 | prop-1-en-2-yl (2-fluoro-5-(7-((2-hydroxyethyl)amino)-2-methyl-1,6-naphthyridin-3-yl)-4-methylphenyl)carbamate | 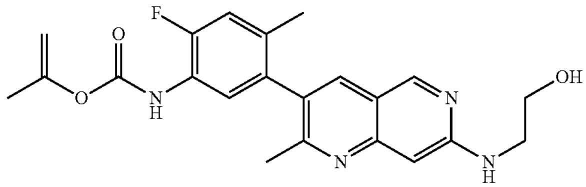 [SMILES: C=C(C)OC(=O)Nc1cc(-c2cc3cnc(NCCO)cc3nc2C)c(C)cc1F] | MS (ESI) m/z: 411.2 (M + H⁺) |
| 90 | prop-1-en-2-yl (2,4-difluoro-5-(7-((2-hydroxyethyl)amino)-2-methyl-1,6-naphthyridin-3-yl)phenyl)carbamate | 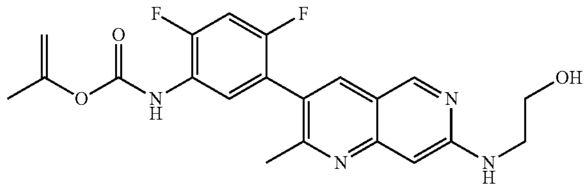 [SMILES: C=C(C)OC(=O)Nc1cc(-c2cc3cnc(NCCO)cc3nc2C)c(F)cc1F] | MS (ESI) m/z: 415.2 (M + H⁺) |

Preparation 91

Synthesis of 3,3-dimethylcyclobutanecarboxamide

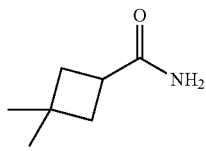

Treat a solution of 3,3-dimethylcyclobutylcarboxylic acid (0.500 g, 3.90 mmol) and oxalyl chloride (0.512 mL, 5.85 mmol) in DCM (30 mL) with catalytic DMF (1 drop), stir at RT for 4 h, concentrate to dryness, add additional DCM and concentrate to dryness again. Dissolve the residue in THF (10 mL), add drop-wise to a solution of NH₄OH (2 mL, 51.4 mmol) in THF (20 mL), and stir at RT overnight. Extract with EtOAc (2×), wash the combined organics with brine, dry over MgSO₄ and concentrate to dryness to afford the title compound (440 mg, 89%) as a white solid. ¹H NMR (400 MHz, DMSO-d₆): δ 7.07 (s, 1H); 6.63 (s, 1H); 2.86 (m, 1H); 1.85 (m, 2H); 1.74 (m, 2H); 1.10 (s, 3H); 1.00 (s, 3H); MS(ESI) m/z: 128.2 (M+H⁺).

Preparation 92

Synthesis of (3,3-dimethylcyclobutyl)methanamine hydrochloride

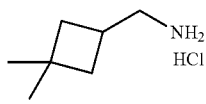

Add a solution 3,3-dimethylcyclobutanecarboxamide (0.438 g, 3.44 mmol) in THF (20 mL) to borane (1.0M in THF, 35 mL, 35.0 mmol) and heat to 65° C. overnight. Cool to RT, quench with the careful addition of MeOH (35 mL) and concentrate to dryness. Dissolve the residue in MeOH (35 mL), treat slowly with 3M HCl (35 mL) and heat at 65° C. overnight. Cool to RT, concentrate under high vacuum to near-dryness and co-evaporate with IPA (4×) to afford a white solid. Triturate the solid with EtOAc, collect via filtration, rinse with a small amount of EtOAc and dry to afford the title compound (317 mg, 61%) as a white solid. ¹H NMR (400 MHz, DMSO-d₆): δ 7.88 (s, 2H); 2.77 (d, J=7.5 Hz, 2H); 2.43 (m, 1H); 1.79 (m, 2H); 1.51 (m, 2H); 1.09 (s, 3H); 1.02 (s, 3H); MS(ESI) m/z: 114.2 (M+H⁺).

Preparation 93

Synthesis of benzyl (2-bromoethyl)carbamate

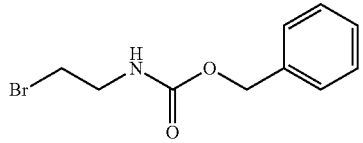 [SMILES: O=C(NCCBr)OCc1ccccc1]

Treat a 0° C. solution of 2-bromoethylamine hydrobromide (50 g, 0.246 mol) in dioxane (500 mL) with aqueous NaOH (1 M, 492 mL, 0.492 mol), add benzyl chloroformate (21.6 g, 0.127 mol) drop-wise, warm to RT and stir overnight. Pour the mixture into H₂O, extract with EtOAc (3×), wash the combined organics with brine, dry over Na₂SO₄, concentrate to dryness and purify via silica gel chromatography (EtOAc/ Petroleum ether) to afford the title compound (60 g, 95%) as a white solid. ¹H NMR (400 MHz, CDCl₃): δ 7.37-7.33 (m, 5H), 5.12 (s, 2H), 3.61 (t, J=5.6 Hz, 2H), 3.47 (t, J=5.6 Hz, 2H).

Preparation 94

Synthesis of benzyl (3-cyano-3-methylbutyl)carbamate

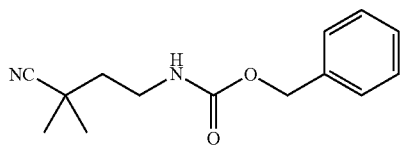 [SMILES: CC(C)(C#N)CCNC(=O)OCc1ccccc1]

Treat a −78° C. solution of diisopropylamine (35 g, 0.346 mol) in THF (300 mL), under N₂, drop-wise with a solution of n-butyllithium (2.5 M, 127 mL, 0.317 mol), warm to −30° C. for 0.5 h, re-cool to −78° C. and treat drop-wise with a solution of isobutyronitrile (19.9 g, 0.288 mol) in THF (100 mL). Stir the mixture at −78° C. for 0.5 h, treat with a solution of benzyl (2-bromoethyl)carbamate (74 g, 0.288 mol) in THF (100 mL), stir at −78° C. for 1 h, then warm to RT and stir overnight. Treat the mixture with H₂O, separate the layers, extract the aqueous layer with EtOAc, wash the combined organics with brine, dry over Na₂SO₄, concentrate to dryness and purify via silica gel chromatography (EtOAc/Petroleum ether) to afford the title compound (15 g, 21% yield). MS (m/z): 247.2 (M+1).

Preparation 95

Synthesis of 4-amino-2,2-dimethylbutanenitrile

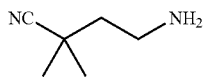

Treat a solution of benzyl (3-cyano-3-methylbutyl)carbamate (2.50 g, 10.15 mmol) in THF (75 mL) with 10% Pd/C (1.080 g) and stir at RT under a hydrogen balloon for 2 h. Filter the mixture through diatomaceous earth, rinse well with THF and concentrate the filtrate to dryness to afford the title compound (assume 100% yield). MS (m/z): 113.2 (M+1).

Preparation 96

Synthesis of 8-methyl-1,4-dioxaspiro[4.5]decane-8-carbonitrile

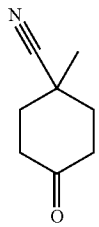

Treat a 0° C. solution of 1,4-dioxa-spiro[4.5]decane-8-carbonitrile (1 g, 5.98 mmol) in THF (12 mL) drop-wise with lithium bis(trimethylsilyl)amide (1M, 6.88 mL, 6.88 mmol), stir at 0° C. for 1 h, add iodomethane (0.374 mL, 5.98 mmol) drop-wise and stir at 0° C. Add satd. NH₄Cl, then brine, extract with EtOAc (2×), dry the combined organics over MgSO₄ and concentrate to dryness to afford crude 8-methyl-1,4-dioxaspiro[4.5]decane-8-carbonitrile (1.33 g, 123%). Add THF (15 mL) and HCl (3M, 15 mL, 45 mmol), heat the mixture at 50° C. for 5 h, cool to RT, make basic with 3M NaOH, extract with DCM (3×), dry the combined organics over Na₂SO₄ and concentrate to dryness to afford the title compound (700 mg, 85%, 2 steps). ¹H NMR (400 MHz, DMSO-d₆): δ 2.48-2.41 (m, 2H), 2.30-2.23 (m, 2H), 2.19-2.12 (m, 2H), 1.84 (td, J=13.3, 4.5 Hz, 2H), 1.41 (s, 3H); MS(ESI) m/z: 138.1 (M+H⁺).

Preparation 97

Synthesis of cis/trans 4-amino-1-methylcyclohexanecarbonitrile

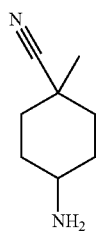

Stir a solution of 1-methyl-4-oxocyclohexanecarbonitrile (0.7 g, 5.10 mmol) and NH₄OAc (3.93 g, 51.0 mmol) in MeOH (10 mL) at RT for 4 h, add sodium cyanoborohydride (0.385 g, 6.12 mmol) and stir at RT overnight. Concentrate the mixture to dryness, dissolve the residue in 2N HCl, stir for 0.5 h and wash with EtOAc. Neutralize the aqueous layer with 2N NaOH, extract with DCM (3×), dry the combined organics over MgSO₄ and concentrate to dryness to afford the title compound as a cis/trans mixture (580 mg, 82%). MS(ESI) m/z: 139.2 (M+H⁻).

Preparation 98

Synthesis of ethyl 3-(dibenzylamino)propanoate

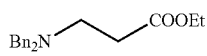

Heat a solution of ethyl 3-aminopropanoate hydrochloride (80.0 g, 0.52 mol), benzylbromide (186.7 g, 1.1 mol) and K₂CO₃ (179.4 g, 1.3 mol) in acetonitrile (1 L) at 40° C. overnight. Concentrate the mixture to dryness, treat with water, extract with EtOAc (3×), wash the combined organics with brine, dry over Na₂SO₄, concentrate to dryness and purify via silica gel chromatography (Pet Ether/EtOAc, 50:1) to afford the title compound (150 g, 97% yield). ¹H NMR (400 MHz, CDCl₃): δ 7.35-7.21 (m, 10H), 4.09 (q, J=7.2 Hz, 2H), 3.58 (s, 4H), 2.82 (t, J=7.2 Hz, 2H), 2.50 (t, J=7.2 Hz, 2H), 1.21 (t, J=7.2 Hz, 3H).

Preparation 99

Synthesis of 4-(dibenzylamino)-2-methylbutan-2-ol

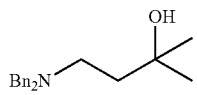

Cool a solution of ethyl 3-(dibenzylamino)propanoate (150 g, 0.51 mol) in THF (1 L) to 0° C. Add methylmagnesium bromide (505 mL, 1.51 mol) drop-wise over 1 h, then heat at 70° C. under N₂ overnight. Re-cool the mixture to 0° C., add saturated NH₄OH drop-wise, extract the mixture with EtOAc (3×), wash the combined organics with brine, dry over Na₂SO₄, concentrate to dryness and purify via silica gel chromatography to afford the title compound (140 g, 98%). MS (m/z): 284.2 (M+1).

Preparation 100

Synthesis of
N,N-dibenzyl-3-methoxy-3-methylbutan-1-amine

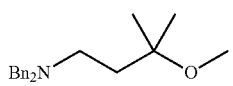

Add potassium hydride (30%, 2.6 g, 19.4 mmol) portion wise under N₂ to a 0° C. solution of 4-(dibenzylamino)-2-methylbutan-2-ol (5 g, 17.6 mmol) in THF (50 mL). Stir the mixture at 0° C. for 0.5 h, treat drop-wise with methyl iodide [MeI] (2.76 g, 19.4 mmol), allow the mixture to warm to RT and stir for 3 h. Re-cool the mixture to 0° C., treat with saturated NH₄Cl, and remove the organics under reduced pressure. Extract the residue with EtOAc (3×), wash the combined organics with brine, dry over Na₂SO₄, concentrate and purify via silica gel chromatography (Pet ether/EtOAc, 50:1) to afford the title compound (3.0 g, 57%). ¹H NMR (400 MHz, DMSO-d₆): δ 7.29 (m, 10H), 3.58 (s, 4H), 3.05 (s, 3H), 2.50 (m, 2H), 1.73 (m, 2H), 1.07 (s, 6H).

Preparation 101

Synthesis of 3-methoxy-3-methylbutan-1-amine hydrochloride

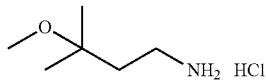

Treat a solution of N,N-dibenzyl-3-methoxy-3-methylbutan-1-amine (3 g, 10.1 mmol) in MeOH (50 mL) with palladium hydroxide on carbon (1 g) and stir the mixture under atmospheric H₂ at RT for 3 h. Remove the solids via filtration, wash with EtOAc, treat the filtrate drop-wise with methanolic HCl and concentrate to dryness to afford the title compound (1.01 g, 66%). ¹H NMR (400 MHz, DMSO-d₆): δ 8.04 (s, 2H), 3.05 (s, 3H), 2.52-2.49 (m, 2H), 1.74-1.70 (m, 2H), 1.07 (s, 6H).

Preparation 102

Synthesis of
N,N-dibenzyl-3-ethoxy-3-methylbutan-1-amine

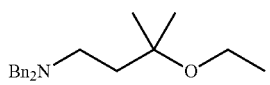

Treat a 0° C. solution of 4-(dibenzylamino)-2-methylbutan-2-ol (13 g, 45.9 mmol) in THF (200 mL), under N₂, portion wise with KH (30%, 6.7 g, 50.9 mmol), stir at 0° C. for 0.5 h, add ethyl iodide (8.5 g, 55 mmol) drop-wise and warm to 60° C. overnight. Cool to 0° C., quench with satd. NH₄Cl and concentrate partially. Extract with EtOAc (3×), wash the combined organics with brine, dry over Na₂SO₄, concentrate and purify via silica gel chromatography to afford the title compound (1.7 g, 12%). ¹H NMR (400 MHz, DMSO-d₆): δ 7.36-7.21 (m, 10H), 3.52 (s, 4H), 3.13 (t, J=7.2 Hz, 2H), 2.40-2.36 (m, 2H), 1.68-1.64 (m, 2H), 0.99 (m, 6H), 0.83 (q, J=7.2 Hz, 3H).

Preparation 103

Synthesis of 3-ethoxy-3-methylbutan-1-amine hydrochloride

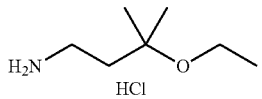

Treat a solution of N,N-dibenzyl-3-ethoxy-3-methylbutan-1-amine (1.7 g, 5.46 mmol) in MeOH (50 mL) with palladium hydroxide on carbon (0.4 g) and hydrogenate (20 psi) at RT overnight. Remove the solids via filtration, wash with MeOH, acidify the filtrate with methanolic HCl until pH=1-2, then concentrate to afford the title compound (862 mg, 94%). ¹H NMR (400 MHz, DMSO-d₆): δ 7.96 (m, 3H), 3.34 (q, J=6.8 Hz, 2H), 2.82-2.73 (m, 2H), 1.76-1.72 (m, 2H), 1.12 (s, 6H), 1.06 (t, J=6.8 Hz, 3H).

Preparation 104

Synthesis of 4-amino-2-methylbutan-2-ol hydrochloride

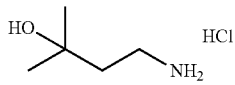

Treat a solution of 4-(dibenzylamino)-2-methylbutan-2-ol (9 g, 31 mmol) in EtOH (90 mL) with palladium hydroxide on carbon (1.5 g) and hydrogenate (30 psi) at RT overnight. Remove the solids via filtration, rinse with EtOAc, add methanolic HCl to the filtrate and concentrated to dryness. Wash the resulting solid with Et₂O to afford the title compound (3.5 g, 79%). ¹H NMR (400 MHz, DMSO-d₆): δ 8.03 (s, 3H), 2.83-2.78 (m, 2H), 1.67-1.63 (m, 2H), 1.09 (s, 6H).

Preparation 105

Synthesis of
N,N-dibenzyl-3-fluoro-3-methylbutan-1-amine

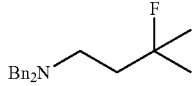

Treat a −78° C. solution of 4-(dibenzylamino)-2-methylbutan-2-ol (110.0 g, 0.39 mol) in DCM (1 L) drop-wise with diethylaminosulfur trifluoride (75 g, 0.47 mol) under N₂, allow it to warm to RT and stir overnight. Re-cool the mixture to −78° C., treat drop-wise with saturated NaHCO₃ (300 mL), warm to RT, extract with EtOAc (3×), wash the combined organics with brine, dry over Na₂SO₄, concentrate to dryness and purify via silica gel chromatography (0.1-0.2% EtOAc/pet ether) to afford the title compound (44.0 g, 40% yield). MS (m/z): 286.2 (M+1).

Preparation 106

Synthesis of 3-fluoro-3-methylbutan-1-amine acetic acid salt

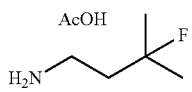

Treat a solution of N,N-dibenzyl-3-fluoro-3-methylbutan-1-amine (18.03 g, 63.2 mmol) in MeOH (150 mL) and acetic acid (7.23 mL, 126 mmol) with 10% Pd/C (3.36 g, 3.16 mmol) and hydrogenate (345 kPa) for 2.5 days. Add additional palladium on carbon (1 g) and hydrogenate the mixture (345 kPa) overnight. Filter the mixture through diatomaceous earth, rinse well with MeOH and concentrate the filtrate to dryness to afford the title compound. MS (m/z): 106.1 (M-AcOH+1).

Preparation 107

Synthesis of 1-(2-(dibenzylamino)ethyl)cyclopropanol

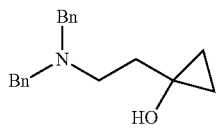

Add titanium isopropoxide (860 mg, 3.03 mmol) to a solution of ethyl 3-(dibenzylamino)propanoate (9.0 g, 30.3 mmol) in ethyl ether, cool to 0° C., add ethyl magnesium bromide (3M in Et₂O, 30.3 mL) drop-wise over 1 h, maintaining the temperature at ~0-4° C., allow to warm to RT and stir overnight. Cool to 0° C., add satd. NH₄Cl, stir at RT for 15 minutes, make basic with satd. NaHCO₃ and extract with EtOAc (2×). Wash the combined organics with brine, dry over MgSO₄, concentrate and purify via silica gel chromatography to give the title compound (7.5 g, 88%) as a pale yellow oil. ¹H NMR (400 MHz, CDCl₃): δ 7.20-7.15 (m, 8H), 7.12-7.07 (m, 2H), 3.45 (s, 4H), 2.61-2.59 (m, 2H), 1.57 (t, J=5.6 Hz, 2H), 0.36-0.33 (m, 2H), 0.30-0.17 (m, 2H).

Preparation 108

Synthesis of N,N-dibenzyl-2-(1-methoxycyclopropyl)ethanamine

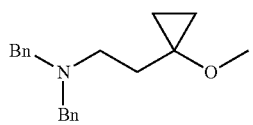

Treat a 0° C. solution of 1-(2-(dibenzylamino)ethyl)cyclopropanol (3 g, 10.6 mmol) in THF (50 mL), under N₂, portion wise with NaH (60%, 0.85 g, 21.3 mmol), stir at 0° C. for 0.5 h, add iodomethane (1.82 g, 12.8 mmol) drop wise, warm to RT and stir for 3 h. Cool the mixture to 0° C., quench with satd. NH₄Cl and partially concentrate. Extract with EtOAc (3×), wash the combined organics with brine, dry over Na₂SO₄, concentrate and purify via silica gel chromatography to afford the title compound (1.2 g, 38%). ¹H NMR (400 MHz, CDCl₃): δ 7.39-7.21 (m, 10H), 3.60 (s, 4H), 3.12 (s, 3H), 2.65 (t, J=8 Hz, 2H), 1.75 (t, J=8 Hz, 2H), 0.68-0.65 (m, 2H), 0.34-0.31 (m, 2H).

Preparation 109

Synthesis of 2-(1-methoxycyclopropyl)ethanamine

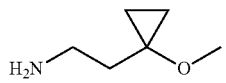

Treat a solution of N,N-dibenzyl-2-(1-methoxycyclopropyl)ethanamine (1.1 g, 3.72 mmol) in MeOH (30 mL) with palladium hydroxide on carbon (0.5 g) and hydrogenate (1 atm) at RT for 3 h. Remove the solids via filtration, wash with MeOH and concentrate the filtrate to afford the title compound (180 mg, 42%). ¹H NMR (400 MHz, DMSO-d₆): δ 3.14 (s, 3H), 2.68 (t, J=7.2 Hz, 2H), 1.63 (t, J=7.2 Hz, 2H), 0.68-0.65 (m, 2H), 0.40-0.37 (m, 2H).

Preparation 110

Synthesis of methyl 4-(dibenzylamino)butanoate

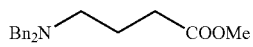

Heat a solution of methyl 4-aminobutanoate hydrochloride (11 g, 71.9 mmol), benzylbromide (25.2 g, 147.3 mmol) and K₂CO₃ (21.8 g, 158.2 mmol) in MeCN (200 mL) at 40° C. overnight. Concentrate the mixture to dryness, pour the residue into water, extract with EtOAc (3×), wash the combined organics with brine, dry over Na₂SO₄, concentrate and purify via silica gel chromatography to give the title compound (19.5 g, 91%). $^1$H NMR (400 MHz, DMSO-d$_6$): δ 7.33-7.18 (m, 10H), 3.57 (s, 3H), 3.52 (s, 4H), 2.43-2.28 (m, 4H), 1.83-1.76 (m, 2H).

Preparation 111

Synthesis of 5-(dibenzylamino)-2-methylpentan-2-ol

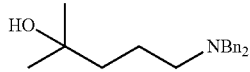

Treat a 0° C. solution of methyl 4-(dibenzylamino)butanoate (19.5 g, 65.6 mmol) in THF (100 mL), under N$_2$, drop-wise with methyl magnesium bromide (65.6 mL, 196.9 mmol) over 1 h, then heat at 70° C. overnight. Cool to 0° C., add satd. NH$_4$Cl drop-wise, extract with EtOAc (3×), wash the combined organics with brine, dry over Na$_2$SO$_4$, concentrate and purify via silica gel chromatography to afford the title compound (15 g, 77%).

Preparation 112

Synthesis of N,N-dibenzyl-4-methoxy-4-methylpentan-1-amine

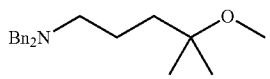

Treat a 0° C. solution of 5-(dibenzylamino)-2-methylpentan-2-ol (3 g, 10.2 mmol) in THF (25 mL), under N$_2$, portion-wise with KH (30%, 1.5 g, 11.3 mmol), stir at 0° C. for 0.5 h, add MeI (1.6 g, 11.3 mmol) drop-wise, warm to RT and stir for 3 h. Cool to 0° C., quench with satd. NH$_4$Cl, partially concentrate under reduced pressure, extract with EtOAc (3×), wash the combined organics with brine, dry over Na$_2$SO$_4$, concentrate and purify via silica gel chromatography to afford the title compound (3.1 g, 97%). $^1$H NMR (400 MHz, DMSO-d$_6$): δ 7.38-7.21 (m, 10H), 3.57 (s, 4H), 3.14 (s, 3H), 2.42 (t, J=7.2 Hz, 2H), 1.58-1.52 (m, 2H), 1.43-1.39 (m, 2H), 1.11 (s, 6H).

Preparation 113

Synthesis of 4-methoxy-4-methylpentan-1-amine hydrochloride

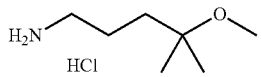

Treat a solution of N,N-dibenzyl-4-methoxy-4-methylpentan-1-amine (3.1 g, 10 mmol) in MeOH (50 mL) with palladium hydroxide on carbon (1 g) and hydrogenate (30 psi) at RT for 3 h. Remove the solids via filtration, wash with MeOH, acidify the filtrate with methanolic HCl and concentrated to dryness. Triturate with ethyl ether, collect the solids via filtration and dry to afford the title compound (816 mg, 51%). $^1$H NMR (400 MHz, DMSO-d$_6$): δ 7.94 (s, 3H), 3.09 (s, 3H), 2.76-2.68 (m, 2H), 1.57-1.49 (m, 2H), 1.43-1.40 (m, 2H), 1.05 (s, 6H).

Preparation 114

Synthesis of N,N-dibenzyl-4-fluoro-4-methylpentan-1-amine

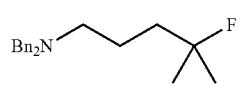

Add diethylaminosulfur trifluoride (17.9 g, 111 mmol) drop-wise to a −78° C. solution of 5-(dibenzylamino)-2-methylpentan-2-ol (11 g, 37 mmol) in DCM (100 mL), under N$_2$, warm to RT and stir overnight. Pour the mixture into ice-water, neutralize with satd. NaHCO$_3$, extract with EtOAc (3×), wash the combined organics with brine, dry over Na$_2$SO$_4$, concentrate and purify via silica gel chromatography to afford the title compound (4.5 g, 41%). $^1$H NMR (400 MHz, DMSO-d$_6$): δ 7.30-7.13 (m, 10H), 3.48 (s, 4H), 2.35 (m, 2H), 1.51-1.48 (m, 4H), 1.22 (d, J=21.2 Hz, 6H).

Preparation 115

Synthesis of 4-fluoro-4-methylpentan-1-amine acetate

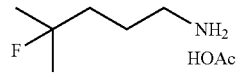

Treat a solution of N,N-dibenzyl-4-fluoro-4-methylpentan-1-amine (400 mg, 1.34 mmol) in MeOH (20 mL) with palladium hydroxide on carbon (200 mg) and hydrogenate (1 atm) at RT overnight. Remove the solids via filtration, wash with EtOAc, add HOAc (80 mg) to the filtrate and concentrate to dryness. Add ether, collect the solid via filtration and dry to afford the title compound (196 mg, 82%). $^1$H NMR (400 MHz, DMSO-d$_6$): δ 3.39-3.36 (m, 2H), 2.36-2.23 (m, 4H), 2.03 (d, J=21.6 Hz, 6H).

Preparation 116

Synthesis of ethyl 4,4-difluoropentanoate

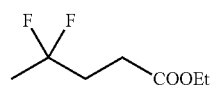

Add diethylaminosulfur trifluoride (29.3 g, 181.7 mmol) drop-wise to a −70° C. solution of ethyl 4-oxopentanoate (21.8 g, 151.4 mmol) in DCM (300 mL), under N$_2$, warm to RT and stir overnight. Pour the mixture slowly into ice-water, separate the layers and extract the aqueous layer with DCM (2×). Wash the combined organics with satd. NaHCO$_3$, then brine, dry over Na$_2$SO$_4$, concentrate and purify via silica gel chromatography (EtOAc/Pet ether) to give the title compound (4.4 g, 17%). $^1$H NMR (400 MHz, CDCl$_3$): δ 4.15 (q, J=7.2 Hz, 2H), 2.52 (t, J=8.0 Hz, 2H), 2.28-2.15 (m, 2H), 1.62 (t, J=18.0 Hz, 3H), 1.27 (t, J=7.2 Hz, 3H).

Preparation 117

Synthesis of 4,4-difluoropentan-1-ol

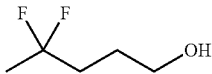

Add lithium aluminum hydride [LAH] (2.3 g, 60 mmol) portion-wise to a 0° C. solution of ethyl 4,4-difluoropentanoate (8.3 g, 50 mmol) in ether (150 mL), under $N_2$, warm to RT and stir overnight. Cool to 0° C., add water (2.3 mL) drop-wise, then 10% NaOH (2.3 mL), remove the solids via filtration and rinse with ether. Wash the filtrate with brine, dry over $Na_2SO_4$ and concentrate to dryness to afford the title compound (5 g, 81%). $^1H$ NMR (400 MHz, $CDCl_3$): δ 3.63 (t, J=6.4 Hz, 2H), 1.95-1.82 (m, 2H), 1.72-1.65 (m, 2H), 1.54 (t, J=18.4 Hz, 3H).

Preparation 118

Synthesis of 4,4-difluoropentyl 4-methylbenzenesulfonate

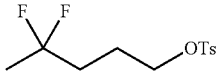 [SMILES: Cc1ccc(S(=O)(=O)OCCCC(C)(F)F)cc1]

Treat a solution of 4,4-difluoropentan-1-ol (5 g, 40.3 mmol) and TsCl (8.4 g, 44.3 mmol) in DCM (80 mL) with TEA (6.1 g, 60 mmol) and DMAP (0.5 g, 4 mmol) and stir at RT overnight. Wash the mixture successively with 2M HCl, satd. $NaHCO_3$, then brine, dry over $Na_2SO_4$, concentrate and purify by silica gel chromatography (EtOAc/Pet ether) to give the title compound (7.1 g, 63%). $^1H$ NMR (400 MHz, $CDCl_3$): δ 7.80 (d, J=8.0 Hz, 2H), 7.36 (d, J=8.0 Hz, 2H), 4.08 (t, J=5.6 Hz, 2H), 2.47 (s, 3H), 1.94-1.84 (m, 4H), 1.57 (t, J=18.4 Hz, 3H).

Preparation 119

Synthesis of N,N-dibenzyl-4,4-difluoropentan-1-amine

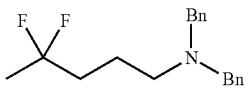 [SMILES: CC(F)(F)CCCN(Cc1ccccc1)Cc1ccccc1]

Treat a solution of 4,4-difluoropentyl 4-methylbenzenesulfonate (7.1 g, 25.5 mmol) in MeCN (100 mL) with $K_2CO_3$ (7.0 g, 51 mmol) and NaI (0.33 g, 2.6 mmol) and heat to reflux overnight. Cool to RT, concentrate under reduced pressure, add water, extract with EtOAc (3×), wash the combined organics with water, then brine, dry, concentrate and purify by silica gel chromatography (EtOAc/Pet ether) to give the title compound (6.6 g, 85%). $^1H$ NMR (400 MHz, $CDCl_3$): δ 7.29-7.14 (m, 10H), 3.48 (s, 4H), 2.37 (t, J=6.8 Hz, 2H), 1.80-1.68 (m, 2H), 1.62-1.55 (m, 2H), 1.48 (t, J=9.2 Hz, 3H).

Preparation 120

Synthesis of 4,4-difluoropentan-1-amine hydrochloride

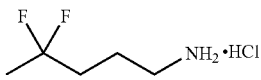

Treat a solution of N,N-dibenzyl-4,4-difluoropentan-1-amine (6.6 g, 21.7 mmol) in MeOH (150 mL) with palladium hydroxide on carbon (50 wt %, 1.6 g) and hydrogenate (30 psi) overnight. Remove the catalyst via filtration, add methanolic HCl drop-wise then concentrate to dryness to afford the title compound (3.18 g). $^1H$ NMR (400 MHz, DMSO-$d_6$): δ 8.05 (s, 3H), 2.76-2.71 (m, 2H), 1.96-1.84 (m, 2H), 1.69-1.62 (m, 2H), 1.54 (t, J=18.8 Hz, 3H); MS (ESI) m/z: 124.0 (M+H$^+$).

Preparation 121

Synthesis of (1-(trifluoromethyl)cyclopropyl)methanol

Treat a 0° C. solution of 1-(trifluoromethyl)cyclopropanecarboxylic acid (9 g, 58.4 mmol) in ether (140 mL), under $N_2$, portion-wise with LAH (2.9 g, 76 mmol), allow to warm to RT and stir overnight. Re-cool to 0° C., slowly add HCl, warm to RT and separate the layers. Extract the aqueous layer with ether (2×), wash the combined organics with brine, dry over $Na_2SO_4$ and concentrate under reduced pressure (water bath temp<30° C.) to afford the title compound (7 g, 86%). $^1$HNMR (400 MHz, DMSO-$d_6$): δ 4.94 (t, J=6.0 Hz, 1H), 3.54 (d, J=6.0 Hz, 2H), 0.87-0.84 (m, 2H), 0.81-0.79 (m, 2H).

Preparation 122

Synthesis of (1-(trifluoromethyl)cyclopropyl)methyl 4-methylbenzenesulfonate

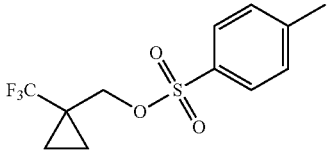 [SMILES: Cc1ccc(S(=O)(=O)OCC2(C(F)(F)F)CC2)cc1]

Treat a solution of (1-(trifluoromethyl)cyclopropyl)methanol (7 g, 50 mmol) and p-toluenesulfonyl chloride (10.4 g, 55 mmol) in DCM (100 mL) with TEA (10 g, 100 mmol) and 4-dimethylaminopyridine (DMAP) (0.6 g, 5 mmol) and stir at RT overnight. Wash successively with 2 M HCl, satd. $NaHCO_3$, and brine, dry over $Na_2SO_4$ and concentrate to give the title compound (12 g, 81%). $^1H$ NMR (400 MHz, DMSO-d₆): δ 7.79 (d, J=8.0 Hz, 2H), 7.50 (d, J=8.0 Hz, 2H), 4.13 (s, 2H), 2.43 (s, 3H), 1.08-1.05 (m, 2H), 0.96-0.94 (m, 2H).

Preparation 123

Synthesis of 2-(1-(trifluoromethyl)cyclopropyl)acetonitrile

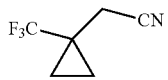

Treat a solution of (1-(trifluoromethyl)cyclopropyl)methyl 4-methylbenzenesulfonate (12 g, 40.8 mmol) in DMF (150 mL) with potassium cyanide (3.5 g, 53 mmol) and heat at 50-70° C. for 3 days. Add water, extract with EtOAc (3×), wash the combined organics with water, then brine, dry and concentrate under reduced pressure to give the title compound (2.4 g, 39%). ¹H NMR (400 MHz, CDCl3): δ 2.81 (s, 2H), 1.24-1.18 (m, 2H), 0.95-0.92 (m, 2H).

Preparation 124

Synthesis of 2-(1-(trifluoromethyl)cyclopropyl)ethanamine hydrochloride

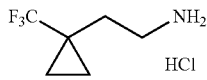

Add borane (10 M in dimethylsulfide, 3 mL, 30 mmol) to a solution of 2-(1-(trifluoromethyl)cyclopropyl)acetonitrile (2.2 g, 14.7 mmol) in THF (60 mL), under N₂, and heat at 70° C. overnight. Cool to 0° C., add methanolic HCl drop-wise, concentrate to dryness, co-evaporate with MeOH, add EtOAc, collect the solids via filtration and dry to afford the title compound (1.1 g, 40%). ¹H NMR (400 MHz, DMSO-d₆): δ 8.05 (s, 3H), 2.87 (t, J=8.4 Hz, 2H), 1.90-1.86 (m, 2H), 0.96-0.93 (m, 2H), 0.82-0.81 (m, 2H).

Preparation 125

Synthesis of (1-methylcyclopropyl)methyl methanesulfonate

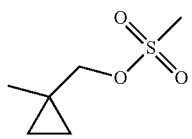

Treat a 0° C. solution of (1-methylcyclopropyl)methanol (1.0 g, 11.61 mmol) in DCM (50 mL) with TEA (1.29 g, 12.77 mmol), add methanesulfonyl chloride (1.46 g, 12.77 mmol) drop-wise and stir at 0° C. for 2 h. Warm the mixture to RT, wash with H₂O, then brine, dry over Na₂SO₄ and concentrate to dryness to afford the title compound (1.85 g, 97%) as an oil.

¹H NMR (400 MHz, DMSO-d₆): δ 4.05 (s, 2H), 3.20 (s, 3H), 1.17 (s, 3H), 0.59 (m, 2H), 0.47 (m, 2H).

Preparation 126

Synthesis of 2-(1-methylcyclopropyl)ethanamine hydrochloride

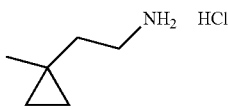

Treat a solution of (1-methylcyclopropyl)methyl methanesulfonate (1.85 g, 11.27 mmol) in DMSO (20 mL) with sodium cyanide (1.104 g, 22.53 mmol) and stir at RT for 4 h. Add H₂O, extract with EtOAc (3×), wash the combined organics with brine, dry over Na₂SO₄ and concentrate carefully to afford a colorless oil. Dissolve the oil in THF (15 mL), add borane dimethylsulfide complex (2.0M in THF, 8.45 mL, 16.90 mmol), heat at 65° C. for 4 h, then cool to RT overnight. Concentrate the mixture to dryness, co-evaporate with EtOAc, triturate with ethyl ether, collect the solid via filtration and dry to afford the title compound (485 mg, 31%). ¹H NMR (400 MHz, DMSO-d₆): δ 7.90 (s, 2H), 2.82 (m, 2H), 1.48 (m, 2H), 0.99 (s, 3H), 0.31-0.22 (m, 4H).

Preparation 127

Synthesis of 4,4,4-trifluoro-3,3-dimethylbutanamide

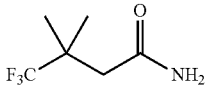

Treat a 0° C. solution of 4,4,4-trifluoro-3,3-dimethylbutanoic acid [See: US2010/0240663] (17 g, 100 mmol) in acetonitrile (200 mL) with 1-(3-dimethylaminopropyl)-3-ethylcarbodiimide hydrochloride (23 g, 120 mmol) and 1-hydroxybenzotriazole (16.2 g, 120 mmol), stir at 0° C. for 2 h, treat with concentrated ammonia in water (25 wt %, 15 mL), allow to warm to RT and stir overnight. Remove the organics under reduced pressure, dissolve the residue in EtOAc, and wash with saturated. NaHCO₃, then brine, dry over MgSO₄, and concentrate to dryness. Treat the material with pet ether, collect the solid via filtration and dry to afford the title compound (13 g, 77% yield). ¹H NMR (400 MHz, DMSO-d6): δ 7.46 (s, 1H), 6.93 (s, 1H), 2.19 (s, 2H), 1.18 (s, 6H).

Preparation 128

Synthesis of 4,4,4-trifluoro-3,3-dimethylbutan-1-amine hydrochloride

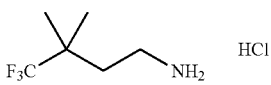

Treat a solution of 4,4,4-trifluoro-3,3-dimethylbutanamide (10 g, 59.1 mmol) in THF (120 mL) with BH₃ (1.0 M in THF, 295 mL, 295 mmol), stir for 15 min at RT, then heat to reflux overnight. Cool the mixture to 0° C., treat drop-wise with MeOH, then methanolic HCl and partially concentrate under reduced pressure. Collect the solids via filtration, rinse with EtOAc and dry to afford the title compound as an off-white solid (5.2 g, 57% yield). ¹H NMR (400 MHz, DMSO-d6): δ 8.10 (s, 3H), 2.83 (m, 2H), 1.81-1.76 (m, 2H), 1.11 (s, 6H).

Preparation 129

Synthesis of benzyl 3-oxocyclobutanecarboxylate

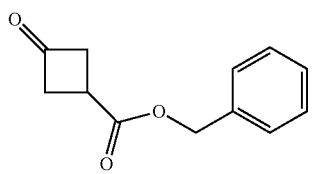 [SMILES: O=C1CC(C(=O)OCc2ccccc2)C1]

Slowly add carbonyldiimidazole (42.6 g, 263 mmol) to a solution of 3-oxo-cyclopropane carboxylic acid (25.0 g, 219 mmol) in DCM (500 mL), stir at RT for 2 h, add benzyl alcohol (24.17 g, 223 mmol) and stir at RT for 16 h. Add water, extract with DCM (2×), wash the combined organics with brine, dry over Na₂SO₄, concentrate to dryness and purify by silica gel chromatography (EtOAc/Hex) to afford the title compound (29.5 g, 66%) as a colorless syrup. ¹H NMR (400 MHz, DMSO-d₆): δ 7.38-7.35 (m, 5H); 5.14 (s, 2H); 3.62 (m, 5H); MS (ESI) m/z: 227.1 (M+Na⁻).

Preparation 130

Synthesis of benzyl 3-hydroxy-3-methylcyclobutanecarboxylate

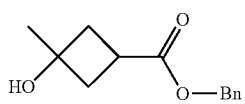

Treat a −78° C. solution of benzyl 3-oxocyclobutanecarboxylate (11.05 g, 54.1 mmol) in THF (155 mL) drop-wise with methyl magnesium bromide (3M in diethyl ether, 27.1 mL, 81 mmol) and stir at −78° C. for 0.5 h. Add satd. NH₄Cl, extract with EtOAc (2×), dry the combined organics, evaporate and purify via silica gel chromatography (acetone/hexanes) to afford the title compound (5.589 g, 47%) as a colorless oil. ¹H NMR (400 MHz, DMSO-d₆): δ 7.36-7.29 (m, 5H); 5.08 (m, 3H); 2.75-2.66 (m, 1H); 2.13-2.12 (m, 4H); 1.21 (s, 3H); MS (ESI) m/z: 243.1 (M+Na⁺).

Preparation 131

Synthesis of benzyl 3-methyl-trans(3-fluorocyclobutanecarboxylate)

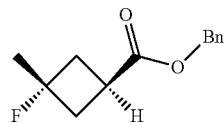 [SMILES: C[C@]1(F)C[C@H](C(=O)OCc2ccccc2)C1]

Treat a −78° C. solution of benzyl 3-hydroxy-3-methylcyclobutanecarboxylate (5.589 g, 25.4 mmol) in DCM (125 mL), under Ar, with diethylaminosulfur trifluoride (5.03 mL, 38.1 mmol), stir at −78° C. for 0.5 h, then allow to warm to RT overnight. Quench the mixture with satd. NaHCO₃, extract with EtOAc (2×), dry the combined organics over MgSO₄, concentrate to dryness and purify via silica gel chromatography (Et₂O/Hex) to afford the title compound (3.82 g, 68%) as a colorless oil. ¹H NMR (400 MHz, DMSO-d₆): δ 7.35 (m, 5H); 5.10 (s, 2H); 3.23 (m, 1H); 2.54 (m, 2H); 2.32 (m, 2H); 1.38 (d, J=22.3 Hz, 3H); MS (ESI) m/z: 245.1 (M+Na⁺).

Preparation 132

Synthesis of 3-methyl-trans(3-fluorocyclobutanecarboxylic acid)

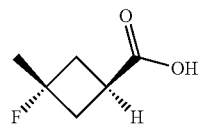

Treat a solution of benzyl 3-methyl-trans(3-fluorocyclobutanecarboxylate) (3.82 g, 17.20 mmol) in MeOH (100 mL) with 10% palladium on carbon (dry) (1.831 g, 1.720 mmol) and hydrogenate at atmospheric pressure (balloon) overnight. Remove the solids via filtration through diatomaceous earth and concentrate the filtrate to dryness to afford the title compound (1.83 g, 81%) as a colorless oil. ¹H NMR (400 MHz, DMSO-d₆): δ 12.29 (s, 1H); 3.10-3.01 (m, 1H); 2.48-2.47 (m, 2H); 2.32-2.21 (m, 2H); 1.39 (d, J=22.3 Hz, 3H).

Preparation 133

Synthesis of benzyl 3-methyl-cis(3-fluoro-cyclobutanecarboxylate)

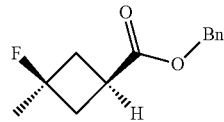

Add diethylaminosulfur trifluoride (1.197 mL, 9.06 mmol) to a −78° C. solution of benzyl 3-hydroxy-3-methylcyclobutanecarboxylate (1.330 g, 6.04 mmol) in DCM (40 mL), under Ar, stir at −78° C. for 0.5 h, then allow to warm to RT overnight. Quench with satd. NaHCO$_3$, extract with EtOAc (2×), dry the combined organics over MgSO$_4$, concentrate to dryness and purify via silica gel chromatography (Et$_2$O/Hex) to afford the title compound (94 mg, 7%) as a colorless oil. $^1$H NMR (400 MHz, DMSO-d$_6$): δ 7.39-7.28 (m, 5H), 5.09 (s, 2H), 2.82 (m, 1H), 2.46-2.28 (m, 4H), 1.43 (d, J=22.2 Hz, 3H); MS (ESI) m/z: 245.1 (M+Na$^+$).

Preparation 134

Synthesis of 3-methyl-cis(3-fluorocyclobutanecarboxylic acid)

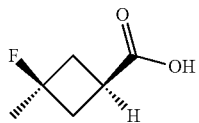

Treat a solution of benzyl 3-methyl-cis(3-fluorocyclobutanecarboxylate) (0.084 g, 0.378 mmol) in MeOH (5 mL) with 10% palladium on carbon (dry) (0.040 g, 0.038 mmol) and hydrogenate at atmospheric pressure (balloon) overnight. Remove the solids via filtration through diatomaceous earth and concentrate the filtrate to dryness to afford the title compound (48 mg, 96%) as a pale yellow solid. $^1$H NMR (400 MHz, DMSO-d$_6$): δ 12.32 (s, 1H), 2.62 (m, 1H), 2.30 (m, 4H), 1.48-1.40 (m, 3H).

Preparation 135

Synthesis of 1-(3,3-dimethylbutyl)-3-(2-fluoro-5-(7-((4-methoxybenzyl)(methyl)amino)-2-methyl-1,6-naphthyridin-3-yl)phenyl)urea

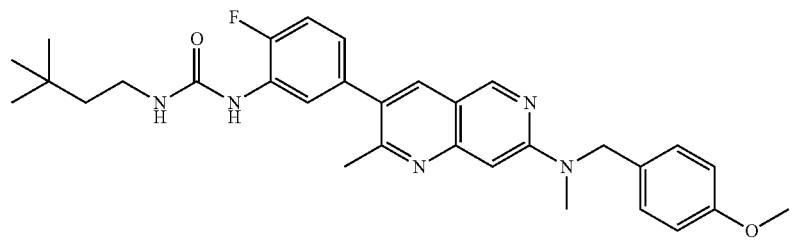 [SMILES: COc1ccc(CN(C)c2cc3nc(C)c(-c4ccc(F)c(NC(=O)NCCC(C)(C)C)c4)cc3cn2)cc1]

Treat a solution of prop-1-en-2-yl(2-fluoro-5-(7-((4-methoxybenzyl)(methyl)amino)-2-methyl-1,6-naphthyridin-3-yl)phenyl)carbamate (0.398 g, 0.818 mmol) and 3,3-dimethylbutylamine (0.166 g, 1.636 mmol) in dioxane (10 mL) with DBU (0.025 ml, 0.164 mmol) and heat at 80° C. overnight. Cool to RT, add EtOAc and wash with 10% LiCl, then brine. Dry the organic layer over MgSO$_4$, concentrate to dryness and purify via silica gel chromatography (EtOAc/Hex) to afford the title compound (370 mg, 85%). $^1$H NMR (400 MHz, DMSO-d$_6$): δ 8.97 (s, 1H), 8.37 (s, 1H), 8.22 (d, J=7.9 Hz, 1H), 7.99 (s, 1H), 7.26 (dd, J=11.4, 8.4 Hz, 1H), 7.15 (d, J=8.4 Hz, 2H), 6.98 (m, 1H), 6.85 (d, J=8.5 Hz, 2H), 6.73 (s, 1H), 6.55 (t, J=5.5 Hz, 1H), 4.86 (s, 2H), 3.69 (s, 3H), 3.08 (m, 5H), 2.48 (s, 3H), 1.33 (m, 2H), 0.88 (s, 9H); MS (ESI) m/z: 530.0 (M+H$^+$).

The following compounds are prepared essentially by the method of Preparation 135.

| Prep No. | Chemical Name | Structure | Physical Data |
|---|---|---|---|
| 136 | 1-(3,3-dimethylbutyl)-3-(2-fluoro-5-(7-((4-methoxybenzyl)(methyl)amino)-2-methyl-1,6-naphthyridin-3-yl)-4-methylphenyl)urea | 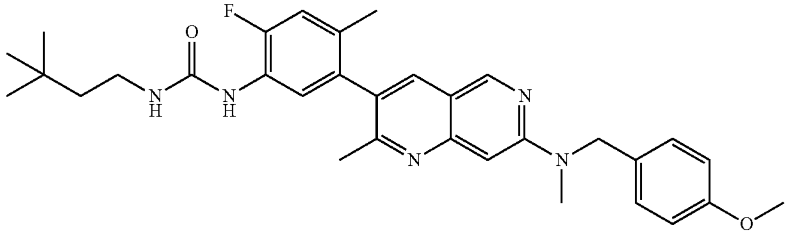 [SMILES: COc1ccc(CN(C)c2cc3nc(C)c(-c4cc(NC(=O)NCCC(C)(C)C)c(F)cc4C)cc3cn2)cc1] | MS (ESI) m/z: 544.3 (M + H$^+$) |

| Prep No. | Chemical Name | Structure | Physical Data |
|---|---|---|---|
| 137 | 1-(3-cyano-3-methylbutyl)-3-(2,4-difluoro-5-(7-((4-methoxybenzyl)(methyl)amino)-2-methyl-1,6-naphthyridin-3-yl)phenyl)urea | 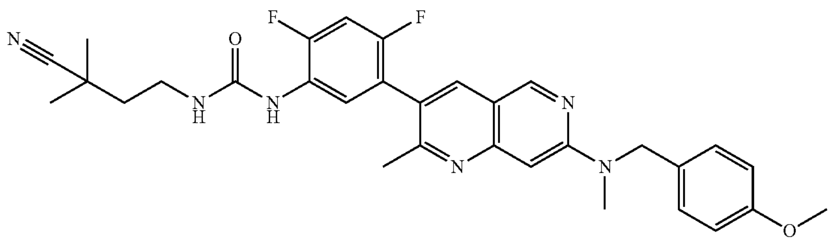 [SMILES: COc1ccc(CN(C)c2cc3nc(C)c(-c4cc(NC(=O)NCCC(C)(C)C#N)c(F)cc4F)cc3cn2)cc1] | MS (ESI) m/z: 559.3 (M + H⁺) |
| 138 | 1-(3,3-dimethylbutyl)-3-(5-(2-ethyl-7-((4-methoxybenzyl)(methyl)amino)-1,6-naphthyridin-3-yl)-2,4-difluorophenyl)urea | 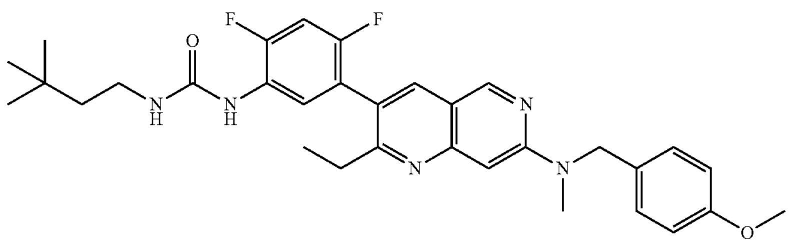 | MS (ESI) m/z: 562.3 (M + H⁺) |
| 139 | 1-(3,3-dimethylbutyl)-3-(5-(2-ethyl-7-((4-methoxybenzyl)(methyl)amino)-1,6-naphthyridin-3-yl)-2-fluoro-4-methylphenyl)urea | 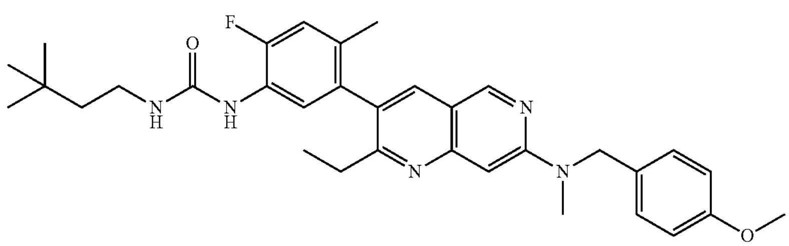 [SMILES: CCc1nc2cc(N(C)Cc3ccc(OC)cc3)ncc2cc1-c1cc(NC(=O)NCCC(C)(C)C)c(F)cc1C] | MS (ESI) m/z: 558.4 (M + H⁺) |
| 140 | 1-cycloheptyl-3-(2-fluoro-5-(7-((4-methoxybenzyl)(methyl)amino)-2-methyl-1,6-naphthyridin-3-yl)-4-methylphenyl)urea | 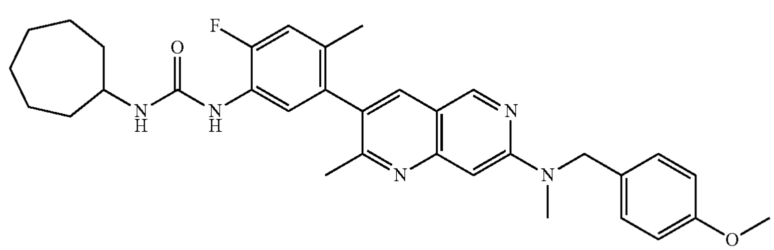 [SMILES: COc1ccc(CN(C)c2cc3nc(C)c(-c4cc(NC(=O)NC5CCCCCC5)c(F)cc4C)cc3cn2)cc1] | MS (ESI) m/z: 556.3 (M + H⁺) |
| 141 | 1-(3,3-dimethylbutyl)-3-(3-(7-((4-methoxybenzyl)(methyl)amino)-2-methyl-1,6-naphthyridin-3-yl)-4-methylphenyl)urea | 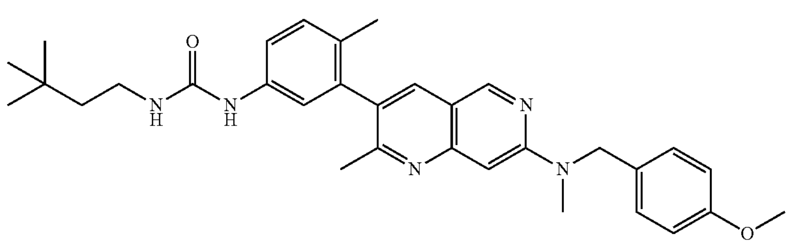 [SMILES: COc1ccc(CN(C)c2cc3nc(C)c(-c4cc(NC(=O)NCCC(C)(C)C)ccc4C)cc3cn2)cc1] | MS (ESI) m/z: 526.3 (M + H⁺) |
| 142 | 1-(3,3-dimethylbutyl)-3-(5-(2-ethyl-7-((4-methoxybenzyl)(methyl)amino)-1,6-naphthyridin-3-yl)-2-fluorophenyl)urea | 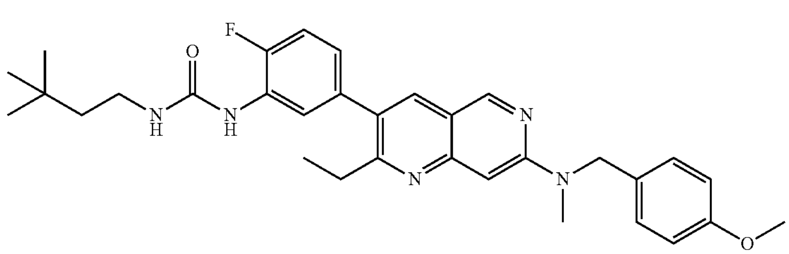 [SMILES: CCc1nc2cc(N(C)Cc3ccc(OC)cc3)ncc2cc1-c1ccc(F)c(NC(=O)NCCC(C)(C)C)c1] | MS (ESI) m/z: 544.3 (M + H⁺) |

| Prep No. | Chemical Name | Structure | Physical Data |
|---|---|---|---|
| 143 | 1-cycloheptyl-3-(2,4-difluoro-5-(7-((4-methoxybenzyl)(methyl)amino)-2-methyl-1,6-naphthyridin-3-yl)phenyl)urea | 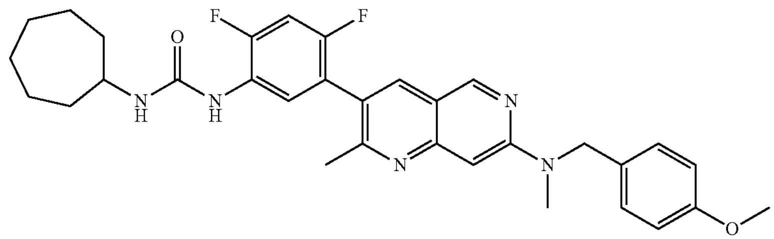 [SMILES: COc1ccc(CN(C)c2cc3nc(C)c(-c4cc(NC(=O)NC5CCCCCC5)c(F)cc4F)cc3cn2)cc1] | MS (ESI) m/z: 560.3 (M + H$^+$) |
| 144 | 1-(3-cyano-3-methylbutyl)-3-(2-fluoro-5-(7-((4-methoxybenzyl)(methyl)amino)-2-methyl-1,6-naphthyridin-3-yl)-4-methylphenyl)urea | 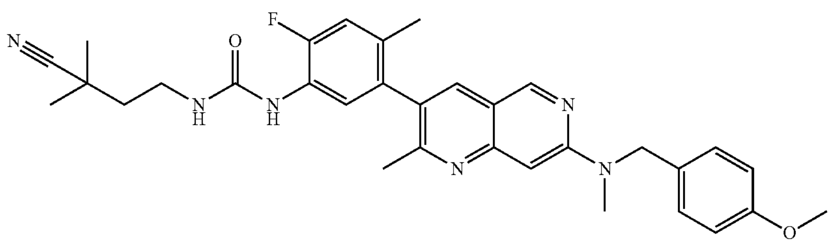 [SMILES: COc1ccc(CN(C)c2cc3nc(C)c(-c4cc(NC(=O)NCCC(C)(C)C#N)c(F)cc4C)cc3cn2)cc1] | MS (ESI) m/z: 555.3 (M + H$^+$) |
| 145 | 1-(3-cyano-3-methylbutyl)-3-(2-fluoro-5-(7-((4-methoxybenzyl)(methyl)amino)-2-methyl-1,6-naphthyridin-3-yl)phenyl)urea | 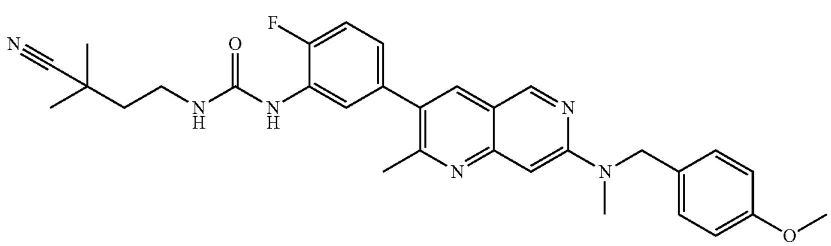 [SMILES: COc1ccc(CN(C)c2cc3nc(C)c(-c4ccc(F)c(NC(=O)NCCC(C)(C)C#N)c4)cc3cn2)cc1] | MS (ESI) m/z: 541.3 (M + H$^+$) |
| 146 | 1-(2-fluoro-5-(7-((4-methoxybenzyl)(methyl)amino)-2-methyl-1,6-naphthyridin-3-yl)-4-methylphenyl)-3-(2-(trifluoromethoxy)ethyl)urea | 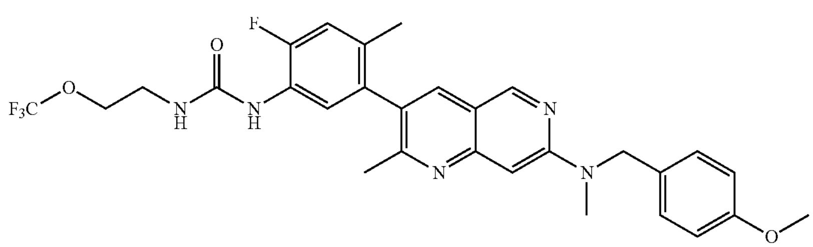 [SMILES: COc1ccc(CN(C)c2cc3nc(C)c(-c4cc(NC(=O)NCCOC(F)(F)F)c(F)cc4C)cc3cn2)cc1] | MS (ESI) m/z: 572.2 (M + H$^+$) |
| 147 | 1-(4,4-difluorocyclohexyl)-3-(2-fluoro-5-(7-((4-methoxybenzyl)(methyl)amino)-2-methyl-1,6-naphthyridin-3-yl)-4-methylphenyl)urea | 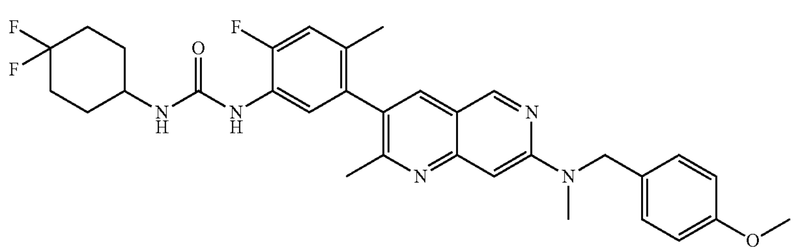 [SMILES: COc1ccc(CN(C)c2cc3nc(C)c(-c4cc(NC(=O)NC5CCC(F)(F)CC5)c(F)cc4C)cc3cn2)cc1] | MS (ESI) m/z: 578.3 (M + H$^+$) |
| 148 | 1-(2,4-difluoro-5-(7-((4-methoxybenzyl)(methyl)amino)-2-methyl-1,6-naphthyridin-3-yl)phenyl)-3-((3,3-dimethylcyclobutyl)methyl)urea | 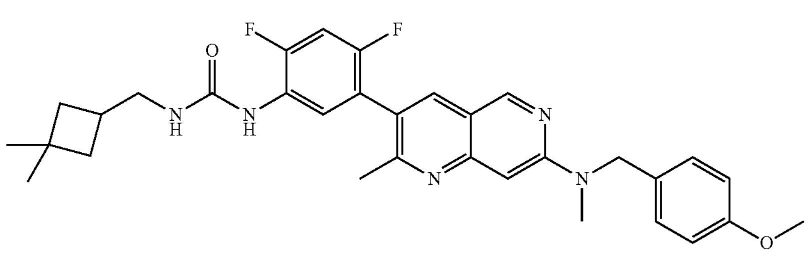 | MS (ESI) m/z: 560.3 (M + H$^+$) |

Preparation 149

Synthesis of 1-(3,3-dimethylcyclobutyl)-3-(2-fluoro-5-(7-((4-methoxybenzyl)(methyl)amino)-2-methyl-1,6-naphthyridin-3-yl)-4-methylphenyl)urea

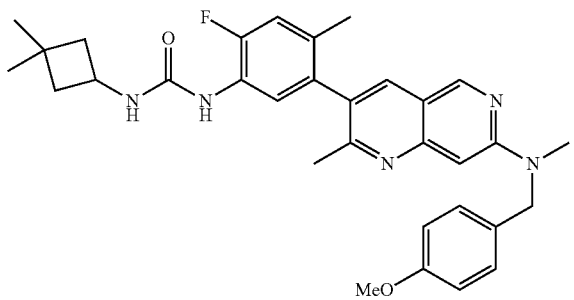

Heat a mixture of 3,3-dimethylcyclobutane carboxylic acid (0.138 g, 1.080 mmol), DPPA (0.233 ml, 1.080 mmol) and TEA (0.100 ml, 0.720 mmol) in dioxane (3 mL) at 100° C. for 15 minutes, add 3-(5-amino-4-fluoro-2-methylphenyl)-N-(4-methoxybenzyl)-N,2-dimethyl-1,6-naphthyridin-7-amine (0.15 g, 0.360 mmol) and heat at 100° C. for an additional 2 h. Cool to RT, add satd. NaHCO$_3$, extract with EtOAc (2×), wash the combined organics with H$_2$O, then brine, dry over Na$_2$SO$_4$, concentrate to dryness and purify via silica gel chromatography (EtOAc/Hex) to afford the title compound (135 mg, 69%) as an orange pasty solid. MS(ESI) m/z: 542.3 (M+H$^+$).

The following compounds are prepared essentially by the method of Preparation 149.

EXAMPLE 1

Synthesis of 1-(3,3-dimethylbutyl)-3-(2-fluoro-5-(2-methyl-7-(methylamino)-1,6-naphthyridin-3-yl)phenyl)urea hydrochloride

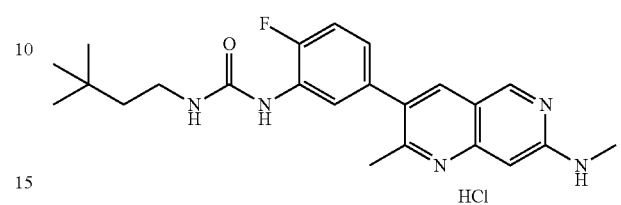

Stir a solution of 1-(3,3-dimethylbutyl)-3-(2-fluoro-5-(7-(4-methoxybenzyl)(methyl)amino)-2-methyl-1,6-naphthyridin-3-yl)phenyl)urea (0.37 g, 0.699 mmol) in TFA (5 mL, 64.9 mmol) at RT for 3 h. Concentrate the mixture to dryness, add satd. NaHCO$_3$ and extract with DCM (3×). Concentrate the combined organics to dryness, triturate with MeCN, collect the solid via filtration and dry to afford the free-base (214 mg, 75%). MS (ESI) m/z: 410.2 (M+H$^+$). Treat a suspension of the free base (0.119 g, 0.291 mmol) in MeCN (3 mL) with 0.1N HCl (3.49 mL, 0.349 mmol), sonicate until all solids dissolve, then freeze and lyophilize. Triturate with Et$_2$O, collect the solid via filtration and dry to afford the title compound (95 mg, 72%) as a pale orange solid. $^1$H NMR (400 MHz, DMSO-d$_6$): δ 9.15 (s, 1H), 8.63 (m, 1H), 8.50 (s, 1H), 8.29 (m, 1H), 7.99 (m, 1H), 7.34-7.31 (m, 1H), 7.05 (m, 1H), 6.66 (m, 2H), 3.08 (m, 2H), 2.91 (s, 3H), 2.67 (s, 3H), 1.33 (t, J=7.9 Hz, 2H), 0.88 (s, 9H); MS (ESI) m/z: 410.2 (M+H$^+$).

| Prep No. | Chemical Name | Structure | Physical Data |
|---|---|---|---|
| 150 | 1-(3,3-dimethylcyclobutyl)-3-(2-fluoro-5-(7-((4-methoxybenzyl)(methyl)amino)-2-methyl-1,6-naphthyridin-3-yl)phenyl)urea | 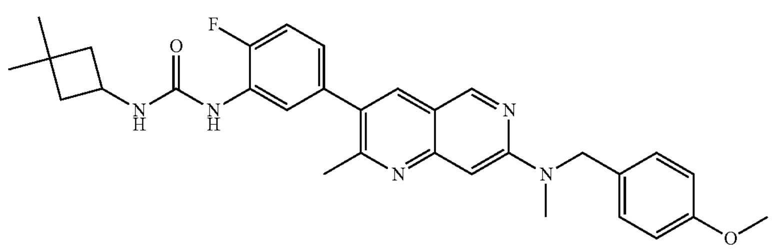 | MS (ESI) m/z: 528.3 (M + H$^+$) |
| 151 | 1-(2,4-difluoro-5-(7-((4-methoxybenzyl)(methyl)amino)-2-methyl-1,6-naphthyridin-3-yl)phenyl)-3-(3-fluoro-cis(3-methylcyclobutyl))urea | 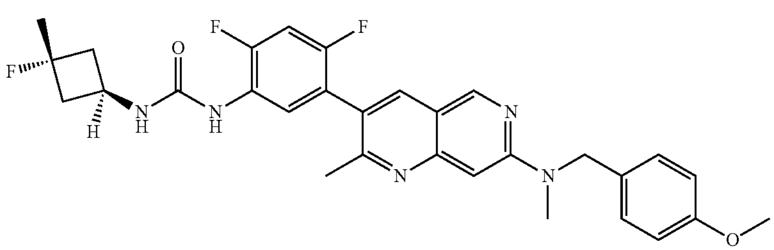 [SMILES: COc1ccc(CN(C)c2cc3nc(C)c(-c4cc(NC(=O)N[C@H]5C[C@](C)(F)C5)c(F)cc4F)cc3cn2)cc1] | MS (ESI) m/z: 550.2 (M + H$^+$) |

The following compounds are prepared essentially by the method of Example 1.

| Ex No. | Chemical Name | Structure | Physical Data |
|---|---|---|---|
| 2 | 1-(3-cyano-3-methylbutyl)-3-(2,4-difluoro-5-(2-methyl-7-(methylamino)-1,6-naphthyridin-3-yl)phenyl)urea hydrochloride | 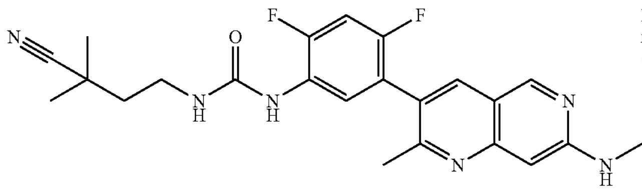 [SMILES: CNc1cc2nc(C)c(-c3cc(NC(=O)NCCC(C)(C)C#N)c(F)cc3F)cc2cn1] | MS (ESI) m/z: 439.2 (M + H⁺) |
| 3 | 1-(3,3-dimethylbutyl)-3-(5-(2-ethyl-7-(methylamino)-1,6-naphthyridin-3-yl)-2,4-difluorophenyl)urea hydrochloride | 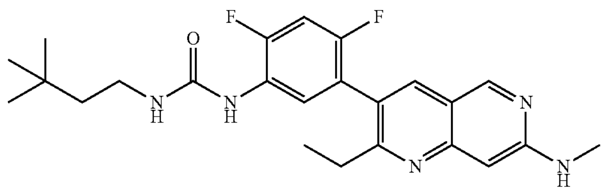 [SMILES: CCc1nc2cc(NC)ncc2cc1-c1cc(NC(=O)NCCC(C)(C)C)c(F)cc1F] | MS (ESI) m/z: 442.2 (M + H⁺) |
| 4 | 1-(3,3-dimethylbutyl)-3-(5-(2-ethyl-7-(methylamino)-1,6-naphthyridin-3-yl)-2-fluoro-4-methylphenyl)urea hydrochloride | 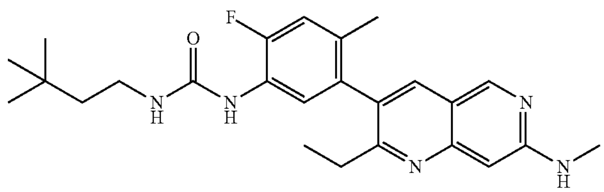 [SMILES: CCc1nc2cc(NC)ncc2cc1-c1cc(NC(=O)NCCC(C)(C)C)c(F)cc1C] | MS (ESI) m/z: 438.3 (M + H⁺) |
| 5 | 1-cycloheptyl-3-(2-fluoro-4-methyl-5-(2-methyl-7-(methylamino)-1,6-naphthyridin-3-yl)phenyl)urea hydrochloride | 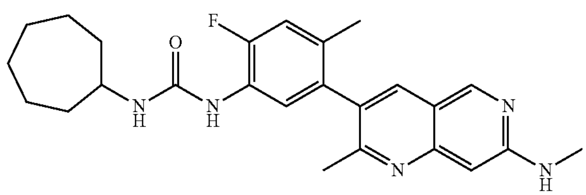 [SMILES: CNc1cc2nc(C)c(-c3cc(NC(=O)NC4CCCCCC4)c(F)cc3C)cc2cn1] | MS (ESI) m/z: 436.2 (M + H⁺) |
| 6 | 1-(3,3-dimethylbutyl)-3-(4-methyl-3-(2-methyl-7-(methylamino)-1,6-naphthyridin-3-yl)phenyl)urea hydrochloride | 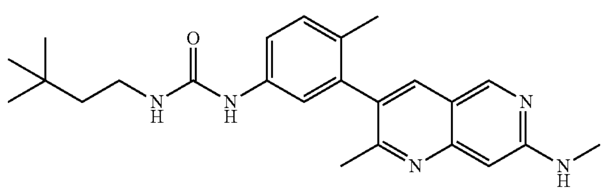 [SMILES: CNc1cc2nc(C)c(-c3cc(NC(=O)NCCC(C)(C)C)ccc3C)cc2cn1] | MS (ESI) m/z: 406.3 (M + H⁺) |
| 7 | 1-(3,3-dimethylbutyl)-3-(5-(2-ethyl-7-(methylamino)-1,6-naphthyridin-3-yl)-2-fluorophenyl)urea hydrochloride | 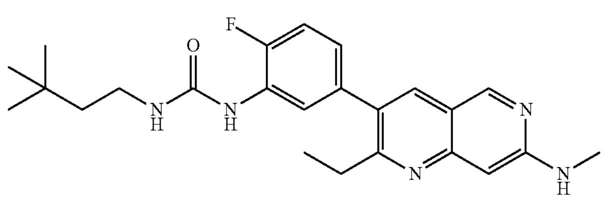 [SMILES: CCc1nc2cc(NC)ncc2cc1-c1ccc(F)c(NC(=O)NCCC(C)(C)C)c1] | MS (ESI) m/z: 424.2 (M + H⁺) |
| 8 | 1-cycloheptyl-3-(2,4-difluoro-5-(2-methyl-7-(methylamino)-1,6-naphthyridin-3-yl)phenyl)urea hydrochloride | 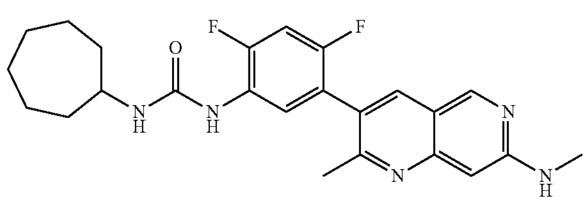 [SMILES: CNc1cc2nc(C)c(-c3cc(NC(=O)NC4CCCCCC4)c(F)cc3F)cc2cn1] | MS (ESI) m/z: 440.2 (M + H⁺) |

| Ex No. | Chemical Name | Structure | Physical Data |
|---|---|---|---|
| 9 | 1-(3-cyano-3-methylbutyl)-3-(2-fluoro-4-methyl-5-(2-methyl-7-(methylamino)-1,6-naphthyridin-3-yl)phenyl)urea | 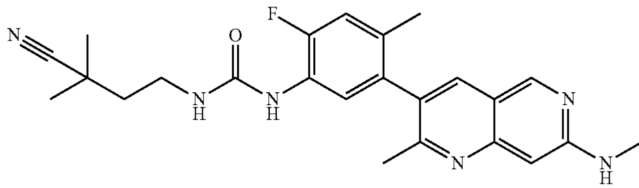 [SMILES: CNc1cc2nc(C)c(-c3cc(NC(=O)NCCC(C)(C)C#N)c(F)cc3C)cc2cn1] | MS (ESI) m/z: 435.3 (M + H⁺) |
| 10 | 1-(3-cyano-3-methylbutyl)-3-(2-fluoro-5-(2-methyl-7-(methylamino)-1,6-naphthyridin-3-yl)phenyl)urea | 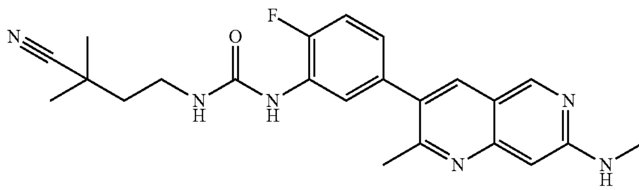 [SMILES: CNc1cc2nc(C)c(-c3ccc(F)c(NC(=O)NCCC(C)(C)C#N)c3)cc2cn1] | MS (ESI) m/z: 421.2 (M + H⁺) |
| 11 | 1-(2-fluoro-4-methyl-5-(2-methyl-7-(methylamino)-1,6-naphthyridin-3-yl)phenyl)-3-(2-(trifluoromethoxy)ethyl)urea hydrochloride | 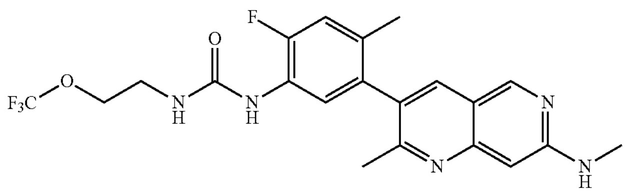 [SMILES: CNc1cc2nc(C)c(-c3cc(NC(=O)NCCOC(F)(F)F)c(F)cc3C)cc2cn1] | MS (ESI) m/z: 452.2 (M + H⁺) |
| 12 | 1-(4,4-difluorocyclohexyl)-3-(2-fluoro-4-methyl-5-(2-methyl-7-(methylamino)-1,6-naphthyridin-3-yl)phenyl)urea hydrochloride | 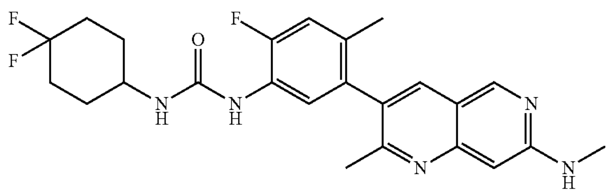 [SMILES: CNc1cc2nc(C)c(-c3cc(NC(=O)NC4CCC(F)(F)CC4)c(F)cc3C)cc2cn1] | MS (ESI) m/z: 458.2 (M + H⁺) |
| 13 | 1-(2,4-difluoro-5-(2-methyl-7-(methylamino)-1,6-naphthyridin-3-yl)phenyl)-3-((3,3-dimethylcyclobutyl)methyl)urea hydrochloride | 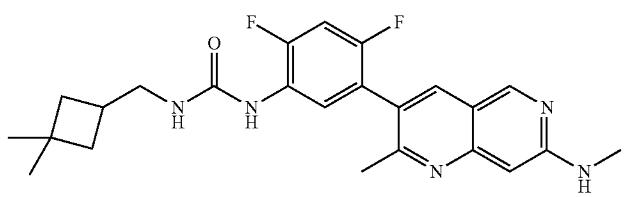 | MS (ESI) m/z: 440.2 (M + H⁺) |
| 14 | 1-(3,3-dimethylcyclobutyl)-3-(2-fluoro-4-methyl-5-(2-methyl-7-(methylamino)-1,6-naphthyridin-3-yl)phenyl)urea | 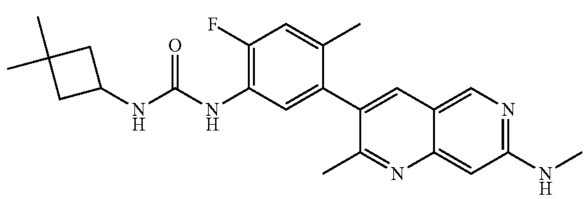 | MS (ESI) m/z: 422.2 (M + H⁺) |
| 15 | 1-(3,3-dimethylcyclobutyl)-3-(2-fluoro-5-(2-methyl-7-(methylamino)-1,6-naphthyridin-3-yl)phenyl)urea hydrochloride | 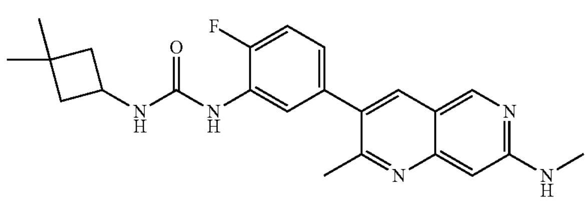 | MS (ESI) m/z: 408.2 (M + H⁺) |
| 16 | 1-(2,4-difluoro-5-(2-methyl-7-(methylamino)-1,6-naphthyridin-3-yl)phenyl)-3-(3-methyl-trans(3-fluorocyclobutyl))urea | 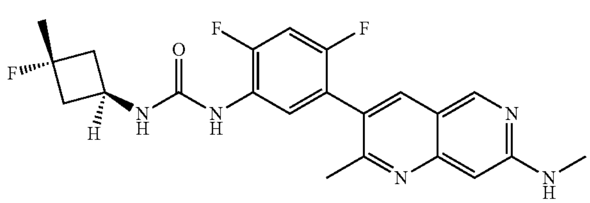 [SMILES: CNc1cc2nc(C)c(-c3cc(NC(=O)N[C@H]4C[C@](C)(F)C4)c(F)cc3F)cc2cn1] | MS (ESI) m/z: 430.2 (M + H⁺) |

| Ex No. | Chemical Name | Structure | Physical Data |
|---|---|---|---|
| 17 | 1-(3,3-dimethylbutyl)-3-(2-fluoro-4-methyl-5-(2-methyl-7-(methylamino)-1,6-naphthyridin-3-yl)phenyl)urea | 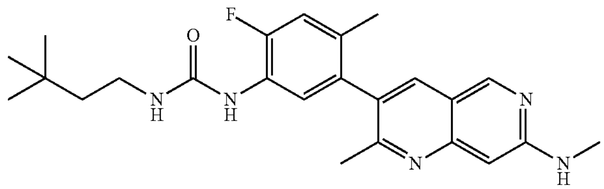 [SMILES: CNc1cc2nc(C)c(-c3cc(NC(=O)NCCC(C)(C)C)c(F)cc3C)cc2cn1] | MS (ESI) m/z: 424.2 (M + H$^+$) |

EXAMPLE 18

Synthesis of 1-(2,4-difluoro-5-(2-methyl-7-(methylamino)-1,6-naphthyridin-3-yl)phenyl)-3-(3,3-dimethylbutyl)urea

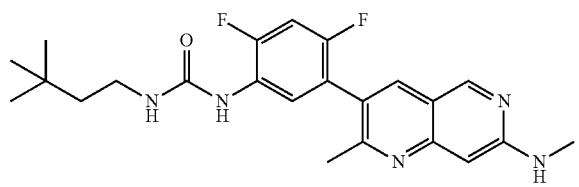 [SMILES: CNc1cc2nc(C)c(-c3cc(NC(=O)NCCC(C)(C)C)c(F)cc3F)cc2cn1]

Heat a solution of prop-1-en-2-yl 2,4-difluoro-5-(2-methyl-7-(methylamino)-1,6-naphthyridin-3-yl)phenylcarbamate (1.449 g, 3.77 mmol), 3,3-dimethylbutylamine (0.572 g, 5.65 mmol), and 1-methylpyrrolidine (0.080 g, 0.942 mmol) in dioxane (30 mL) at 80° C. overnight. Cool to RT, collect the precipitate via filtration and dry. Concentrate the filtrate, treat with DCM, sonicate for 0.5 h, collect the solid via filtration and combine with the solid above to afford the title compound (1.43 g, 89%). $^1$H NMR (400 MHz, DMSO-d$_6$): δ 8.86 (s, 1H), 8.35 (s, 1H), 8.13 (t, 1H), 8.00 (s, 1H), 7.40 (t, 1H), 8.85-8.82 (m, 1H), 6.52-6.49 (m, 2H), 3.07-3.04 (m, 2H), 2.82 (d, 3H), 2.38 (s, 3H), 1.34-1.30 (m, 2H), 0.87 (s, 9H); MS (ESI) m/z: 428.2 (M+H$^+$).

The following compounds are prepared essentially by the method of Example 18.

| Ex No. | Chemical Name | Structure | Physical Data |
|---|---|---|---|
| 19 | 1-(3,3-dimethylbutyl)-3-(4-fluoro-3-(2-methyl-7-(methylamino)-1,6-naphthyridin-3-yl)phenyl)urea hydrochloride | 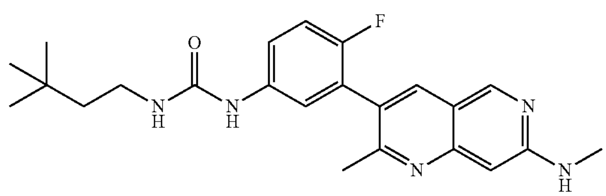 [SMILES: CNc1cc2nc(C)c(-c3cc(NC(=O)NCCC(C)(C)C)ccc3F)cc2cn1] | MS (ESI) m/z: 410.2 (M + H$^+$) |
| 20 | 1-(2,2-dimethyltetrahydro-2H-pyran-4-yl)-3-(2-fluoro-4-methyl-5-(2-methyl-7-(methylamino)-1,6-naphthyridin-3-yl)phenyl)urea hydrochloride | 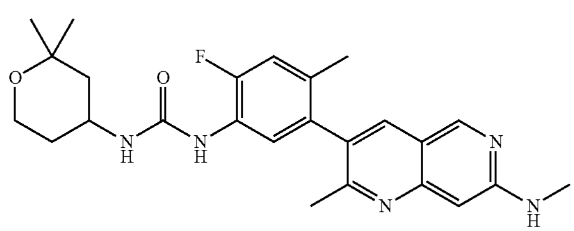 [SMILES: CNc1cc2nc(C)c(-c3cc(NC(=O)NC4CCOC(C)(C)C4)c(F)cc3C)cc2cn1] | MS (ESI) m/z: 452.3 (M + H$^+$) |
| 21 | 1-((3,3-dimethylcyclobutyl)methyl)-3-(2-fluoro-4-methyl-5-(2-methyl-7-(methylamino)-1,6-naphthyridin-3-yl)phenyl)urea hydrochloride | 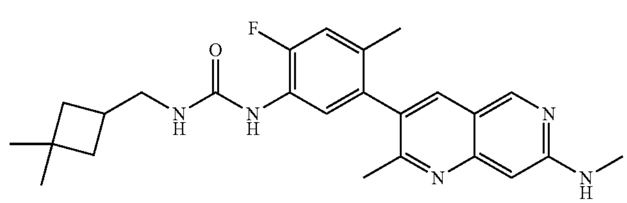 | MS (ESI) m/z: 436.2 (M + H$^+$) |

-continued

| Ex No. | Chemical Name | Structure | Physical Data |
|---|---|---|---|
| 22 | 1-(4,4-difluorocyclohexyl)-3-(2-fluoro-4-methyl-5-(7-(methylamino)-1,6-naphthyridin-3-yl)phenyl)urea hydrochloride | 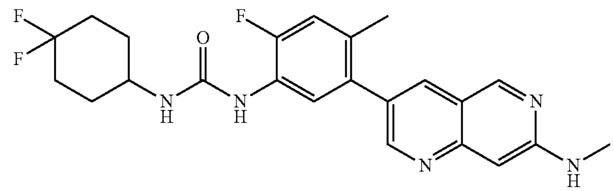 [SMILES: CNc1cc2ncc(-c3cc(NC(=O)NC4CCC(F)(F)CC4)c(F)cc3C)cc2cn1] | MS (ESI) m/z: 444.2 (M + H⁺) |
| 23 | 1-(2-fluoro-4-methyl-5-(2-methyl-7-(methylamino)-1,6-naphthyridin-3-yl)phenyl)-3-(2-(1-(trifluoromethyl)cyclopropyl)ethyl)urea hydrochloride | 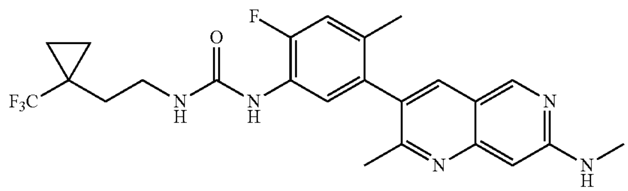 [SMILES: CNc1cc2nc(C)c(-c3cc(NC(=O)NCCC4(C(F)(F)F)CC4)c(F)cc3C)cc2cn1] | MS (ESI) m/z: 476.2 (M + H⁺) |
| 24 | 1-(2,4-difluoro-5-(2-methyl-7-(methylamino)-1,6-naphthyridin-3-yl)phenyl)-3-(3-methoxy-3-methylbutyl)urea hydrochloride | 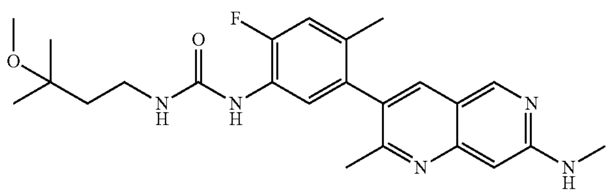 | MS (ESI) m/z: 444.2 (M + H⁺) |
| 25 | 1-(trans-4-cyano-4-methylcyclohexyl)-3-(2-fluoro-4-methyl-5-(2-methyl-7-(methylamino)-1,6-naphthyridin-3-yl)phenyl)urea | 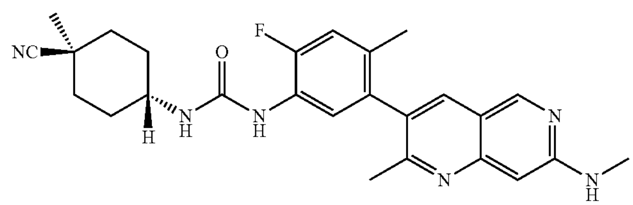 [SMILES: CNc1cc2nc(C)c(-c3cc(NC(=O)N[C@H]4CC[C@](C)(C#N)CC4)c(F)cc3C)cc2cn1] | MS (ESI) m/z: 461.2 (M + H⁺) |
| 26 | 1-(cis-4-cyano-4-methylcyclohexyl)-3-(2-fluoro-4-methyl-5-(2-methyl-7-(methylamino)-1,6-naphthyridin-3-yl)phenyl)urea | 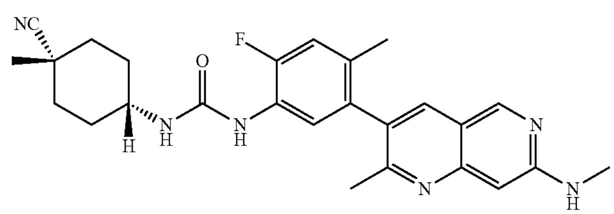 | MS (ESI) m/z: 461.2 (M + H⁺) |
| 27 | 1-(2-fluoro-4-methyl-5-(2-methyl-7-(methylamino)-1,6-naphthyridin-3-yl)phenyl)-3-(2-(1-methylcyclopropyl)ethyl)urea hydrochloride | 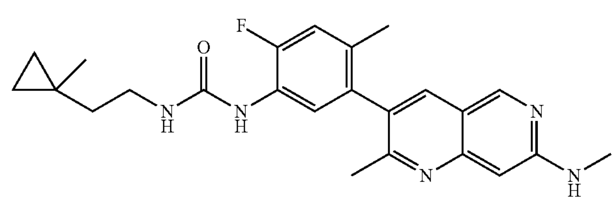 [SMILES: CNc1cc2nc(C)c(-c3cc(NC(=O)NCCC4(C)CC4)c(F)cc3C)cc2cn1] | MS (ESI) m/z: 422.2 (M + H⁺) |
| 28 | 1-(2,4-difluoro-5-(2-methyl-7-(methylamino)-1,6-naphthyridin-3-yl)phenyl)-3-(2-(1-methoxycyclopropyl)ethyl)urea | 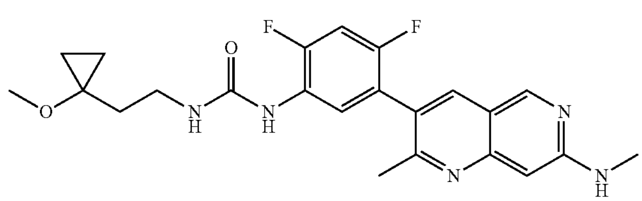 | MS (ESI) m/z: 442.1 (M + H⁺) |

-continued

| Ex No. | Chemical Name | Structure | Physical Data |
|---|---|---|---|
| 29 | 1-(cyclohexylmethyl)-3-(2-fluoro-4-methyl-5-(2-methyl-7-(methylamino)-1,6-naphthyridin-3-yl)phenyl)urea hydrochloride | 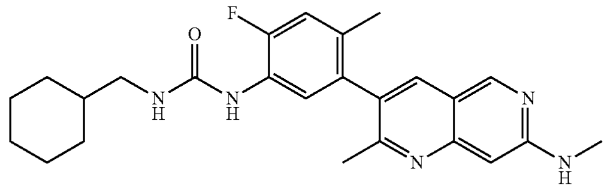 [SMILES: CNc1cc2nc(C)c(-c3cc(NC(=O)NCC4CCCCC4)c(F)cc3C)cc2cn1] | MS (ESI) m/z: 436.2 (M + H+) |
| 30 | 1-(3-ethoxy-3-methylbutyl)-3-(2-fluoro-4-methyl-5-(2-methyl-7-(methylamino)-1,6-naphthyridin-3-yl)phenyl)urea hydrochloride | 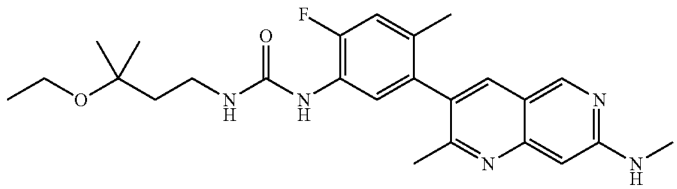 [SMILES: CCOC(C)(C)CCNC(=O)Nc1cc(-c2cc3cnc(NC)cc3nc2C)c(C)cc1F] | MS (ESI) m/z: 454.2 (M + H+) |
| 31 | 1-(2-fluoro-4-methyl-5-(2-methyl-7-(methylamino)-1,6-naphthyridin-3-yl)phenyl)-3-(2-(1-methoxycyclopropyl)ethyl)urea hydrochloride | 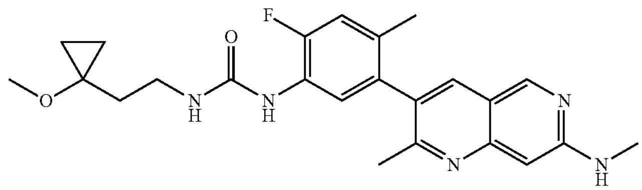 | MS (ESI) m/z: 438.2 (M + H+) |
| 32 | 1-(2-fluoro-4-methyl-5-(7-(methylamino)-1,6-naphthyridin-3-yl)phenyl)-3-(3-methoxy-3-methylbutyl)urea | 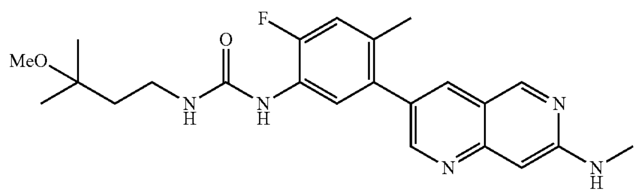 [SMILES: CNc1cc2ncc(-c3cc(NC(=O)NCCC(C)(C)OC)c(F)cc3C)cc2cn1] | MS (ESI) m/z: 426.2 (M + H+) |
| 33 | 1-(2-fluoro-4-methyl-5-(2-methyl-7-(methylamino)-1,6-naphthyridin-3-yl)phenyl)-3-(4-methoxy-4-methylpentyl)urea hydrochloride | 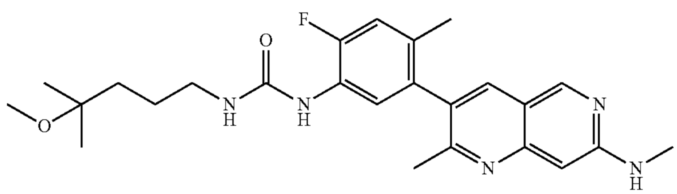 | MS (ESI) m/z: 454.2 (M + H+) |
| 34 | 1-(2,4-difluoro-5-(2-methyl-7-((6-methylpyridin-3-yl)amino)-1,6-naphthyridin-3-yl)phenyl)-3-(3,3-dimethylbutyl)urea dihydrochloride | 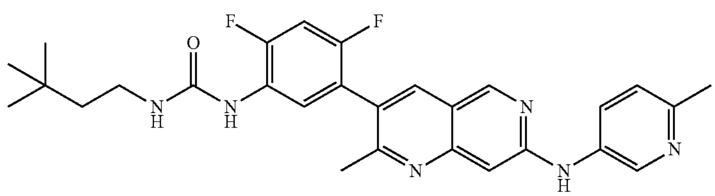 [SMILES: Cc1ccc(Nc2cc3nc(C)c(-c4cc(NC(=O)NCCC(C)(C)C)c(F)cc4F)cc3cn2)cn1] | MS (ESI) m/z: 505.3 (M + H+) |
| 35 | N-(3-(5-(3-(3,3-dimethylbutyl)ureido)-2-fluorophenyl)-2-methyl-1,6-naphthyridin-7-yl)acetamide | 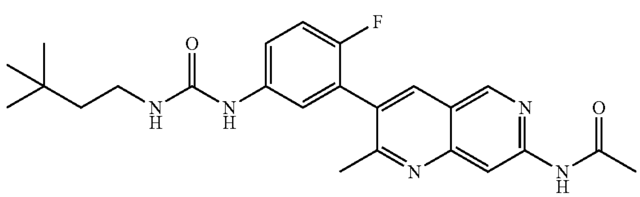 [SMILES: CC(=O)Nc1cc2nc(C)c(-c3cc(NC(=O)NCCC(C)(C)C)ccc3F)cc2cn1] | MS (ESI) m/z: 438.3 (M + H+) |
| 36 | N-(3-(3-(3-(3,3-dimethylbutyl)ureido)-4-fluorophenyl)-2-ethyl-1,6-naphthyridin-7-yl)acetamide | 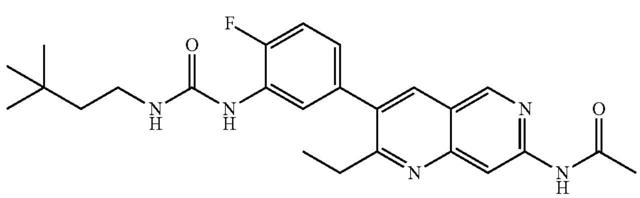 [SMILES: CCc1nc2cc(NC(C)=O)ncc2cc1-c1ccc(F)c(NC(=O)NCCC(C)(C)C)c1] | MS (ESI) m/z: 452.2 (M + H+) |

-continued

| Ex No. | Chemical Name | Structure | Physical Data |
|---|---|---|---|
| 37 | N-(3-(5-(3-(3,3-dimethylbutyl)ureido)-2-fluorophenyl)-2-ethyl-1,6-naphthyridin-7-yl)acetamide | 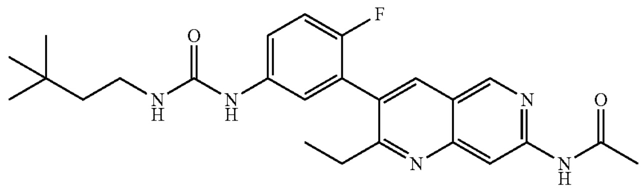 [SMILES: CCc1nc2cc(NC(C)=O)ncc2cc1-c1cc(NC(=O)NCCC(C)(C)C)ccc1F] | MS (ESI) m/z: 452.2 (M + H⁺) |
| 38 | N-(3-(4-fluoro-3-(3-(3-fluoro-3-methylbutyl)ureido)phenyl)-2-methyl-1,6-naphthyridin-7-yl)isobutyramide | 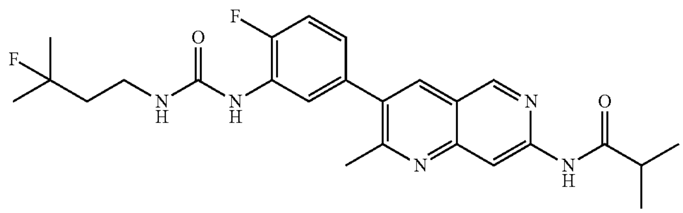 [SMILES: Cc1nc2cc(NC(=O)C(C)C)ncc2cc1-c1ccc(F)c(NC(=O)NCCC(C)(C)F)c1] | MS (ESI) m/z: 470.3 (M + H⁺) |
| 39 | N-(3-(5-(3-(4,4-difluorocyclohexyl)ureido)-4-fluoro-2-methylphenyl)-2-methyl-1,6-naphthyridin-7-yl)cyclopropanecarboxamide | 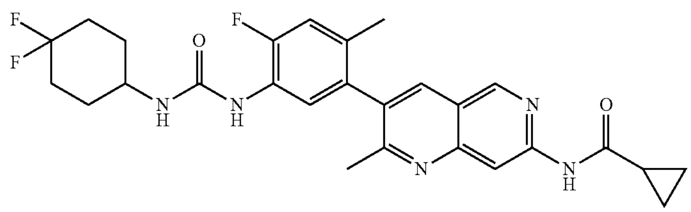 [SMILES: Cc1cc(F)c(NC(=O)NC2CCC(F)(F)CC2)cc1-c1cc2cnc(NC(=O)C3CC3)cc2nc1C] | MS (ESI) m/z: 512.2 (M + H⁺) |
| 40 | N-(3-(5-(3-(2-cyclopropylethyl)ureido)-4-fluoro-2-methylphenyl)-2-methyl-1,6-naphthyridin-7-yl)cyclopropanecarboxamide | 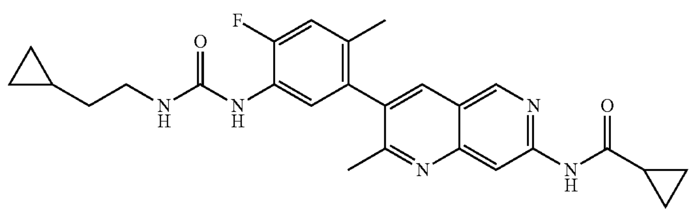 [SMILES: Cc1cc(F)c(NC(=O)NCCC2CC2)cc1-c1cc2cnc(NC(=O)C3CC3)cc2nc1C] | MS (ESI) m/z: 462.2 (M + H⁺) |
| 41 | N-(3-(3-(3-(4,4-difluorocyclohexyl)ureido)-4-fluorophenyl)-2-methyl-1,6-naphthyridin-7-yl)cyclopropanecarboxamide | 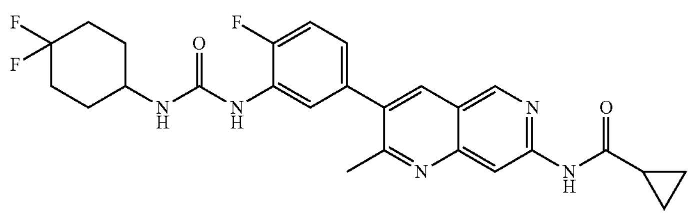 [SMILES: Cc1nc2cc(NC(=O)C3CC3)ncc2cc1-c1ccc(F)c(NC(=O)NC2CCC(F)(F)CC2)c1] | MS (ESI) m/z: 498.2 (M + H⁺) |
| 42 | N-(3-(4-fluoro-2-methyl-5-(3-(2-(trifluoromethoxy)ethyl)ureido)phenyl)-2-methyl-1,6-naphthyridin-7-yl)cyclopropanecarboxamide | 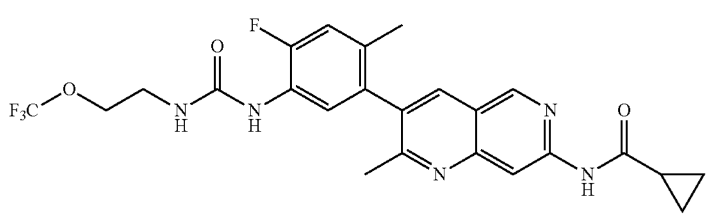 [SMILES: Cc1cc(F)c(NC(=O)NCCOC(F)(F)F)cc1-c1cc2cnc(NC(=O)C3CC3)cc2nc1C] | MS (ESI) m/z: 506.2 (M + H⁺) |
| 43 | N-(3-(5-(3-(3-cyano-3-methylbutyl)ureido)-2,4-difluorophenyl)-2-methyl-1,6-naphthyridin-7-yl)acetamide | 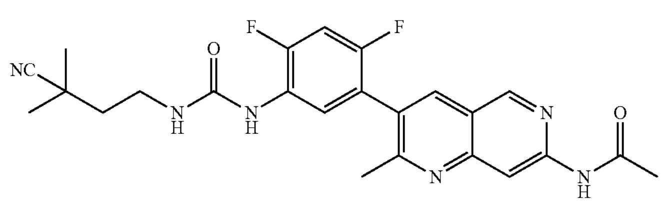 [SMILES: CC(=O)Nc1cc2nc(C)c(-c3cc(NC(=O)NCCC(C)(C)C#N)c(F)cc3F)cc2cn1] | MS (ESI) m/z: 467.2 (M + H⁺) |

-continued

| Ex No. | Chemical Name | Structure | Physical Data |
|---|---|---|---|
| 44 | 1-(5-(7-amino-2-methyl-1,6-naphthyridin-3-yl)-2-fluoro-4-methylphenyl)-3-(3-cyano-3-methylbutyl)urea | 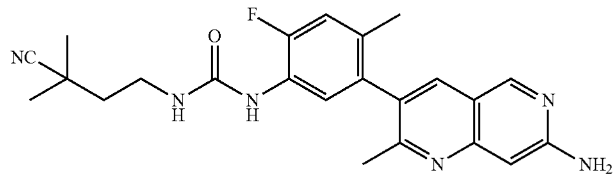 [SMILES: Cc1cc(F)c(NC(=O)NCCC(C)(C)C#N)cc1-c1cc2cnc(N)cc2nc1C] | MS (ESI) m/z: 421.2 (M + H+) |
| 45 | 1-(2-fluoro-4-methyl-5-(2-methyl-7-(methylamino)-1,6-naphthyridin-3-yl)phenyl)-3-isopentylurea | 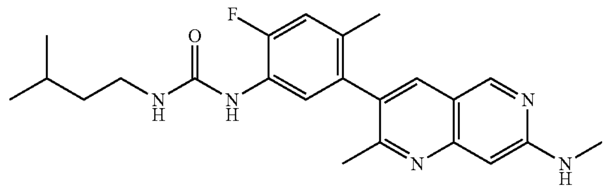 [SMILES: CNc1cc2nc(C)c(-c3cc(NC(=O)NCCC(C)C)c(F)cc3C)cc2cn1] | MS (ESI) m/z: 410.0 (M + H+) |
| 46 | 1-(2,4-difluoro-5-(2-methyl-7-(methylamino)-1,6-naphthyridin-3-yl)phenyl)-3-isopentylurea | 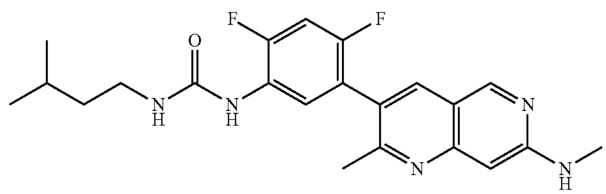 | MS (ESI) m/z: 414.0 (M + H+) |
| 47 | 1-(2,4-difluoro-5-(7-(2-hydroxyethylamino)-2-methyl-1,6-naphthyridin-3-yl)phenyl)-3-(3,3-dimethylbutyl)urea | 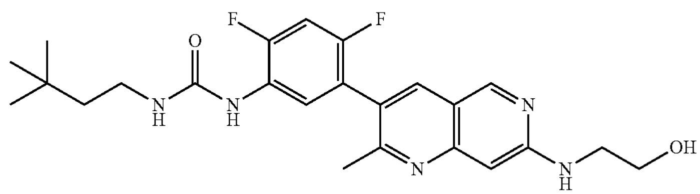 [SMILES: Cc1nc2cc(NCCO)ncc2cc1-c1cc(NC(=O)NCCC(C)(C)C)c(F)cc1F] | MS (ESI) m/z: 458.2 (M + H+) |
| 48 | 1-(2-fluoro-4-methyl-5-(2-methyl-7-(methylamino)-1,6-naphthyridin-3-yl)phenyl)-3-(tetrahydro-2H-pyran-4-yl)urea | 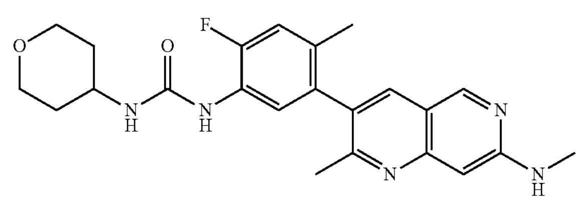 [SMILES: CNc1cc2nc(C)c(-c3cc(NC(=O)NC4CCOCC4)c(F)cc3C)cc2cn1] | MS (ESI) m/z: 424.2 (M + H+) |
| 49 | 1-(3-cyano-3-methylbutyl)-3-(2,4-difluoro-5-(7-((2-hydroxyethyl)amino)-2-methyl-1,6-naphthyridin-3-yl)phenyl)urea | 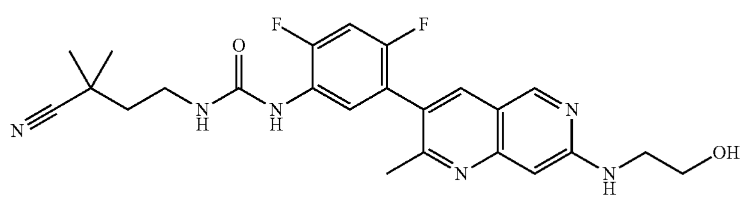 [SMILES: Cc1nc2cc(NCCO)ncc2cc1-c1cc(NC(=O)NCCC(C)(C)C#N)c(F)cc1F] | MS (ESI) m/z: 469.2 (M + H+) |
| 50 | 1-(2,4-difluoro-5-(7-((2-hydroxyethyl)amino)-2-methyl-1,6-naphthyridin-3-yl)phenyl)-3-(3-fluoro-3-methylbutyl)urea | 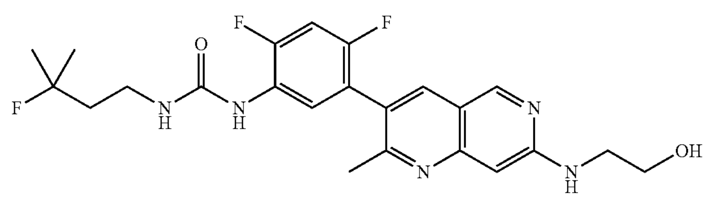 [SMILES: Cc1nc2cc(NCCO)ncc2cc1-c1cc(NC(=O)NCCC(C)(C)F)c(F)cc1F] | MS (ESI) m/z: 462.2 (M + H+) |
| 51 | 1-(2,4-difluoro-5-(7-((2-hydroxyethyl)amino)-2-methyl-1,6-naphthyridin-3-yl)phenyl)-3-((3,3-difluorocyclobutyl)methyl)urea | 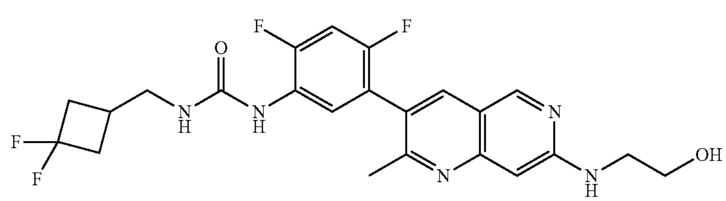 [SMILES: Cc1nc2cc(NCCO)ncc2cc1-c1cc(NC(=O)NCC2CC(F)(F)C2)c(F)cc1F] | MS (ESI) m/z: 478.2 (M + H+) |

| Ex No. | Chemical Name | Structure | Physical Data |
|---|---|---|---|
| 52 | 1-(2-fluoro-4-methyl-5-(2-methyl-7-(methylamino)-1,6-naphthyridin-3-yl)phenyl)-3-(oxetan-2-ylmethyl)urea | 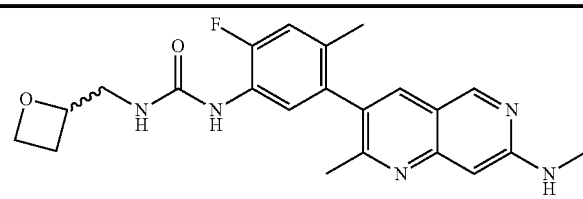 | MS (ESI) m/z: 410.2 (M + H+) |
| 53 | 1-(2-fluoro-4-methyl-5-(2-methyl-7-(methylamino)-1,6-naphthyridin-3-yl)phenyl)-3-((tetrahydro-2H-pyran-2-yl)methyl)urea | 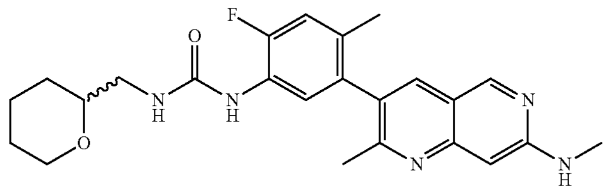 [SMILES: CNc1cc2nc(C)c(-c3cc(NC(=O)NCC4CCCCO4)c(F)cc3C)cc2cn1] | MS (ESI) m/z: 438.2 (M + H+) |
| 54 | 1-(2-fluoro-4-methyl-5-(2-methyl-7-(methylamino)-1,6-naphthyridin-3-yl)phenyl)-3-(tetrahydrofuran-3-yl)urea | 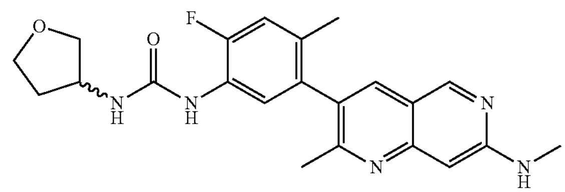 [SMILES: CNc1cc2nc(C)c(-c3cc(NC(=O)NC4CCOC4)c(F)cc3C)cc2cn1] | MS (ESI) m/z: 410.2 (M + H+) |
| 55 | 1-(2-fluoro-4-methyl-5-(2-methyl-7-(methylamino)-1,6-naphthyridin-3-yl)phenyl)-3-(2-hydroxy-3,3-dimethylbutyl)urea | 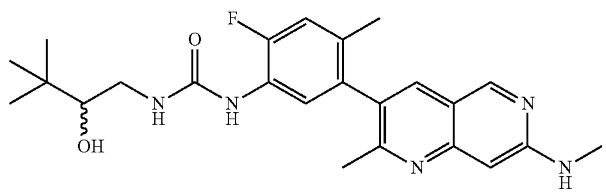 [SMILES: CNc1cc2nc(C)c(-c3cc(NC(=O)NCC(O)C(C)(C)C)c(F)cc3C)cc2cn1] | MS (ESI) m/z: 440.0 (M + H+) |
| 56 | (S)-1-(2-fluoro-4-methyl-5-(2-methyl-7-(methylamino)-1,6-naphthyridin-3-yl)phenyl)-3-(2-hydroxy-3,3-dimethylbutyl)urea | 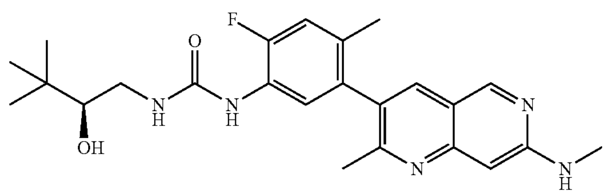 [SMILES: CNc1cc2nc(C)c(-c3cc(NC(=O)NC[C@@H](O)C(C)(C)C)c(F)cc3C)cc2cn1] | MS (ESI) m/z: 440.2 (M + H+) |
| 57 | (R)-1-(2-fluoro-4-methyl-5-(2-methyl-7-(methylamino)-1,6-naphthyridin-3-yl)phenyl)-3-(2-hydroxy-3,3-dimethylbutyl)urea | 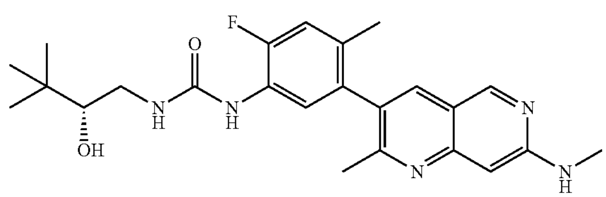 [SMILES: CNc1cc2nc(C)c(-c3cc(NC(=O)NC[C@H](O)C(C)(C)C)c(F)cc3C)cc2cn1] | MS (ESI) m/z: 440.2 (M + H+) |
| 58 | 1-(2-fluoro-4-methyl-5-(2-methyl-7-(methylamino)-1,6-naphthyridin-3-yl)phenyl)-3-(2-(1-hydroxycyclopropyl)ethyl)urea | 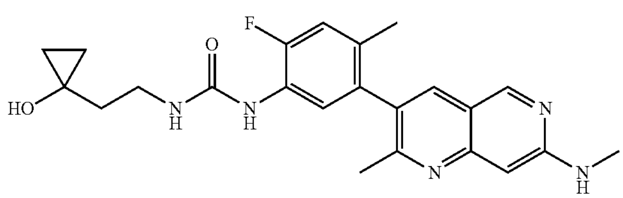 [SMILES: CNc1cc2nc(C)c(-c3cc(NC(=O)NCCC4(O)CC4)c(F)cc3C)cc2cn1] | MS (ESI) m/z: 424.2 (M + H+) |
| 59 | 1-(4,4-dimethylpentan-2-yl)-3-(2-fluoro-4-methyl-5-(2-methyl-7-(methylamino)-1,6-naphthyridin-3-yl)phenyl)urea | 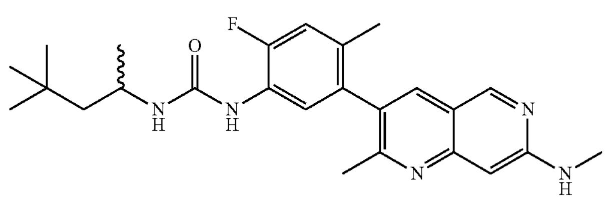 [SMILES: CNc1cc2nc(C)c(-c3cc(NC(=O)NC(C)CC(C)(C)C)c(F)cc3C)cc2cn1] | MS (ESI) m/z: 438.2 (M + H+) |

| Ex No. | Chemical Name | Structure | Physical Data |
|---|---|---|---|
| 60 | 1-(2-fluoro-4-methyl-5-(2-methyl-7-(methylamino)-1,6-naphthyridin-3-yl)phenyl)-3-(2-hydroxy-3-methylbutyl)urea | 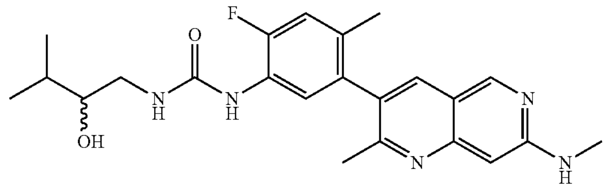 [SMILES: CNc1cc2nc(C)c(-c3cc(NC(=O)NCC(O)C(C)C)c(F)cc3C)cc2cn1] | MS (ESI) m/z: 426.2 (M + H+) |
| 61 | 1-(2-fluoro-4-methyl-5-(2-methyl-7-(methylamino)-1,6-naphthyridin-3-yl)phenyl)-3-(3,3,3-trifluoro-2-hydroxypropyl)urea | 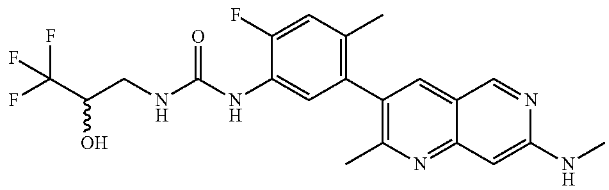 [SMILES: CNc1cc2nc(C)c(-c3cc(NC(=O)NCC(O)C(F)(F)F)c(F)cc3C)cc2cn1] | MS (ESI) m/z: 452.0 (M + H+) |
| 62 | 1-(5-(7-amino-2-methyl-1,6-naphthyridin-3-yl)-2-fluoro-4-methylphenyl)-3-(2-hydroxy-3,3-dimethylbutyl)urea | 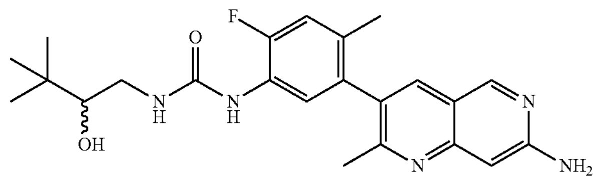 [SMILES: Cc1cc(F)c(NC(=O)NCC(O)C(C)(C)C)cc1-c1cc2cnc(N)cc2nc1C] | MS (ESI) m/z: 426.2 (M + H+) |
| 63 | 1-(2-cyclopropyl-2-hydroxyethyl)-3-(2-fluoro-4-methyl-5-(2-methyl-7-(methylamino)-1,6-naphthyridin-3-yl)phenyl)urea | 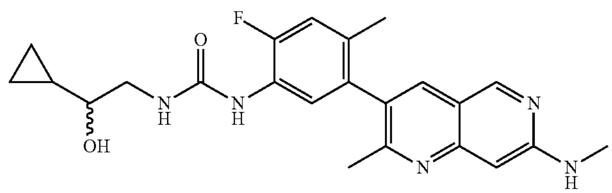 [SMILES: CNc1cc2nc(C)c(-c3cc(NC(=O)NCC(O)C4CC4)c(F)cc3C)cc2cn1] | MS (ESI) m/z: 424.0 (M + H+) |
| 64 | 1-(3,3-dimethylbutyl)-3-(2-fluoro-5-(7-((2-hydroxyethyl)amino)-2-methyl-1,6-naphthyridin-3-yl)-4-methylphenyl)urea | 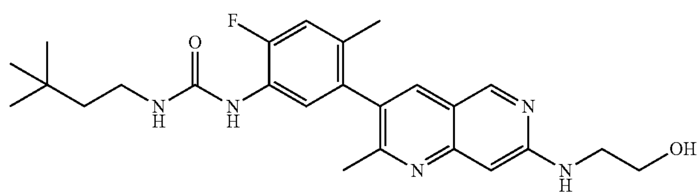 [SMILES: Cc1cc(F)c(NC(=O)NCCC(C)(C)C)cc1-c1cc2cnc(NCCO)cc2nc1C] | MS (ESI) m/z: 454.2 (M + H+) |
| 65 | 1-(3-fluoro-3-methylbutyl)-3-(2-fluoro-5-(7-((2-hydroxyethyl)amino)-2-methyl-1,6-naphthyridin-3-yl)-4-methylphenyl)urea | 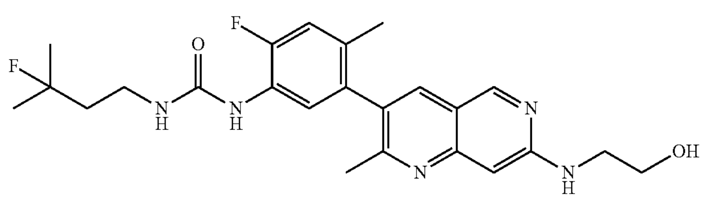 [SMILES: Cc1cc(F)c(NC(=O)NCCC(C)(C)F)cc1-c1cc2cnc(NCCO)cc2nc1C] | MS (ESI) m/z: 458.0 (M + H+) |
| 66 | 1-((3,3-difluorocyclobutyl)methyl)-3-(2-fluoro-5-(7-((2-hydroxyethyl)amino)-2-methyl-1,6-naphthyridin-3-yl)-4-methylphenyl)urea | 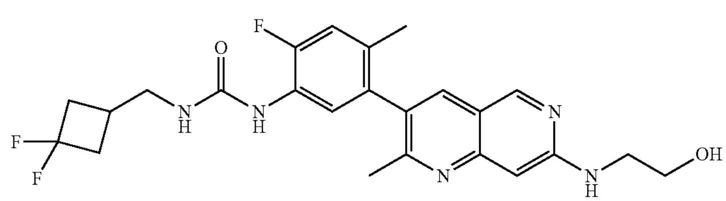 [SMILES: Cc1cc(F)c(NC(=O)NCC2CC(F)(F)C2)cc1-c1cc2cnc(NCCO)cc2nc1C] | MS (ESI) m/z: 474.2 (M + H+) |
| 67 | 1-(3-cyano-3-methylbutyl)-3-(2-fluoro-5-(7-((2-hydroxyethyl)amino)-2-methyl-1,6-naphthyridin-3-yl)-4-methylphenyl)urea | 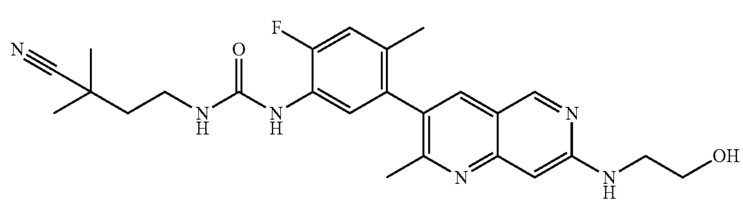 [SMILES: Cc1cc(F)c(NC(=O)NCCC(C)(C)C#N)cc1-c1cc2cnc(NCCO)cc2nc1C] | MS (ESI) m/z: 465.0 (M + H+) |

| Ex No. | Chemical Name | Structure | Physical Data |
|---|---|---|---|
| 68 | 1-(2-fluoro-4-methyl-5-(2-methyl-7-(methylamino)-1,6-naphthyridin-3-yl)phenyl)-3-(2,4,4-trimethylpentan-2-yl)urea hydrochloride | 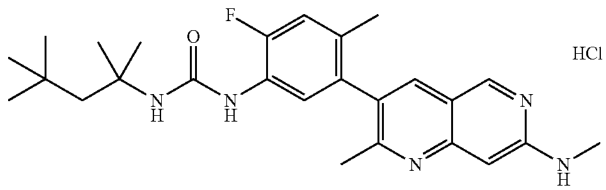 [SMILES: CNc1cc2nc(C)c(-c3cc(NC(=O)NC(C)(C)CC(C)(C)C)c(F)cc3C)cc2cn1 ; Cl] | MS (ESI) m/z: 452.0 (M + H+) |
| 69 | 1-(2-fluoro-4-methyl-5-(2-methyl-7-(methylamino)-1,6-naphthyridin-3-yl)phenyl)-3-(2-morpholinoethyl)urea | 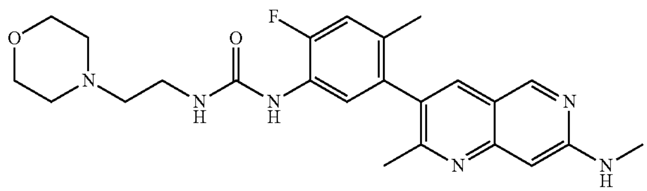 [SMILES: CNc1cc2nc(C)c(-c3cc(NC(=O)NCCN4CCOCC4)c(F)cc3C)cc2cn1] | MS (ESI) m/z: 453.0 (M + H+) |

EXAMPLE 70

Synthesis of (R)-1-(5-(7-amino-2-methyl-1,6-naphthyridin-3-yl)-2-fluoro-4-methylphenyl)-3-(2-hydroxy-3,3-dimethylbutyl)urea

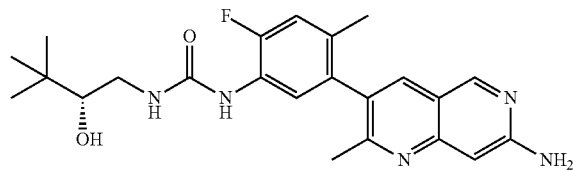 [SMILES: Cc1cc(F)c(NC(=O)NC[C@H](O)C(C)(C)C)cc1-c1cc2cnc(N)cc2nc1C]

Purify 1-(5-(7-amino-2-methyl-1,6-naphthyridin-3-yl)-2-fluoro-4-methylphenyl)-3-(2-hydroxy-3,3-dimethylbutyl)urea on a Chiralpak AS-H column eluting with MeOH/IPA/CO$_2$ to obtain the separated isomer. MS (m/z): 426.2 (M+1).

The following compounds are prepared essentially by the procedure of Example 70.

| Ex No. | Chemical Name | Structure | Physical Data |
|---|---|---|---|
| 71 | (S)-1-(5-(7-amino-2-methyl-1,6-naphthyridin-3-yl)-2-fluoro-4-methylphenyl)-3-(2-hydroxy-3,3-dimethylbutyl)urea | 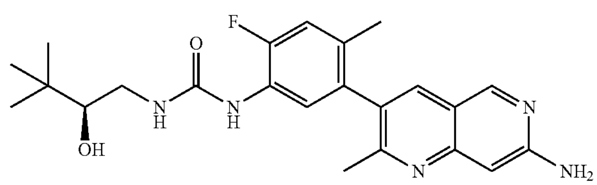 [SMILES: Cc1cc(F)c(NC(=O)NC[C@@H](O)C(C)(C)C)cc1-c1cc2cnc(N)cc2nc1C] | MS (ESI) m/z: 426.2 (M + H+) |
| 72 | (R)-1-(4,4-dimethylpentan-2-yl)-3-(2-fluoro-4-methyl-5-(2-methyl-7-(methylamino)-1,6-naphthyridin-3-yl)phenyl)urea | 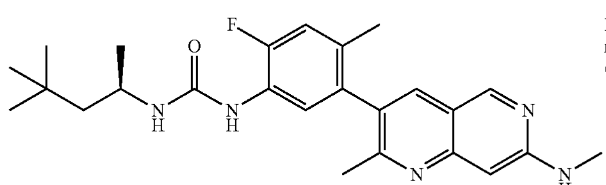 | MS (ESI) m/z: 438.2 (M + H+) |
| 73 | (S)-1-(4,4-dimethylpentan-2-yl)-3-(2-fluoro-4-methyl-5-(2-methyl-7-(methylamino)-1,6-naphthyridin-3-yl)phenyl)urea | 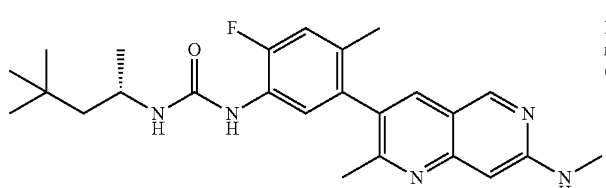 | MS (ESI) m/z: 438.2 (M + H+) |

| Ex No. | Chemical Name | Structure | Physical Data |
|---|---|---|---|
| 74 | (R)-1-(2-fluoro-4-methyl-5-(2-methyl-7-(methylamino)-1,6-naphthyridin-3-yl)phenyl)-3-(2-hydroxy-3-methylbutyl)urea | 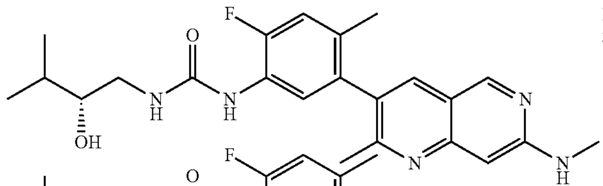 | MS (ESI) m/z: 426.2 (M + H+) |
| 75 | (S)-1-(2-fluoro-4-methyl-5-(2-methyl-7-(methylamino)-1,6-naphthyridin-3-yl)phenyl)-3-(2-hydroxy-3-methylbutyl)urea | 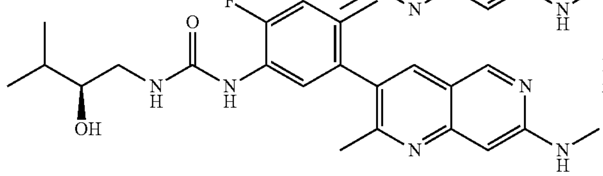 | MS (ESI) m/z: 426.0 (M + H+) |

EXAMPLE 76

Synthesis of 1-(3-fluoro-3-methylbutyl)-3-(2-fluoro-4-methyl-5-(2-methyl-7-(methylamino)-1,6-naphthyridin-3-yl)phenyl)urea

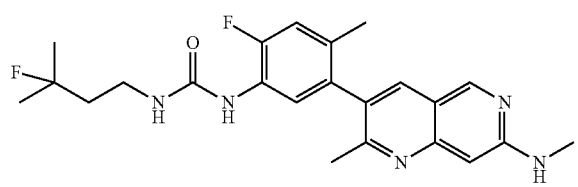 [SMILES: CNc1cc2nc(C)c(-c3cc(NC(=O)NCCC(C)(C)F)c(F)cc3C)cc2cn1]

Combine prop-1-en-2-yl(2-fluoro-4-methyl-5-(2-methyl-7-(methylamino)-1,6-naphthyridin-3-yl)phenyl)carbamate (2.5 g, 6.6 mmol), 3-fluoro-3-methylbutan-1-amine diacetate (1.8 g, 7.9 mmol), and N-methylpyrrolidine (2.7 mL, 26.0 mmole) in THF (50 mL) and heat at 50° C. overnight. Evaporate under reduced pressure and partition between NaHCO₃ and EtOAc. Wash the organic layer with brine, dry over Na₂SO₄, concentrate in vacuo, and purify by silica gel chromatography (50-100% EtOAc/DCM) to obtain the title compound (2.0 g, 71%). ¹H NMR (400 MHz, DMSO-d₆): δ 8.82 (s, 1H), 8.33 (s, 1H), 7.93 (d, J=8 Hz, 1H), 7.83 (s, 1H), 7.16 (d, J=8 Hz, 1H), 6.73 (m, 1H), 6.56 (m, 1H), 6.52 (s, 1H), 3.15 (m, 2H), 2.82 (d, J=5 Hz, 3H), 2.27 (s, 3H), 1.94 (s, 3H), 1.73 (m, 2H), 1.30 (d, J=21.6 Hz, 6H); MS (ESI) m/z: 428.2 (M+H⁺).

EXAMPLE 77

Synthesis of 1-(3-fluoro-cis(3-methylcyclobutyl))-3-(2-fluoro-4-methyl-5-(2-methyl-7-(methylamino)-1,6-naphthyridin-3-yl)phenyl)urea

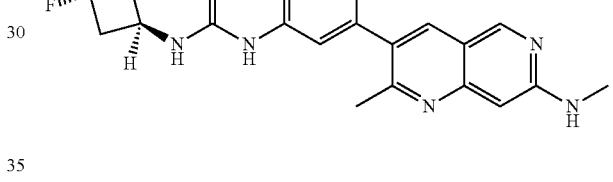

Treat a solution of 3-methyl-(trans-3-fluorocyclobutanecarboxylic acid) (0.499 g, 3.78 mmol) in dioxane (20 mL) with TEA (1 mL, 7.19 mmol) and DPPA (0.800 mL, 3.71 mmol) and heat at 80° C. until gas evolution ceases. Add 3-(5-amino-4-fluoro-2-methylphenyl)-N,2-dimethyl-1,6-naphthyridin-7-amine (1.0 g, 3.37 mmol) and heat the mixture at 50° C. overnight. Concentrate the mixture to dryness, purify by silica gel chromatography (EtOAc/Hex). Add MeCN (20 mL), sonicate and collect the solid via filtration to afford the title compound (500 mg, 35%) as a pale yellow solid. ¹H NMR (400 MHz, DMSO-d₆): δ 8.82 (s, 1H), 8.23 (s, 1H), 7.90 (d, J=8.5 Hz, 1H), 7.85 (s, 1H), 7.17 (d, J=12.3 Hz, 1H), 6.91 (d, J=6.8 Hz, 1H), 6.78-6.72 (m, 1H), 6.52 (s, 1H), 4.14-4.13 (m, 1H), 2.82 (d, J=5.0 Hz, 3H), 2.59-2.50 (m, 2H), 2.48 (s, 3H), 2.26 (s, 3H), 2.07-1.96 (m, 2H), 1.95 (s, 3H), 1.45 (d, J=22.3 Hz, 3H); MS (ESI) m/z: 426.2 (M+H⁺).

The following compound is prepared essentially by the method of Example 77.

| Ex No. | Chemical Name | Structure | Physical Data |
|---|---|---|---|
| 78 | 1-(2,4-difluoro-5-(2-methyl-7-(methylamino)-1,6-naphthyridin-3-yl)phenyl)-3-(3,3-dimethylcyclobutyl)urea hydrochloride | 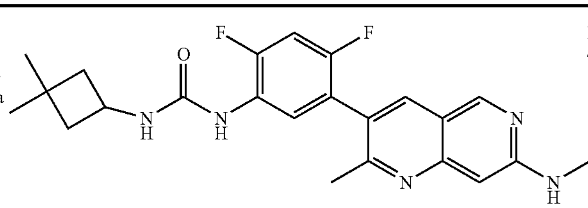 | MS (ESI) m/z: 426.0 (M + H⁺) |

Preparation 152

Synthesis of 1-cycloheptyl-3-(2-fluoro-5-(4,4,5,5-tetramethyl-1,3,2-dioxaborolan-2-yl)phenyl)urea

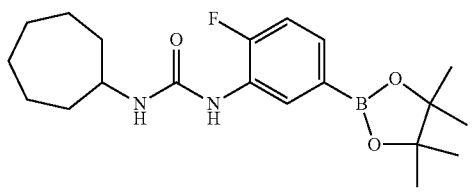 [SMILES: CC1(C)OB(c2ccc(F)c(NC(=O)NC3CCCCCC3)c2)OC1(C)C]

Treat a solution of prop-1-en-2-yl(2-fluoro-5-(4,4,5,5-tetramethyl-1,3,2-dioxaborolan-2-yl)phenyl)carbamate (0.460 g, 1.432 mmol) in THF (5 mL) with cycloheptylamine (0.195 g, 1.719 mmol) followed by a catalytic amount of 1-methylpyrrolidine (0.012 g, 0.143 mmol) and heat at 60° C. for 2 h. Concentrate the mixture to dryness, add MeCN, collect the solid via filtration and dry to afford the title compound (420 mg, 78%) as a white solid. $^1$H NMR (400 MHz, DMSO-$d_6$): δ 8.50 (dd, J=9, 1.7 Hz, 1H), 8.33 (s, 1H), 7.16 (m, 2H), 6.60 (d, J=7.0 Hz, 1H), 3.64 (m, 1H), 1.80 (m, 2H), 1.50 (m, 10H), 1.26 (s, 12H); MS(ESI) m/z: 377.2 (M+H$^+$).

The following compounds are prepared essentially by the method of Preparation 152.

| Prep No. | Chemical Name | Structure | Physical Data |
|---|---|---|---|
| 153 | 1-(3-fluoro-3-methylbutyl)-3-(2-fluoro-4-methyl-5-(4,4,5,5-tetramethyl-1,3,2-dioxaborolan-2-yl)phenyl)urea | 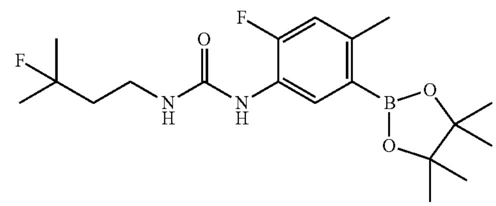 [SMILES: Cc1cc(F)c(NC(=O)NCCC(C)(C)F)cc1B1OC(C)(C)C(C)(C)O1] | MS (ESI) m/z: 383.2 (M + H$^+$) |
| 154 | 1-(3-fluoro-3-methylbutyl)-3-(2-fluoro-5-(4,4,5,5-tetramethyl-1,3,2-dioxaborolan-2-yl)phenyl)urea | 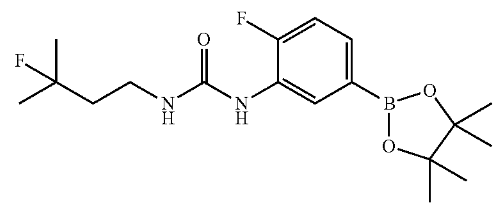 [SMILES: CC(C)(F)CCNC(=O)Nc1cc(B2OC(C)(C)C(C)(C)O2)ccc1F] | MS (ESI) m/z: 369.2 (M + H$^+$) |
| 155 | 1-(2,4-difluoro-5-(4,4,5,5-tetramethyl-1,3,2-dioxaborolan-2-yl)phenyl)-3-(4,4,4-trifluoro-3,3-dimethylbutyl)urea | 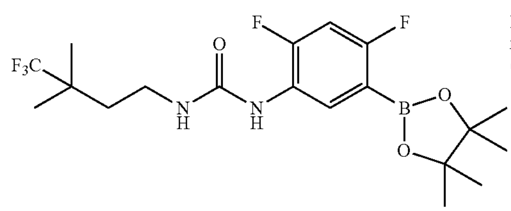 [SMILES: CC(C)(CCNC(=O)Nc1cc(B2OC(C)(C)C(C)(C)O2)c(F)cc1F)C(F)(F)F] | MS (ESI) m/z: 437.2 (M + H$^+$) |
| 156 | 1-(3,3-dimethylbutyl)-3-(2-fluoro-5-(4,4,5,5-tetramethyl-1,3,2-dioxaborolan-2-yl)phenyl)urea | 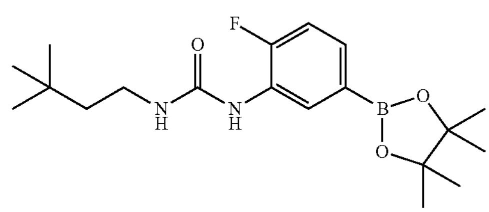 [SMILES: CC(C)(C)CCNC(=O)Nc1cc(B2OC(C)(C)C(C)(C)O2)ccc1F] | MS (ESI) m/z: 365.2 (M + H$^+$) |
| 157 | 1-(2-fluoro-4-methyl-5-(4,4,5,5-tetramethyl-1,3,2-dioxaborolan-2-yl)phenyl)-3-(2-(1(trifluoromethyl)cyclopropyl)ethyl)urea | 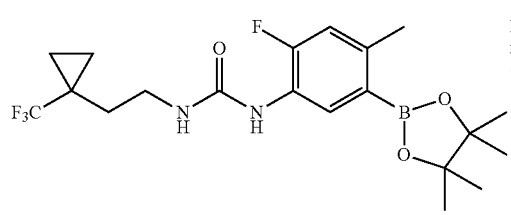 [SMILES: Cc1cc(F)c(NC(=O)NCCC2(C(F)(F)F)CC2)cc1B1OC(C)(C)C(C)(C)O1] | MS (ESI) m/z: 431.2 (M + H$^+$) |

Preparation 158

Synthesis of 1-(5-(7-chloro-2-methyl-1,6-naphthyridin-3-yl)-2-fluorophenyl)-3-cycloheptylurea

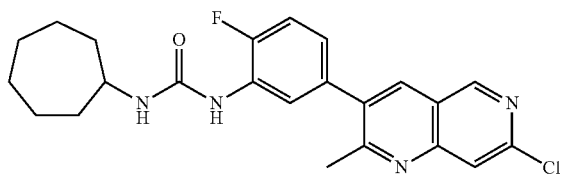 [SMILES: Cc1nc2cc(Cl)ncc2cc1-c1ccc(F)c(NC(=O)NC2CCCCCC2)c1]

Sparge a suspension of 1-cycloheptyl-3-(2-fluoro-5-(4,4,5,5-tetramethyl-1,3,2-dioxaborolan-2-yl)phenyl)urea (0.420 g, 1.116 mmol), 7-chloro-2-methyl-1,6-naphthyridin-3-yl trifluoromethanesulfonate (0.438 g, 1.339 mmol) and $K_2CO_3$ (0.463 g, 3.35 mmol) in dioxane (4 mL) and $H_2O$ (1 mL) with Ar, add $Pd(PPh_3)_4$ (0.064 g, 0.056 mmol) and heat at 60° C. for 3 h. Concentrate the mixture to dryness and purify via silica gel chromatography (EtOAc/Hex) to afford the title compound (679 mg, 61%) as a white solid. MS(ESI) m/z: 427.1 (M+H$^+$).

The following compounds are prepared essentially by the method of Preparation 158.

| Prep No. | Chemical Name | Structure | Physical Data |
|---|---|---|---|
| 159 | 1-(5-(7-chloro-2-methyl-1,6-naphthyridin-3-yl)-2-fluoro-4-methylphenyl)-3-(3-fluoro-3-methylbutyl)urea | 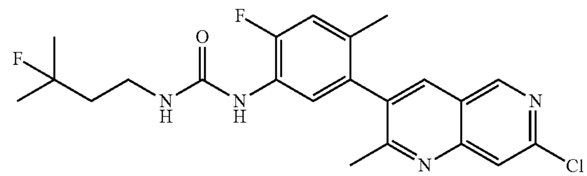 [SMILES: Cc1cc(F)c(NC(=O)NCCC(C)(C)F)cc1-c1cc2cnc(Cl)cc2nc1C] | MS (ESI) m/z: 433.1 (M + H$^+$) |
| 160 | 1-(5-(7-chloro-2-methyl-1,6-naphthyridin-3-yl)-2-fluorophenyl)-3-(3-fluoro-3-methylbutyl)urea | 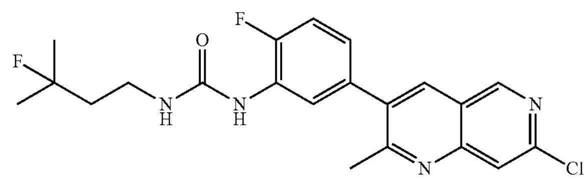 [SMILES: Cc1nc2cc(Cl)ncc2cc1-c1ccc(F)c(NC(=O)NCCC(C)(C)F)c1] | MS (ESI) m/z: 419.1 (M + H$^+$) |
| 161 | 1-(5-(7-chloro-1,6-naphthyridin-3-yl)-2-fluoro-4-methylphenyl)-3-(3-fluoro-3-methylbutyl)urea | 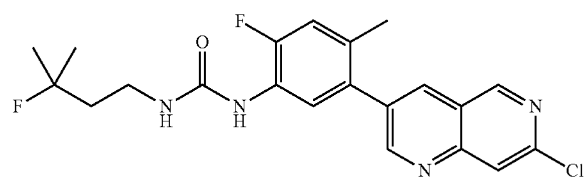 [SMILES: Cc1cc(F)c(NC(=O)NCCC(C)(C)F)cc1-c1cnc2cc(Cl)ncc2c1] | MS (ESI) m/z: 419.1 (M + H$^+$) |
| 162 | 1-(5-(7-chloro-2-methyl-1,6-naphthyridin-3-yl)-2,4-difluorophenyl)-3-(4,4,4-trifluoro-3,3-dimethylbutyl)urea | 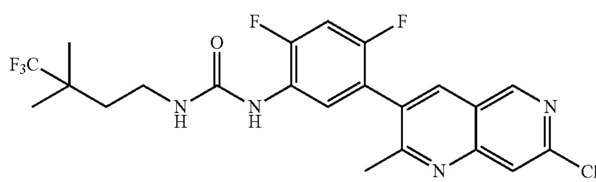 [SMILES: Cc1nc2cc(Cl)ncc2cc1-c1cc(NC(=O)NCCC(C)(C)C(F)(F)F)c(F)cc1F] | MS (ESI) m/z: 487.1 (M + H$^+$) |
| 163 | 1-(5-(7-chloro-2-methyl-1,6-naphthyridin-3-yl)-2-fluorophenyl)-3-(3,3-dimethylbutyl)urea | 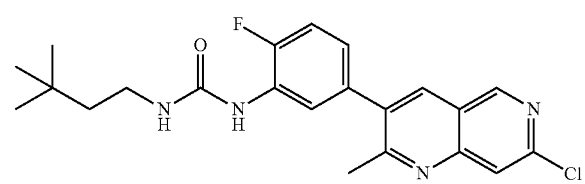 [SMILES: Cc1nc2cc(Cl)ncc2cc1-c1ccc(F)c(NC(=O)NCCC(C)(C)C)c1] | MS (ESI) m/z: 415.2 (M + H$^+$) |
| 164 | 1-(5-(7-chloro-2-methyl-1,6-naphthyridin-3-yl)-2-fluoro-4-methylphenyl)-3-(2-(1-(trifluoromethyl)cyclopropyl)ethyl)urea | 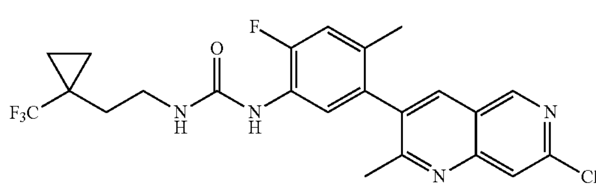 [SMILES: Cc1cc(F)c(NC(=O)NCCC2(C(F)(F)F)CC2)cc1-c1cc2cnc(Cl)cc2nc1C] | MS (ESI) m/z: 481.1 (M + H$^+$) |

Preparation 165

Synthesis of prop-1-en-2-yl(5-(7-chloro-2-methyl-1,6-naphthyridin-3-yl)-2-fluoro-4-methylphenyl)carbamate

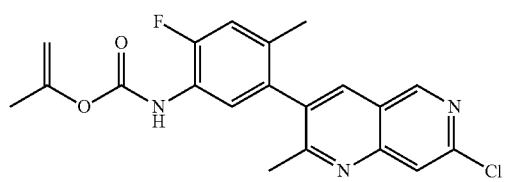 [SMILES: C=C(C)OC(=O)Nc1cc(-c2cc3cnc(Cl)cc3nc2C)c(C)cc1F]

Treat a solution of 5-(7-chloro-2-methyl-1,6-naphthyridin-3-yl)-2-fluoro-4-methylaniline (0.5 g, 1.657 mmol) in EtOAc (10 mL) with satd. NaHCO$_3$ (10 mL) followed by isopropenyl chloroformate (0.199 mL, 1.823 mmol) and stir the bi-phasic mixture at RT overnight. Separate the layers, extract the aqueous with EtOAc (2×), dry the combined organics over MgSO$_4$ and concentrate to dryness to the title compound (646 mg, 101%). MS (ESI) m/z: 386.1 (M+H$^+$).
The following compounds are prepared essentially by the method of Preparation 165.

Preparation 169

Synthesis of 1-(5-(7-chloro-2-methyl-1,6-naphthyridin-3-yl)-2-fluoro-4-methylphenyl)-3-(3,3,3-trifluoropropyl)urea

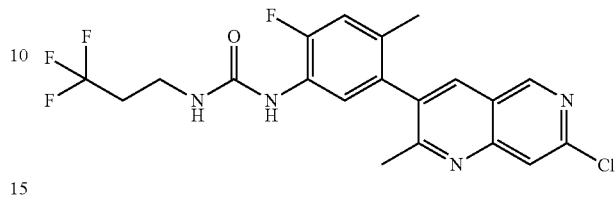

Heat a mixture of prop-1-en-2-yl(5-(7-chloro-2-methyl-1,6-naphthyridin-3-yl)-2-fluoro-4-methylphenyl)carbamate (0.20 g, 0.518 mmol), 3,3,3-trifluoropropylamine hydrochloride (0.093 g, 0.622 mmol) and 1-methylpyrrolidine (0.068 mL, 0.648 mmol) in THF (5 mL) at 55° C. overnight. Cool to RT, add H$_2$O, extract with EtOAc (2×), wash the combined organics with brine (2×), dry over MgSO$_4$ and concentrate to dryness to afford the title compound (220 mg, 96%). $^1$H NMR (400 MHz, DMSO-d$_6$): δ 9.23 (s, 1H), 8.53 (s, 1H), 8.31 (s, 1H), 8.01 (s, 1H), 7.97 (d, J=8.4 Hz, 1H), 7.23 (d, J=12.3 Hz, 1H), 6.75 (t, J=5.9 Hz, 1H), 3.58-3.02 (m, 2H), 2.42 (m, 2H), 2.41 (s, 3H), 1.95 (s, 3H).
The following compounds are prepared essentially by the method of Preparation 169.

| Prep No. | Chemical Name | Structure | Physical Data |
|---|---|---|---|
| 166 | prop-1-en-2-yl (5-(7-chloro-2-methyl-1,6-naphthyridin-3-yl)-2,4-difluorophenyl)carbamate | 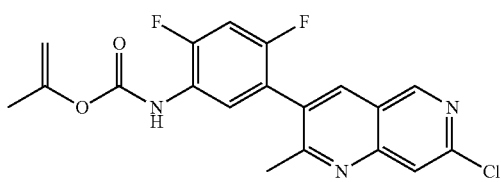 [SMILES: C=C(C)OC(=O)Nc1cc(-c2cc3cnc(Cl)cc3nc2C)c(F)cc1F] | MS (ESI) m/z: 390.1 (M + H$^+$) |
| 167 | prop-1-en-2-yl (3-(7-chloro-2-methyl-1,6-naphthyridin-3-yl)-4-methylphenyl)carbamate | 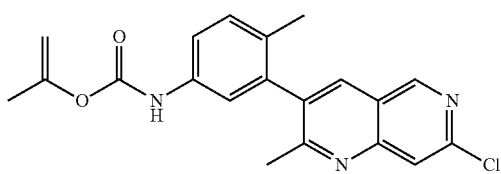 [SMILES: C=C(C)OC(=O)Nc1ccc(C)c(-c2cc3cnc(Cl)cc3nc2C)c1] | MS (ESI) m/z: 368.2 (M + H$^+$) |
| 168 | prop-1-en-2-yl (5-(7-chloro-2-methyl-1,6-naphthyridin-3-yl)-2-fluorophenyl)carbamate | 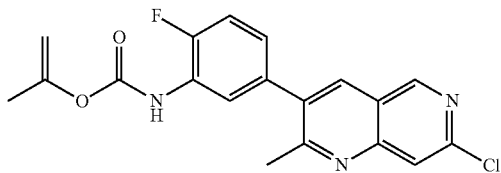 [SMILES: C=C(C)OC(=O)Nc1cc(-c2cc3cnc(Cl)cc3nc2C)ccc1F] | MS (ESI) m/z: 372.1 (M + H$^+$) |

| Prep No. | Chemical Name | Structure | Physical Data |
|---|---|---|---|
| 170 | 1-(5-(7-chloro-2-methyl-1,6-naphthyridin-3-yl)-2,4-difluorophenyl)-3-(4,4-difluorocyclohexyl)urea | 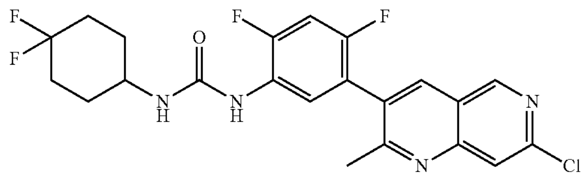 [SMILES: Cc1nc2cc(Cl)ncc2cc1-c1cc(NC(=O)NC2CCC(F)(F)CC2)c(F)cc1F] | MS(ESI) m/z: 467.2 (M + H$^+$) |
| 171 | 1-(5-(7-chloro-2-methyl-1,6-naphthyridin-3-yl)-2,4-difluorophenyl)-3-(4,4,4-trifluorobutyl)urea | 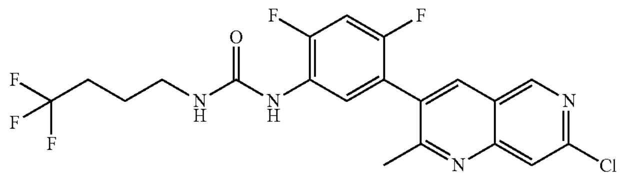 [SMILES: Cc1nc2cc(Cl)ncc2cc1-c1cc(NC(=O)NCCCC(F)(F)F)c(F)cc1F] | MS(ESI) m/z: 459.1 (M + H$^+$) |
| 172 | 1-(5-(7-chloro-2-methyl-1,6-naphthyridin-3-yl)-2-fluoro-4-methylphenyl)-3-(2-cyclopropylethyl)urea | 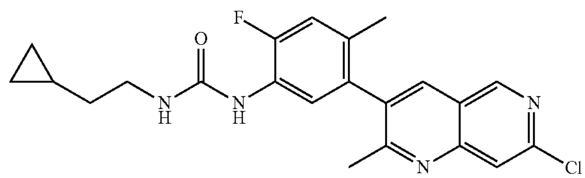 [SMILES: Cc1cc(F)c(NC(=O)NCCC2CC2)cc1-c1cc2cnc(Cl)cc2nc1C] | MS(ESI) m/z: 413.1 (M + H$^+$) |
| 173 | 1-(5-(7-chloro-2-methyl-1,6-naphthyridin-3-yl)-2-fluoro-4-methylphenyl)-3-(4,4,4-trifluorobutyl)urea | 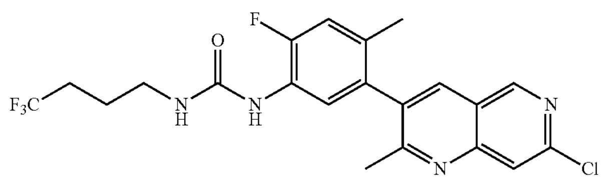 [SMILES: Cc1cc(F)c(NC(=O)NCCCC(F)(F)F)cc1-c1cc2cnc(Cl)cc2nc1C] | MS(ESI) m/z: 455.1 (M + H$^+$) |
| 174 | 1-(5-(7-chloro-2-methyl-1,6-naphthyridin-3-yl)-2-fluoro-4-methylphenyl)-3-(3-methoxy-3-methylbutyl)urea | 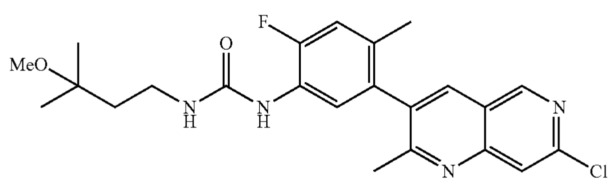 [SMILES: COC(C)(C)CCNC(=O)Nc1cc(-c2cc3cnc(Cl)cc3nc2C)c(C)cc1F] | MS(ESI) m/z: 445.2 (M + H$^+$) |
| 175 | 1-(5-(7-chloro-2-methyl-1,6-naphthyridin-3-yl)-2,4-difluorophenyl)-3-(2-(1-methylcyclopropyl)ethyl)urea | 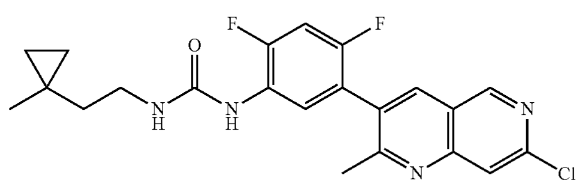 [SMILES: Cc1nc2cc(Cl)ncc2cc1-c1cc(NC(=O)NCCC2(C)CC2)c(F)cc1F] | MS(ESI) m/z: 431.1 (M + H$^+$) |
| 176 | 1-(5-(7-chloro-2-methyl-1,6-naphthyridin-3-yl)-2-fluoro-4-methylphenyl)-3-(4,4-difluoropentyl)urea | 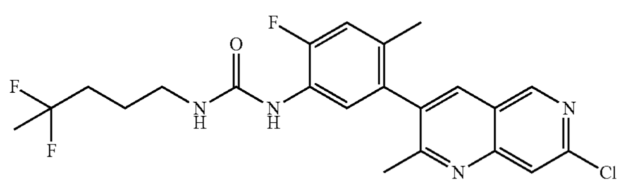 | MS(ESI) m/z: 451.1 (M + H$^+$) |
| 177 | 1-(5-(7-chloro-2-methyl-1,6-naphthyridin-3-yl)-2-fluoro-4-methylphenyl)-3-(4-fluoro-4-methylpentyl)urea | 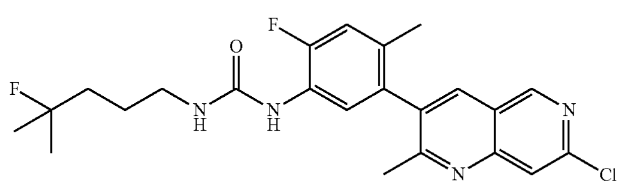 [SMILES: Cc1cc(F)c(NC(=O)NCCCC(C)(C)F)cc1-c1cc2cnc(Cl)cc2nc1C] | MS(ESI) m/z: 447.2 (M + H$^+$) |

| Prep No. | Chemical Name | Structure | Physical Data |
|---|---|---|---|
| 178 | 1-(5-(7-chloro-2-methyl-1,6-naphthyridin-3-yl)-2-fluoro-4-methylphenyl)-3-(4,4,4-trifluoro-3,3-dimethylbutyl)urea | 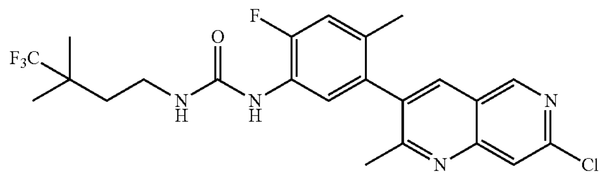 [SMILES: Cc1cc(F)c(NC(=O)NCCC(C)(C)C(F)(F)F)cc1-c1cc2cnc(Cl)cc2nc1C] | MS(ESI) m/z: 483.2 (M + H⁺) |
| 179 | 1-(5-(7-chloro-2-methyl-1,6-naphthyridin-3-yl)-2,4-difluorophenyl)-3-(3,3-dimethylbutyl)urea | 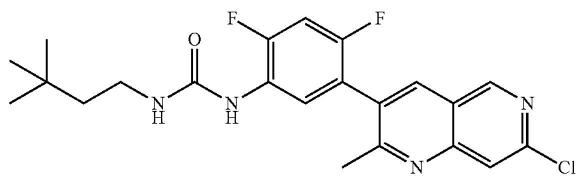 [SMILES: Cc1nc2cc(Cl)ncc2cc1-c1cc(NC(=O)NCCC(C)(C)C)c(F)cc1F] | MS (ESI) m/z: 433.2 (M + H⁺) |
| 180 | 1-(3-(7-chloro-2-methyl-1,6-naphthyridin-3-yl)-4-methylphenyl)-3-(3,3-dimethylbutyl)urea | 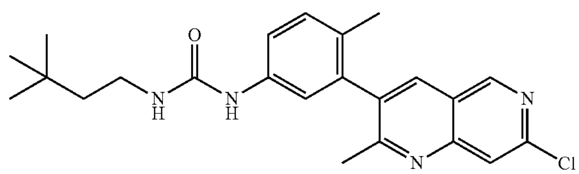 [SMILES: Cc1ccc(NC(=O)NCCC(C)(C)C)cc1-c1cc2cnc(Cl)cc2nc1C] | MS (ESI) m/z: 411.2 (M + H⁺) |
| 181 | 1-(5-(7-chloro-2-methyl-1,6-naphthyridin-3 yl)-2 fluorophenyl)-3-cyclohexylurea | 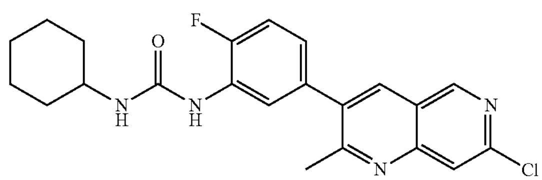 [SMILES: Cc1nc2cc(Cl)ncc2cc1-c1ccc(F)c(NC(=O)NC2CCCCC2)c1] | MS(ESI) m/z: 413.2 (M + H⁺) |
| 182 | 1-(5-(7-chloro-2-methyl-1,6-naphthyridin-3-yl)-2-fluorophenyl)-3-cyclopentylurea | 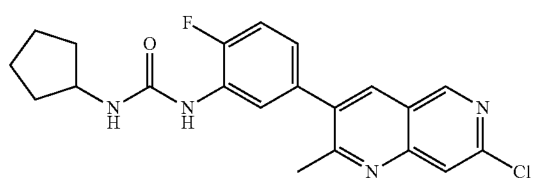 [SMILES: Cc1nc2cc(Cl)ncc2cc1-c1ccc(F)c(NC(=O)NC2CCCC2)c1] | MS(ESI) m/z: 399.1 (M + H⁺) |
| 183 | 1-(5-(7-chloro-2-methyl-1,6-naphthyridin-3-yl)-2-fluorophenyl)-3-(2-cyclopentylethyl)urea | 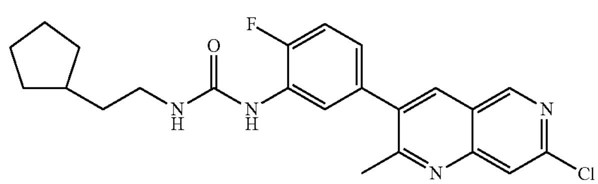 [SMILES: Cc1nc2cc(Cl)ncc2cc1-c1ccc(F)c(NC(=O)NCCC2CCCC2)c1] | MS (ESI) m/z: 427.2 (M + H⁺) |
| 184 | 1-(5-(7-chloro-2-methyl-1,6-naphthyridin-3-yl)-2-fluorophenyl)-3-(2-cyclopropylethyl)urea | 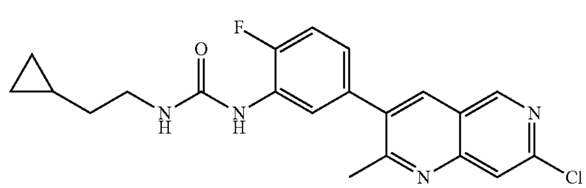 [SMILES: Cc1nc2cc(Cl)ncc2cc1-c1ccc(F)c(NC(=O)NCCC2CC2)c1] | MS(ESI) m/z: 399.1 (M + H⁺) |
| 185 | 1-(5-(7-chloro-2-methyl-1,6-naphthyridin-3-yl)-2,4-difluorophenyl)-3-(3-fluoro-3-methylbutyl)urea | 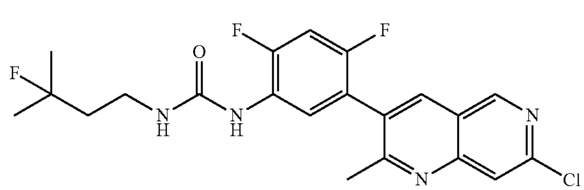 [SMILES: Cc1nc2cc(Cl)ncc2cc1-c1cc(NC(=O)NCCC(C)(C)F)c(F)cc1F] | MS(ESI) m/z: 437.1 (M + H⁺) |

| Prep No. | Chemical Name | Structure | Physical Data |
|---|---|---|---|
| 186 | 1-(5-(7-chloro-2-methyl-1,6-naphthyridin-3-yl)-2,4-difluorophenyl)-3-(3-hydroxy-3-methylbutyl)urea | 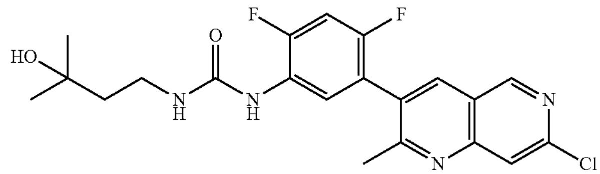 [SMILES: Cc1nc2cc(Cl)ncc2cc1-c1cc(NC(=O)NCCC(C)(C)O)c(F)cc1F] | MS(ESI) m/z: 435.1 (M + H⁺) |
| 187 | 1-(5-(7-chloro-2-methyl-1,6-naphthyridin-3-yl)-2-fluorophenyl)-3-(3,3,3-trifluoropropyl)urea | 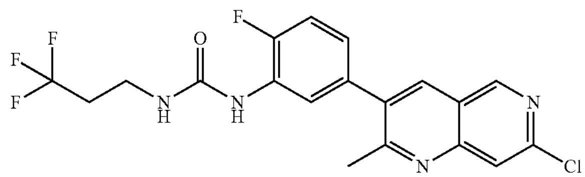 | MS(ESI) m/z: 427.1 (M + H⁺) |
| 188 | 1-(5-(7-chloro-2-methyl-1,6-naphthyridin-3-yl)-2,4-difluorophenyl)-3-(2-cyclopropylethyl)urea | 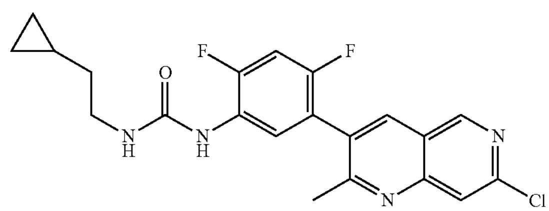 [SMILES: Cc1nc2cc(Cl)ncc2cc1-c1cc(NC(=O)NCCC2CC2)c(F)cc1F] | MS(ESI) m/z: 417.1 (M + H⁺) |
| 189 | 1-(5-(7-chloro-2-methyl-1,6-naphthyridin-3-yl)-2-fluoro-4-methylphenyl)-3-(3,3-dimethylbutyl)urea | 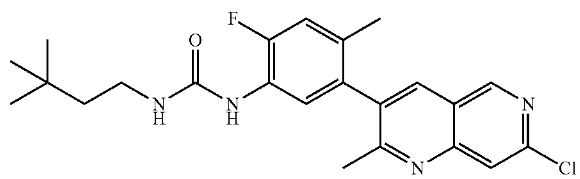 [SMILES: Cc1cc(F)c(NC(=O)NCCC(C)(C)C)cc1-c1cc2cnc(Cl)cc2nc1C] | MS (ESI) m/z: 429.2 (M + H⁺) |
| 190 | 1-(5-(7-chloro-2-methyl-1,6-naphthyridin-3-yl)-2-fluoro-4-methylphenyl)-3-cycloheptylurea | 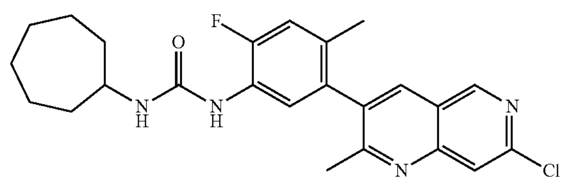 [SMILES: Cc1cc(F)c(NC(=O)NC2CCCCCC2)cc1-c1cc2cnc(Cl)cc2nc1C] | MS (ESI) m/z: 441.2 (M + H⁺) |

Preparation 191

Synthesis of 1-(5-(7-chloro-2-methyl-1,6-naphthyridin-3-yl)-2-fluoro-4-methylphenyl)-3-(2-cyclobutylethyl)urea

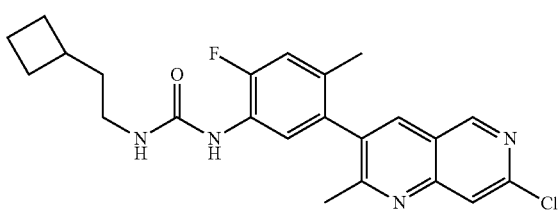 [SMILES: Cc1cc(F)c(NC(=O)NCCC2CCC2)cc1-c1cc2cnc(Cl)cc2nc1C]

Treat a suspension of 3-cyclobutylpropanoic acid (0.204 g, 1.591 mmol) in dioxane (5 mL) with DPPA (0.438 g, 1.591 mmol), 5-(7-chloro-2-methyl-1,6-naphthyridin-3-yl)-2-fluoro-4-methylaniline (0.400 g, 1.326 mmol) and TEA (0.268 g, 2.65 mmol), stir at RT for 0.5 h then heat at 90° C. for 4 h. Concentrate the mixture to dryness and purify via silica gel chromatography (EtOAc/Hex) to afford the title compound (348 mg, 61%) as a white solid. ¹H NMR (400 MHz, DMSO-d₆): δ 9.23 (d, J=0.7 Hz, 1H), 8.30 (m, 2H), 7.98 (m, 2H), 7.22 (d, J=12.3 Hz, 1H), 6.52 (t, J=5.6 Hz, 1H), 2.95 (q, J=6.5 Hz, 2H), 2.42 (s, 3H), 2.25 (m, 1H), 1.96 (m, 2H), 1.94 (s, 3H), 1.75 (m, 2H), 1.52 (m, 4H); MS(ESI) m/z: 427.1 (M+H⁺).

The following compounds are prepared essentially by the method of Preparation 191.

| Prep No. | Chemical Name | Structure | Physical Data |
|---|---|---|---|
| 192 | 1-(5-(7-chloro-2-methyl-1,6-naphthyridin-3-yl)-2-fluorophenyl)-3-(2-cyclobutylethyl)urea | 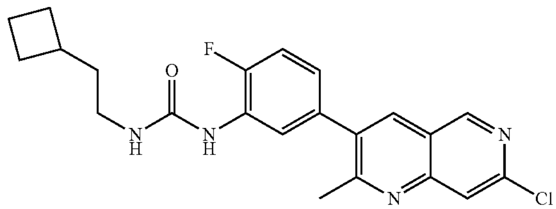 [SMILES: Cc1nc2cc(Cl)ncc2cc1-c1ccc(F)c(NC(=O)NCCC2CCC2)c1] | MS(ESI) m/z: 413.1 (M + H+) |
| 193 | 1-(5-(7-chloro-2-methyl-1,6-naphthyridin-3-yl)-2-fluoro-4-methylphenyl)-3-(3-fluoro-trans(3-methylcyclobutyl))urea | 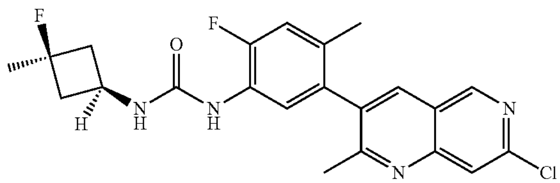 [SMILES: Cc1cc(F)c(NC(=O)N[C@H]2C[C@@](C)(F)C2)cc1-c1cc2cnc(Cl)cc2nc1C] | MS(ESI) m/z: 431.1 (M + H+) |
| 194 | 1-(5-(7-chloro-2-methyl-1,6-naphthyridin-3-yl)-2-fluorophenyl)-3-(3,3-dimethylcyclobutyl)urea | 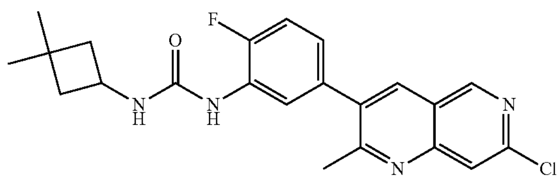 [SMILES: Cc1nc2cc(Cl)ncc2cc1-c1ccc(F)c(NC(=O)NC2CC(C)(C)C2)c1] | MS(ESI) m/z: 413.2 (M + H+) |

Preparation 195

Synthesis of tert-butyl (3-(4-fluoro-5-(3-(3-fluoro-3-methylbutyl)ureido)-2-methylphenyl)-2-methyl-1,6-naphthyridin-7-yl)carbamate

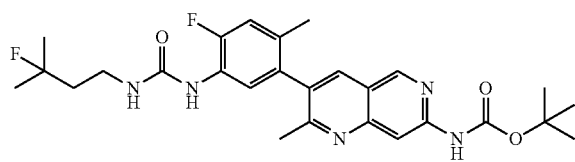 [SMILES: Cc1cc(F)c(NC(=O)NCCC(C)(C)F)cc1-c1cc2cnc(NC(=O)OC(C)(C)C)cc2nc1C]

Combine 1-(5-(7-chloro-2-methyl-1,6-naphthyridin-3-yl)-2-fluoro-4-methylphenyl)-3-(3-fluoro-3-methylbutyl)urea (8.1 g, 18.71 mmol), t-butylcarbamate (6.58 g, 56.1 mmol), potassium carbonate (7.76 g, 56.1 mmol), palladium (II) acetate (0.420 g, 1.871 mmol), and Xantphos (1.083 g, 1.871 mmol) in dioxane (100 mL). Sparge the mixture with argon and sonication for 10 min, then heat at 95° C. overnight. Dilute with EtOAc (100 mL), filter through diatomaceous earth, and wash the filter cake with EtOAc. Evaporate the filtrate and purify by silica gel chromatography (hexane/EtOAc) to yield the title compound (5.81 g, 60.5%). Dissolve the title compound (5.81 g, 11.31 mmol) in THF (100 mL), treat with Si-Thiol (Pd Scavenger) (1.3 mM/g, 9.4 mmol) and stir overnight at RT. Remove the solids via filtration, concentrate the filtrate and dry under high vacuum to afford the title compound (5.81 g, 100%). $^1$H NMR (400 MHz, DMSO-$d_6$): δ 10.02 (s, 1H); 9.06 (d, J=0.8 Hz, 1H); 8.37 (s, 1H); 8.13 (d, J=24.9 Hz, 2H); 7.96 (d, J=8.5 Hz, 1H); 7.20 (d, J=12.3 Hz, 1H); 6.57 (t, J=5.7 Hz, 1H); 3.11-3.18 (m, 2H); 2.36 (s, 3H); 1.95 (s, 3H); 1.74 (dt, J=19.9, 7.5 Hz, 2H); 1.50 (s, 9H); 1.29 (d, J=22 Hz, 6H; MS (ESI) m/z: 514.3 (M+H+).

The following compounds are prepared essentially by the method of Preparation 195.

| Prep No. | Chemical Name | Structure | Physical Data |
|---|---|---|---|
| 196 | tert-butyl (3-(5-(3-cycloheptylureido)-4-fluoro-2-methylphenyl)-2-methyl-1,6-naphthyridin-7-yl)carbamate | 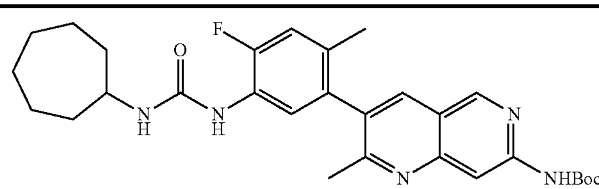 | MS (ESI) m/z: 552.2 (M + H+) |
| 197 | tert-butyl (3-(4-fluoro-2-methyl-5-(3-(2-(1-(trifluoromethyl)cyclopropyl)ethyl)ureido)phenyl)-2-methyl-1,6-naphthyridin-7-yl)carbamate | 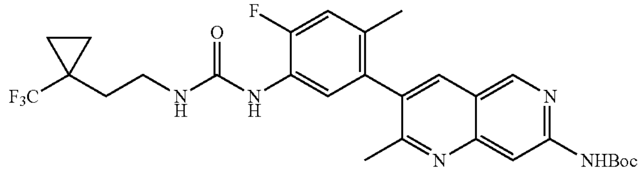 [SMILES: Cc1cc(F)c(NC(=O)NCCC2(C(F)(F)F)CC2)cc1-c1cc2cnc(NC(=O)OC(C)(C)C)cc2nc1C] | MS(ESI) m/z: 562.2 (M + H+) |

| Prep No. | Chemical Name | Structure | Physical Data |
|---|---|---|---|
| 198 | tert-butyl (3-(4-fluoro-5-(3-(3-methoxy-3-methylbutyl)ureido)-2-methylphenyl)-2-methyl-1,6-naphthyridin-7-yl)carbamate | 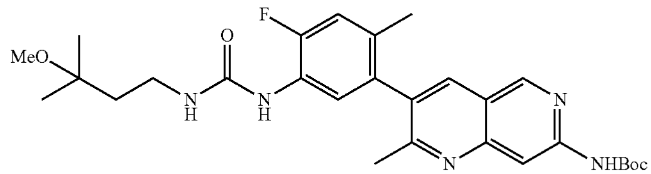 [SMILES: COC(C)(C)CCNC(=O)Nc1cc(-c2cc3cnc(NC(=O)OC(C)(C)C)cc3nc2C)c(C)cc1F] | MS (ESI) m/z: 526.3 (M + H$^+$) |
| 199 | tert-butyl (3-(4-fluoro-5-(3-(3-fluoro-3-methylbutyl)ureido)-2-methylphenyl)-1,6-naphthyridin-7-yl)carbamate | 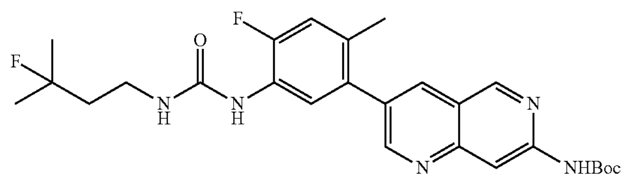 [SMILES: Cc1cc(F)c(NC(=O)NCCC(C)(C)F)cc1-c1cnc2cc(NC(=O)OC(C)(C)C)ncc2c1] | MS (ESI) m/z: 500.3 (M + H$^+$) |

EXAMPLE 79

Synthesis of 1-(5-(7-amino-2-methyl-1,6-naphthyridin-3-yl)-2-fluoro-4-methylphenyl)-3-(3-fluoro-3-methylbutyl)urea

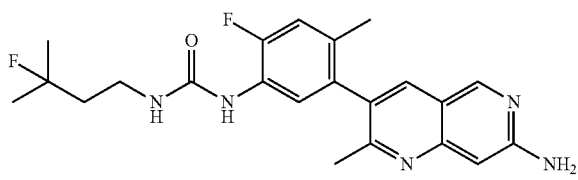 [SMILES: Cc1cc(F)c(NC(=O)NCCC(C)(C)F)cc1-c1cc2cnc(N)cc2nc1C]

Combine tert-butyl (3-(4-fluoro-5-(3-(3-fluoro-3-methylbutyl)ureido)-2-methylphenyl)-2-methyl-1,6-naphthyridin-7-yl)carbamate t-Butyl (3-(4-fluoro-5-(3-(3-fluoro-3-methylbutyl)ureido)-2-methylphenyl)-2-methyl-1,6-naphthyridin-7-yl)carbamate (5.81 g, 11.3 mmol) and a solution of tetrabutylammonium fluoride in THF (1 M, 91 mL, 91 mmol) and heat at 60° C. overnight, then at ~68° C. for an additional 24 h. Dilute the mixture with EtOAc (250 mL) and wash with water (2x) and brine. Back-extract the combined aqueous with EtOAc (100 mL), combine the organics, dry, concentrate, and purify by silica gel chromatography (0-2% MeOH/EtOAc). Triturate with acetonitrile (50 mL) and dry under high vacuum at 80° C. to yield the title compound (2.88 g, 61.5%). $^1$H NMR (400 MHz, DMSO-d$_6$): δ 8.78 (d, J=0.8 Hz, 1H); 8.33 (s, 1H); 7.92 (d, J=8.5 Hz, 1H); 7.83 (s, 1H); 7.16 (d, J=12.4 Hz, 1H); 6.65 (s, 1H); 6.55 (t, J=5.7 Hz, 1H); 6.23 (s, 2H); 3.15 (q, J=7.0 Hz, 2H); 2.25 (s, 3H); 1.95 (s, 3H); 1.74 (dt, J=19.9, 7.5 Hz, 2H); 1.29 (d, J=22 Hz, 6H); MS (ESI) m/z: 414.2 (M+H$^+$).

The following compounds are prepared essentially by the method of Example 79.

| Ex No. | Chemical Name | Structure | Physical Data |
|---|---|---|---|
| 80 | 1-(5-(7-amino-2-methyl-1,6-naphthyridin-3-yl)-2-fluoro-4-methylphenyl)-3-(3-methoxy-3-methylbutyl)urea hydrochloride | 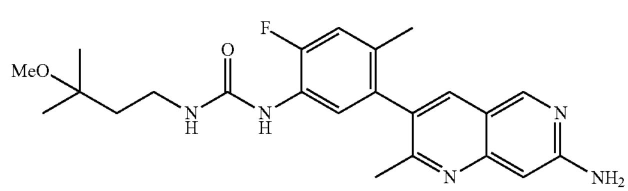 [SMILES: COC(C)(C)CCNC(=O)Nc1cc(-c2cc3cnc(N)cc3nc2C)c(C)cc1F] | MS (ESI) m/z: 426.2 (M + H$^+$) |
| 81 | 1-(5-(7-amino-1,6-naphthyridin-3-yl)-2-fluoro-4-methylphenyl)-3-(3-fluoro-3-methylbutyl)urea | 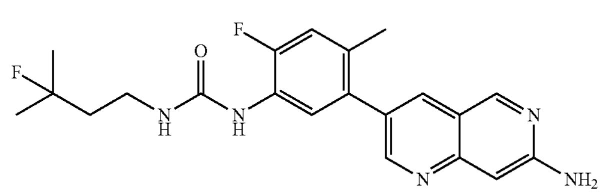 [SMILES: Cc1cc(F)c(NC(=O)NCCC(C)(C)F)cc1-c1cnc2cc(N)ncc2c1] | MS (ESI) m/z: 400.2 (M + H$^+$) |

EXAMPLE 82

Synthesis of 1-(5-(7-amino-2-methyl-1,6-naphthyridin-3-yl)-2-fluoro-4-methylphenyl)-3-cycloheptylurea

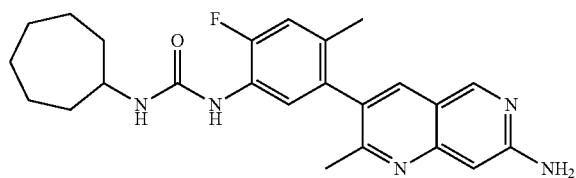 [SMILES: Cc1cc(F)c(NC(=O)NC2CCCCCC2)cc1-c1cc2cnc(N)cc2nc1C]

Add HCl (6.0 M, 1.058 mL, 6.35 mmol) to a solution of tert-butyl (3-(5-(3-cycloheptylureido)-4-fluoro-2-methylphenyl)-2-methyl-1,6-naphthyridin-7-yl)carbamate (0.331 g, 0.635 mmol) in MeOH (10 mL) and heat at 50° C. for 1 h. Cool to RT, concentrate to dryness, add DCM and TEA and concentrate to dryness again. Add water to the residue, extract with DCM (4×), dry the combined organics over $Na_2SO_4$, concentrate to dryness and purify via silica gel chromatography (MeOH/DCM) to afford the title compound (202 mg, 76%) as a yellow solid. $^1$H NMR (400 MHz, DMSO-$d_6$): δ 8.82 (s, 1H), 8.21 (s, 1H), 7.95 (m, 2H), 7.16 (d, J=12.3 Hz, 1H), 6.65-6.62 (m, 2H), 6.39 (s, 2H), 3.62 (s, 1H), 2.28 (s, 3H), 1.95 (s, 3H), 1.76 (m, 2H), 1.44-1.41 (m, 10H); MS (ESI) m/z: 422.2 (M+H$^+$).

The following compounds is prepared essentially by the method of Example 82.

EXAMPLE 84

Synthesis of 1-(2-cyclopropylethyl)-3-(2-fluoro-4-methyl-5-(2-methyl-7-(methylamino)-1,6-naphthyridin-3-yl)phenyl)urea hydrochloride

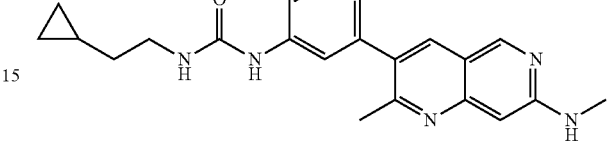

Add $Pd_2(dba)_3$ (0.020 g, 0.022 mmol), 2-di-tert-butylphosphino-2',4',6'-triisopropylbiphenyl [t-butyl X-Phos] (0.019 g, 0.045 mmol), methylamine (2.0M in THF, 1.114 mL, 2.228 mmol) and $Cs_2CO_3$ (0.436 g, 1.337 mmol) to a solution of 1-(5-(7-chloro-2-methyl-1,6-naphthyridin-3-yl)-2-fluoro-4-methylphenyl)-3-(2-cyclopropylethyl)urea (0.184 g, 0.446 mmol) in dioxane (4 mL) and heat at 90° C. for 3 h. Cool to RT, remove the solids via filtration, rinse with DCM, then THF, concentrate the filtrate to dryness and purify via silica gel chromatography (EtOAc/Hex) to afford 1-(2-cyclopropylethyl)-3-(2-fluoro-4-methyl-5-(2-methyl-7-(methylamino)-1,6-naphthyridin-3-yl)phenyl)urea (108 mg, 59%) as a light yellow solid. $^1$H NMR (400 MHz, DMSO-$d_6$): δ 8.82 (s, 1H), 8.28 (d, J=2.4 Hz, 1H), 7.95 (d, J=8.5 Hz, 1H), 7.85 (s, 1H), 7.16 (d, J=12.4 Hz, 1H), 6.78-6.72 (m, 1H), 6.59 (m, 1H), 6.52 (s, 1H), 3.10 (q, J=6.5 Hz, 2H), 2.82 (d, J=5.0 Hz, 3H), 2.26 (s, 3H), 1.95 (s, 3H), 1.37 (m, 2H), 0.70 (m, 1H), 0.35 (m, 2H), 0.04 (m, 2H); MS(ESI) m/z: 408.2 (M+H$^+$). Suspend 1-(2-cyclopropylethyl)-3-(2-fluoro-4-methyl-5-(2-methyl-7-(methylamino)-1,6-naphthyridin-3-yl)phenyl)urea, (0.108 g, 0.265 mmol) in acetonitrile (4 mL), treat with 0.5 M HCl (0.53 mL, 0.265 mmol), freeze and lyophilize the resulting clear solution to provide the title compound. MS(ESI) m/z: 408.2 (M+H$^+$).

| Ex No. | Chemical Name | Structure | Physical Data |
|---|---|---|---|
| 83 | 1-(5-(7-amino-2-methyl-1,6-naphthyridin-3-yl)-2-fluoro-4-methylphenyl)-3-(2-(1-(trifluoromethyl)cyclopropyl)ethyl)urea hydrochloride | 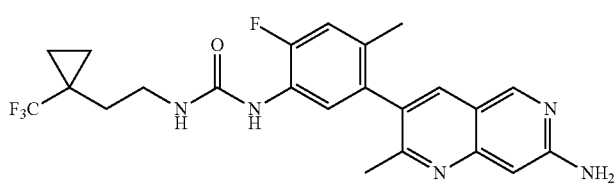 [SMILES: Cc1cc(F)c(NC(=O)NCCC2(C(F)(F)F)CC2)cc1-c1cc2cnc(N)cc2nc1C] | MS (ESI) m/z: 462.2 (M + H$^+$) |

The following compounds are prepared essentially by the method of Example 84.

| Ex No. | Chemical Name | Structure | Physical Data |
|---|---|---|---|
| 85 | 1-cycloheptyl-3-(2-fluoro-5-(2-methyl-7-(methylamino)-1,6-naphthyridin-3-yl)phenyl)urea hydrochloride | 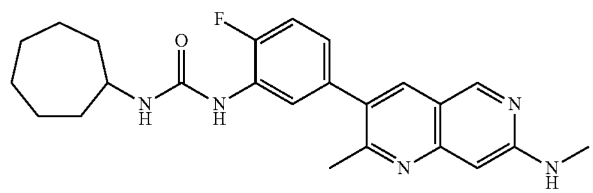 [SMILES: CNc1cc2nc(C)c(-c3ccc(F)c(NC(=O)NC4CCCCCC4)c3)cc2cn1] | MS(ESI) m/z: 422.2 (M + H+) |
| 86 | 1-(3-fluoro-3-methylbutyl)-3-(2-fluoro-5-(2-methyl-7-(methylamino)-1,6-naphthyridin-3-yl)phenyl)urea hydrochloride | 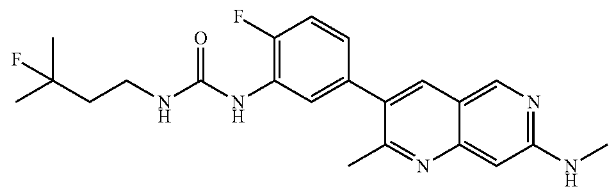 [SMILES: CNc1cc2nc(C)c(-c3ccc(F)c(NC(=O)NCCC(C)(C)F)c3)cc2cn1] | MS (ESI) m/z: 414.2 (M + H+) |
| 87 | 1-(2-fluoro-4-methyl-5-(2-methyl-7-(methylamino)-1,6-naphthyridin-3-yl)phenyl)-3-(3,3,3-trifluoropropyl)urea hydrochloride | 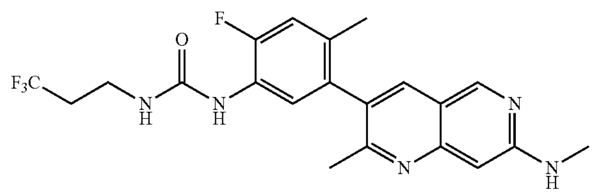 [SMILES: CNc1cc2nc(C)c(-c3cc(NC(=O)NCCC(F)(F)F)c(F)cc3C)cc2cn1] | MS(ESI) m/z: 436.2 (M + H+) |
| 88 | 1-(2,4-difluoro-5-(2-methyl-7-(methylamino)-1,6-naphthyridin-3-yl)phenyl)-3-(4,4-difluorocyclohexyl)urea hydrochloride | 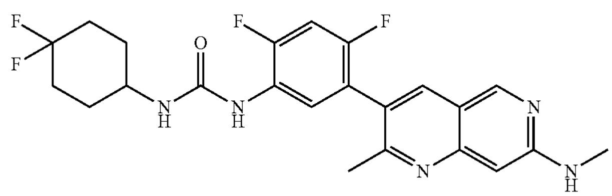 [SMILES: CNc1cc2nc(C)c(-c3cc(NC(=O)NC4CCC(F)(F)CC4)c(F)cc3F)cc2cn1] | MS(ESI) m/z: 462.2 (M + H+) |
| 89 | 1-(2-fluoro-4-methyl-5-(2-methyl-7-(methylamino)-1,6-naphthyridin-3-yl)phenyl)-3-(4,4,4-trifluoro-3,3-dimethylbutyl)urea hydrochloride | 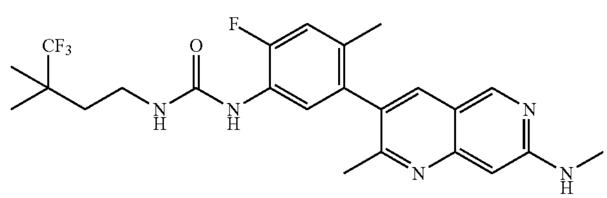 [SMILES: CNc1cc2nc(C)c(-c3cc(NC(=O)NCCC(C)(C)C(F)(F)F)c(F)cc3C)cc2cn1] | MS(ESI) m/z: 478.2 (M + H+) |
| 90 | 1-(2,4-difluoro-5-(2-methyl-7-(methylamino)-1,6-naphthyridin-3-yl)phenyl)-3-(4,4,4-trifluorobutyl)urea hydrochloride | 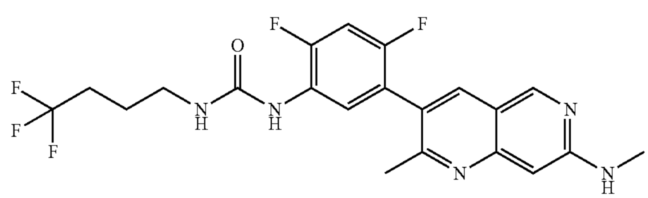 [SMILES: CNc1cc2nc(C)c(-c3cc(NC(=O)NCCCC(F)(F)F)c(F)cc3F)cc2cn1] | MS(ESI) m/z: 454.2 (M + H+) |
| 91 | 1-(2-fluoro-4-methyl-5-(2-methyl-7-(methylamino)-1,6-naphthyridin-3-yl)phenyl)-3-(3,3,3-trifluoropropyl)urea hydrochloride | 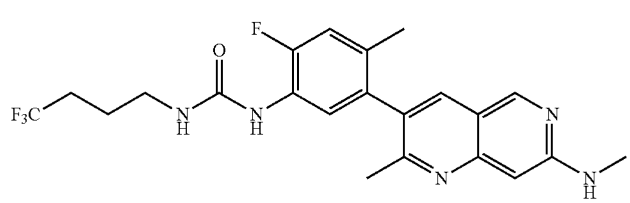 [SMILES: CNc1cc2nc(C)c(-c3cc(NC(=O)NCCCC(F)(F)F)c(F)cc3C)cc2cn1] | MS(ESI) m/z: 450.2 (M + H+) |

-continued

| Ex No. | Chemical Name | Structure | Physical Data |
|---|---|---|---|
| 92 | 1-(2-fluoro-4-methyl-5-(2-methyl-7-(methylamino)-1,6-naphthyridin-3-yl)phenyl)-3-(3-methoxy-3-methylbutyl)urea hydrochloride | 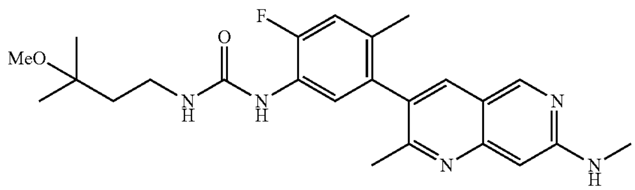 [SMILES: CNc1cc2nc(C)c(-c3cc(NC(=O)NCCC(C)(C)OC)c(F)cc3C)cc2cn1] | MS(ESI) m/z: 440.2 (M + H$^+$) |
| 93 | 1-(3-fluoro-3-methylbutyl)-3-(2-fluoro-4-methyl-5-(7-(methylamino)-1,6-naphthyridin-3-yl)phenyl)urea | 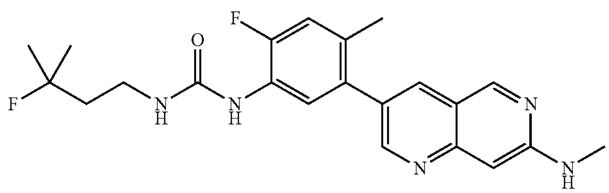 [SMILES: CNc1cc2ncc(-c3cc(NC(=O)NCCC(C)(C)F)c(F)cc3C)cc2cn1] | MS(ESI) m/z: 414.2 (M + H$^+$) |
| 94 | 1-(2,4-difluoro-5-(2-methyl-7-(methylamino)-1,6-naphthyridin-3-yl)phenyl)-3-(2-(1-methylcyclopropyl)ethyl)urea hydrochloride | 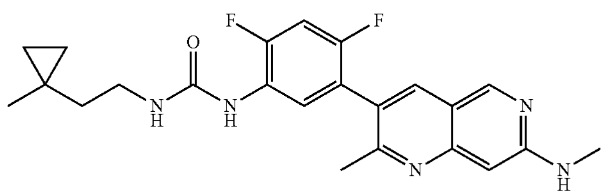 | MS(ESI) m/z: 426.2 (M + H$^+$) |
| 95 | 1-(5-(7-(ethylamino)-2-methyl-1,6-naphthyridin-3-yl)-2-fluoro-4-methylphenyl)-3-(3-fluoro-3-methylbutyl)urea | 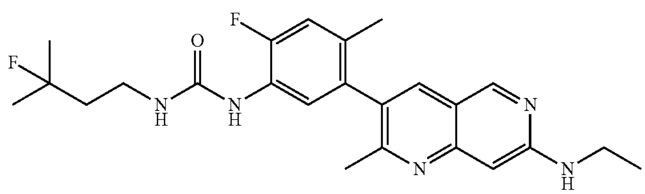 [SMILES: CCNc1cc2nc(C)c(-c3cc(NC(=O)NCCC(C)(C)F)c(F)cc3C)cc2cn1] | MS(ESI) m/z: 442.2 (M + H$^+$) |
| 96 | 1-(3-fluoro-3-methylbutyl)-3-(2-fluoro-5-(7-(isopropylamino)-2-methyl-1,6-naphthyridin-3-yl)-4-methylphenyl)urea | 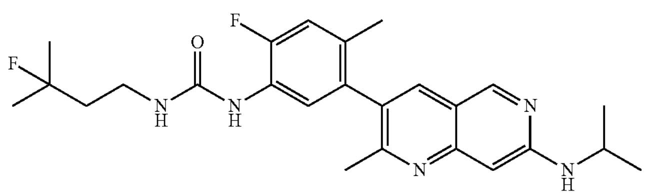 [SMILES: Cc1cc(F)c(NC(=O)NCCC(C)(C)F)cc1-c1cc2cnc(NC(C)C)cc2nc1C] | MS(ESI) m/z: 456.3 (M + H$^+$) |
| 97 | 1-(2-cyclobutylethyl)-3-(2-fluoro-4-methyl-5-(2-methyl-7-(methylamino)-1,6-naphthyridin-3-yl)phenyl)urea hydrochloride | 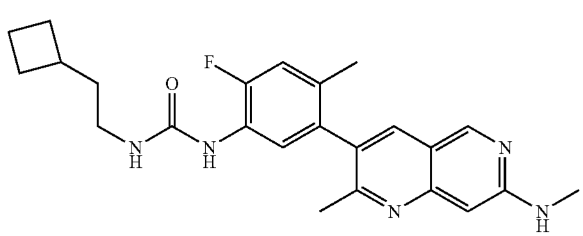 [SMILES: CNc1cc2nc(C)c(-c3cc(NC(=O)NCCC4CCC4)c(F)cc3C)cc2cn1] | MS(ESI) m/z: 422.2 (M + H$^+$) |
| 98 | 1-(2-cyclobutylethyl)-3-(2-fluoro-5-(2-methyl-7-(methylamino)-1,6-naphthyridin-3-yl)phenyl)urea hydrochloride | 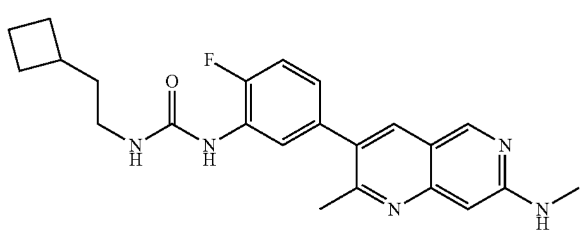 [SMILES: CNc1cc2nc(C)c(-c3ccc(F)c(NC(=O)NCCC4CCC4)c3)cc2cn1] | MS(ESI) m/z: 408.2 (M + H$^+$) |

-continued

| Ex No. | Chemical Name | Structure | Physical Data |
|---|---|---|---|
| 99 | 1-(4,4-difluoropentyl)-3-(2-fluoro-4-methyl-5-(2-methyl-7-(methylamino)-1,6-naphthyridin-3-yl)phenyl)urea hydrochloride | 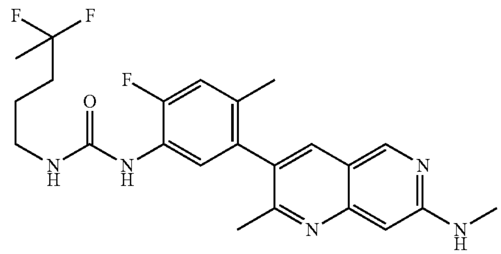 [SMILES: CNc1cc2nc(C)c(-c3cc(NC(=O)NCCCC(C)(F)F)c(F)cc3C)cc2cn1] | MS(ESI) m/z: 446.2 (M + H$^+$) |
| 100 | 1-(3-fluoro-trans(3-methylcyclobutyl))-3-(2-fluoro-4-methyl-5-(2-methyl-7-(methylamino)-1,6-naphthyridin-3-yl)phenyl)urea | 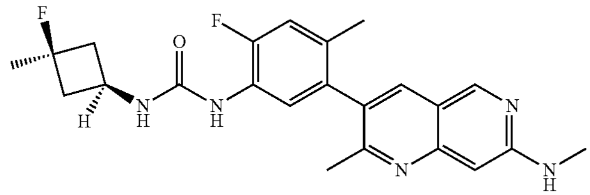 | MS(ESI) m/z: 426.2 (M + H$^+$) |
| 101 | 1-(2-fluoro-4-methyl-5-(2-methyl-7-(methylamino)-1,6-naphthyridin-3-yl)phenyl)-3-(4-fluoro-4-methylpentyl)urea hydrochloride | 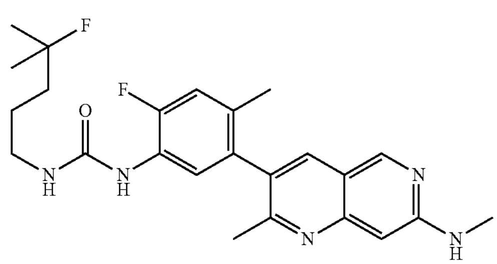 [SMILES: CNc1cc2nc(C)c(-c3cc(NC(=O)NCCCC(C)(C)F)c(F)cc3C)cc2cn1] | MS(ESI) m/z: 442.2 (M + H$^+$) |
| 102 | 1-(2,4-difluoro-5-(2-methyl-7-(methylamino)-1,6-naphthyridin-3-yl)phenyl)-3-(4,4,4-trifluoro-3,3-dimethylbutyl)urea hydrochloride | 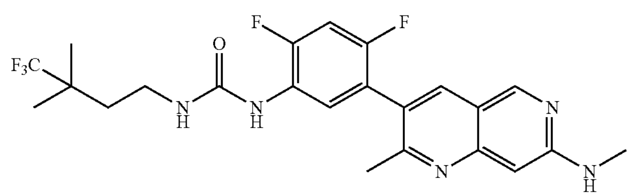 [SMILES: CNc1cc2nc(C)c(-c3cc(NC(=O)NCCC(C)(C)C(F)(F)F)c(F)cc3F)cc2cn1] | MS(ESI) m/z: 482.2 (M + H$^+$) |

EXAMPLE 103

Synthesis of N-(3-(3-(3-(3,3-dimethylbutyl)ureido)-4-fluorophenyl)-2-methyl-1,6-naphthyridin-7-yl)acetamide

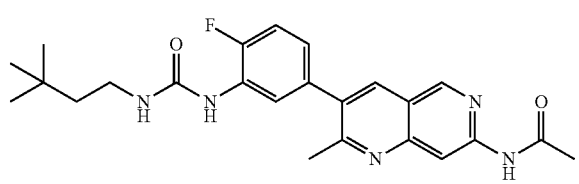 [SMILES: CC(=O)Nc1cc2nc(C)c(-c3ccc(F)c(NC(=O)NCCC(C)(C)C)c3)cc2cn1]

Sprage a mixture of 1-(5-(7-chloro-2-methyl-1,6-naphthyridin-3-yl)-2-fluorophenyl)-3-(3,3-dimethylbutyl)urea (0.200 g, 0.482 mmol), XantPhos (0.028 g, 0.048 mmol), Cs$_2$CO$_3$ (0.314 g, 0.964 mmol) and acetamide (0.142 g, 2.410 mmol) in dioxane (5 mL) with Ar, add Pd$_2$(dba)$_3$ (0.022 g, 0.024 mmol), heat at 100° C. for 7 h, then cool to RT overnight. Remove the solids via filtration through diatomaceous earth, rinse well with THF, wash the filtrate with brine (2×), dry over MgSO$_4$, concentrate to dryness and purify via silica gel chromatography (MeOH/DCM). Triturate with MTBE, collect the solid via filtration and dry to afford the title compound (105 mg, 49%) as a pale yellow solid. $^1$H NMR (400 MHz, DMSO-d$_6$): δ 10.74 (s, 1H), 9.15 (d, J=0.8 Hz, 1H), 8.49 (s, 1H), 8.41 (d, J=2.6 Hz, 1H), 8.26 (dd, J=7.9, 2.3 Hz, 1H), 8.20 (s, 1H), 7.30 (dd, J=11.4, 8.4 Hz, 1H), 7.03 (ddd, J=8.4, 4.7, 2.3 Hz, 1H), 6.57 (t, J=5.6 Hz, 1 H), 3.11-3.05 (m, 2H), 2.57 (s, 3H), 2.15 (s, 3H), 1.36-1.31 (m, 2H), 0.88 (s, 9H); MS (ESI) m/z: 438.3 (M+H$^+$).

The following compounds are prepared essentially by the method of Example 103.

| Ex No. | Chemical Name | Structure | Physical Data |
|---|---|---|---|
| 104 | N-(3-(5-(3-(3,3-dimethylbutyl)ureido)-4-fluoro-2-methylphenyl)-2-methyl-1,6-naphthyridin-7-yl)acetamide hydrochloride | 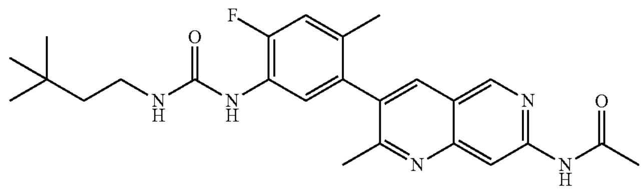 [SMILES: CC(=O)Nc1cc2nc(C)c(-c3cc(NC(=O)NCCC(C)(C)C)c(F)cc3C)cc2cn1] | MS (ESI) m/z: 452.2 (M + H$^+$) |
| 105 | N-(3-(5-(3-(3,3-dimethylbutyl)ureido)-2,4-difluorophenyl)-2-methyl-1,6-naphthyridin-7-yl)acetamide | 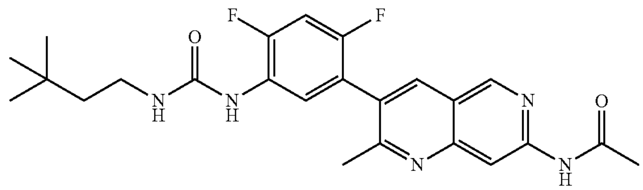 [SMILES: CC(=O)Nc1cc2nc(C)c(-c3cc(NC(=O)NCCC(C)(C)C)c(F)cc3F)cc2cn1] | MS (ESI) m/z: 456.2 (M + H$^+$) |
| 106 | N-(3-(5-(3-(3,3-dimethylbutyl)ureido)-2-methylphenyl)-2-methyl-1,6-naphthyridin-7-yl)acetamide hydrochloride | 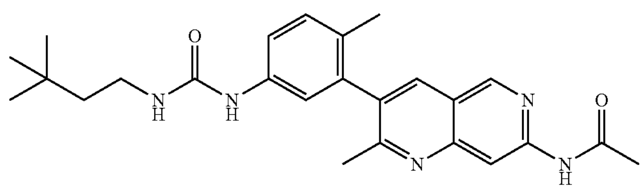 [SMILES: CC(=O)Nc1cc2nc(C)c(-c3cc(NC(=O)NCCC(C)(C)C)ccc3C)cc2cn1] | MS (ESI) m/z: 434.3 (M + H$^+$) |
| 107 | N-(3-(3-(3-cycloheptylureido)-4-fluorophenyl)-2-methyl-1,6-naphthyridin-7-yl)acetamide hydrochloride | 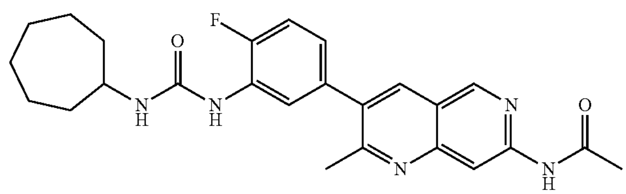 [SMILES: CC(=O)Nc1cc2nc(C)c(-c3ccc(F)c(NC(=O)NC4CCCCCC4)c3)cc2cn1] | MS(ESI) m/z: 450.2 (M + H$^+$) |
| 108 | N-(3-(3-(3-cyclohexylureido)-4-fluorophenyl)-2-methyl-1,6-naphthyridin-7-yl)acetamide hydrochloride | 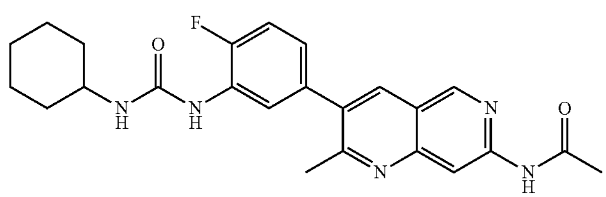 [SMILES: CC(=O)Nc1cc2nc(C)c(-c3ccc(F)c(NC(=O)NC4CCCCC4)c3)cc2cn1] | MS(ESI) m/z: 436.2 (M + H$^+$) |
| 109 | N-(3-(3-(3-cyclopentylureido)-4-fluorophenyl)-2-methyl-1,6-naphthyridin-7-yl)acetamide hydrochloride | 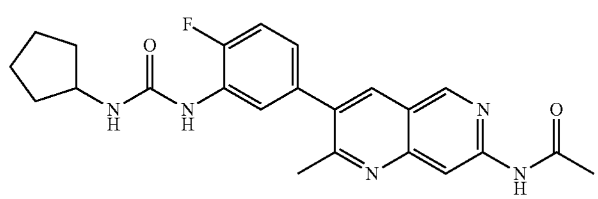 [SMILES: CC(=O)Nc1cc2nc(C)c(-c3ccc(F)c(NC(=O)NC4CCCC4)c3)cc2cn1] | MS(ESI) m/z: 422.2 (M + H$^+$) |
| 110 | N-(3-(3-(3-(2-cyclopentylethyl)ureido)-4-fluorophenyl)-2-methyl-1,6-naphthyridin-7-yl)acetamide hydrochloride | 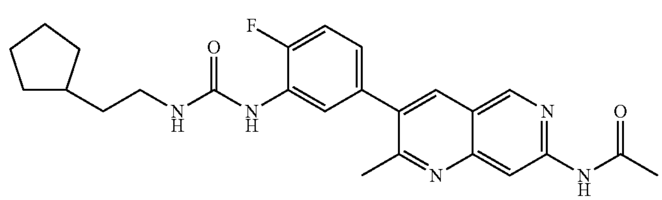 [SMILES: CC(=O)Nc1cc2nc(C)c(-c3ccc(F)c(NC(=O)NCCC4CCCC4)c3)cc2cn1] | MS(ESI) m/z: 450.2 (M + H$^+$) |
| 111 | N-(3-(3-(3-(2-cyclopropylethyl)ureido)-4-fluorophenyl)-2-methyl-1,6-naphthyridin-7-yl)acetamide hydrochloride | 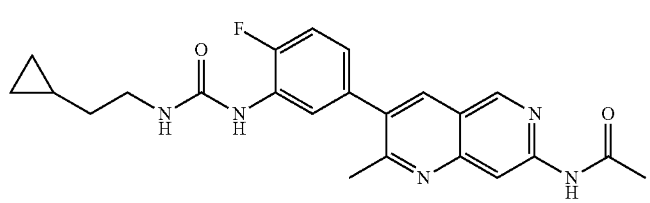 [SMILES: CC(=O)Nc1cc2nc(C)c(-c3ccc(F)c(NC(=O)NCCC4CC4)c3)cc2cn1] | MS(ESI) m/z: 422.2 (M + H$^+$) |

-continued

| Ex No. | Chemical Name | Structure | Physical Data |
|---|---|---|---|
| 112 | N-(3-(3-(3-(3,3-dimethylcyclobutyl)ureido)-4-fluorophenyl)-2-methyl-1,6-naphthyridin-7-yl)acetamide | 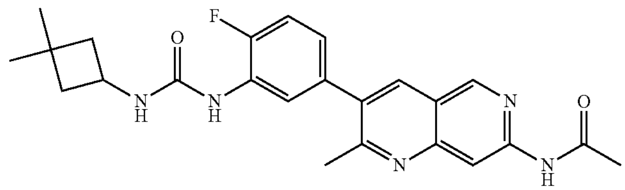 [SMILES: CC(=O)Nc1cc2nc(C)c(-c3ccc(F)c(NC(=O)NC4CC(C)(C)C4)c3)cc2cn1] | MS(ESI) m/z: 436.2 (M + H$^+$) |
| 113 | N-(3-(4-fluoro-5-(3-(3-fluoro-3-methylbutyl)ureido)-2-methylphenyl)-2-methyl-1,6-naphthyridin-7-yl)propionamide hydrochloride | 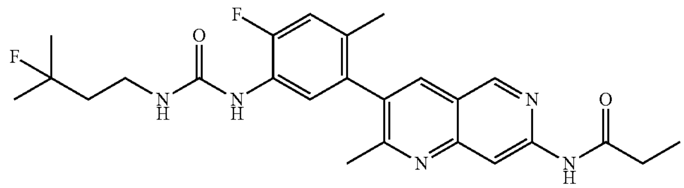 [SMILES: CCC(=O)Nc1cc2nc(C)c(-c3cc(NC(=O)NCCC(C)(C)F)c(F)cc3C)cc2cn1] | MS(ESI) m/z: 470.3 (M + H$^+$) |
| 114 | N-(3-(2,4-difluoro-5-(3-(3-fluoro-3-methylbutyl)ureido)phenyl)-2-methyl-1,6-naphthyridin-7-yl)acetamide | 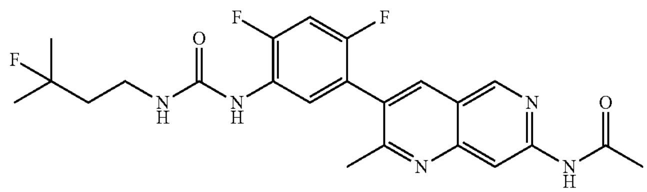 [SMILES: CC(=O)Nc1cc2nc(C)c(-c3cc(NC(=O)NCCC(C)(C)F)c(F)cc3F)cc2cn1] | MS (ESI) m/z: 460.2 (M + H$^+$) |
| 115 | N-(3-(2,4-difluoro-5-(3-(3-hydroxy-3-methylbutyl)ureido)phenyl)-2-methyl-1,6-naphthyridin-7-yl)acetamide | 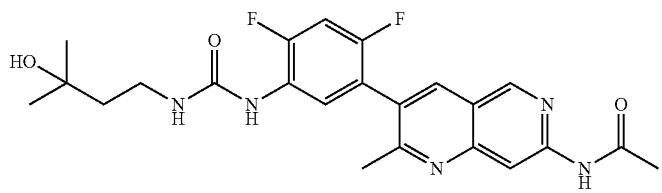 [SMILES: CC(=O)Nc1cc2nc(C)c(-c3cc(NC(=O)NCCC(C)(C)O)c(F)cc3F)cc2cn1] | MS (ESI) m/z: 458.2 (M + H$^+$) |
| 116 | N-(3-(4-fluoro-2-methyl-5-(3-(3,3,3-trifluoropropyl)ureido)phenyl)-2-methyl-1,6-naphthyridin-7-yl)cyclopropanecarboxamide hydrochloride | 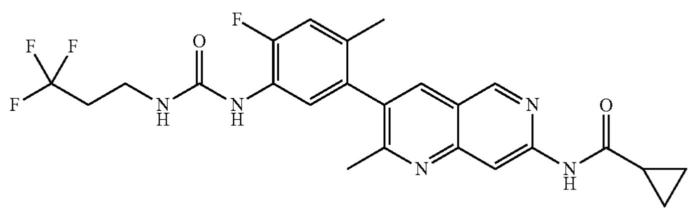 [SMILES: Cc1cc(F)c(NC(=O)NCCC(F)(F)F)cc1-c1cc2cnc(NC(=O)C3CC3)cc2nc1C] | MS(ESI) m/z: 490.2 (M + H$^+$) |
| 117 | N-(3-(4-fluoro-5-(3-(3-fluoro-3-methylbutyl)ureido)-2-methylphenyl)-2-methyl-1,6-naphthyridin-7-yl)acetamide hydrochloride | 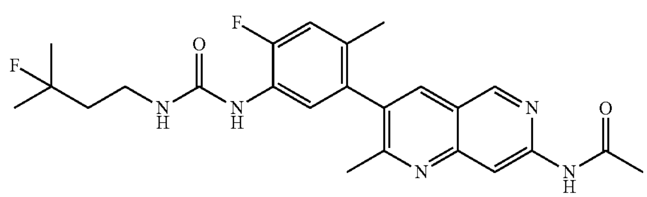 [SMILES: CC(=O)Nc1cc2nc(C)c(-c3cc(NC(=O)NCCC(C)(C)F)c(F)cc3C)cc2cn1] | MS(ESI) m/z: 456.3 (M + H$^+$) |
| 118 | N-(3-(4-fluoro-5-(3-(3-fluoro-3-methylbutyl)ureido)-2-methylphenyl)-2-methyl-1,6-naphthyridin-7-yl)cyclopropanecarboxamide hydrochloride | 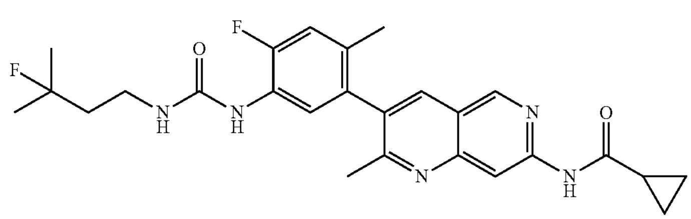 [SMILES: Cc1cc(F)c(NC(=O)NCCC(C)(C)F)cc1-c1cc2cnc(NC(=O)C3CC3)cc2nc1C] | MS(ESI) m/z: 482.3 (M + H$^+$) |

| Ex No. | Chemical Name | Structure | Physical Data |
|---|---|---|---|
| 119 | N-(3-(4-fluoro-5-(3-(3-fluoro-3-methylbutyl)ureido)-2-methylphenyl)-2-methyl-1,6-naphthyridin-7-yl)isobutyramide hydrochloride | 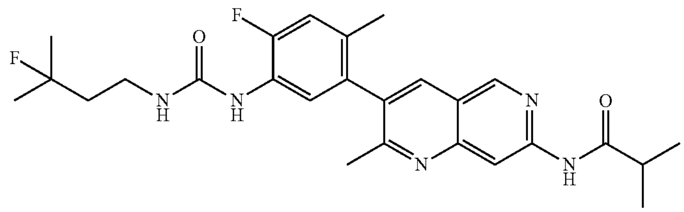 [SMILES: Cc1cc(F)c(NC(=O)NCCC(C)(C)F)cc1-c1cc2cnc(NC(=O)C(C)C)cc2nc1C] | MS(ESI) m/z: 484.2 (M + H⁺) |
| 120 | N-(3-(4-fluoro-3-(3-(3,3,3-trifluoropropyl)ureido)phenyl)-2-methyl-1,6-naphthyridin-7-yl)cyclopropanecarboxamide hydrochloride | 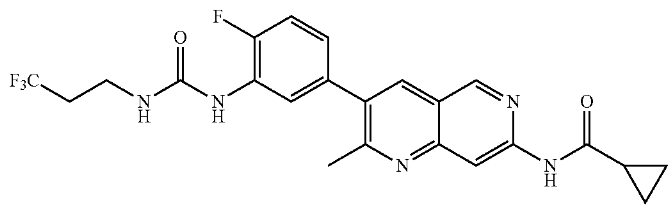 [SMILES: Cc1nc2cc(NC(=O)C3CC3)ncc2cc1-c1ccc(F)c(NC(=O)NCCC(F)(F)F)c1] | MS(ESI) m/z: 476.2 (M + H⁺) |
| 121 | N-(3-(2,4-difluoro-5-(3-(3-fluoro-3-methylbutyl)ureido)phenyl)-2-methyl-1,6-naphthyridin-7-yl)cyclopropanecarboxamide hydrochloride | 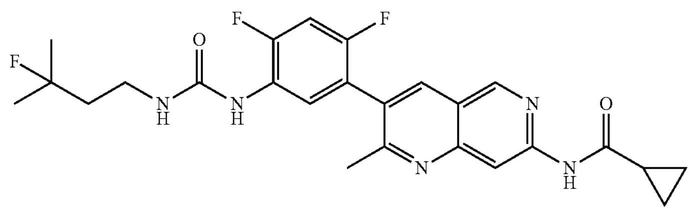 [SMILES: Cc1nc2cc(NC(=O)C3CC3)ncc2cc1-c1cc(NC(=O)NCCC(C)(C)F)c(F)cc1F] | MS(ESI) m/z: 486.2 (M + H⁺) |
| 122 | N-(3-(2,4-difluoro-5-(3-(4,4,4-trifluorobutyl)ureido)phenyl)-2-methyl-1,6-naphthyridin-7-yl)cyclopropanecarboxamide hydrochloride | 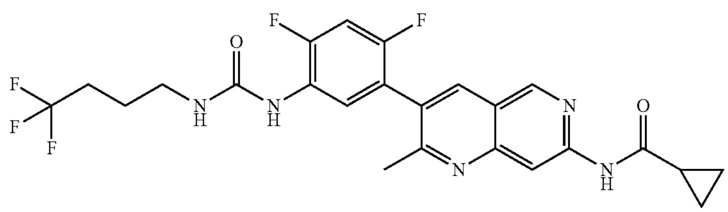 [SMILES: Cc1nc2cc(NC(=O)C3CC3)ncc2cc1-c1cc(NC(=O)NCCCC(F)(F)F)c(F)cc1F] | MS(ESI) m/z: 508.2 (M + H⁺) |
| 123 | N-(3-(5-(3-(2-cyclopropylethyl)ureido)-2,4-difluorophenyl)-2-methyl-1,6-naphthyridin-7-yl)cyclopropanecarboxamid hydrochloride | 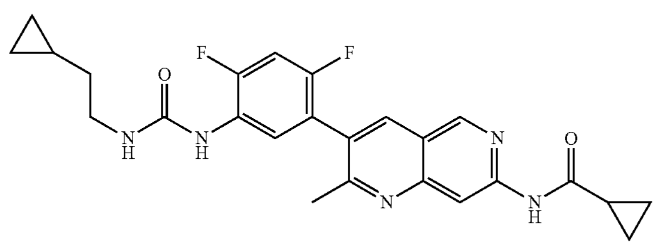 [SMILES: Cc1nc2cc(NC(=O)C3CC3)ncc2cc1-c1cc(NC(=O)NCCC2CC2)c(F)cc1F] | MS(ESI) m/z: 466.2 (M + H⁺) |
| 124 | N-(3-(4-fluoro-2-methyl-5-(3-(4,4,4-trifluoro-3,3-dimethylbutyl)ureido)phenyl)-2-methyl-1,6-naphthyridin-7-yl)acetamide | 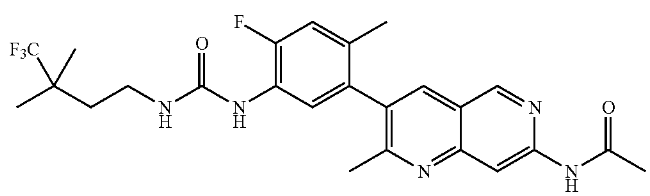 [SMILES: CC(=O)Nc1cc2nc(C)c(-c3cc(NC(=O)NCCC(C)(C)C(F)(F)F)c(F)cc3C)cc2cn1] | MS (ESI) m/z: 506.2 (M + H⁺) |
| 125 | N-(3-(4-fluoro-5-(3-(3-fluoro-3-methylbutyl)ureido)-2-methylphenyl)-2-methyl-1,6-naphthyridin-7-yl)formamide hydrochloride | 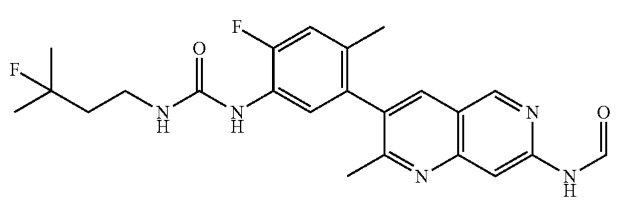 [SMILES: Cc1cc(F)c(NC(=O)NCCC(C)(C)F)cc1-c1cc2cnc(NC=O)cc2nc1C] | MS(ESI) m/z: 442.1 (M + H⁺) |

EXAMPLE 126

Synthesis of 1-(5-(7-amino-2-methyl-1,6-naphthyridin-3-yl)-2-fluorophenyl)-3-(3,3-dimethylbutyl)urea

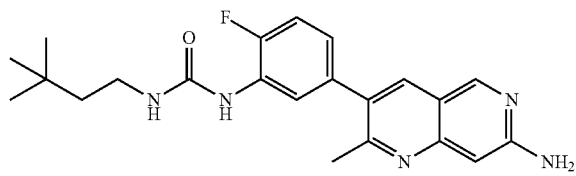 [SMILES: Cc1nc2cc(N)ncc2cc1-c1ccc(F)c(NC(=O)NCCC(C)(C)C)c1]

Add HCl (3M, 4 mL, 12 mmol) to a suspension of N-(3-(3-(3-(3,3-dimethylbutyl)ureido)-4-fluorophenyl)-2-methyl-1,6-naphthyridin-7-yl)acetamide (70 mg, 0.160 mmol) in EtOH (4 mL), stir at RT for 1.5 h, then heat at 50° C. for 4 h. Cool to RT, remove the organics under reduced pressure and filter the aqueous residue. Add satd. NaHCO₃ to the filtrate until pH=8, extract with THF (3×), wash the combined organics with brine, dry over MgSO₄ and concentrate to dryness. Suspend the material in 4:1 MeCN/H₂O, collect the solid via filtration and dry to afford the title compound (47 mg, 74%) as a golden-tan solid. MS (ESI) m/z: 396.2 (M+H⁺).

The following compounds are prepared essentially by the method of Example 126.

Sparge a suspension of 1-(5-(7-chloro-2-methyl-1,6-naphthyridin-3-yl)-2-fluoro-4-methylphenyl)-3-(3,3-dimethylbutyl)urea (0.267 g, 0.622 mmol), trifluoroacetamide (0.704 g, 6.22 mmol), Pd₂(dba)₃ (0.029 g, 0.031 mmol), XantPhos (0.036 g, 0.062 mmol) and Cs₂CO₃ (1.014 g, 3.11 mmol) in dioxane (5 mL) with argon and heat at 95° C. overnight. Add additional trifluoroacetamide (0.704 g, 6.22 mmol), Pd₂(dba)₃ (0.029 g, 0.031 mmol), XantPhos (0.036 g, 0.062 mmol), Cs₂CO₃ (1.014 g, 3.11 mmol) and dioxane (5 mL) and heat at 110° C. overnight. Cool to RT, add water, extract with 4:1 EtOAc/THF (3×), wash the combined organics with satd. Na₂CO₃, then brine, dry over Na₂SO₄, concentrate to dryness and purify via silica gel chromatography (MeOH/DCM). Re-purify via reverse-phase chromatography (MeCN/H₂O with 0.1% TFA), remove the organics under reduced pressure, neutralize the aqueous material with satd. Na₂CO₃, collect the resulting solid via filtration and dry to afford the free base (43 mg, 17%). Add HCl (0.5 M, 0.252 mL, 0.126 mmol) to a solution of the free base (0.043 g, 0.105 mmol) in MeCN (2

| Ex No. | Chemical Name | Structure | Physical Data |
|---|---|---|---|
| 127 | 1-(5-(7-amino-2-methyl-1,6-naphthyridin-3-yl)-2-fluoro-4-methylphenyl)-3-(4,4,4-trifluoro-3,3-dimethylbutyl)urea hydrochloride | 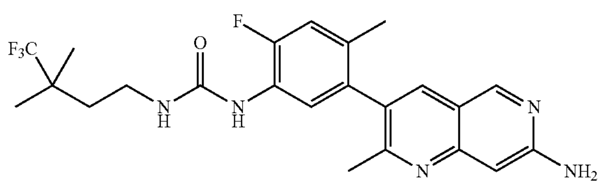 [SMILES: Cc1cc(F)c(NC(=O)NCCC(C)(C)C(F)(F)F)cc1-c1cc2cnc(N)cc2nc1C] | MS (ESI) m/z: 464.2 (M + H⁺) |
| 128 | 1-(5-(7-amino-2-methyl-1,6-naphthyridin-3-yl)-2,4-difluorophenyl)-3-(3,3-dimethylbutyl)urea hydrochloride | 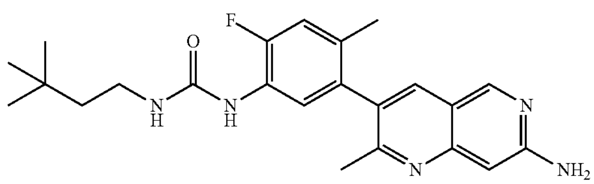 | MS (ESI) m/z: 414.2 (M + H⁺) |

EXAMPLE 129

Synthesis of 1-(5-(7-amino-2-methyl-1,6-naphthyridin-3-yl)-2-fluoro-4-methylphenyl)-3-(3,3-dimethylbutyl)urea hydrochloride

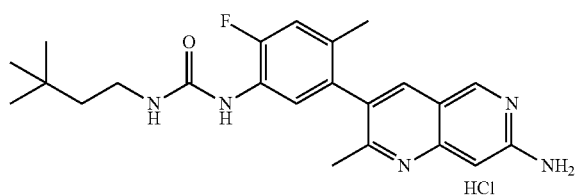 [SMILES: Cc1cc(F)c(NC(=O)NCCC(C)(C)C)cc1-c1cc2cnc(N)cc2nc1C ; Cl]

mL), dilute with H₂O (4 mL), freeze, lyophilize and dry to afford the title compound (44 mg, 94%) as a yellow solid. ¹H NMR (400 MHz, DMSO-d₆): δ 9.07 (s, 1H), 8.52 (s, 1H), 8.34 (s, 1H), 8.03 (d, J=8.4 Hz, 1H), 7.45 (br s, 2H), 7.23 (d, J=12.3 Hz, 1H), 6.74 (s, 1H), 6.54 (t, J=5.6 Hz, 1H), 3.05 (m, 2H), 2.45 (s, 3H), 2.01 (s, 3H), 1.31 (m, 2H), 0.86 (s, 9H); MS (ESI) m/z: 410.2 (M+H⁺).

The following compound is prepared essentially by the method of Example 129.

| Ex No. | Chemical Name | Structure | Physical Data |
|---|---|---|---|
| 130 | 1-(5-(7-amino-2-methyl-1,6-naphthyridin-3-yl)-2,4-difluorophenyl)-3-(3-fluoro-3-methylbutyl)urea hydrochloride | 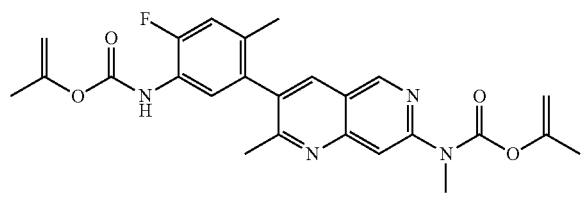 | MS (ESI) m/z: 418.2 (M + H$^+$) |

Preparation 200

Synthesis of prop-1-en-2-yl(3-(4-fluoro-2-methyl-5-(((prop-1-en-2-yloxy)carbonyl)amino)phenyl)-2-methyl-1,6-naphthyridin-7-yl)(methyl)carbamate Add isopropenyl chloroformate (0.269 mL, 2.463 mmol) to a 0° C. suspension of 3-(5-amino-4-fluoro-2-methylphenyl)-N,2-dimethyl-1,6-naphthyridin-7-amine (0.73 g, 2.463 mmol) in pyridine (8 mL, 99 mmol), stir for 1 h at 0° C., warm to RT and concentrate to dryness. Add DCM, wash with H$_2$O (2×), back-extract the combined aqueous layers with DCM, wash the combined organics with brine, dry over Na$_2$SO$_4$, concentrate to dryness and purify via silica gel chromatography (EtOAc/Hex) to afford the title compound (337 mg, 29%). MS(ESI) m/z: 465.2 (M+H$^+$).

EXAMPLE 131

Synthesis of 1-(2-fluoro-4-methyl-5-(2-methyl-7-(methylamino)-1,6-naphthyridin-3-yl)phenyl)-3-phenethylurea hydrochloride

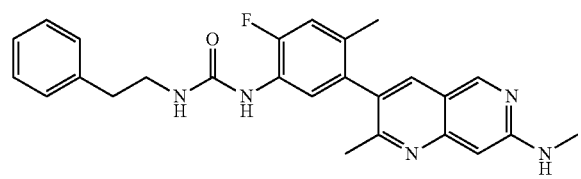 [SMILES: CNc1cc2nc(C)c(-c3cc(NC(=O)NCCc4ccccc4)c(F)cc3C)cc2cn1]

Add 1-methylpyrrolidine (0.075 mL, 0.717 mmol) to a solution of prop-1-en-2-yl(3-(4-fluoro-2-methyl-5-(((prop-1-en-2-yloxy)carbonyl)amino)phenyl)-2-methyl-1,6-naphthyridin-7-yl)(methyl)carbamate (0.333 g, 0.717 mmol) and phenethylamine (0.091 g, 0.753 mmol) in dioxane (6 mL) and heat at 50° C. overnight. Cool to RT, add satd. NaHCO$_3$, extract with EtOAc (3×), dry the combined organics over MgSO$_4$ and concentrate to dryness. Dissolve the residue in dioxane (10 mL), add NaOH (1.0M, 2 mL), stir at RT for 2 h, then heat to 50° C. overnight. Add NaOH (3M, 0.5 mL), heat the mixture at 55° C. for 24 h, then add additional NaOH (3M, 0.25 mL) and heat at 60° C. for 24 h. Cool the mixture to RT, add brine, extract with EtOAc (3×), dry the combined organics over MgSO$_4$, concentrate to dryness and purify via silica gel chromatography (EtOAc/Hex) to afford 1-(2-fluoro-4-methyl-5-(2-methyl-7-(methylamino)-1,6-naphthyridin-3-yl)phenyl)-3-phenethylurea (245 mg, 77%). MS(ESI) m/z: 444.2 (M+H$^+$). Add 0.1N HCl (6.08 mL, 0.608 mmol) to a suspension of 1-(2-fluoro-4-methyl-5-(2-methyl-7-(methylamino)-1,6-naphthyridin-3-yl)phenyl)-3-phenethylurea (0.245 g, 0.552 mmol) in MeCN (2 mL), sonicate for 5 min, freeze, lyophilize and dry to afford the title compound (244 mg, 92%) as an orange solid. $^1$H NMR (400 MHz, DMSO-d$_6$): δ 9.13 (s, 1H), 8.58 (s, 1H), 8.44 (s, 1H), 8.04 (m, 2H), 7.32-7.17 (m, 6H), 6.66 (m, 2H), 3.29 (m, 2H), 2.91 (s, 3H), 2.71 (t, J=7.1 Hz, 2H), 2.51 (s, 3H), 2.01 (s, 3H).

Preparation 201

Synthesis of prop-1-en-2-yl(3-(3-(3-(3,3-dimethylbutyl)ureido)-4-fluorophenyl)-2-methyl-1,6-naphthyridin-7-yl)carbamate

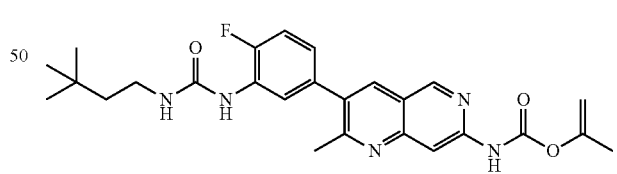

Add isopropenyl chloroformate (0.193 mL, 1.769 mmol) to a 0° C. solution of 1-(5-(7-amino-2-methyl-1,6-naphthyridin-3-yl)-2-fluorophenyl)-3-(3,3-dimethylbutyl)urea (0.636 g, 1.608 mmol) in pyridine (10 mL) and stir the mixture for 1 h as it warms to RT. Add water, extract with DCM (3×), dry the combined organics over MgSO$_4$ and concentrate to dryness to afford the title compound (585 mg, 76%). MS(ESI) m/z: 480.2 (M+H$^+$).

The following compounds are prepared essentially by the method of Preparation 201.

| Prep No. | Chemical Name | Structure | Physical Data |
|---|---|---|---|
| 202 | prop-1-en-2-yl (3-(4-fluoro-5-(3-(3-fluoro-3-methylbutyl)ureido)-2-methylphenyl)-2-methyl-1,6-naphthyridin-7-yl)carbamate | 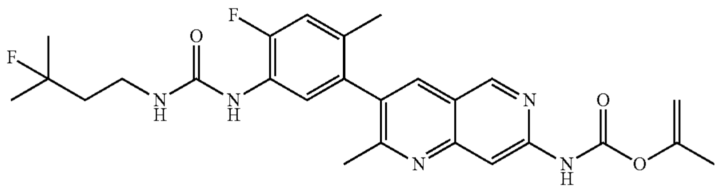 [SMILES: C=C(C)OC(=O)Nc1cc2nc(C)c(-c3cc(NC(=O)NCCC(C)(C)F)c(F)cc3C)cc2cn1] | MS(ESI) m/z: 498.3 (M + H$^+$) |

EXAMPLE 132

Synthesis of 3-(3-(3-(3-(3,3-dimethylbutyl)ureido)-4-fluorophenyl)-2-methyl-1,6-naphthyridin-7-yl)-1,1-dimethylurea hydrochloride

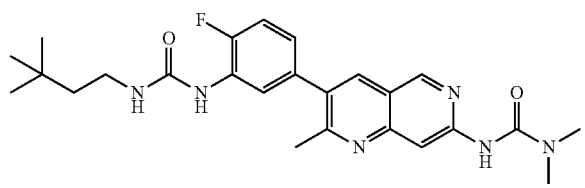 [SMILES: Cc1nc2cc(NC(=O)N(C)C)ncc2cc1-c1ccc(F)c(NC(=O)NCCC(C)(C)C)c1]

Add 1-methylpyrrolidine (0.355 mL, 3.34 mmol) to a suspension of prop-1-en-2-yl(3-(3-(3-(3,3-dimethylbutyl)ureido)-4-fluorophenyl)-2-methyl-1,6-naphthyridin-7-yl)carbamate (0.2 g, 0.417 mmol) and dimethylamine hydrochloride (0.136 g, 1.668 mmol) in dioxane (4 mL) and heat at 60° C. overnight. Cool to RT, add satd. NaHCO$_3$, extract with EtOAc (3×), dry the combined organics over MgSO$_4$, concentrate to dryness and purify via silica gel chromatography (EtOAc/Hex) to afford 3-(3-(3-(3-(3,3-dimethylbutyl)ureido)-4-fluorophenyl)-2-methyl-1,6-naphthyridin-7-yl)-1,1-dimethylurea (99 mg, 51%). MS(ESI) m/z: 467.3 (M+H$^+$). Treat the solid with MeCN (2 mL), add 0.1N HCl (2.33 mL, 0.233 mmol), freeze, lyophilize and dry to afford the title compound (76 mg, 71%). $^1$H NMR (400 MHz, DMSO-d$_6$): δ 9.52 (s, 1H), 9.30 (s, 1H), 8.64 (s, 1H), 8.50 (s, 1H), 8.41 (s, 1H), 8.32 (dd, J=7.9, 2.4 Hz, 1H), 7.35 (dd, J=11.3, 8.4 Hz, 1H), 7.07 (m, 1H), 6.66 (m, 1H), 3.08 (m, 2H), 3.00 (s, 6H), 2.70 (s, 3H), 1.34 (m, 2H), 0.88 (s, 9H); MS(ESI) m/z: 467.3 (M+H$^+$).

The following compounds are prepared essentially by the method of Example 132.

| Ex No. | Chemical Name | Structure | Physical Data |
|---|---|---|---|
| 133 | N-(3-(3-(3-(3,3-dimethylbutyl)ureido)-4-fluorophenyl)-2-methyl-1,6-naphthyridin-7-yl)azetidine-1-carboxamide | 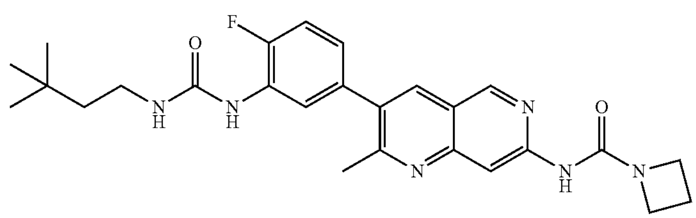 [SMILES: Cc1nc2cc(NC(=O)N3CCC3)ncc2cc1-c1ccc(F)c(NC(=O)NCCC(C)(C)C)c1] | MS(ESI) m/z: 479.3 (M + H$^+$) |
| 134 | 3-(3-(4-fluoro-5-(3-(3-fluoro-3-methylbutyl)ureido)-2-methylphenyl)-2-methyl-1,6-naphthyridin-7-yl)-1,1-dimethylurea hydrochloride | 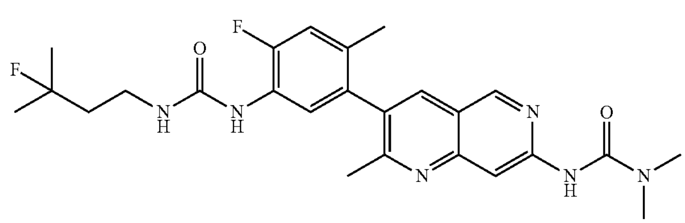 [SMILES: Cc1cc(F)c(NC(=O)NCCC(C)(C)F)cc1-c1cc2cnc(NC(=O)N(C)C)cc2nc1C] | MS(ESI) m/z: 485.2 (M + H$^+$) |

It is generally known that bioavailability of a poorly soluble compound may be enhanced by formulating it as a solid dispersion in a polymer matrix. Such solid dispersions are dispersions of drug in an inert carrier matrix prepared by melting (fusion) of drug-polymer mixtures followed by solidification of the homogeneous molten mixture by rapid cooling (for example using processes such as hot melt extrusion), or by dissolving the drug and polymer in appropriate organic solvent followed by either solvent removal by evaporation (for example spray-drying) or by precipitation using antisolvent. Solid dispersions typically render the drug in an amorphous form which results in faster dissolution rate and/or higher degree (extent) and duration of super saturation leading to enhanced oral bioavailability of poorly soluble compounds relative to the undispersed crystalline drug. Polymers that have been successfully used for solid dispersions include (but are not limited to) polyvinyl pyrrolidone (PVP), polyvinyl pyrrolidone-vinyl acetate (PVP-VA), hydroxypropyl methylcellulose (HPMC), hydroxypropyl methylcellulose acetate succinate (HPMCAS), hydroxypropyl methylcellulose phthalate (HPMCP-55), cellulose acetate phthalate (CAP), and Eudragit® EPO.

Physical and chemical stability of a solid dispersion are factors in the suitability of such formulations. Drug loading is another variable that can impact physical stability of the metastable amorphous form of drug as well as its in vivo performance. A preferred way to administer a solid dispersion in humans is by further formulating it as a capsule or a tablet by adding a pharmaceutically acceptable carrier, and optionally other excipients, suitable for such dosage form manufacturing and performance.

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenvironments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site: http://cgap.nci.nih.gov). The database includes chromosomal aberrations for at least some of the malignancies of the present invention. The Wellcome Trust Sanger Institute Cancer Genome Project maintains a detailed online "Cancer Gene Census" of all human genes that have been causally linked to tumorigenesis (see http://www.sanger.ac.uklgenetics/CGP/Census) as well as the COSMIC (Catalogue of Somatic Mutations in Cancer) database of somatic mutations in human cancer (see http://www.sanger.ac.uklgenetics/CGP/cosmic). A further source containing abundant information on cytogenetic changes causally linked to various cancers is the Atlas of Genetics and Cytogenetics in Oncology and Haematology (http://atlasgeneticsoncology.org//Anomalies/Anomliste.html#MDS). These databases also include chromosomal aberrations for at least some of the malignancies of the present invention.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

The Ras/Raf/MEK/MAPK signaling pathway relays extracellular stimuli to the nucleus, thereby regulating diverse cellular responses including cell proliferation, differentiation and apoptosis. Perturbation of these processes by aberrant MAPK signaling such as genetic alterations often leads to malignant transformation. The importance of this signaling pathway in neoplasms is evident through the discovery of many mutant alleles that activate this pathway in a variety of human malignancies. Oncogenic mutations in receptor tyrosine kinases (RTKs), such as EGFR and cMet, or overexpression of RTKs and their ligands abnormally activate Ras and its downstream components. Activating Ras mutations have been detected in approximately 30% of human cancers. These mutations markedly diminish GTPase activity, thereby rendering Ras in the GTP-bound and active state. In mammals, the Ras family consists of three genes: K-Ras, N-Ras and H-Ras. K-Ras is often mutated in epithelial cancers, such as pancreatic, lung and colorectal cancer, while N-Ras mutations often occur in melanoma, liver and myeloid (AML, CML) malignancies. Activating mutations of B-Raf, a member of Raf family, have been discovered with high frequency in melanoma and thyroid carcinoma and, to a lesser extent, in colorectal, ovarian and lung cancer. Somatic mutations of MEK1 and MEK2 have been identified in melanoma patients. Finally, loss of negative regulators, such as members of the Sprouty family and GAPs (GTPase-activating proteins) such as NF1, can indirectly activate this pathway. It is believed that many tumors exhibit deregulation of Ras/Raf/MEK/MAPK pathway, making it an attractive target for therapeutic intervention.

The Raf proteins are composed of three members, A-Raf, B-Raf and C-Raf (also called Raf1), that play a pivotal role in transducing signals from Ras to downstream components MEK1/2 and ERK1/ERK2. Raf protein kinases have been shown to play a role in tumorigenesis including tumor cell proliferation, survival, invasion and angiogenesis, Sebolt-Leopold et al, *Nat Rev Cancer,* 2004, 4: 937-947; Wellbrock et al, *Nat Rev Mol Cell Biol,* 2004, 5: 875-885. MAPK pathway activation in tumor cells by multiple mechanisms such as mutations or overexpression of RTKs and Ras mutations, all go through Raf proteins. More importantly, activating mutations of B-RAF, Davies et al, *Nature,* 2002, 417: 949-954, are often observed in several malignancies including melanoma, colorectal, lung, ovarian and thyroid carcinomas. Almost 90% of the B-Raf mutations are a T1799A change in exon 15 which results is a Val to Glu amino acid substitution (B-Raf V600E). This mutation in B-Raf leads to constitutive kinase activity approximately 500 fold greater than that of wild type protein, and malignant transformation. Additional mutations, such as T529I, a B-Raf gatekeeper mutation and G468A, a B-Raf secondary mutation are also known and believed to play a role in causing, maintaining, or exacerbating malignant transformation, Whittaker et al, *Sci. Transl. Med.*, 2010, 2(35) ra41; Wan et al, *Cell*, 2004, 116: 855-867.

Recently, a B-Raf specific kinase inhibitor vemurafenib (also called PLX-4032) was approved by the United States Food and Drug Administration (FDA) for treatment of melanoma patients with B-Raf V600E mutation. Vemurafenib is efficacious and provides survival benefit in these patients. However, patients responsive to this drug generally develop drug resistance which leads to disease relapse in an average of 7 months. Similar to many other targeted therapies, the acquired resistance to B-Raf inhibition presents a therapeutic challenge to long-term survival benefit in this patient population.

To improve the benefit of B-Raf inhibitors, research continues to identify the mechanisms which render mutant B-Raf expressing melanoma cells resistant to vemurafenib. Recent studies have indicated that reactivation of the MAPK pathway is a mechanism of resistance to B-Raf inhibition. Resistant mechanisms primarily involve reactivation of ERK signaling through bypass mechanisms that are either Ras/Raf dependent, such as N-Ras activation, Nazarian et al, *Nature*. 2010, 468: 973-7, H-Ras activation (Su et al, *New England Journal of Medicine*. 2012, 366: 207-215), C-Raf upregulation, (Johannessen et al, *Nature*. 2010, 468: 968-72; Montagut et al, *Cancer Res*. 2008, 68: 4853-61), aberrantly spliced variants of B-Raf V600E (Poulikakos et al, *Nature*. 2011, 480: 387-390) or Ras/Raf independent (Tp12/COT overexpression) Johannessen et al, *Nature*. 2010, 468: 968-72. Consequently, multiple mechanisms could attenuate the effect of B-Raf inhibition on MAPK signaling in B-RAF mutant cancers. Although a gatekeeper mutation of B-Raf (T529I) that could cause resistance to BRAF inhibition has not yet been clinically identified, such a mutation has been experimentally demonstrated to cause resistance, Whittaker et al, *Sci Transl Med*. 2010, 2(35): ra41. Recent studies have also suggested that activation of MAPK-redundant signaling pathways by RTKs such as IGF-1R or PDGFRβ could play a role in acquired resistance to B-Raf inhibition; Nazarian et al, *Nature*. 2010, 468: 973-7; Villanueva et al, *Cancer Cell*. 2010, 18: 683-95; Shi et al, *Cancer Res*. 2011, 71: 5067-74. It is clear that MAPK reactivation is involved in many of these resistance mechanisms. A pan Raf inhibitor is expected to block MAPK reactivation.

Additionally, B-Raf specific inhibitors including vemurafenib and its close analogue N-[3-(5-chloro-1H-pyrrolo[2,3-b]pyridine-3-carbonyl)-2,4-difluorophenyl]propane-1-sulfonamide (PLX4720; a commercially available selective B-Raf inhibitor) were demonstrated to induce paradoxical pathway activation through dimerization with other Raf isoforms in a B-Raf wild type background, Hatzivassiliou G, et al. *Nature*, 2010, 464: 431-435; Poulikakos et al, *Nature*, 2010, 464: 427-430; Heidorn, et al, *Cell*, 2010, 140: 209-221. Vemurafenib is believed to activate the Raf/MEK/ERK pathway through binding B-Raf wild type and stimulating B-Raf-C-Raf dimerization. This paradoxical pathway activation by B-Raf specific inhibition is believed to be a major reason of skin side effects (such as squamous cell carcinoma) in some melanoma patients treated with vemurafenib. Vemurafenib is not approved for treatment of cancer patients with B-Raf wild type genetic background due to its paradoxical pathway activation activity in this genetic background.

Certain exemplified compounds of Formula I are Raf kinase inhibitors inhibiting all isoforms of Raf proteins including A-Raf, B-Raf, C-Raf, and B-Raf V600E mutation. Due to their pan Raf activities, certain exemplified compounds of Formula I are active against tumor cells with MAPK pathway activation by upstream signaling such as N-Ras mutation and K-Ras mutation. Therefore, the exemplified compounds of Formula I have the potential for treating cancer patients with B-Raf mutation (such as melanoma, colorectal, lung, ovarian and thyroid carcinoma), N-Ras mutation (such as melanoma, AML, CML, acute lymphocytic leukemia (ALL), CLL, liver cancer), (Schubbert et al, *Nature Reviews Cancer*, 2007, 7: 295; Pylayeva-Gupta et al, *Nature Reviews Cancer*, 2011, 11: 761); or K-Ras mutation (such as biliary tract, cervical, colorectal, endometrial, lung, ovarian, pancreatic, and liver; Schubbert et al, *Nature Reviews Cancer*, 2007, 7: 295; Pylayeva-Gupta et al, *Nature Reviews Cancer*, 2011, 11: 761) or other upstream MAPK pathway activating RTK mutation/overexpression. The exemplified compounds of Formula I are also active against melanoma tumor cells which developed resistance to vemurafenib. Therefore, it is believed that the exemplified compounds will be effective for melanoma patients who have failed vemurafenib or other B-Raf inhibitors.

The exemplified compounds of Formula I are also inhibitors of c-KIT. C-KIT is a receptor tyrosine kinase that normally controls the function of primitive hematopoietic cells, melanocytes and germ cells. Overexpression and genetic mutations (such as L576P, K642E, T670I, and V654A) of c-KIT occur in melanoma, acute myelogenous leukemia, and gastrointestinal stromal tumors (GIST), therefore, the exemplified compounds have the potential to treat melanoma, acute myelogenous leukemia and GIST patients, Lennartsson et al, *Current Cancer Drug Targets*, 2006, 6: 65.

Exemplified compounds of Formula I can be used as a single agent or in combination with one or more other approved drugs for treatment of cancer patients. These cancer patients include: melanoma patients with B-Raf mutation, melanoma patients who failed vemurafenib or other B-Raf inhibitors, melanoma patients with N-Ras mutation, melanoma patients with c-KIT overexpression or c-KIT mutation; colorectal cancer patients with B-Raf mutation or K-Ras mutation; ovarian cancer patients with B-Raf mutation or K-Ras mutation; lung cancer patients with B-Raf mutation or K-Ras mutation; myeloid leukemia patients with N-Ras mutation, or c-KIT overexpression or c-KIT mutation; liver cancer patients with N-Ras or K-Ras mutation; pancreatic cancer patients with K-Ras mutation; thyroid carcinoma patients with B-Raf or N-Ras mutation; biliary tract cancer patients with K-Ras mutation; GIST patients with c-KIT mutation or overexpression.

The following studies demonstrate the Ras/Raf/MEK/ERK pathway signaling inhibitory activity of the exemplified compounds of Formula I. Assays evidencing pan Raf inhibition and pathway signaling inhibitory activity may be carried out substantially as follows or by similar assays affording similar data.

Expression and Purification of B-Raf Proteins

B-Raf V600E (residues 433-726 containing V600E mutation) containing an N-terminal purification tag (MDRGSH-HHHHHGS (SEQ ID NO: 8)) is expressed and purified essentially as described previously (Wan et al, *Cell*, 2004, 116, 855-867).

B-Raf V600E constructs containing a secondary T529I mutation or G468A mutation are generated by site directed mutagenesis (Quikchange, Strategene) of the base B-Raf (433-726, V600E) construct.

Sequence IDs of Screening Constructs:

B-Raf-V600E (Seq ID No. 1)

MDRGSHHHHHHGSEDRNRMKTLGRRDSSDDWEIPDGQITVGQRIGSGSFGTVYK
GKWHGDVAVKMLNVTAPTPQQLQAFKNEVGVLRKTRHVNILLFMGYSTKPQLAI
VTQWCEGSSLYHHLHIIETKFEMIKLIDIARQTAQGMDYLHAKSIIHRDLKSNNIFLH
EDLTVKIGDFGLAT<u>E</u>KSRWSGSHQFEQLSGSILWMAPEVIRMQDKNPYSFQSDVYA
FGIVLYELMTGQLPYSNINNRDQIIFMVGRGYLSPDLSKVRSNCPKAMKRLMAECL
KKKRDERPLFPQILASIELLARSLPKIHR

B-Raf-V600E+T529I (Seq ID No. 2)

MDRGSHHHHHHGSEDRNRMKTLGRRDSSDDWEIPDGQITVGQRIGSGSFGTVYK
GKWHGDVAVKMLNVTA PTPQQLQAFK NEVGVLRKTR
HVNILLFMGYSTKPQLAIV<u>I</u>Q WCEGSSLYHHLHIIETKFE MIKLIDIARQ
TAQGMDYLHA KSIIHRDLKSNNIFLHEDLT VKIGDFGLAT <u>E</u>KSRWSGSHQ
FEQLSGSILW MAPEVIRMQD KNPYSFQSDV YAFGIVLYEL MTGQLPYSNI
NNRDQIIFMVGRGYLSPDLS KVRSNCPKAM KRLMAECLKK KRDERPLFPQ
ILASIELLARSLPKIHR

B-Raf-V600E+G468A (Seq ID No. 3)

MDRGSHHHHHHGSEDRNRMKTLGRRDSSDDWEIPDGQITVGQRIGSGSFATVYK
GKWHGDVAVKMLNVTAPTPQQLQAFKNEVGVLRKTRHVNILLFMGYSTKPQLAI
VTQWCEGSSLYHHLHIIETKFEMIKLIDIARQTAQGMDYLHAKSIIHRDLKSNNIFLH
EDLTVKIGDFGLAT<u>E</u>KSRWSGSHQFEQLSGSILWMAPEVIRMQDKNPYSFQSDVYA
FGIVLYELMTGQLPYSNINNRDQIIFMVGRGYLSPDLSKVRSNCPKAMKRLMAECL
KKKRDERPLFPQILASIELLARSLPKIHR

B-Raf-wild type, full length
(Seq ID No. 4, Invitrogen, PV3848)
MAPILGYWKI KGLVQPTRLL LEYLEEKYEE HLYERDEGDK WRNKKFELGL
EFPNLPYYID GDVKLTQSMA IIRYIADKHN MLGGCPKERA EISMLEGAVL
DIRYGVSRIA YSKDFETLKV DFLSKLPEML KMFEDRLCHK TYLNGDHVTH
PDFMLYDALD VVLYMDPMCL DAFPKLVCFK KRIEAIPQID KYLKSSKYIA
WPLQGWQATF GGGDHPPKSD LVPRHNQTSL YKKAGSAAAV VEENLYFQGS
FTMAALSGGG GGGAEPGQAL FNGDMEPEAG AGAGAAASSA
NIKQMIKLTQ EHIEALLDKF GGEHNPPSIY LEAYEEYTSK LDALQQREQQ
LLESLGNGTD FSVSSSASMD TVTSSSSSSL SVLPSSLSVF QNPTDVARSN
PKSPQKPIVR VFLPNKQRTV VPARCGVTVR DSLKKALMMR GLIPECCAVY
RIQDGEKKPI GWDTDISWLT GEELHVEVLE NVPLTTHNFV RKTFFTLAFC
DFCRKLLFQG FRCQTCGYKF HQRCSTEVPL MCVNYDQLDL LFVSKFFEHH
PIPQEEASLA ETALTSGSSP SAPASDSIGP QILTSPSPSK SIPIPQPFRP
ADEDHRNQFG QRDRSSSAPN VHINTIEPVN IDDLIRDQGF RGDGGSTTGL
SATPPASLPG SLTNVKALQK SPGPQRERKS SSSSEDRNRM KTLGRRDSSD
DWEIPDGQIT VGQRIGSGSF GTVYKGKWHG DVAVKMLNVT APTPQQLQAF
KNEVGVLRKT RHVNILLFMG YSTKPQLAIV TQWCEGSSLY HHLHIIETKF
EMIKLIDIAR QTAQGMDYLH AKSIIHRDLK SNNIFLHEDL TVKIGDFGLA -continued

```
TVKSRWSGSH QFEQLSGSIL WMAPEVIRMQ DKNPYSFQSD VYAFGIVLYE

LMTGQLPYSN INNRDQIIFM VGRGYLSPDL SKVRSNCPKA MKRLMAECLK

KKRDERPLFP QILASIELLA RSLPKIHRSA SEPSLNRAGF QTEDFSLYAC

ASPKTPIQAG GYGAFPVH.

C-Raf
                              (Seq ID No. 5, Millipore, # 14-352)
MSPILGYWKI KGLVQPTRLL LEYLEEKYEE HLYERDEGDK WRNKKFELGL

EFPNLPYYID GDVKLTQSMA IIRYIADKHN MLGGCPKERA EISMLEGAVL

DIRYGVSRIA YSKDFETLKV DFLSKLPEML KMFKDRLCHK TYLNGDHVTH

PDFMLYDALD VVLYMDPMCL DAFPKLVCFK KRIEAIPQID KYLKSSKYIA

WPLQGWQATF GGGDHPPKSD LVPRGSQPKT PVPAQRERAP VSGTQEKNKI

RPRGQRDSSD DWEIEASEVM LSTRIGSGSF GTVYKGKWHG DVAVKILKVV

DPTPEQFQAF RNEVAVLRKT RHVNILLFMG YMTKDNLAIV TQWCEGSSLY

KHLHVQETKF QMFQLIDIAR QTAQGMDYLH AKNIIHRDMK SNNIFLHEGL

TVKIGDFGLA TVKSRWSGSQ QVEQPTGSVL WMAPEVIRMQ DNNPFSFQSD

VYSYGIVLYE LMTGELPYSH INNRDQIIFM VGRGYASPDL SKLYKNCPKA

MKRLVADCVK KVKEERPLFP QILSSIELLQ HSLPKINRSA SEPSLHRAAH

TEDINACTLT TSPRLPVF

MEK1 protein sequence used for screening
                                                 (Seq ID no. 6)
MELKDDDFEKISELGAGNGGVVFKVSHKPSGLVMARKLIHLEIKPAIRNQIIRELQ

VLHECNSPYIVGFYGAFYSDGEISICMEHMDGGSLDQVLKKAGRIPEQILGKVSIA

VIKGLTYLREKHKIMHRDVKPSNILVNSRGEIKLCDFGVSGQLIDSMANSFVGTRS

YMSPERLQGTHYSVQSDIWSMGLSLVEMAVGRYPIPPPDAKELELMFGCQVEGD

AAETPPRPRTPGRPLSSYGMDSRPPMAIFELLDYIVNEPPPKLPSGVFSLEFQDFVN

KCLIKNPAERADLKQLMVHAFIKRSDAEEVDFAGWLCSTIGLNQPSTPTHAAGV
```

Enzymatic Assays Measuring Raf Kinase Activity

Test compounds are evaluated for their inhibitory activities against one or more of wild type B-Raf, wild type C-Raf, B-Raf V600E, B-Raf V600E+T529I and B-Raf V600E+G468A. T529I is a B-Raf gatekeeper mutation and G468A is a B-Raf secondary mutation. The enzymatic assays of B-Raf, C-Raf and B-Raf mutations evaluate a property of a Raf/MEK1 complex, which in the presence of ATP, catalyzes an enhanced ATP hydrolysis (Rominger, et al, *Arch. Biochem. Biophys.* 2007, 464: 130-137). The ADP formed is monitored by the well-known coupled PK/LDH (pyruvate kinase/lactate dehydrogenase) system in the form of NADH oxidation, which can be monitored and detected by absorbance at 340 nm (A340; for principal of the method see Schindler et al, *Science*, 2000, 289: 1938-1942). Raf activated MEK1 ATPase activity is a property shared by all forms of Raf proteins. In the B-Raf wild type enzymatic assay, the reaction mixture contains 1.2 nM B-Raf (Seq ID No. 4), 30 nM MEK1, 1000 uM ATP, 3.5 units (per 100 ul) of PK, 5 units (per 100 ul) of LDH, 1 mM phosphoenol pyruvate (PEP), and 280 uM of NADH. In the C-Raf assay, the reaction mixture contains 0.6 nM C-Raf (Seq ID No. 5), 26 nM MEK1, 2000 uM ATP, and the same amount of PK, LDH, PEP and NADH as above. In the B-Raf V600E assay, the reaction mixture contains 1.6 nM B-Raf V600E (Seq ID No. 1), 26 nM MEK1, 200 uM ATP and the same amount of PK, LDH, PEP and NADH as above. In the B-Raf V600E+T529I (Seq ID No. 2) assay, the reaction mixture contains 6.2 nM B-Raf V600E+T529I, 30 nM MEK1, 200 uM ATP and the same amount of PK, LDH, PEP and NADH as above. In the B-Raf V600E+G468A (Seq ID No. 3) assay, the reaction mixture contains 3.5 nM B-Raf, 30 nM MEK1, 200 uM ATP and the same amount of PK, LDH, PEP and NADH as above. All assays are started by mixing the above mixture with test compound and monitoring at A340 continuously for approximately 5 hr. Reaction data at the 3 to 4 hour time frame are collected to calculate $IC_{50}$ values.

The exemplified compounds of the invention exhibit $IC_{50}s < 100$ nM against one or more of wild type B-Raf, wild type C-Raf, B-Raf V600E, B-Raf V600E+T529I and B-Raf V600E+G468A.

These data evidence that the exemplified compounds of Formula I inhibit B-Raf V600E and C-Raf in these assays.

Enzymatic Assay of c-KIT Kinase Activity c-KIT is an important oncogene, and its overexpression and genetic mutations often occur in melanoma and gastrointestinal stromal tumor (GIST) patients. In the c-KIT enzymatic assay, the phosphorylation of poly E4Y by ATP catalyzed by c-KIT is monitored. The ADP produced from the kinase reaction is coupled to pyruvate kinase/lactate dehydrogenase (PK/LDH) reactions where NAD is formed from pyruvate and NADH. NADH can be detected by absorbance at 340 nm (for principal of the method see Schindler et al, *Science*, 2000, 289: 1938-1942). The assay reaction mixture includes 6 nM c-KIT (Seq ID No. 7, generated by methods known and used by those of ordinary skill in the art), 1 mg/mL Poly (Glu,Tyr) (Sigma), 1 mM Phosphoenol-pyruvate, 280 µM NADH, 5 U/3.5 U (per 100 ul) Pyruvate Kinase/Lactate Dehydrogenase, 85 mM Tris, pH 7.5, 17 mM $MgCl_2$, 0.0042% Triton® X-100, 0.005% BSA, 1% DMSO. Test compound is incubated with the reaction mixture for 0.5 hour before adding 200 µM ATP to start the reaction at 30° C. Reaction rates at 0.5 to 1 h are used to calculate % inhibition and $IC_{50}$ values.

The exemplified compounds of the invention inhibit c-KIT with $IC_{50}$s<100 nM.

```
c-KIT with N-terminal GST fusion
                                             (Seq ID No. 7)
LGYWKIKGLVQPTRLLLEYLEEKYEEHLYERDEGDKWRNKKFELGLEFP

NLPYYIDGDVKLTQSMAIIRYIADKHNMLGGCPKERAEISMLEGAVDIR

YGVSRIAYSKDFETLKVDFLSKLPEMLKMFEDRLCHKTYLNGDHVTHPD

FMLYDALDVVLYMDPMCLDAFPKLVCFKKRIEAIPQIDKYLKSSKYIWP

LQGWQATFGGGDHPPKSDLVPRHNQTSLYKKAGSAAAVLEENLYFQGTY

KYLQKPMYEVQWKVVEEINGNNYVYIDPTQLPYDHKWEFPRNRLSFGKT

LGAGAFGKVVEATAYGLIKSDAAMTVAVKMLKPSAHLTEREALMSELKV

LSYLGNHMNIVNLLGACTIGGPTLVITEYCCYGDLLNFLRRKRDSFICS

KQEDHAEAALYKNLLHSKESSCSDSTNEYMDMKPGVSYVVPTKADKRRS

VRIGSYIERDVTPAIMEDDELALDLEDLLSFSYQVAKGMAFLASKNCIH

RDLAARNILLTHGRITKICDFGLARDIKNDSNYVVKGNARLPVKWMAPE

SIFNCVYTFESDVWSYGIFLWELFSLGSSPYPGMPVDSKFYKMIKEGFR

MLSPEHAPAEMYDIMKTCWDADPLKRPTFKQIVQLIEKQISESTNHIYS

NLANCSPNRQKPVVDHSVRINSVGSTASSSQPLLVHDDV.
```

Measurement of Raf Kinase Activities with Native Whole Enzymes Using KiNativ Assay of ActivX Biosciences Inc To further evaluate the enzymatic pan Raf activities of test compounds, they are evaluated in a KiNativ assay developed and carried out by ActivX Biosciences Inc. using whole cell lysates of A375 cells. A375 cells are human melanoma cells with a B-Raf V600E mutation.

Sample preparation: A375 cells from ATCC are lysed by sonication in commercially available lysis buffer, cleared by centrifugation, and the resulting supernatant gel filtered into a commercially available kinase reaction buffer containing 20 mM $MnCl_2$. Final protein concentration of lysates are 10 mg/mL. 5 µL of each test compound is added from 100 µM, 10 µM, 1 µM, or 0.1 µM stock solutions in DMSO to 500 uL of lysate in duplicate for final concentrations of 1 µM, 0.1 µM, 0.01 µM, and 0.001 µM. 5 µL of DMSO is added to 500 µL of lysate in quadruplicate for controls. After 15 minute incubation, desthiobiotin-ATP acylphosphate probe is added to each sample to a final concentration of 5 µM and incubated with the samples for 10 minutes. Following the probe reaction, samples are prepared for targeted mass spectrum analysis using ActivX standard protocol. Briefly, samples are prepared for trypsin digestion (denature, reduce alkylate), digested with trypsin, and desthio-biotinylated peptides are enriched on streptavidin resin.

Data collection: Enriched peptide samples are analyzed by LC-MS/MS on a Thermo-LTQ Velos ion trap mass spectrometer using ActivX data collection methodology for A375 cells.

Data analysis: All quantitation is performed by extracting characteristic fragment ion signals from targeted MS/MS spectra and comparing signals in control and treated samples. ActivX software is used with manual validation/visual inspection performed as needed based on data flagging/filtering measures. All inhibition data points are visually verified, as are all data points showing variability outside of normal limits. Significance of data points showing >35% inhibition is determined according to the following formula: |average control peak areas−average treated peak areas|/(2*StdDev(Control peak areas)+|treated replicate one peak area−treated replicate two peak area|>0.8. $IC_{50}$ values are determined using IGOR® software.

TABLE 1

Pan Raf activities of Examples in ActivX KiNativ A375 whole cell lysate assay

| | IC50 (nM) | | | |
|---|---|---|---|---|
| Ex No. | B-Raf (V600E) | B-Raf (V600E) | A-Raf | C-Raf |
| 18 | 35 | 37 | 31 | 20 |
| 76 | 16 | 22 | 120 | 170 |

As shown in Table 1, Examples 18 and 76 inhibited A-Raf, B-RafV600E and C-Raf in A375 cells with $IC_{50}$ values <170 nM.

Cell Proliferation Assays

To investigate if the in vitro biochemical activities translate into cellular activities, the examples are used to treat cancerous cell lines with MAPK pathway activation. The A375, HT-29, Colo-205 cells (ATCC) harbor a B-Raf V600E mutation. The HCT-116 cells (ATCC) harbor a K-Ras mutation/B-Raf wild type, and the SK-Mel-2 cells (ATCC) harbor an N-Ras mutation/B-Raf wild type. The exemplified compounds of Formula I inhibit proliferation of one or more of A375, HT-29, Colo-205, HCT-116 and MEL-2 cells with $IC_{50}$s <1 uM.

A375 Cell Proliferation Assay

A375 cells (catalog #CRL-1619) are obtained from the American Type Culture Collection (ATCC, Manassas, Va.). Briefly, cells are grown in DMEM High Glucose supplemented with 10% characterized fetal bovine serum (Invitrogen, Carlsbad, Calif.) and 1% Penicillin/Streptomycin/L-Glutamine at 37 degrees Celsius, 5% $CO_2$, and 95% humidity. Cells are allowed to expand until reaching 70-95% confluency at which point they are subcultured or harvested for assay use. A serial dilution of test compound is dispensed into a 384-well black clear bottom plate in triplicate. Six hundred twenty-five cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.)

using an excitation of 540 nm and an emission of 600 nm. Data is analyzed using Prism software (Graphpad, San Diego, Calif.) to calculate $IC_{50}$ values.

HT-29 Cell Proliferation Assay

HT-29 cells (catalog #HTB-38) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

Colo205 Cell Proliferation Assay

Colo205 cells (catalog #HB-8307) are obtained from the American Type Culture Collection (ATCC, Manassas, Va.). Briefly, cells are grown in RPMI 1640 supplemented with 10% characterized fetal bovine serum (Invitrogen, Carlsbad, Calif.), 1 mM sodium pyruvate, and 1% Penicillin/Streptomycin/L-Glutamine at 37 degrees Celsius, 5% $CO_2$, and 95% humidity. Cells are allowed to expand until reaching 30-60% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

HCT-116 Cell Proliferation Assay

HCT-116 cells (catalog #CCL-247) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. A serial dilution of test compound is dispensed into a 384-well black clear bottom plate in triplicate. Six hundred twenty-five cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

SK-Mel-2 Cell Proliferation Assay

SK-Mel-2 cells (catalog #HTB-68) are obtained from the American Type Culture Collection (ATCC, Manassas, Va.). Briefly, cells are grown in MEM supplemented with 10% characterized fetal bovine serum (Invitrogen, Carlsbad, Calif.), 1 mM sodium pyruvate, 0.1 mM non-essential amino acids, and 1% Penicillin/Streptomycin/L-Glutamine at 37 degrees Celsius, 5% $CO_2$, and 95% humidity. Cells are allowed to expand until reaching 70-95% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

Inhibition in Vemurafenib-Resistant Melanoma Cells

Vemurafenib (PLX4032) and PLX4720 are inhibitors of mutant B-Raf V600E (Johannessen et al, *Nature,* 2010, 468: 968-72; Montagut et al, *Cancer Res.* 2008, 68: 4853-61; Wagle et al, *Journal of Clinical Oncology,* 2011, 29: 3085-96). Some of the patients who initially respond to vemurafenib therapy develop drug resistance and become refractory within an average of 7 months, Whittaker et al, *Sci Transl Med.* 2010, 2: 35-41. A vemurafenib-resistant cell line is generated by chronic treatment of the human melanoma cell line A375 (ATCC) harboring the B-Raf V600E mutation with increasing concentrations PLX4720.

Generation of B-Raf V600E Melanoma Cell Lines Resistant to B-Raf Inhibition

To generate resistant cells, A375 cells are cultured in growth medium, essentially as described above for the A375 cell proliferation assay, in the presence of gradually increasing concentrations of N-[3-(5-chloro-1H-pyrrolo[2,3-b]pyridine-3-carbonyl)-2,4-difluorophenyl]propane-1-sulfonamide (PLX4720; a commercially available selective B-Raf inhibitor) from 0.02 to 2 µM through approximately 4 months and 30 passages to afford a resistant cell line designated as A375res. The resistance of A375res to vemurafenib and PLX4720 is confirmed by the shift of $IC_{50}$ values in Cell Titer Blue cell proliferation assay.

In these A375res cells, PLX4720 loses much of its activity shifting more than 27-fold from an $IC_{50}$ of 369 nM to greater than 10 uM in a 72 hour proliferation assay performed essentially as described above for the A375 cell line. Similarly, the $IC_{50}$ of vemurafenib shifts from 175 nM to greater than 10 uM, a change of more than 57-fold. In contrast, the $IC_{50}$ shift of tested examples 9, 12, 13, 17, 20, 23, 24, 25, 26, 27, 28, 29, 30, 31, 32, 33, 44, 45, 47, 55, 57, 59, 60, 61, 65, 7276, 77, 79, 80, 81, 82, 83, 84, 88, 89, 91, 92, 93, 94, 97, 99, 100, 101, 123, 125, and 129, falls in a narrow range between 0.5 to 4.9 fold, with absolute $IC_{50}$ values between 9 nM and 504 nM. These data evidence that the examples of the invention inhibit cell proliferation in A375res cells in this assay.

Utility of Compounds of Formula I in the Treatment of Wt B-Raf Tumor Cells

Recent published studies (see above) suggest that B-Raf specific inhibitors, such as vemurafenib (PLX-4032) induce "paradoxical pathway activation" through B-Raf dimerization with other Raf isoforms in B-Raf wild type backgrounds. Vemurafenib is not approved for treatment of melanoma cancer patients with B-Raf wild type genetic background. This paradoxical pathway activation is also believed to be a cause of skin side effects (such as squamous cell carcinoma) in some melanoma patients treated with vemurafenib.

Examples of Formula I are tested against HCT-116 cells harboring wild type B-Raf and K-Ras mutation. The phospho-ERK activities are evaluated as described below.

HCT-116 Cell pERK Assay

HCT-116 cells (catalog #CCL-247) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. HCT-116 cells suspended in complete media are added to 384-well tissue culture treated plates ($3\times10^5$ cells/mL; 7,500 cells per well). The cells are incubated overnight at 37 degrees Celsius, 5% $CO_2$, and 95% humidity. Next, test compound or DMSO diluted in complete media is added to the wells (0.25% final DMSO concentration). The plates are then incubated for 4 hours at 37 degrees Celsius, 5% $CO_2$, and 95% humidity. Following compound incubation, the cells are lysed at 4° C. for 20 minutes with shaking Cell lysates are centrifuged and the supernatant is transferred to a new plate. An aliquot of each lysate is transferred to a white 384-well assay plate. Using the AlphaScreen SureFire pERK kit (Perkin-Elmer, Waltham, Mass.), an acceptor bead mixture is added to each well and incubated for 2 h at room temperature in the dark. A donor bead mixture is then added to each well and incubated for 2 h at room temperature in the dark. Plates are read using a Synergy2 plate reader (Biotek, Winooski, Vt.) in Plate Mode with Timing Control. Read: (F)1: excitation: 680/30 nm, emission: Plug. 2: Excitation: Plug, emission: 570/100 nm. Top mirror 635 nm. Data is analyzed using Prism software (Graphpad, San Diego, Calif.) to calculate $IC_{50}$ values and Excel software (Microsoft, Redmond, Wash.) to calculate stimulation compared to control.

Examples of Formula I have Minimal Paradoxical Pathway Activation in the Hct-116 Cell pERK Assay Examples of the invention evidence minimal paradoxical pathway stimulation, and maintain phospho-ERK inhibiting activities in HCT-116 cells harboring B-Raf wild type and K-Ras genetic background. Tested examples 9, 12, 13, 18, 20, 23, 24, 45, 47, 55, 56, 57, 64, 76, 77, 79, 83, 84, 88, 89, 92, 93, 94, 125, and 129 substantially reduce phospho-ERK signal with $IC_{50}$s between 2 nM and 96 nM in this assay. In contrast, vemurafenib stimulates the pERK signal in this assay at concentrations up to about 3 uM. Since compounds of Formula I also evidence c-Raf inhibition (prior assays, above) it is believed that paradoxical pathway activation will be minimal, or will occur at only very low inhibitor concentrations, consistent with the potent suppression of pERK measured in the HCT-116 cells.

In Vivo Activity

A375 Mouse Xenograft Pharmacodynamic Assay

To evaluate the in vivo pharmacodynamic (PD) effects of compounds of Formula I, an A375 (B-Raf V600E) xenograft model is employed. Briefly, $10\times10^6$ A375 tumor cells (ATCC) are prepared in a 1:1 matrigel mix (0.2 mL total volume) and implanted by subcutaneous injection in hind leg of nude female mice. A total of 4 mice each for each dosing group are employed. Treatment is initiated with oral administration (gavage) of test compound or vehicle (20% captisol, 25 mM phosphate, pH2.0) in 0.2 mL volume when average tumor size reaches approximately 300 mg. After a fixed time interval, the tumors are harvested and the phospho-ERK levels are measured by ELISA (Enzyme-linked immunosorbent assay). Treated groups are compared to the vehicle control group to calculate % inhibition. Data for compounds of Formula 1 are presented in table 2.

TABLE 2

Inhibition of tumor pERK levels in A375 xenografts 2 h post dose

| Example | Dose | Measured pERK inhibition 2 h post dose |
|---|---|---|
| Ex 9 | 20 mg/kg | 78% inhibition |
| Ex 12 | 20 mg/kg | 58% inhibition |
| Ex 17 | 20 mg/kg | 89% inhibition |
| Ex 18 | 20 mg/kg | 93% inhibition |
| Ex 24 | 20 mg/kg | 45% inhibition |
| Ex 43 | 20 mg/kg | 55% inhibition |
| Ex 47 | 20 mg/kg | 50% inhibition |
| Ex 56 | 6 mg/kg | 75% inhibition |
| Ex 57 | 20 mg/kg | 96% inhibition |
| Ex 64 | 20 mg/kg | 79% inhibition |
| Ex 75 | 20 mg/kg | 89% inhibition |
| Ex 77 | 20 mg/kg | 96% inhibition |
| Ex 78 | 20 mg/kg | 68% inhibition |
| Ex 79 | 20 mg/kg | 87% inhibition |
| Ex 89 | 20 mg/kg | 84% inhibition |
| Ex 92 | 20 mg/kg | 77% inhibition |
| Ex 103 | 20 mg/kg | 90% inhibition |
| Ex 105 | 20 mg/kg | 87% inhibition |

To further evaluate in vivo activity of compounds of Formula I, an A375 xenograft tumor model is utilized. Briefly, $10\times10^6$ cells in a 1:1 matrigel mix (0.2 mL total volume) are implanted by subcutaneous injection in the hind leg of nude female mice. A total of 8-10 mice in each group are used. Treatment is initiated with oral administration (gavage) of a test compound or vehicle (20% captisol, 25 mM phosphate, pH2.0) in 0.2 mL volume when tumor size reaches approximately 300-500 mg. Test compound is orally dosed twice or thrice a day for 21 days. Tumor growth and body weight are monitored over time to evaluate efficacy and signs of toxicity. Bidimensional measurements of tumors are performed twice a week and tumor volumes are calculated based on the following formula: (Tumor Volume)=$[(L)\times(W^2)\times(\pi/6)]$ where L is mid-axis length and W is mid-axis width. Tumor volume data are transformed to a log scale to equalize variance across time and treatment groups. The log volume data are analyzed with a two-way repeated measures analysis of variance by time and treatment using the MIXED procedures in SAS software (version 8.2). The correlation model for the repeated measures is spatial power. Treated groups are compared to the control group at each time point. The MIXED procedure is also used separately for each treatment group to calculate adjusted means and standard errors at each time point. Both analyses account for the autocorrelation within each animal and the loss of data that occurs when animals with large tumors are removed from the study early. The adjusted means and standard errors are plotted for each treatment group versus time.

Example 18 was orally dosed twice a day at 12 mg/kg for 21 days or thrice per day at 8 or 12 mg/kg in the A375 mouse xenograft efficacy model. All three dosing groups evidenced tumor growth inhibition with minimal animal body weight loss. Example 76 was orally dosed twice a day at 10 or 30 mg/kg for 21 days in the A375 mouse xenograft efficacy model. Both dosing groups evidenced tumor growth inhibition and tumor growth regression with minimal animal body weight loss. Example 79 was orally dosed twice a day at 15 or 30 mg/kg for 21 days in the A375 mouse xenograft efficacy model. Both dosing groups evidenced tumor growth inhibition with minimal animal body weight loss. These data evidence in vivo activity by Examples 18, 76 and 79 and support that the enzymatic, cell lysate and cell proliferation data correlates to in vivo activity.

We claim:

1. A compound of formula I

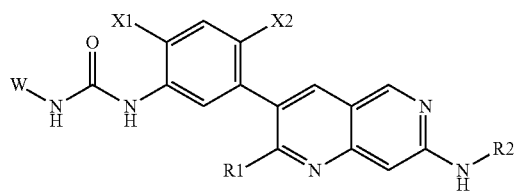

wherein
W is C1-C6 alkyl, optionally substituted with one or more of Z1A, Z1B, Z1C, Z1D, or Z1E; C4-C8 cycloalkyl optionally substituted with one or two Z2A or Z2B substituents; or W is C4-C8 heterocyclyl optionally substituted with one or two Z2A or Z2B substituents;

each Z1A, Z1B, Z1C, Z1D, Z1E is individually and independently C1-C6 alkyl, halogen, fluoro-C1-C6 alkyl wherein the alkyl chain is partially or completely fluorinated, C1-C4alkoxy, hydroxyl, fluoroC1-C4alkoxy wherein the alkyl chain is partially or completely fluorinated, cyano, C3-C8 cycloalkyl optionally substituted with one or two Z2A or Z2B substituents, phenyl optionally substituted with one to three Z2A or Z2B, or R5;

each Z2A and Z2B is individually and independently hydrogen, C1-C6 alkyl, halogen, fluoro-C1-C6 alkyl wherein the alkyl chain is partially or completely fluorinated, hydrogen, C1-C4alkoxy, hydroxyl, or cyano;

X1 is fluoro or H;

X2 is methyl, halogen, or hydrogen;

R1 is selected from C1-C4alkyl, or hydrogen;
R2 is C1-C6 alkyl, hydrogen, —(CH$_2$)$_n$—OR3, —(CH$_2$)$_n$—NR3(R4), —(CH$_2$)$_q$—R5, —C(O)—R7, or R6-substituted C5-C6heteroaryl;
each R3 and R4 is individually and independently H, C1-C6 alkyl;
each R5 is independently and individually selected from the group consisting of

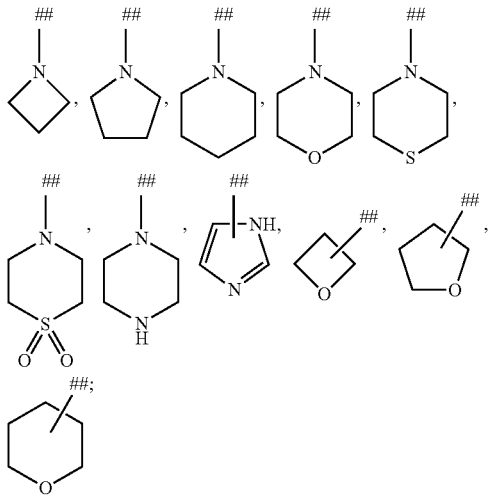

and wherein the symbol (##) is the point of attachment to —(CH$_2$)$_q$— or Z1A-E;
each R5 is optionally substituted with —(R6)$_p$;
each R6 is individually and independently C1-C6 alkyl, —(CH$_2$)$_m$—CN, —(CH$_2$)$_m$—OR3, —(CH$_2$)$_m$—NR3(R4), —(CH$_2$)$_m$—C(O)NR3(R4), or —(CH$_2$)$_m$—C(O)—R3, wherein each alkyl or alkylene is optionally substituted with one or two C1-C6 alkyl;
R7 is C1-C6alkyl, C3-C8 cycloalkyl, hydrogen, —(CH$_2$)$_m$—NR3(R4), —(CH$_2$)$_m$—R5, or —(CH$_2$)$_m$—OR3;
each m is individually and independently 0, 1, 2, or 3;
n is 2, 3, or 4;
p is 0, 1, 2, 3, or 4;
q is 0, 1, or 2.

2. The compound of claim 1 wherein W is C1-C6 alkyl, optionally substituted with Z1A, Z1B, Z1C, and Z1D.

3. The compound of claim 2 having formula Ia

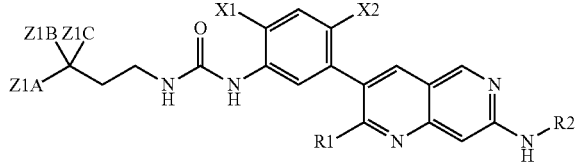

wherein each Z1A, Z1B, Z1C is individually and independently C1-C2 alkyl, fluorine, trifluoromethyl, C1-C2alkoxy, hydroxyl, or cyano.

4. The compound of claim 3 wherein X1 is fluorine and X2 is hydrogen, fluorine, or methyl.

5. The compound of claim 4 wherein R1 and R2 are each methyl.

6. The compound of claim 1 having formula Ib

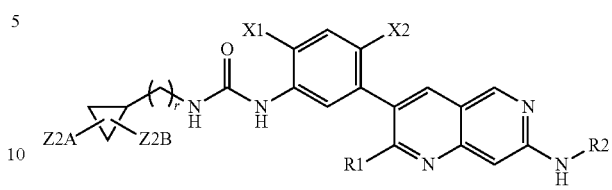

wherein Z2A and Z2B are individually and independently hydrogen, C1-C2 alkyl, trifluoromethyl, or C1-C2 alkoxy; and wherein r is 1 or 2.

7. The compound of claim 6 wherein X1 is fluorine and X2 is hydrogen, fluorine, or methyl.

8. The compound of claim 7 wherein R1 and R2 are each methyl.

9. The compound of claim 1 wherein W is C4-C8 cycloalkyl optionally substituted by Z2A and Z2B substituents.

10. The compound of claim 9 having formula Ic

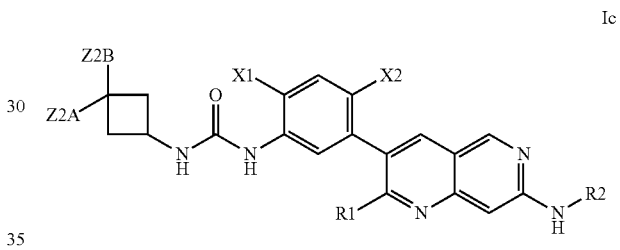

wherein each Z2A and Z2B is individually and independently C1-C2 alkyl, hydrogen, trifluoromethyl, or fluorine.

11. The compound of claim 10 wherein X1 is fluorine and X2 is hydrogen, fluorine, or methyl.

12. The compound of claim 11 wherein R1 and R2 are each methyl.

13. A compound selected from 1-(3,3-dimethylbutyl)-3-(2-fluoro-5-(2-methyl-7-(methylamino)-1,6-naphthyridin-3-yl)phenyl)urea, 1-(3-cyano-3-methylbutyl)-3-(2,4-difluoro-5-(2-methyl-7-(methylamino)-1,6-naphthyridin-3-yl)phenyl)urea, 1-(3,3-dimethylbutyl)-3-(5-(2-ethyl-7-(methylamino)-1,6-naphthyridin-3-yl)-2,4-difluorophenyl)urea, 1-(3,3-dimethylbutyl)-3-(5-(2-ethyl-7-(methylamino)-1,6-naphthyridin-3-yl)-2-fluoro-4-methylphenyl)urea, 1-cycloheptyl-3-(2-fluoro-4-methyl-5-(2-methyl-7-(methylamino)-1,6-naphthyridin-3-yl)phenyl)urea, 1-(3,3-dimethylbutyl)-3-(4-methyl-3-(2-methyl-7-(methylamino)-1,6-naphthyridin-3-yl)phenyl)urea, 1-(3,3-dimethylbutyl)-3-(5-(2-ethyl-7-(methylamino)-1,6-naphthyridin-3-yl)-2-fluorophenyl)urea, 1-cycloheptyl-3-(2,4-difluoro-5-(2-methyl-7-(methylamino)-1,6-naphthyridin-3-yl)phenyl)urea, 1-(3-cyano-3-methylbutyl)-3-(2-fluoro-4-methyl-5-(2-methyl-7-(methylamino)-1,6-naphthyridin-3-yl)phenyl)urea, 1-(3-cyano-3-methylbutyl)-3-(2-fluoro-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-(trifluoromethoxy)ethyl)urea, 1-(4,4-difluorocyclohexyl)-3-(2-fluoro-4-methyl-5-(2-methyl-7-(methylamino)-1,6-naphthyridin-3-yl)phenyl)urea, 1-(2,4-difluoro-5-(2-methyl-7-(methylamino)-1,6- naphthyridin-3-yl)phenyl)-3-((3,3-dimethylcyclobutyl)methyl)urea, 1-(3,3-dimethylcyclobutyl)-3-(2-fluoro-4-methyl-5-(2-methyl-7-(methylamino)-1,6-naphthyridin-3-yl)phenyl)urea, 1-(3,3-dimethylcyclobutyl)-3-(2-fluoro-5-(2-methyl-7-(methylamino)-1,6-naphthyridin-3-yl)phenyl)urea, 1-(2,4-difluoro-5-(2-methyl-7-(methylamino)-1,6-naphthyridin-3-yl)phenyl)-3-(3-methyl-trans(3-fluorocyclobutyl))urea, 1-(3,3-dimethylbutyl)-3-(2-fluoro-4-methyl-5-(2-methyl-7-(methylamino)-1,6-naphthyridin-3-yl)phenyl)urea, 1-(2,4-difluoro-5-(2-methyl-7-(methylamino)-1,6-naphthyridin-3-yl)phenyl)-3-(3,3-dimethylbutyl)urea, 1-(3,3-dimethylbutyl)-3-(4-fluoro-3-(2-methyl-7-(methylamino)-1,6-naphthyridin-3-yl)phenyl)urea, 1-(2,2-dimethyltetrahydro-2H-pyran-4-yl)-3-(2-fluoro-4-methyl-5-(2-methyl-7-(methylamino)-1,6-naphthyridin-3-yl)phenyl)urea, 1-((3,3-dimethylcyclobutyl)methyl)-3-(2-fluoro-4-methyl-5-(2-methyl-7-(methylamino)-1,6-naphthyridin-3-yl)phenyl)urea, 1-(4,4-difluorocyclohexyl)-3-(2-fluoro-4-methyl-5-(7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-(1-(trifluoromethyl)cyclopropyl)ethyl)urea, 1-(2,4-difluoro-5-(2-methyl-7-(methylamino)-1,6-naphthyridin-3-yl)phenyl)-3-(3-methoxy-3-methylbutyl)urea, 1-(trans-4-cyano-4-methylcyclohexyl)-3-(2-fluoro-4-methyl-5-(2-methyl-7-(methylamino)-1,6-naphthyridin-3-yl)phenyl)urea, 1-(cis-4-cyano-4-methylcyclohexyl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-(1-methylcyclopropyl)ethyl)urea, 1-(2,4-difluoro-5-(2-methyl-7-(methylamino)-1,6-naphthyridin-3-yl)phenyl)-3-(2-(1-methoxycyclopropyl)ethyl)urea, 1-(cyclohexylmethyl)-3-(2-fluoro-4-methyl-5-(2-methyl-7-(methylamino)-1,6-naphthyridin-3-yl)phenyl)urea, 1-(3-ethoxy-3-methylbutyl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-(1-methoxycyclopropyl)ethyl)urea, 1-(2-fluoro-4-methyl-5-(7-(methylamino)-1,6-naphthyridin-3-yl)phenyl)-3-(3-methoxy-3-methylbutyl)urea, 1-(2-fluoro-4-methyl-5-(2-methyl-7-(methylamino)-1,6-naphthyridin-3-yl)phenyl)-3-(4-methoxy-4-methylpentyl)urea, 1-(2,4-difluoro-5-(2-methyl-7-((6-methylpyridin-3-yl)amino)-1,6-naphthyridin-3-yl)phenyl)-3-(3,3-dimethylbutyl)urea, N-(3-(5-(3-(3,3-dimethylbutyl)ureido)-2-fluorophenyl)-2-methyl-1,6-naphthyridin-7-yl)acetamide, N-(3-(3-(3-(3,3-dimethylbutyl)ureido)-4-fluorophenyl)-2-ethyl-1,6-naphthyridin-7-yl)acetamide, N-(3-(5-(3-(3,3-dimethylbutyl)ureido)-2-fluorophenyl)-2-ethyl-1,6-naphthyridin-7-yl)acetamide, N-(3-(4-fluoro-3-(3-(3-fluoro-3-methylbutyl)ureido)phenyl)-2-methyl-1,6-naphthyridin-7-yl)isobutyramide, N-(3-(5-(3-(4,4-difluorocyclohexyl)ureido)-4-fluoro-2-methylphenyl)-2-methyl-1,6-naphthyridin-7-yl)cyclopropanecarboxamide, N-(3-(5-(3-(2-cyclopropylethyl)ureido)-4-fluoro-2-methylphenyl)-2-methyl-1,6-naphthyridin-7-yl)cyclopropanecarboxamide, N-(3-(3-(3-(4,4-difluorocyclohexyl)ureido)-4-fluorophenyl)-2-methyl-1,6-naphthyridin-7-yl)cyclopropanecarboxamide, N-(3-(4-fluoro-2-methyl-5-(3-(2-(trifluoromethoxy)ethyl)ureido)phenyl)-2-methyl-1,6-naphthyridin-7-yl)cyclopropanecarboxamide, N-(3-(5-(3-(3-cyano-3-methylbutyl)ureido)-2,4-difluorophenyl)-2-methyl-1,6-naphthyridin-7-yl)acetamide, 1-(5-(7-amino-1,6-naphthyridin-3-yl)-2-fluoro-4-methylphenyl)-3-(3-cyano-3-methylbutyl)urea, 1-(3-fluoro-3-methylbutyl)-3-(2-fluoro-4-methyl-5-(2-methyl-7-(methylamino)-1,6-naphthyridin-3-yl)phenyl)urea, 1-(3-fluoro-cis(3-methylcyclobutyl))-3-(2-fluoro-4-methyl-5-(2-methyl-7-(methylamino)-1,6-naphthyridin-3-yl)phenyl)urea, 1-(2,4-difluoro-5-(2-methyl-7-(methylamino)-1,6-naphthyridin-3-yl)phenyl)-3-(3,3-dimethylcyclobutyl)urea, 1-(5-(7-amino-2-methyl-1,6-naphthyridin-3-yl)-2-fluoro-4-methylphenyl)-3-(3-fluoro-3-methylbutyl)urea, 1-(5-(7-amino-2-methyl-1,6-naphthyridin-3-yl)-2-fluoro-4-methylphenyl)-3-(3-methoxy-3-methylbutyl)urea, 1-(5-(7-amino-1,6-naphthyridin-3-yl)-2-fluoro-4-methylphenyl)-3-(3-fluoro-3-methylbutyl)urea, 1-(5-(7-amino-2-methyl-1,6-naphthyridin-3-yl)-2-fluoro-4-methylphenyl)-3-cycloheptylurea, 1-(5-(7-amino-2-methyl-1,6-naphthyridin-3-yl)-2-fluoro-4-methylphenyl)-3-(2-(1-(trifluoromethyl)cyclopropyl)ethyl)urea, 1-(2-cyclopropylethyl)-3-(2-fluoro-4-methyl-5-(2-methyl-7-(methylamino)-1,6-naphthyridin-3-yl)phenyl)urea, 1-cycloheptyl-3-(2-fluoro-5-(2-methyl-7-(methylamino)-1,6-naphthyridin-3-yl)phenyl)urea, 1-(3-fluoro-3-methylbutyl)-3-(2-fluoro-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(3,3,3-trifluoropropyl)urea, 1-(2,4-difluoro-5-(2-methyl-7-(methylamino)-1,6-naphthyridin-3-yl)phenyl)-3-(4,4-difluorocyclohexyl)urea, 1-(2-fluoro-4-methyl-5-(2-methyl-7-(methylamino)-1,6-naphthyridin-3-yl)phenyl)-3-(4,4,4-trifluoro-3,3-dimethylbutyl)urea, 1-(2,4-difluoro-5-(2-methyl-7-(methylamino)-1,6-naphthyridin-3-yl)phenyl)-3-(4,4,4-trifluorobutyl)urea, 1-(2-fluoro-4-methyl-5-(2-methyl-7-(methylamino)-1,6-naphthyridin-3-yl)phenyl)-3-(3,3,3-trifluoropropyl)urea, 1-(2-fluoro-4-methyl-5-(2-methyl-7-(methylamino)-1,6-naphthyridin-3-yl)phenyl)-3-(3-methoxy-3-methylbutyl)urea, 1-(3-fluoro-3-methylbutyl)-3-(2-fluoro-4-methyl-5-(7-(methylamino)-1,6-naphthyridin-3-yl)phenyl)urea, 1-(2,4-difluoro-5-(2-methyl-7-(methylamino)-1,6-naphthyridin-3-yl)phenyl)-3-(2-(1-methylcyclopropyl)ethyl)urea, 1-(5-(7-(ethylamino)-2-methyl-1,6-naphthyridin-3-yl)-2-fluoro-4-methylphenyl)-3-(3-fluoro-3-methylbutyl)urea, 1-(3-fluoro-3-methylbutyl)-3-(2-fluoro-5-(7-(isopropylamino)-2-methyl-1,6-naphthyridin-3-yl)-4-methylphenyl)urea, 1-(2-cyclobutylethyl)-3-(2-fluoro-4-methyl-5-(2-methyl-7-(methylamino)-1,6-naphthyridin-3-yl)phenyl)urea, 1-(2-cyclobutylethyl)-3-(2-fluoro-5-(2-methyl-7-(methylamino)-1,6-naphthyridin-3-yl)phenyl)urea, 1-(4,4-difluoropentyl)-3-(2-fluoro-4-methyl-5-(2-methyl-7-(methylamino)-1,6-naphthyridin-3-yl)phenyl)urea, 1-(3-fluoro-trans(3-methylcyclobutyl))-3-(2-fluoro-4-methyl-5-(2-methyl-7-(methylamino)-1,6-naphthyridin-3-yl)phenyl)urea, 1-(2-fluoro-4-methyl-5-(7-(methylamino)-1,6-naphthyridin-3-yl)phenyl)-3-(4-fluoro-4-methylpentyl)urea, 1-(2,4-difluoro-5-(2-methyl-7-(methylamino)-1,6-naphthyridin-3-yl)phenyl)-3-(4,4,4-trifluoro-3,3-dimethylbutyl)urea, N-(3-(3-(3-(3,3-dimethylbutyl)ureido)-4-fluorophenyl)-2-methyl-1,6-naphthyridin-7-yl)acetamide, N-(3-(5-(3-(3,3-dimethylbutyl)ureido)-4-fluoro-2-methylphenyl)-2-methyl-1,6-naphthyridin-7-yl)acetamide, N-(3-(5-(3-(3,3-dimethylbutyl)ureido)-2,4-difluorophenyl)-2-methyl-1,6-naphthyridin-7-yl)acetamide, N-(3-(5-(3-(3,3-dimethylbutyl)ureido)-2-methylphenyl)-2-methyl-1,6-naphthyridin-7-yl)acetamide, N-(3-(3-(3-cycloheptylureido)-4-fluorophenyl)-2-methyl-1,6-naphthyridin-7-yl)acetamide, N-(3-(3-(3-cyclohexylureido)-4-fluorophenyl)-2-methyl-1,6-naphthyridin-7-yl)acetamide, N-(3-(3-(3-cyclopentylureido)-4-fluorophenyl)-2-methyl-1,6-naphthyridin-7-yl)acetamide, N-(3-(3-(3-(2-cyclopentylethyl)ureido)-4-fluorophenyl)-2-methyl-1,6-naphthyridin-7-yl)acetamide, N-(3-(3-(3-(2-cyclopropylethyl)ureido)-4- fluorophenyl)-2-methyl-1,6-naphthyridin-7-yl)acetamide, N-(3-(3-(3-(3,3-dimethylcyclobutyl)ureido)-4-fluorophenyl)-2-methyl-1,6-naphthyridin-7-yl)acetamide, N-(3-(4-fluoro-5-(3-(3-fluoro-3-methylbutyl)ureido)-2-methylphenyl)-2-methyl-1,6-naphthyridin-7-yl)propionamide, N-(3-(2,4-difluoro-5-(3-(3-fluoro-3-methylbutyl)ureido)phenyl)-2-methyl-1,6-naphthyridin-7-yl)acetamide, N-(3-(2,4-difluoro-5-(3-(3-hydroxy-3-methylbutyl)ureido)phenyl)-2-methyl-1,6-naphthyridin-7-yl)acetamide, N-(3-(4-fluoro-2-methyl-5-(3-(3,3,3-trifluoropropyl)ureido)phenyl)-2-methyl-1,6-naphthyridin-7-yl)cyclopropanecarboxamide, N-(3-(4-fluoro-5-(3-(3-fluoro-3-methylbutyl)ureido)-2-methylphenyl)-2-methyl-1,6-naphthyridin-7-yl)acetamide, N-(3-(4-fluoro-5-(3-(3-fluoro-3-methylbutyl)ureido)-2-methylphenyl)-2-methyl-1,6-naphthyridin-7-yl)cyclopropanecarboxamide, N-(3-(4-fluoro-5-(3-(3-fluoro-3-methylbutyl)ureido)-2-methylphenyl)-2-methyl-1,6-naphthyridin-7-yl)isobutyramide, N-(3-(4-fluoro-3-(3-(3,3,3-trifluoropropyl)ureido)phenyl)-2-methyl-1,6-naphthyridin-7-yl)cyclopropanecarboxamide, N-(3-(2,4-difluoro-5-(3-(3-fluoro-3-methylbutyl)ureido)phenyl)-2-methyl-1,6-naphthyridin-7-yl)cyclopropanecarboxamide, N-(3-(2,4-difluoro-5-(3-(4,4,4-trifluorobutyl)ureido)phenyl)-2-methyl-1,6-naphthyridin-7-yl)cyclopropanecarboxamide, N-(3-(5-(3-(2-cyclopropylethyl)ureido)-2,4-difluorophenyl)-2-methyl-1,6-naphthyridin-7-yl)cyclopropanecarboxamide, N-(3-(4-fluoro-5-(3-(3-fluoro-3-methylbutyl)ureido)-2-methylphenyl)-2-methyl-1,6-naphthyridin-7-yl)formamide, 1-(5-(7-amino-2-methyl-1,6-naphthyridin-3-yl)-2-fluorophenyl)-3-(3,3-dimethylbutyl)urea, 1-(5-(7-amino-2-methyl-1,6-naphthyridin-3-yl)-2-fluoro-4-methylphenyl)-3-(4,4,4-trifluoro-3,3-dimethylbutyl)urea, 1-(5-(7-amino-2-methyl-1,6-naphthyridin-3-yl)-2,4-difluorophenyl)-3-(3,3-dimethylbutyl)urea, 1-(5-(7-amino-2-methyl-1,6-naphthyridin-3-yl)-2-fluoro-4-methylphenyl)-3-(3,3-dimethylbutyl)urea, 1-(5-(7-amino-2-methyl-1,6-naphthyridin-3-yl)-2,4-difluorophenyl)-3-(3-fluoro-3-methylbutyl)urea, 1-(2-fluoro-4-methyl-5-(2-methyl-7-(methylamino)-1,6-naphthyridin-3-yl)phenyl)-3-phenethylurea, 3-(3-(3-(3-(3,3-dimethylbutyl)ureido)-4-fluorophenyl)-2-methyl-1,6-naphthyridin-7-yl)-1,1-dimethylurea, N-(3-(3-(3-(3,3-dimethylbutyl)ureido)-4-fluorophenyl)-2-methyl-1,6-naphthyridin-7-yl)azetidine-1-carboxamide, 3-(3-(4-fluoro-5-(3-(3-fluoro-3-methylbutyl)ureido)-2-methylphenyl)-2-methyl-1,6-naphthyridin-7-yl)-1,1-dimethylurea, 1-(3,3-dimethylbutyl)-3-(2-fluoro-5-(7-((2-hydroxyethyl)amino)-2-methyl-1,6-naphthyridin-3-yl)-4-methylphenyl)urea, 1-(2,4-difluoro-5-(7-(2-hydroxyethylamino)-2-methyl-1,6-naphthyridin-3-yl)phenyl)-3-(3,3-dimethylbutyl)urea, 1-(2-fluoro-4-methyl-5-(2-methyl-7-(methylamino)-1,6-naphthyridin-3-yl)phenyl)-3-(2-hydroxy-3,3-dimethylbutyl)urea, 1-(2-fluoro-4-methyl-5-(2-methyl-7-(methylamino)-1,6-naphthyridin-3-yl)phenyl)-3-isopentylurea, 1-(2-fluoro-4-methyl-5-(2-methyl-7-(methylamino)-1,6-naphthyridin-3-yl)phenyl)-3-(2,4,4-trimethylpentan-2-yl)urea, 1-(2,4-difluoro-5-(2-methyl-7-(methylamino)-1,6-naphthyridin-3-yl)phenyl)-3-isopentylurea, 1-(3-fluoro-3-methylbutyl)-3-(2-fluoro-5-(7-((2-hydroxyethyl)amino)-2-methyl-1,6-naphthyridin-3-yl)-4-methylphenyl)urea, 1-((3,3-difluorocyclobutyl)methyl)-3-(2-fluoro-5-(7-((2-hydroxyethyl)amino)-2-methyl-1,6-naphthyridin-3-yl)-4-methylphenyl)urea, 1-(3-cyano-3-methylbutyl)-3-(2-fluoro-5-(7-((2-hydroxyethyl)amino)-2-methyl-1,6-naphthyridin-3-yl)-4-methylphenyl)urea, (S)-1-(2-fluoro-4-methyl-5-(2-methyl-7-(methylamino)-1,6-naphthyridin-3-yl)phenyl)-3-(2-hydroxy-3,3-dimethylbutyl)urea, (R)-1-(2-fluoro-4-methyl-5-(2-methyl-7-(methylamino)-1,6-naphthyridin-3-yl)phenyl)-3-(2-hydroxy-3,3-dimethylbutyl)urea, 1-(2-fluoro-4-methyl-5-(2-methyl-7-(methylamino)-1,6-naphthyridin-3-yl)phenyl)-3-(2-morpholinoethyl)urea, 1-(2-fluoro-4-methyl-5-(2-methyl-7-(methylamino)-1,6-naphthyridin-3-yl)phenyl)-3-(2-(1-hydroxycyclopropyl)ethyl)urea, 1-(4,4-dimethylpentan-2-yl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(2-hydroxy-3-methylbutyl)urea, 1-(2-fluoro-4-methyl-5-(2-methyl-7-(methylamino)-1,6-naphthyridin-3-yl)phenyl)-3-(3,3,3-trifluoro-2-hydroxypropyl)urea, (R)-1-(4,4-dimethylpentan-2-yl)-3-(2-fluoro-4-methyl-5-(2-methyl-7-(methylamino)-1,6-naphthyridin-3-yl)phenyl)urea, (S)-1-(4,4-dimethylpentan-2-yl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(tetrahydro-2H-pyran-4-yl)urea, 1-(3-cyano-3-methylbutyl)-3-(2,4-difluoro-5-(7-((2-hydroxyethyl)amino)-2-methyl-1,6-naphthyridin-3-yl)phenyl)urea, 1-(2,4-difluoro-5-(7-((2-hydroxyethyl)amino)-2-methyl-1,6-naphthyridin-3-yl)phenyl)-3-(3-fluoro-3-methylbutyl)urea, 1-(2,4-difluoro-5-(7-((2-hydroxyethyl)amino)-2-methyl-1,6-naphthyridin-3-yl)phenyl)-3-((3,3-difluorocyclobutyl)methyl)urea, (R)-1-(2-fluoro-4-methyl-5-(2-methyl-7-(methylamino)-1,6-naphthyridin-3-yl)phenyl)-3-(2-hydroxy-3-methylbutyl)urea, (S)-1-(2-fluoro-4-methyl-5-(2-methyl-7-(methylamino)-1,6-naphthyridin-3-yl)phenyl)-3-(2-hydroxy-3-methylbutyl)urea, (R)-1-(5-(7-amino-2-methyl-1,6-naphthyridin-3-yl)-2-fluoro-4-methylphenyl)-3-(2-hydroxy-3,3-dimethylbutyl)urea, (S)-1-(5-(7-amino-2-methyl-1,6-naphthyridin-3-yl)-2-fluoro-4-methylphenyl)-3-(2-hydroxy-3,3-dimethylbutyl)urea, 1-(5-(7-amino-2-methyl-1,6-naphthyridin-3-yl)-2-fluoro-4-methylphenyl)-3-(2-hydroxy-3,3-dimethylbutyl)urea, 1-(2-cyclopropyl-2-hydroxyethyl)-3-(2-fluoro-4-methyl-5-(2-methyl-7-(methylamino)-1,6-naphthyridin-3-yl)phenyl)urea, 1-(2-fluoro-4-methyl-5-(2-methyl-7-(methylamino)-1,6-naphthyridin-3-yl)phenyl)-3-(oxetan-2-ylmethyl)urea, 1-(2-fluoro-4-methyl-5-(2-methyl-7-(methylamino)-1,6-naphthyridin-3-yl)phenyl)-3-((tetrahydro-2H-pyran-2-yl)methyl)urea, or 1-(2-fluoro-4-methyl-5-(2-methyl-7-(methylamino)-1,6-naphthyridin-3-yl)phenyl)-3-(tetrahydrofuran-3-yl)urea.

14. A compound selected from 1-(3,3-dimethylbutyl)-3-(2-fluoro-4-methyl-5-(2-methyl-7-(methylamino)-1,6-naphthyridin-3-yl)phenyl)urea, 1-(2,4-difluoro-5-(2-methyl-7-(methylamino)-1,6-naphthyridin-3-yl)phenyl)-3-(3,3-dimethylbutyl)urea, 1-(3-fluoro-3-methylbutyl)-3-(2-fluoro-4-methyl-5-(2-methyl-7-(methylamino)-1,6-naphthyridin-3-yl)phenyl)urea, 1-(3-fluoro-cis(3-methylcyclobutyl))-3-(2-fluoro-4-methyl-5-(2-methyl-7-(methylamino)-1,6-naphthyridin-3-yl)phenyl)urea, 1-(3-fluoro-3-methylbutyl)-3-(2-fluoro-4-methyl-5-(7-(methylamino)-1,6-naphthyridin-3-yl)phenyl)urea, N-(3-(3-(3-(3,3-dimethylbutyl)ureido)-4-fluorophenyl)-2-methyl-1,6-naphthyridin-7-yl)acetamide, 1-(5-(7-amino-2-methyl-1,6-naphthyridin-3-yl)-2-fluoro-4-methylphenyl)-3-(2-(1-(trifluoromethyl)cyclopropyl)ethyl)urea, 1-(5-(7-amino-2-methyl-1,6-naphthyridin-3-yl)-2-fluoro-4-methylphenyl)-3-(3-fluoro-3-methylbutyl)urea, (S)-1-(2-fluoro-4-methyl-5-(2-methyl-7-(methylamino)-1,6-naphthyridin-3-yl)phenyl)-3-(2-hydroxy-3,3-dimethylbutyl)urea, or (R)-1-(2-fluoro-4-methyl-5-(2-methyl-7-(methylamino)-1,6-naphthyridin-3-yl)phenyl)-3-(2-hydroxy-3,3-dimethylbutyl)urea.

15. A pharmaceutical composition comprising a compound of claim 1, or a pharmaceutically acceptable salt thereof, in association with a pharmaceutically acceptable carrier.

16. A method of treating mammalian diseases including melanoma, thyroid cancer, colon cancer, gastrointestinal stromal tumors, solid tumors, blood-borne cancers, AML, or other cancers caused by activation of the RAS-RAF-MEK-ERK signaling pathway comprising administering to a patient in need thereof a therapeutically effective amount of a compound of claim 1, or a pharmaceutically acceptable salt thereof.

17. The compound of claim 1, or a pharmaceutically acceptable salt thereof, for use in therapy.

18. The compound of claim 1, or a pharmaceutically acceptable salt thereof, for use in the treatment of a cancer which is thyroid cancer, ovarian cancer, melanoma, AML or colorectal cancer.

19. The method of claim 16, wherein the compound is administered orally, parenterally, by inhalation, or subcutaneously.

* * * * *